(12) United States Patent
Rüegg

(10) Patent No.: US 6,890,885 B2
(45) Date of Patent: May 10, 2005

(54) HERBICIDAL COMPOSITION

(75) Inventor: Willy T. Rüegg, Greensboro, NC (US)

(73) Assignee: Syngenta Corp Protection, Inc., Greensboro, NC (US)

( * ) Notice: Subject to any disclaimer, the term of this patent is extended or adjusted under 35 U.S.C. 154(b) by 20 days.

(21) Appl. No.: 10/201,405

(22) Filed: Jul. 23, 2002

(65) Prior Publication Data

US 2004/0106519 A1 Jun. 3, 2004

Related U.S. Application Data

(63) Continuation-in-part of application No. PCT/EP01/00720, filed on Jan. 23, 2001.

(30) Foreign Application Priority Data

Jan. 25, 2000 (CH) ................................................ 139/00
Jun. 9, 2000 (CH) ............................................... 1150/00

(51) Int. Cl.⁷ ........................ A01N 25/32; A01N 43/40; A01N 43/72; A01N 43/80; A01N 43/90

(52) U.S. Cl. ........................ 504/103; 504/104; 504/105; 504/106; 504/107; 504/108; 504/109; 504/110; 504/111; 504/112; 504/128; 504/132; 504/134; 504/136; 504/137

(58) Field of Search ................................ 504/104, 105, 504/106, 107, 108, 109, 110, 111, 112, 128, 132, 134, 136, 137, 103, 135

(56) References Cited

U.S. PATENT DOCUMENTS

| | | | |
|---|---|---|---|
| 3,790,571 A | 2/1974 | Diskus et al. | 260/250 |
| 4,448,960 A | 5/1984 | Rohr et al. | 544/282 |
| 4,639,266 A | 1/1987 | Heubach et al. | 71/92 |
| 4,995,902 A | 2/1991 | Brunner | 71/94 |
| 5,183,492 A | 2/1993 | Suchy et al. | 504/243 |
| 5,194,085 A | 3/1993 | Lindig et al. | 504/273 |
| 5,215,570 A | 6/1993 | Burckhardt et al. | 504/104 |
| 5,324,843 A | 6/1994 | Rueb et al. | 548/452 |
| 5,441,922 A | 8/1995 | Ort et al. | 504/104 |
| 5,461,019 A | 10/1995 | Willms et al. | 504/130 |
| 5,498,773 A | 3/1996 | Noveroske et al. | 504/103 |
| 5,516,750 A | 5/1996 | Willms et al. | 504/106 |
| 5,530,126 A | 6/1996 | Woodard et al. | 544/52 |
| 5,696,051 A | 12/1997 | Willms et al. | 504/130 |
| 5,700,762 A | * 12/1997 | Lee et al. | 504/292 |
| 5,741,756 A | 4/1998 | Shribbs | 504/149 |
| 2001/0044382 A1 | 11/2001 | Ruegg | 504/139 |

FOREIGN PATENT DOCUMENTS

| | | |
|---|---|---|
| CA | 2064636 | 12/1997 |
| EP | 0 206 251 | 12/1986 |
| EP | 0 338 992 | 10/1989 |
| EP | 0 436 483 | 7/1991 |
| EP | 0 613 618 | 9/1994 |
| EP | 0 646 315 | 4/1995 |
| EP | 0 929 543 | 10/2001 |
| WO | WO 97/08953 | 3/1997 |
| WO | WO 97/34485 | 9/1997 |
| WO | WO 99/00020 | 1/1999 |
| WO | WO 00/00029 | 1/2000 |
| WO | WO 00/15615 | 3/2000 |

OTHER PUBLICATIONS

AGROW Nr. 296, Jan. 16, 1998, p 22.
The British Crop Protection Conference—weeds, Conference Proceedings vol. 1, 2–8, pp. 67–72.
The 1997 British Crop Prtoection Conference—Weeds, Conference Proceedings vol. 1, 3A–2, pp. 93–98.
Abstracts of Papers American Chemical Society, (2000) vol. 220, No. Part 1, pp AGRO 174.
Pesticide Manual, Eleventh Ed., British Crop Protection Council, 1997, Entry No. 61, 154, 213, 304, 350, 363, 377, 462.

* cited by examiner

*Primary Examiner*—S. Mark Clardy
(74) *Attorney, Agent, or Firm*—Thomas Hamilton

(57) ABSTRACT

A herbicidal composition that, in addition to comprising customary inert formulation adjuvants, comprises a) a compound of formula I

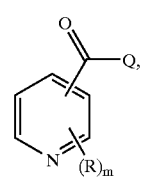

(I)

wherein the substituents are as defined in claim 1, and
b) a synergistically effective amount of one or more compounds of formulae 2.1 to 2.51. The compositions according to the invention may also comprise a safener.

10 Claims, No Drawings

HERBICIDAL COMPOSITION

This application is a continuation-in-part of PCT International Application No. PCT/EP01/00720, filed Jan. 23, 2001, claiming priority of Swiss Patent Application Nos. 139/00, filed Jan. 25, 2000, and 1150/00, filed Jun. 9. 2000, all of which are herein incorporated by reference.

The present invention relates to a novel herbicidal composition comprising a herbicidal active ingredient combination that is suitable for the selective control of weeds in crops of useful plants, for example in maize crops. The invention relates also to a method of controlling weeds in crops of useful plants, and to the use of the novel composition for that purpose.

The compounds of formula I

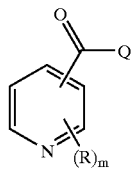

(I)

wherein the definitions of the substituents are given hereinbelow have herbicidal activity.

Surprisingly, it has now been shown that a combination of variable amounts of active ingredients, that is, of an active ingredient of formula I with one or more of the active ingredients of formulae 2.1 to 2.51 listed below, which are known and some of which are also commercially available, exhibits a synergistic action that is capable of controlling, both pre-emergence and post-emergence, the majority of weeds occurring especially in crops of useful plants.

There is therefore proposed in accordance with the present invention a novel synergistic composition for selective weed control that, in addition to customary inert formulation adjuvants, comprises as active ingredient a mixture of a) a herbicidally effective amount of a compound of formula I

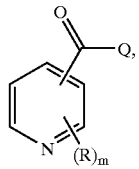

(I)

wherein each R is independently hydrogen, $C_1$–$C_6$alkyl, $C_2$–$C_6$alkenyl, $C_2$–$C_6$haloalkenyl, $C_2$–$C_6$alkynyl, $C_2$–$C_6$haloalkynyl, $C_3$–$C_6$cycloalkyl, $C_1$–$C_6$alkoxy, $C_1$–$C_6$haloalkoxy, $C_1$–$C_6$alkylthio, $C_1$–$C_6$alkylsulfinyl, $C_1$–$C_6$alkylsulfonyl, $C_1$–$C_6$haloalkyl, $C_1$–$C_6$haloalkylthio, $C_1$–$C_6$haloalkylsulfinyl, $C_1$–$C_6$haloalkylsulfonyl, $C_1$–$C_6$alkoxycarbonyl, $C_1$–$C_6$alkylcarbonyl, $C_1$–$C_6$alkylamino, di($C_1$–$C_6$alkyl)amino, $C_1$–$C_6$alkylaminosulfonyl, di($C_1$–$C_6$alkyl)aminosulfonyl, —N($R_1$)—S—$R_2$, —N($R_3$)—SO—$R_4$, —N($R_5$)—$SO_2$—$R_6$, nitro, cyano, halogen, hydroxy, amino, benzylthio, benzylsulfinyl, benzylsulfonyl, phenyl, phenoxy, phenylthio, phenylsulfinyl or phenylsulfonyl; wherein the phenyl group may itself be mono-, di- or tri-substituted by $C_1$–$C_6$alkyl, $C_1$–$C_6$haloalkyl, $C_3$–$C_6$alkenyl, $C_3$–$C_6$haloalkenyl, $C_3$–$C_6$alkynyl, $C_3$–$C_6$haloalkynyl, $C_1$–$C_6$alkoxy, $C_1$–$C_6$haloalkoxy, $C_3$–$C_6$alkenyloxy, $C_3$–$C_6$alkynyloxy, mercapto, $C_1$–$C_6$alkylthio, $C_1$–$C_6$haloalkylthio, $C_3$–$C_6$alkenylthio, $C_3$–$C_6$haloalkenylthio, $C_3$–$C_6$alkynylthio, $C_2$–$C_5$alkoxyalkylthio, $C_3$–$C_5$acetylalkylthio, $C_3$–$C_6$alkoxycarbonylalkylthio, $C_2$–$C_4$cyanoalkylthio, $C_1$–$C_6$alkylsulfinyl, $C_1$–$C_6$haloalkylsulfinyl, $C_1$–$C_6$alkylsulfonyl, $C_1$–$C_6$haloalkylsulfonyl, aminosulfonyl, $C_1$–$C_2$alkylaminosulfonyl, $C_2$–$C_4$dialkylaminosulfonyl, $C_1$–$C_3$alkylene-$R_{45}$, $NR_{46}R_{47}$, halogen, cyano, nitro, phenyl or by benzylthio, wherein the latter phenyl and benzylthio groups may themselves be substituted on the phenyl ring by $C_1$–$C_3$alkyl, $C_1$–$C_3$haloalkyl, $C_1$–$C_3$alkoxy, $C_1$–$C_3$haloalkoxy, halogen, cyano or by nitro;

or each R is independently a monocyclic or fused bicyclic ring system having from 5 to 10 members, which may be aromatic or partially saturated and may contain from 1 to 4 hetero atoms selected from nitrogen, oxygen and sulfur; wherein the ring system either is bound directly to the pyridine ring or is bound to the pyridine ring via a $C_1$–$C_4$alkylene group, and each ring system may not contain more than two oxygen atoms and may not contain more than two sulfur atoms, and the ring system may itself be mono-, di- or tri-substituted by $C_1$–$C_6$alkyl, $C_1$–$C_6$haloalkyl, $C_3$–$C_6$alkenyl, $C_3$–$C_6$haloalkenyl, $C_3$–$C_6$alkynyl, $C_3$–$C_6$haloalkynyl, $C_1$-alkyl, $C_1$–$C_6$haloalkoxy, $C_3$–$C_6$alkenyloxy, $C_3$–$C_6$alkynyloxy, mercapto, $C_1$–$C_6$alkylthio, $C_1$–$C_6$haloalkylthio, $C_3$–$C_6$alkenylthio, $C_3$–$C_6$haloalkenylthio, $C_3$–$C_6$alkynylthio, $C_2$–$C_5$alkoxyalkylthio, $C_3$–$C_5$acetylalkylthio, $C_3$–$C_6$alkoxycarbonylalkylthio, $C_2$–$C_4$cyanoalkylthio, $C_1$–$C_6$alkylsulfinyl, $C_1$–$C_6$haloalkylsulfinyl, $C_1$–$C_6$alkylsulfonyl, $C_1$–$C_6$haloalkylsulfonyl, aminosulfonyl, $C_1$–$C_2$alkylamino-sulfonyl, $C_2$–$C_4$dialkylaminosulfonyl, $C_1$–$C_3$alkylene-$R_7$, $NR_8R_9$, halogen, cyano, nitro, phenyl or by benzylthio, wherein phenyl and benzylthio may themselves be substituted on the phenyl ring by $C_1$–$C_3$alkyl, $C_1$–$C_3$haloalkyl, $C_1$–$C_3$alkoxy, $C_1$–$C_3$haloalkoxy, halogen, cyano or by nitro, and wherein the substituents on the nitrogen in the heterocyclic ring are other than halogen; or each R is independently $C_1$–$C_4$alkoxy-$C_1$–$C_4$alkyl or $C_1$–$C_4$alkoxy-$C_1$–$C_4$alkoxy-$C_1$–$C_4$alkyl;

m is 1, 2, 3 or 4;

$R_1$, $R_3$ and $R_5$ are each independently of the others hydrogen or $C_1$–$C_6$alkyl;

$R_2$ is $NR_{10}R_{11}$, $C_1$–$C_6$alkoxy, $C_1$–$C_6$haloalkoxy, $C_1$–$C_6$alkyl, $C_1$–$C_6$haloalkyl, $C_3$–$C_6$alkenyl, $C_3$–$C_6$-haloalkenyl, $C_3$–$C_6$alkynyl, $C_3$–$C_6$haloalkynyl, $C_3$–$C_6$cycloalkyl or phenyl, wherein phenyl may itself be substituted by $C_1$–$C_3$alkyl, $C_1$–$C_3$haloalkyl, $C_1$–$C_3$alkoxy, $C_1$–$C_3$haloalkoxy, halogen, cyano or by nitro;

$R_4$ is $NR_{12}R_{13}$, $C_1$–$C_6$alkoxy, $C_1$–$C_6$haloalkoxy, $C_1$–$C_6$alkyl, $C_1$–$C_6$haloalkyl, $C_3$–$C_6$alkenyl, $C_3$–$C_6$-haloalkenyl, $C_3$–$C_6$alkynyl, $C_3$–$C_6$haloalkynyl, $C_3$–$C_6$cycloalkyl or phenyl, wherein phenyl may itself be substituted by $C_1$–$C_3$alkyl, $C_1$–$C_3$haloalkyl, $C_1$–$C_3$alkoxy, $C_1$–$C_3$haloalkoxy, halogen, cyano or by nitro;

$R_6$ is $NR_{14}R_{15}$, $C_1$–$C_6$alkoxy, $C_1$–$C_6$haloalkoxy, $C_1$–$C_6$alkyl, $C_3$–$C_6$haloalkyl, $C_3$–$C_6$-haloalkenyl, $C_3$–$C_6$alkynyl, $C_3$–$C_6$haloalkynyl, $C_3$–$C_6$cycloalkyl or phenyl, wherein phenyl may itself be substituted by $C_1$–$C_3$alkyl, $C_1$–$C_3$haloalkyl, $C_1$–$C_3$alkoxy, $C_1$–$C_3$haloalkoxy, halogen, cyano or by nitro;

$R_7$ and $R_{45}$ are each independently of the other $C_1$–$C_3$alkoxy, $C_2$–$C_4$alkoxycarbonyl, $C_1$–$C_3$-alkylthio, $C_1$–$C_3$alkylsulfinyl, $C_1$–$C_3$alkylsulfonyl or phenyl, wherein phenyl may itself be substituted by $C_1$–$C_3$alkyl, $C_1$–$C_3$haloalkyl, $C_1$–$C_3$alkoxy, $C_1$–$C_3$haloalkoxy, halogen, cyano or by nitro;

$R_8$, $R_{10}$, $R_{12}$, $R_{14}$ and $R_{46}$ are each independently of the others hydrogen or $C_1$–$C_6$alkyl;

$R_9$, $R_{11}$, $R_{13}$, $R_{15}$ and $R_{47}$ are each independently of the others $C_1$–$C_6$alkyl or $C_1$–$C_6$alkoxy;

Q is the group $Q_1$

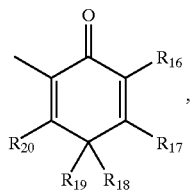

(Q₁)

wherein $R_{16}$, $R_{17}$, $R_{18}$ and Rig are each independently of the others hydrogen, hydroxy, $C_1$–$C_4$alkyl, $C_2$–$C_6$alkenyl, $C_2$–$C_6$alkynyl, $C_1$–$C_4$alkoxycarbonyl, $C_1$–$C_6$alkylthio, $C_1$–$C_6$alkylsulfinyl, $C_1$–$C_6$alkylsulfonyl, $C_1$–$C_4$alkyl-NHS(O)$_2$, $C_1$–$C_4$haloalkyl, —NH—$C_1$–$C_4$alkyl, —N($C_1$–$C_4$alkyl)$_2$, $C_1$–$C_6$alkoxy, cyano, nitro, halogen, or phenyl which may itself be substituted by $C_1$–$C_4$alkyl, $C_1$–$C_4$haloalkyl, $C_1$–$C_4$alkoxy, $C_1$–$C_4$haloalkoxy, $C_1$–$C_4$alkylcarbonyl, $C_1$–$C_4$alkoxycarbonyl, amino, $C_1$–$C_4$alkylamino, di($C_1$–$C_4$alkyl)amino, $C_1$–$C_6$alkylthio, $C_1$–$C_6$alkylsulfinyl, $C_1$–$C_6$alkylsulfonyl, $C_1$–$C_4$alkyl-S(O)$_2$O, $C_1$–$C_4$haloalkylthio, $C_1$–$C_4$haloalkylsulfinyl, $C_1$–$C_4$haloalkylsulfonyl, $C_1$–$C_4$haloalkyl-S(O)$_2$O, $C_1$–$C_4$alkyl-S(O)$_2$NH, $C_1$–$C_4$alkyl-S(O)$_2$N($C_1$–$C_4$alkyl), halogen, nitro, COOH or by cyano; or two adjacent substituents out of $R_{16}$, $R_{17}$, $R_{18}$ and $R_{19}$ form a $C_2$–$C_6$alkylene bridge;

$R_{20}$ is hydroxy, O⁻M⁺, halogen, $C_1$–$C_{12}$alkoxy, $C_1$–$C_{12}$alkylcarbonyloxy, $C_2$–$C_4$-alkenylcarbonyloxy, $C_3$–$C_6$cycloalkylcarbonyloxy, $C_1$–$C_{12}$alkoxycarbonyloxy, $C_1$–$C_{12}$alkylcarbonyloxy, $R_{21}R_{22}N$—C(O)O, $C_1$–$C_{12}$alkylthio, $C_1$–$C_{12}$alkylsulfinyl, $C_1$–$C_{12}$alkylsulfonyl, $C_1$–$C_4$haloalkylthio, $C_1$–$C_4$haloalkylsulfinyl, $C_1$–$C_4$haloalkylsulfonyl, $C_2$–$C_{12}$alkenylthio, $C_2$–$C_{12}$alkenylsulfinyl, $C_2$–$C_{12}$alkenylsulfonyl, $C_2$–$C_{12}$haloalkenylthio, $C_2$–$C_{12}$haloalkenylsulfinyl, $C_2$–$C_{12}$haloalkenylsulfonyl, $C_2$–$C_{12}$alkynylthio, $C_2$–$C_{12}$alkynylsulfinyl, $C_2$–$C_{12}$alkynylsulfonyl, $C_1$–$C_4$alkyl-S(O)$_2$O, phenyl-S(O)$_2$O, ($C_1$–$C_4$alkoxy)$_2$P(O)O, $C_1$–$C_4$alkyl($C_1$–$C_4$alkoxy)P(O)O, H($C_1$–$C_4$alkoxy)P(O)O, $C_1$–$C_{12}$-alkyl-S(CO)O, benzyloxy, phenoxy, phenylthio, phenylsulfinyl or phenylsulfonyl, wherein the phenyl group may itself be substituted by $C_1$–$C_4$alkyl, $C_1$–$C_4$haloalkyl, $C_1$–$C_4$alkoxy, $C_1$–$C_4$haloalkoxy, $C_1$–$C_4$alkylcarbonyl, $C_1$–$C_4$alkoxycarbonyl, $C_1$–$C_4$alkylamino, di($C_1$–$C_4$alkyl)amino, $C_1$–$C_4$alkylthio, $C_1$–$C_4$alkylsulfinyl, $C_1$–$C_4$alkylsulfonyl, $C_1$–$C_4$alkyl-S(O)$_2$O, $C_1$–$C_4$haloalkylthio, $C_1$–$C_4$haloalkylsulfinyl, $C_1$–$C_4$haloalkylsulfonyl, $C_1$–$C_4$haloalkyl-S(O)$_2$O, $C_1$–$C_4$alkyl-S(O)$_2$NH, $C_1$–$C_4$alkyl-S(O)$_2$N($C_1$–$C_4$alkyl), halogen, nitro or by cyano; and $R_{21}$ and $R_{22}$ are each independently of the other hydrogen or $C_1$–$C_4$alkyl;

or is the group $Q_2$

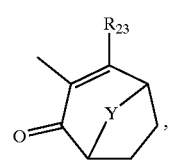

(Q₂)

wherein $R_{23}$ is hydroxy, O⁻M⁺, halogen, $C_1$–$C_{12}$alkoxy, $C_1$–$C_{12}$alkylcarbonyloxy, $C_2$–$C_4$-alkenylcarbonyloxy, $C_3$–$C_6$cycloalkylcarbonyloxy, $C_1$–$C_{12}$alkoxycarbonyloxy, $C_1$–$C_{12}$alkyl-carbonyloxy, $R_{24}R_{25}N$—C(O)O, $C_1$–$C_{12}$alkylthio, $C_1$–$C_{12}$alkylsulfinyl, $C_1$–$C_{12}$alkylsulfonyl, $C_1$–$C_4$haloalkylthio, $C_1$–$C_4$haloalkylsulfinyl, $C_1$–$C_4$haloalkylsulfonyl, $C_2$–$C_{12}$alkenylthio, $C_2$–$C_{12}$alkenylsulfinyl, $C_2$–$C_{12}$alkenylsulfonyl, $C_2$–$C_{12}$haloalkenylthio, $C_2$–$C_{12}$haloalkenylsulfinyl, $C_2$–$C_{12}$-haloalkenylsulfonyl, $C_2$–$C_{12}$alkynylthio, $C_2$–$C_{12}$alkynylsulfinyl, $C_2$–$C_{12}$alkynylsulfonyl, $C_1$–$C_4$alkyl-S(O)$_2$O, phenyl-S(O)$_2$O, ($C_1$–$C_4$alkoxy)$_2$P(O)O, $C_1$–$C_4$alkyl($C_1$–$C_4$alkoxy)P(O)O, H($C_1$–$C_4$alkoxy)P(O)O, $C_1$–$C_{12}$-alkyl-S(CO)O, benzyloxy, phenoxy, phenylthio, phenylsulfinyl or phenylsulfonyl, wherein the phenyl group may itself be substituted by $C_1$–$C_4$alkyl, $C_1$–$C_4$haloalkyl, $C_1$–$C_4$alkoxy, $C_1$–$C_4$haloalkoxy, $C_1$–$C_4$alkylcarbonyl, $C_1$–$C_4$alkoxycarbonyl, $C_1$–$C_4$alkylamino, di($C_1$–$C_4$alkyl)amino, $C_1$–$C_4$alkylthio, $C_1$–$C_4$alkylsulfinyl, $C_1$–$C_4$alkylsulfonyl, $C_1$–$C_4$alkyl-S(O)$_2$O, $C_1$–$C_4$haloalkylthio, $C_1$–$C_4$haloalkylsulfinyl, $C_1$–$C_4$haloalkylsulfonyl, $C_1$–$C_4$haloalkyl-S(O)$_2$O, $C_1$–$C_4$alkyl-S(O)$_2$NH, $C_1$–$C_4$alkyl-S(O)$_2$N($C_1$–$C_4$alkyl), halogen, nitro or by cyano;

$R_{24}$ and $R_{25}$ are each independently of the other hydrogen or $C_1$–$C_4$alkyl; and Y is oxygen, sulfur, a chemical bond or a $C_1$–$C_4$alkylene bridge;

or is the group $Q_3$

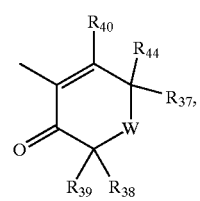

(Q₃)

wherein $R_{44}$, $R_{37}$, $R_{38}$ and $R_{39}$ are each independently of the others hydrogen, $C_1$–$C_6$alkyl, $C_1$–$C_6$haloalkyl, $C_2$–$C_6$alkenyl, $C_2$–$C_6$alkynyl, $C_1$–$C_6$alkoxycarbonyl, $C_1$–$C_6$alkylthio, $C_1$–$C_6$alkyl-sulfinyl, $C_1$–$C_6$alkylsulfonyl, $C_1$–$C_6$alkyl-NHS(O)$_2$, $C_1$–$C_6$alkylamino, di($C_1$–$C_6$alkyl)amino, hydroxy, $C_1$–$C_6$alkoxy, $C_3$–$C_6$alkenyloxy, $C_3$–$C_6$alkynyloxy, hydroxy-$C_1$–$C_6$alkyl, $C_1$–$C_4$alkylsulfonyloxy,-$C_1$–$C_6$alkyl, tosyloxy-$C_1$–$C_6$alkyl, halogen, cyano, nitro, phenyl, or phenyl substituted by $C_1$–$C_4$alkyl, $C_1$–$C_4$haloalkyl, $C_1$–$C_4$alkoxy, $C_1$–$C_4$haloalkoxy, $C_1$–$C_4$alkylcarbonyl, $C_1$–$C_4$alkoxycarbonyl, amino, $C_1$–$C_4$alkylamino, di($C_1$–$C_4$alkyl)amino, $C_1$–$C_6$alkylthio, $C_1$–$C_6$alkylsulfinyl, $C_1$–$C_6$alkylsulfonyl, $C_1$–$C_4$alkyl-S (O)$_2$O, C$_1$–C$_6$haloalkylthio, C$_1$–C$_6$haloalkylsulfinyl, C$_1$–C$_6$haloalkylsulfonyl, C$_1$–C$_4$haloalkyl-S(O)$_2$O, C$_1$–C$_4$alkyl-S(O)$_2$NH, C$_1$–C$_6$alkylthio-N(C$_1$–C$_4$alkyl), C$_1$–C$_6$alkylsulfinyl-N(C$_1$–C$_4$alkyl), C$_1$–C$_6$alkylsulfonyl-N(C$_1$–C$_4$alkyl), halogen, nitro, COOH or by cyano; or adjacent R$_{44}$ and R$_{37}$ or R$_{38}$ and R$_{39}$ together are C$_3$–C$_6$alkylene;

W is oxygen, sulfur, sulfinyl, sulfonyl, —CR$_{41}$R$_{42}$—, —C(O)— or —NR$_{43}$—;

R$_{41}$ is hydrogen, C$_1$–C$_4$alkyl, C$_1$–C$_4$haloalkyl, C$_1$–C$_4$alkoxy-C$_1$–C$_4$alkyl, C$_1$–C$_4$alkylthio-C$_1$–C$_4$alkyl, C$_1$–C$_4$alkylcarbonyloxy-C$_1$–C$_4$alkyl, C$_1$–C$_4$alkylsulfonyloxy-C$_1$–C$_4$alkyl, tosyloxy-C$_1$–C$_4$alkyl, di(C$_1$–C$_3$alkoxyalkyl)methyl, di(C$_1$–C$_3$alkylthioalkyl)methyl, (C$_1$–C$_3$alkoxyalkyl)-(C$_1$–C$_3$alkylthioalkyl)-methyl, C$_3$–C$_5$oxacycloalkyl, C$_3$–C$_5$thiacycloalkyl, C$_3$–C$_4$dioxacycloalkyl, C$_3$–C$_4$dithiacycloalkyl, C$_3$–C$_4$oxathiacycloalkyl, formyl, C$_1$–C$_4$alkoxycarbonyl, or phenyl which may itself be substituted by C$_1$–C$_4$alkyl, C$_1$–C$_4$haloalkyl, C$_1$–C$_4$alkoxy, C$_1$–C$_4$haloalkoxy, C$_1$–C$_4$alkylcarbonyl, C$_1$–C$_4$alkoxycarbonyl, amino, C$_1$–C$_4$alkylamino, di(C$_1$–C$_4$alkyl)amino, C$_1$–C$_4$alkylthio, C$_1$–C$_4$alkylsulfinyl, C$_1$–C$_4$alkylsulfonyl, C$_1$–C$_4$alkyl-S(O)$_2$O, C$_1$–C$_4$haloalkylthio, C$_1$–C$_4$haloalkylsulfinyl, C$_1$–C$_4$haloalkylsulfonyl, C$_1$–C$_4$haloalkyl-S(O)$_2$O, C$_1$–C$_4$alkyl-S(O)$_2$NH, C$_1$–C$_6$alkylthio-N(C$_1$–C$_4$alkyl), C$_1$–C$_6$alkylsulfinyl-N(C$_1$–C$_4$alkyl), C$_1$–C$_6$alkylsulfonyl-N(C$_1$–C$_4$alkyl), halogen, nitro, COOH or by cyano; or R$_{42}$ together with R$_{39}$ is C$_1$–C$_6$alkylene;

R$_{42}$ is hydrogen, C$_1$–C$_4$alkyl or C$_1$–C$_4$haloalkyl;

R$_{40}$ is hydroxy, O$^-$M$^+$, halogen, C$_1$–C$_{12}$alkoxy, C$_1$–C$_{12}$alkylcarbonyloxy, C$_2$–C$_4$alkenylcarbonyloxy, C$_3$–C$_6$cycloalkylcarbonyloxy, C$_1$–C$_{12}$alkoxycarbonyloxy, C$_1$–C$_{12}$alkylcarbonyloxy, R$_{96}$R$_{97}$N—C(O)O, C$_1$–C$_{12}$alkylthio, C$_1$–C$_{12}$alkylsulfinyl, C$_1$–C$_{12}$alkylsulfonyl, C$_1$–C$_4$haloalkylthio, C$_1$–C$_4$haloalkylsulfinyl, C$_1$–C$_4$haloalkylsulfonyl, C$_2$–C$_{12}$alkenylthio, C$_2$–C$_{12}$alkenylsulfinyl, C$_2$–C$_{12}$alkenylsulfonyl, C$_2$–C$_{12}$haloalkenylthio, C$_2$–C$_{12}$haloalkenylsulfinyl, C$_2$–C$_{12}$haloalkenylsulfonyl, C$_2$–C$_{12}$alkynylthio, C$_2$–C$_{12}$alkynylsulfinyl, C$_2$–C$_{12}$alkynylsulfonyl, C$_1$–C$_4$alkyl-S(O)$_2$O, phenyl-S(O)$_2$O, (C$_1$–C$_4$alkoxy)$_2$P(O)O, C$_1$–C$_4$alkyl(C$_1$–C$_4$alkoxy)P(O)O, H(C$_1$–C$_4$alkoxy)P(O)O, C$_1$–C$_{12}$-alkyl-S(CO)O, benzyloxy, phenoxy, phenylthio, phenylsulfinyl or phenylsulfonyl, wherein the phenyl group may itself be substituted by C$_1$–C$_4$alkyl, C$_1$–C$_4$haloalkyl, C$_1$–C$_4$alkoxy, C$_1$–C$_4$haloalkoxy, C$_1$–C$_4$alkylcarbonyl, C$_1$–C$_4$alkoxycarbonyl, C$_1$–C$_4$alkylamino, di(C$_1$–C$_4$alkyl)amino, C$_1$–C$_4$alkylthio, C$_1$–C$_4$alkylsulfinyl, C$_1$–C$_4$alkylsulfonyl, C$_1$–C$_4$alkyl-S(O)$_2$O, C$_1$–C$_4$haloalkylthio, C$_1$–C$_4$haloalkylsulfinyl, C$_1$–C$_4$haloalkylsulfonyl, C$_1$–C$_4$haloalkyl-S(O)$_2$O, C$_1$–C$_4$alkyl-S(O)$_2$NH, C$_1$–C$_4$alkyl-S(O)$_2$N(C$_1$–C$_4$alkyl), halogen, nitro or by cyano;

R$_{96}$ and R$_{97}$ are each independently of the other hydrogen or C$_1$–C$_4$alkyl;

R$_{43}$ is hydrogen, C$_1$–C$_4$alkyl, C$_1$–C$_4$alkoxycarbonyl, or phenyl which may itself be substituted by C$_1$–C$_4$alkyl, C$_1$–C$_4$haloalkyl, C$_1$–C$_4$alkoxy, C$_1$–C$_4$haloalkoxy, C$_1$–C$_4$alkylcarbonyl, C$_1$–C$_4$alkoxy-carbonyl, C$_1$–C$_4$alkylamino, di(C$_1$–C$_4$alkyl)amino, C$_1$–C$_4$alkylthio, C$_1$–C$_4$alkylsulfinyl, C$_1$–C$_4$alkyl-sulfonyl, C$_1$–C$_4$alkyl-S(O)$_2$O, C$_1$–C$_4$haloalkylthio, C$_1$–C$_4$haloalkylsulfinyl, C$_1$–C$_4$haloalkylsulfonyl, C$_1$–C$_4$haloalkyl-S(O)$_2$O, C$_1$–C$_4$alkyl-S(O)$_2$NH, C$_1$–C$_4$alkyl-S(O)$_2$N(C$_1$–C$_4$alkyl), halogen, nitro or by cyano;

or is the group Q$_4$

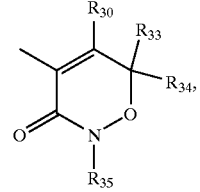

(Q$_4$)

wherein R$_{30}$ hydroxy, O$^-$M$^+$, halogen, C$_1$–C$_{12}$alkoxy, C$_1$–C$_{12}$alkylcarbonyloxy; C$_2$–C$_4$alkenyl-carbonyloxy, C$_3$–C$_6$cycloalkylcarbonyloxy, C$_1$–C$_{12}$alkoxycarbonyloxy, C$_1$–C$_{12}$alkylcarbonyloxy, R$_{31}$R$_{32}$N—C(O)O, C$_1$–C$_{12}$alkylthio, C$_1$–C$_{12}$alkylsulfinyl, C$_1$–C$_{12}$alkylsulfonyl, C$_1$–C$_4$haloalkylthio, C$_1$–C$_4$haloalkylsulfinyl, C$_1$–C$_4$haloalkylsulfonyl, C$_2$–C$_{12}$alkenylthio, C$_2$–C$_{12}$alkenylsulfinyl, C$_2$–C$_{12}$-alkenylsulfonyl, C$_2$–C$_{12}$haloalkenylthio, C$_2$–C$_{12}$haloalkenylsulfinyl, C$_2$–C$_{12}$haloalkenylsulfonyl, C$_2$–C$_{12}$alkynylthio, C$_2$–C$_{12}$alkynylsulfinyl, C$_2$–C$_{12}$alkynylsulfonyl, C$_1$–C$_4$alkyl-S(O)$_2$O, phenyl-S(O)$_2$O, (C$_1$–C$_4$alkoxy)$_2$P(O)O, C$_1$–C$_4$alkyl(C$_1$–C$_4$alkoxy)P(O)O, H(C$_1$–C$_4$alkoxy)P(O)O, C$_1$–C$_{12}$-alkyl-S(CO)O, benzyloxy, phenoxy, phenylthio, phenylsulfinyl or phenylsulfonyl, wherein the phenyl group may itself be substituted by C$_1$–C$_4$alkyl, C$_1$–C$_4$haloalkyl, C$_1$–C$_4$alkoxy, C$_1$–C$_4$haloalkoxy, C$_1$–C$_4$alkylcarbonyl, C$_1$–C$_4$alkoxycarbonyl, C$_1$–C$_4$alkylamino, di(C$_1$–C$_4$alkyl) amino, C$_1$–C$_4$alkylthio, C$_1$–C$_4$alkylsulfinyl, C$_1$–C$_4$alkylsulfonyl, C$_1$–C$_4$alkyl-S(O)$_2$O, C$_1$–C$_4$haloalkylthio, C$_1$–C$_4$haloalkylsulfinyl, C$_1$–C$_4$haloalkylsulfonyl, C$_1$–C$_4$haloalkyl-S(O)$_2$O, C$_1$–C$_4$alkyl-S(O)$_2$NH, C$_1$–C$_4$alkyl-S(O)$_2$N(C$_1$–C$_4$alkyl), halogen, nitro or by cyano; and R$_{31}$, and R$_{32}$ are each independently of the other hydrogen or C$_1$–C$_4$alkyl;

R$_{33}$ and R$_{34}$ are each independently of the other hydrogen, hydroxy, C$_1$–C$_4$alkyl, C$_2$–C$_6$alkenyl, C$_2$–C$_6$alkynyl, C$_1$–C$_4$alkoxycarbonyl, C$_1$–C$_6$alkylthio, C$_1$–C$_6$alkylsulfinyl, C$_1$–C$_6$alkylsulfonyl, C$_1$–C$_4$alkyl-NHS(O)$_2$, C$_1$–C$_4$haloalkyl, —NH—C$_1$–C$_4$alkyl, —N(C$_1$–C$_4$alkyl)$_2$, C$_1$–C$_6$alkoxy, cyano, nitro, halogen, or phenyl which may itself be substituted by C$_1$–C$_4$alkyl, C$_1$–C$_4$haloalkyl, C$_1$–C$_4$alkoxy, C$_1$–C$_4$haloalkoxy, C$_1$–C$_4$alkylcarbonyl, C$_1$–C$_4$alkoxycarbonyl, amino, C$_1$–C$_4$alkylamino, di(C$_1$–C$_4$alkyl)amino, C$_1$–C$_6$alkylthio, C$_1$–C$_6$alkylsulfinyl, C$_1$–C$_6$alkylsulfonyl, C$_1$–C$_4$alkyl-S(O)$_2$O, C$_1$–C$_4$haloalkylthio, C$_1$–C$_4$haloalkylsulfinyl, C$_1$–C$_4$haloalkylsulfonyl, C$_1$–C$_4$haloalkyl-S(O)$_2$O, C$_1$–C$_4$alkyl-S(O)$_2$NH, C$_1$–C$_4$alkyl-S(O)$_2$N(C$_1$–C$_4$alkyl), halogen, nitro, COOH or by cyano; or R$_{33}$ and R$_{34}$ together form a C$_2$–C$_6$alkylene bridge; and R$_{35}$ is hydrogen, C$_1$–C$_4$alkyl, C$_1$–C$_4$alkoxycarbonyl, or phenyl which may itself be substituted by C$_1$–C$_4$alkyl, C$_1$–C$_4$haloalkyl, C$_1$–C$_4$alkoxy, C$_1$–C$_4$haloalkoxy, C$_1$–C$_4$alkylcarbonyl, C$_1$–C$_4$alkoxy-carbonyl, amino, C$_1$–C$_4$alkylamino, di(C$_1$–C$_4$alkyl)amino, C$_1$–C$_4$alkylthio, C$_1$–C$_4$alkylsulfinyl, C$_1$–C$_4$alkylsulfonyl, C$_1$–C$_4$alkyl-S(O)$_2$O, C$_1$–C$_4$haloalkylthio, C$_1$–C$_4$haloalkylsulfinyl, C$_1$–C$_4$halo-alkylsulfonyl, C$_1$–C$_4$haloalkyl-S(O)$_2$O, $C_1$–$C_4$alkyl-S(O)$_2$NH, $C_1$–$C_4$alkyl-S(O)$_2$N($C_1$–$C_4$alkyl), halogen, nitro, COOH or by cyano;

or is the group $Q_5$

($Q_5$)

wherein Z is sulfur, SO or SO$_2$;

$R_{01}$ is hydrogen, $C_1$–$C_8$alkyl, $C_1$–$C_8$alkyl substituted by halogen, $C_1$–$C_4$alkoxy, $C_1$–$C_4$alkylthio, $C_1$–$C_4$alkylsulfonyl, $C_1$–$C_4$alkylsulfinyl, hydroxy, cyano, nitro, —CHO, —CO$_2R_{02}$, —COR$_{03}$, —COSR$_{04}$, —NR$_{05}R_{06}$, CONR$_{036}R_{037}$, or by phenyl which may itself be substituted by $C_1$–$C_4$alkyl, $C_1$–$C_6$haloalkyl, $C_1$–$C_4$alkoxy, $C_1$–$C_4$haloalkoxy, $C_2$–$C_6$alkenyl, $C_3$–$C_6$alkynyl, $C_3$–$C_6$alkenyloxy, $C_3$–$C_6$alkynyloxy, halogen, nitro, cyano, —COOH, COOC$_1$–$C_4$alkyl, COOphenyl, $C_1$–$C_4$alkoxy, phenoxy, ($C_1$–$C_4$alkoxy)-$C_1$–$C_4$alkyl, ($C_1$–$C_4$alkylthio)-$C_1$–$C_4$alkyl, ($C_1$–$C_4$alkylsulfinyl)-$C_1$–$C_4$alkyl, ($C_1$–$C_4$alkylsulfonyl)-$C_1$–$C_4$alkyl, NHSO$_2$—$C_1$–$C_4$alkyl, NHSO$_2$-phenyl, N($C_1$–$C_6$alkyl)SO$_2$—$C_1$–$C_4$alkyl, N($C_1$–$C_6$alkyl)SO$_2$-phenyl, N($C_2$–$C_6$alkenyl)SO$_2$—$C_1$–$C_4$alkyl, N($C_2$–$C_6$alkenyl)SO$_2$-phenyl, N($C_3$–$C_6$alkynyl)SO$_2$—$C_1$–$C_4$alkyl, N($C_3$–$C_6$alkynyl)SO$_2$-phenyl, N($C_3$–$C_7$cycloalkyl)SO$_2$—$C_1$–$C_4$alkyl, N($C_3$–$C_7$cycloalkyl)SO$_2$-phenyl, N(phenyl)SO$_2$—$C_1$–$C_4$alkyl, N(phenyl)SO$_2$-phenyl, OSO$_2$—$C_1$–$C_4$alkyl, CONR$_{025}R_{026}$, OSO$_2$—$C_1$–$C_4$haloalkyl, OSO$_2$-phenyl, $C_1$–$C_4$alkylthio, $C_1$–$C_4$haloalkylthio, phenylthio, $C_1$–$C_4$alkylsulfonyl, $C_1$–$C_4$haloalkylsulfonyl, phenylsulfonyl, $C_1$–$C_4$alkylsulfinyl, $C_1$–$C_4$haloalkylsulfinyl, phenylsulfinyl, $C_1$–$C_4$alkylenephenyl or by —NR$_{015}$CO$_2R_{027}$;

or $R_{01}$ is $C_2$–$C_8$alkenyl or $C_2$–$C_8$alkenyl substituted by halogen, $C_1$–$C_4$alkoxy, $C_1$–$C_4$alkylthio, $C_1$–$C_4$alkylsulfonyl, $C_1$–$C_4$alkylsulfinyl, —CONR$_{032}R_{033}$, cyano, nitro, —CHO, —CO$_2R_{038}$, —COR$_{039}$, —COS—$C_1$–$C_4$alkyl, —NR$_{034}R_{035}$, or by phenyl which may itself be substituted by $C_1$–$C_4$alkyl, $C_1$–$C_6$haloalkyl, $C_1$–$C_4$alkoxy, $C_1$–$C_4$haloalkoxy, $C_2$–$C_6$alkenyl, $C_3$–$C_6$alkynyl, $C_3$–$C_6$alkenyloxy, $C_3$–$C_6$alkynyloxy, halogen, nitro, cyano, —COOH, COOC$_1$–$C_4$alkyl, COOphenyl, $C_1$–$C_4$alkoxy, phenoxy, ($C_1$–$C_4$alkoxy)-$C_1$–$C_4$alkyl, ($C_1$–$C_4$alkylthio)-$C_1$–$C_4$alkyl, ($C_1$–$C_4$alkylsulfinyl)-$C_1$–$C_4$alkyl, ($C_1$–$C_4$alkylsulfonyl)-$C_1$–$C_4$alkyl, NHSO$_2$—$C_1$–$C_4$alkyl, NHSO$_2$-phenyl, N($C_1$–$C_6$alkyl)SO$_2$—$C_1$–$C_4$alkyl, N($C_1$–$C_6$alkyl)SO$_2$-phenyl, N($C_2$–$C_6$alkenyl)SO$_2$—$C_1$–$C_4$alkyl, N($C_2$–$C_6$alkenyl)SO$_2$-phenyl, N($C_3$–$C_6$alkynyl)SO$_2$—$C_1$–$C_4$alkyl, N($C_3$–$C_6$alkynyl)SO$_2$-phenyl, N($C_3$–$C_7$cycloalkyl)SO$_2$—$C_1$–$C_4$alkyl, N($C_3$–$C_7$cycloalkyl)SO$_2$-phenyl, N(phenyl)SO$_2$—$C_1$–$C_4$alkyl, N(phenyl)SO$_2$-phenyl, OSO$_2$—$C_1$–$C_4$alkyl, CONR$_{040}R_{041}$, OSO$_2$—$C_1$–$C_4$haloalkyl, OSO$_2$-phenyl, $C_1$–$C_4$alkylthio, $C_1$–$C_4$haloalkylthio, phenylthio, $C_1$–$C_4$alkylsulfonyl, $C_1$–$C_4$haloalkylsulfonyl, phenylsulfonyl, $C_1$–$C_4$alkylsulfinyl, $C_1$–$C_4$haloalkylsulfinyl, phenylsulfinyl, $C_1$–$C_4$alkylenephenyl or by —NR$_{043}$CO$_2R_{042}$;

or $R_{01}$ is $C_3$–$C_6$alkynyl or $C_3$–$C_6$alkynyl substituted by halogen, $C_1$–$C_4$haloalkyl, cyano, —CO$_2R_{044}$, or by phenyl which may itself be substituted by $C_1$–$C_4$alkyl, $C_1$–$C_6$haloalkyl, $C_1$–$C_4$alkoxy, $C_1$–$C_4$haloalkoxy, $C_2$–$C_6$alkenyl, $C_3$–$C_6$alkynyl, $C_3$–$C_6$alkenyloxy, $C_3$–$C_6$alkynyloxy, halogen, nitro, cyano, —COOH, COOC$_1$–$C_4$alkyl, COOphenyl, $C_1$–$C_4$alkoxy, phenoxy, ($C_1$–$C_4$alkoxy)-$C_1$–$C_4$alkyl, ($C_1$–$C_4$alkylthio)-$C_1$–$C_4$alkyl, ($C_1$–$C_4$alkylsulfinyl)-$C_1$–$C_4$alkyl, ($C_1$–$C_4$alkylsulfonyl)-$C_1$–$C_4$alkyl, NHSO$_2$—$C_1$–$C_4$alkyl, NHSO$_2$-phenyl, N($C_1$–$C_6$alkyl)SO$_2$—$C_1$–$C_4$alkyl, N($C_1$–$C_6$alkyl)SO$_2$-phenyl, N($C_2$–$C_6$alkenyl)SO$_2$—$C_1$–$C_4$alkyl, N($C_2$–$C_6$alkenyl)SO$_2$-phenyl, N($C_3$–$C_6$alkynyl)SO$_2$—$C_1$–$C_4$alkyl, N($C_3$–$C_6$alkynyl)SO$_2$-phenyl, N($C_3$–$C_7$cycloalkyl)SO$_2$—$C_1$–$C_4$alkyl, N($C_3$–$C_7$cycloalkyl)SO$_2$-phenyl, N(phenyl)SO$_2$—$C_1$–$C_4$alkyl, N(phenyl)SO$_2$-phenyl, OSO$_2$—$C_1$–$C_4$alkyl, CONR$_{028}R_{029}$, OSO$_2$—$C_1$–$C_4$haloalkyl, OSO$_2$-phenyl, $C_1$–$C_4$alkylthio, $C_1$–$C_4$haloalkylthio, phenylthio, $C_1$–$C_4$alkylsulfonyl, $C_1$–$C_4$haloalkylsulfonyl, phenylsulfonyl, $C_1$–$C_4$alkylsulfinyl, $C_1$–$C_4$haloalkylsulfinyl, phenylsulfinyl, $C_1$–$C_4$alkylenephenyl or by —NR$_{031}$CO$_2R_{030}$;

or $R_{01}$ is $C_3$–$C_7$cycloalkyl or $C_3$–$C_7$cycloalkyl substituted by $C_1$–$C_4$alkyl, $C_1$–$C_4$alkoxy, $C_1$–$C_4$alkyl-thio, $C_1$–$C_4$alkylsulfinyl, $C_1$–$C_4$alkylsulfonyl, or by phenyl which may itself be substituted by halogen, nitro, cyano, $C_1$–$C_4$alkoxy, $C_1$–$C_4$haloalkoxy, $C_1$–$C_4$alkylthio, $C_1$–$C_4$haloalkylthio, $C_1$–$C_4$alkyl or by $C_1$–$C_4$haloalkyl; or $R_{01}$ is $C_1$–$C_4$alkylene-$C_3$–$C_7$cycloalkyl, phenyl, or phenyl substituted by $C_1$–$C_4$alkyl, $C_1$–$C_6$haloalkyl, $C_1$–$C_4$alkoxy, $C_1$–$C_4$haloalkoxy, $C_2$–$C_6$alkenyl, $C_3$–$C_6$alkynyl, $C_3$–$C_6$alkenyloxy, $C_3$–$C_6$alkynyloxy, halogen, nitro, cyano, —COOH, COOC$_1$–$C_4$alkyl, COOphenyl, $C_1$–$C_4$alkoxy, phenoxy, ($C_1$–$C_4$alkoxy)-$C_1$–$C_4$alkyl, ($C_1$–$C_4$alkylthio)-$C_1$–$C_4$alkyl, ($C_1$–$C_4$alkylsulfinyl)-$C_1$–$C_4$alkyl, ($C_1$–$C_4$alkylsulfonyl)-$C_1$–$C_4$alkyl, NHSO$_2$—$C_1$–$C_4$alkyl, NHSO$_2$-phenyl, N($C_1$–$C_6$alkyl)SO$_2$—$C_1$–$C_4$alkyl, N($C_1$–$C_6$alkyl)SO$_2$-phenyl, N($C_2$–$C_6$alkenyl)SO$_2$—$C_1$–$C_4$alkyl, N($C_2$–$C_6$alkenyl)SO$_2$-phenyl, N($C_3$–$C_6$alkynyl)SO$_2$—$C_1$–$C_4$alkyl, N($C_3$–$C_6$alkynyl)SO$_2$-phenyl, N($C_3$–$C_7$cycloalkyl)SO$_2$—$C_1$–$C_4$alkyl, N($C_3$–$C_7$cycloalkyl)SO$_2$-phenyl, N(phenyl)SO$_2$—$C_1$–$C_4$alkyl, N(phenyl)SO$_2$-phenyl, OSO$_2$—$C_1$–$C_4$alkyl, CONR$_{045}R_{046}$, OSO$_2$—$C_1$–$C_4$haloalkyl, OSO$_2$-phenyl, $C_1$–$C_4$alkylthio, $C_1$–$C_4$haloalkylthio, phenylthio, $C_1$–$C_4$alkylsulfonyl, $C_1$–$C_4$haloalkylsulfonyl, phenylsulfonyl, $C_1$–$C_4$alkylsulfinyl, $C_1$–$C_4$haloalkylsulfinyl, phenylsulfinyl or by —NR$_{048}$CO$_2R_{047}$; or $R_{01}$ is $C_1$–$C_4$alkylenephenyl, COR$_{07}$ or from 4- to 6-membered heterocyclyl;

$R_{02}$, $R_{038}$, $R_{044}$ and $R_{066}$ are each independently of the others hydrogen, $C_1$–$C_4$alkyl, phenyl, or phenyl substituted by $C_1$–$C_4$alkyl, $C_1$–$C_6$haloalkyl, $C_1$–$C_4$alkoxy, $C_1$–$C_4$haloalkoxy, $C_2$–$C_6$alkenyl, $C_3$–$C_6$alkynyl, $C_3$–$C_6$alkenyloxy, $C_3$–$C_6$alkynyloxy, halogen, nitro, cyano, —COOH, COOC$_1$–$C_4$alkyl, COOphenyl, $C_1$–$C_4$alkoxy, phenoxy, ($C_1$–$C_4$alkoxy)-$C_1$–$C_4$alkyl, ($C_1$–$C_4$alkylthio)-$C_1$–$C_4$alkyl, ($C_1$–$C_4$alkylsulfinyl)-$C_1$–$C_4$alkyl, ($C_1$–$C_4$alkylsulfonyl)-$C_1$–$C_4$alkyl, NHSO$_2$—$C_1$–$C_4$alkyl, NHSO$_2$-phenyl, N($C_1$–$C_6$alkyl) SO$_2$—$C_1$–$C_4$alkyl, N($C_1$–$C_6$alkyl)SO$_2$-phenyl, N($C_2$–$C_6$alkenyl)SO$_2$—$C_1$–$C_4$alkyl, N($C_2$–$C_6$alkenyl) SO$_2$-phenyl, N($C_3$–$C_6$alkynyl)SO$_2$—$C_1$–$C_4$alkyl, N($C_3$–$C_6$alkynyl)SO$_2$-phenyl, N($C_3$–$C_7$cycloalkyl)SO$_2$—$C_1$–$C_4$alkyl, N($C_3$–$C_7$cycloalkyl)SO$_2$-phenyl, N(phenyl) SO$_2$—$C_1$–$C_4$alkyl, N(phenyl)SO$_2$-phenyl, OSO$_2$—$C_1$–$C_4$alkyl, CONR$_{049}R_{050}$, OSO$_2$—$C_1$–$C_4$haloalkyl, OSO$_2$phenyl, $C_1$–$C_4$alkylthio, $C_1$–$C_4$haloalkylthio, phenylthio, $C_1$–$C_4$alkylsulfonyl, $C_1$–$C_4$haloalkylsulfonyl, phenylsulfonyl, $C_1$–$C_4$alkylsulfinyl, $C_1$–$C_4$haloalkylsulfinyl, phenylsulfinyl, —$C_1$–$C_4$-alkylphenyl or by —$NR_{052}CO_2R_{053}$;

$R_{03}$, $R_{039}$ and $R_{067}$ are each independently of the others $C_1$–$C_4$alkyl, phenyl, or phenyl substituted by $C_1$–$C_4$alkyl, $C_1$–$C_6$haloalkyl, $C_1$–$C_4$alkoxy, $C_1$–$C_4$haloalkoxy, $C_2$–$C_6$alkenyl, $C_3$–$C_6$alkyl, $C_3$–$C_6$alkenyloxy, $C_3$–$C_6$alkynyloxy, halogen, nitro, cyano, —COOH, $COOC_1$–$C_4$alkyl, COOphenyl, $C_1$–$C_4$alkoxy, phenoxy, ($C_1$–$C_4$alkoxy)-$C_1$–$C_4$alkyl, ($C_1$–$C_4$alkylthio)-$C_1$–$C_4$alkyl, ($C_1$–$C_4$alkylsulfinyl)-$C_1$–$C_4$alkyl, ($C_1$–$C_4$alkylsulfonyl)-$C_1$–$C_4$alkyl, $NHSO_2$—$C_1$–$C_4$alkyl, $NHSO_2$-phenyl, $N(C_1$–$C_6$alkyl$)SO_2$ $C_1$–$C_4$alkyl, $N(C_1$–$C_6$alkyl$)SO_2$-phenyl, $N(C_2$–$C_6$alkenyl$)SO_2$—$C_1$–$C_4$alkyl, $N(C_2$–$C_6$alkenyl$)SO_2$-phenyl, $N(C_3$–$C_6$alkynyl$)SO_2$—$C_1$–$C_4$alkyl, $N(C_3$–$C_6$alkynyl$)SO_2$-phenyl, $N(C_3$–$C_7$cycloalkyl$)SO_2$—$C_4$alkyl, $N(C_3$–$C_7$cycloalkyl$)SO_2$-phenyl, $N($phenyl$)SO_2$—$C_1$–$C_4$alkyl, $N($phenyl$)SO_2$-phenyl, $OSO_2$—$C_1$–$C_4$alkyl, $CONR_{068}R_{054}$, $OSO_2$—$C_1$–$C_4$haloalkyl, $OSO_2$-phenyl, $C_1$–$C_4$alkylthio, $C_1$–$C_4$haloalkylthio, phenylthio, $C_1$–$C_4$alkylsulfonyl, $C_1$–$C_4$haloalkylsulfonyl, phenylsulfonyl, $C_1$–$C_4$alkylsulfinyl, $C_1$–$C_4$haloalkylsulfinyl, phenylsulfinyl, —$(CH_2)_t$-phenyl or by —$NR_{056}CO_2R_{055}$;

$R_{04}$ is $C_1$–$C_4$alkyl;

$R_{05}$ is hydrogen, $C_1$–$C_4$alkyl, $C_2$–$C_6$alkenyl, $C_3$–$C_6$alkynyl, $C_3$–$C_7$cycloalkyl, phenyl, or phenyl substituted by $C_1$–$C_4$alkyl, $C_1$–$C_6$haloalkyl, $C_1$–$C_4$alkoxy, $C_1$–$C_4$haloalkoxy, $C_2$–$C_6$alkenyl, $C_3$–$C_6$-alkynyl, $C_3$–$C_6$alkenyloxy, $C_3$–$C_6$alkynyloxy, halogen, nitro, cyano, —COOH, $COOC_1$–$C_4$alkyl, COOphenyl, $C_1$–$C_4$alkoxy, phenoxy, ($C_1$–$C_4$alkoxy)-$C_1$–$C_4$alkyl, ($C_1$–$C_4$alkylthio)-$C_1$–$C_4$alkyl, ($C_1$–$C_4$alkylsulfinyl)-$C_1$–$C_4$alkyl, ($C_1$–$C_4$alkylsulfonyl)-$C_1$–$C_4$alkyl, $NHSO_2$–$C_1$–$C_4$alkyl, $NHSO_2$-phenyl, $N(C_1$–$C_6$alkyl$)SO_2$—$C_1$–$C_4$alkyl, $N(C_1$–$C_6$alkyl$)SO_2$-phenyl, $N(C_2$–$C_6$alkenyl$)SO_2$—$C_1$–$C_4$alkyl, $N(C_2$–$C_6$alkenyl$)SO_2$-phenyl, $N(C_3$–$C_6$alkynyl$)SO_2H$, $N(C_3$–$C_6$alkynyl$)SO_2$—$C_1$–$C_4$alkyl, $N(C_3$–$C_6$alkynyl$)SO_2$-phenyl, $N(C_3$–$C_7$cycloalkyl$)SO_2H$, $N(C_3$–$C_7$cycloalkyl$)SO_2$—$C_1$–$C_4$alkyl, $N(C_3$–$C_7$cycloalkyl$)SO_2$-phenyl, $N($phenyl$)SO_2$—$C_1$–$C_4$alkyl, $N($phenyl$)SO_2$-phenyl, $OSO_2$—$C_1$–$C_4$alkyl, $CONR_{057}R_{058}$, $OSO_2$—$C_1$–$C_4$haloalkyl, $OSO_2$-phenyl, $C_1$–$C_4$alkylthio, $C_1$–$C_4$haloalkylthio, phenylthio, $C_1$–$C_4$alkylsulfonyl, $C_1$–$C_4$haloalkylsulfonyl, phenylsulfonyl, $C_1$–$C_4$alkylsulfinyl, $C_1$–$C_4$haloalkylsulfinyl, phenylsulfinyl, $C_1$–$C_4$alkylenephenyl or by —$NR_{060}CO_2R_{059}$;

$R_{06}$ is hydrogen, $C_1$–$C_4$alkyl, $C_2$–$C_6$alkenyl, $C_3$–$C_6$alkynyl, $C_3$–$C_7$cycloalkyl, phenyl, or phenyl substituted by $C_1$–$C_4$alkyl, $C_1$–$C_6$haloalkyl, $C_1$–$C_4$alkoxy, $C_1$–$C_4$haloalkoxy, $C_2$–$C_6$alkenyl, $C_3$–$C_6$alkynyl, $C_3$–$C_6$alkenyloxy, $C_3$–$C_6$alkynyloxy, halogen, nitro, cyano, —COOH, $COOC_1$–$C_4$alkyl, COOphenyl, $C_1$–$C_4$alkoxy, phenoxy, ($C_1$–$C_4$alkoxy)-$C_1$–$C_4$alkyl, ($C_1$–$C_4$alkylthio)-$C_1$–$C_4$alkyl, ($C_1$–$C_4$alkylsulfinyl)-$C_1$–$C_4$alkyl, ($C_1$–$C_4$alkylsulfonyl)-$C_1$–$C_4$alkyl, $NHSO_2$—$C_1$–$C_4$alkyl, $NHSO_2$phenyl, $N(C_1$–$C_6$alkyl$)SO_2$—$C_1$–$C_4$alkyl, $N(C_1$–$C_6$alkyl$)SO_2$-phenyl, $N(C_2$–$C_6$alkenyl$)SO_2$—$C_1$–$C_4$alkyl, $N(C_2$–$C_6$alkenyl$)SO_2$-phenyl, $N(C_3$–$C_6$alkynyl$)SO_2$—$C_1$–$C_4$alkyl, $N(C_3$–$C_6$alkynyl$)SO_2$-phenyl, $N(C_3$–$C_7$cycloalkyl$)SO_2$—$C_1$–$C_4$alkyl, $N(C_3$–$C_7$cycloalkyl$)SO_2$-phenyl, $N($phenyl$)SO_2$—$C_1$–$C_4$alkyl, $N($phenyl$)SO_2$-phenyl, $OSO_2$—$C_1$–$C_4$alkyl, $CONR_{061}R_{062}$, $OSO_2$—$C_1$–$C_4$haloalkyl, $OSO_2$-phenyl, $C_1$–$C_4$alkylthio, $C_1$–$C_4$haloalkylthio, phenylthio, $C_1$–$C_4$alkylsulfonyl, $C_1$–$C_4$haloalkylsulfonyl, phenylsulfonyl, $C_1$–$C_4$alkylsulfinyl, $C_1$–$C_4$haloalkylsulfinyl, phenylsulfinyl, $C_1$–$C_4$alkylenephenyl or by —$NR_{064}CO_2R_{063}$;

$R_{07}$ is phenyl, $C_1$–$C_4$alkyl, $C_1$–$C_4$alkoxy or —$NR_{08}R_{09}$;

$R_{08}$ and $R_{09}$ are each independently of the other $C_1$–$C_4$alkyl, phenyl, or phenyl substituted by halogen, nitro, cyano, $C_1$–$C_4$alkyl, $C_1$–$C_4$alkoxy, $C_1$–$C_4$thioalkyl, —$CO_2R_{066}$, —$COR_{067}$, $C_1$–$C_4$-alkylsulfonyl, $C_1$–$C_4$alkylsulfinyl or by $C_1$–$C_4$haloalkyl; or $R_{08}$ and $R_{09}$ together form a 5- or 6-membered ring, which may be interrupted by oxygen, $NR_{065}$ or by S;

$R_{015}$, $R_{031}$, $R_{043}$, $R_{048}$, $R_{052}$, $R_{056}$, $R_{060}$ and $R_{064}$ are each independently of the others hydrogen, $C_1$–$C_4$alkyl, $C_2$–$C_6$alkenyl, $C_3$–$C_6$alkynyl or $C_3$–$C_7$cycloalkyl;

$R_{025}$, $R_{026}$, $R_{027}$, $R_{028}$, $R_{029}$, $R_{030}$, $R_{032}$, $R_{033}$, $R_{034}$, $R_{035}$, $R_{036}$, $R_{037}$, $R_{040}$, $R_{041}$, $R_{042}$, $R_{045}$, $R_{046}$, $R_{047}$, $R_{049}$, $R_{050}$, $R_{053}$, $R_{054}$, $R_{055}$, $R_{057}$, $R_{058}$, $R_{059}$, $R_{061}$, $R_{062}$, $R_{063}$ are each independently of the others hydrogen, $C_1$–$C_4$alkyl, $C_2$–$C_6$alkenyl, $C_3$–$C_6$alkynyl, $C_3$–$C_7$cycloalkyl, phenyl, or phenyl substituted by halogen, nitro, cyano, $C_1$–$C_4$alkoxy, $C_1$–$C_4$haloalkoxy, $C_1$–$C_4$alkylthio, $C_1$–$C_4$haloalkylthio, $C_1$–$C_4$alkyl or by $C_1$–$C_4$haloalkyl; and $R_{36}$ is $C_1$–$C_4$alkyl, $C_1$–$C_4$haloalkyl, $C_3$–$C_6$alkenyl, $C_3$–$C_6$haloalkenyl, $C_3$–$C_6$alkynyl, $CR_3$–$CR_6$haloalkynyl, $C_3$–$C_6$cycloalkyl, or $C_3$–$C_6$cycloalkyl substituted by halogen, $C_1$–$C_4$alkyl, $C_1$–$C_4$haloalkyl, $C_3$–$C_6$alkenyl, $C_3$–$C_6$haloalkenyl, $C_3$–$C_6$alkynyl, $C_3$–$C_6$haloalkynyl, $C_1$–$C_4$alkoxycarbonyl, $CR_1$–$C_4$alkylthio, $C_1$–$C_4$alkylsulfinyl, $C_1$–$C_4$alkylsulfonyl, $C_1$–$C_4$haloalkylthio, $C_1$–$C_4$haloalkylsulfinyl, $C_1$–$C_4$haloalkylsulfonyl, $C_1$–$C_4$alkylcarbonyl, di($C_1$–$C_4$alkyl)amino, $C_1$–$C_4$alkoxy, $C_1$–$C_4$haloalkoxy, $C_1$–$C_4$alkyl-$S(O)_2O$, $C_1$–$C_4$haloalkyl-$S(O)_2O$, or by phenyl which may itself be substituted by halogen, $C_1$–$C_4$alkyl, $C_1$–$C_4$haloalkyl, $C_3$–$C_6$alkenyl, $C_3$–$C_6$alkynyl, cyano, nitro or by COOH;

or an agronomically acceptable salt of such a compound, and b) a synergistically effective amount of one or more compounds selected from a compound of formula 2.1

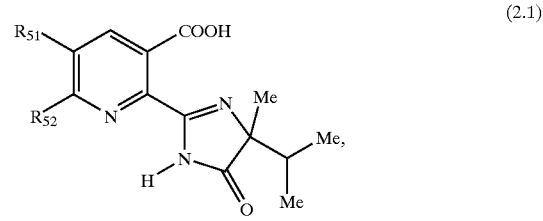

(2.1)

wherein $R_{51}$ is $CH_2$—OMe, ethyl or hydrogen;

$R_{52}$ is hydrogen or $R_{51}$ and $R_{52}$ together are the group —CH=CH—CH=CH—;

and a compound of formula 2.2

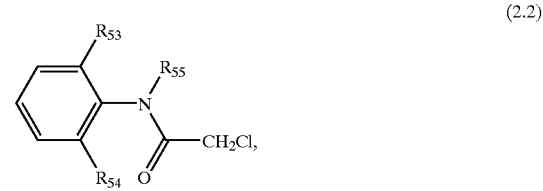

(2.2)

wherein $R_{53}$ is ethyl, $R_{54}$ is methyl or ethyl and $R_{55}$ is —CH(Me)—$CH_2$OMe, <S>—CH(Me)—$CH_2$OMe, $CH_2$OMe or $CH_2$O—$CH_2CH_3$;

and a compound of formula 2.3

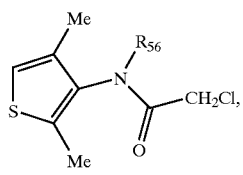
(2.3)

wherein $R_{56}$ is CH(Me)—CH$_2$OMe or <S>CH(Me)—CH$_2$OMe;

and a compound of formula 2.4

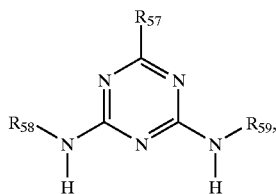
(2.4)

wherein $R_{57}$ is chlorine, methoxy or methylthio, $R_{58}$ is ethyl and $R_{59}$ is ethyl, isopropyl, —C(CN)(CH$_3$)—CH$_3$ or tert-butyl;

and a compound of formula 2.5

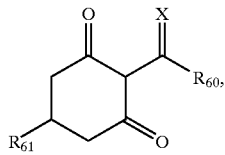
(2.5)

wherein $R_{60}$ is ethyl or n-propyl, $R_{61}$ is COO$^-$½ Ca$^{++}$, —CH$_2$—CH(Me)S—CH$_2$CH$_3$ or the group

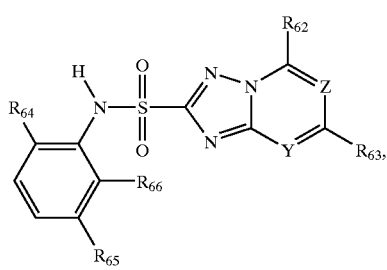

and X is oxygen, N—O—CH$_2$CH$_3$ or N—O—CH$_2$CH=CH—Cl;

and a compound of formula 2.6

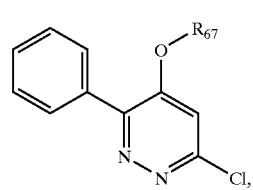
(2.6)

wherein $R_{62}$ is hydrogen, methoxy or ethoxy, $R_{63}$ is hydrogen, methyl, methoxy or fluorine, $R_{64}$ is COOMe, fluorine or chlorine, $R_{65}$ is hydrogen or methyl, Y is methine, C—F or nitrogen, Z is methine or nitrogen and $R_{66}$ is fluorine or chlorine;

and a compound of formula 2.7

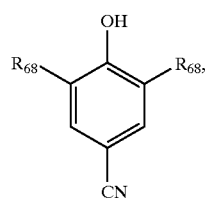
(2.7)

wherein $R_{67}$ is hydrogen or —C(O)—S-n-octyl;

and a compound of formula 2.8

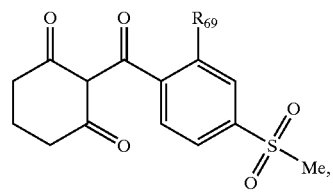
(2.8)

wherein $R_{68}$ is either bromine or iodine;

and a compound of formula 2.9

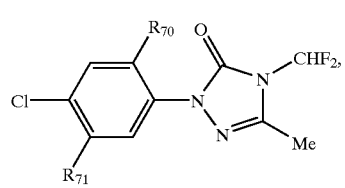
(2.9)

wherein $R_{69}$ is chlorine or nitro;

and a compound of formula 2.10

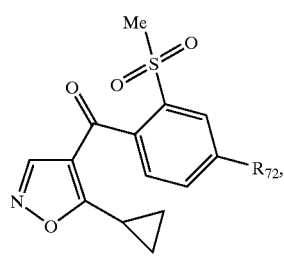
(2.10)

wherein $R_{70}$ is fluorine or chlorine and $R_{71}$ is —CH$_2$—CH(Cl)—COOCH$_2$CH$_3$ or —NH—SO$_2$Me;

and a compound of formula 2.11

(2.11)

wherein $R_{72}$ is trifluoromethyl or chlorine;

and a compound of formula 2.12

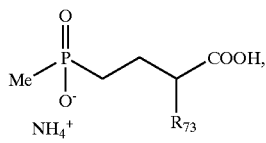
(2.12)

wherein R$_{73}$ is NH$_2$ or <S>NH$_2$;
and a compound of formula 2.13

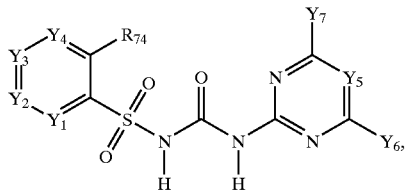
(2.13)

wherein Y$_1$ is nitrogen, methine, NH—CHO or N—Me, Y$_2$ is nitrogen, methine or C—I, Y$_3$ is methine, Y$_4$ is methine or Y$_3$ and Y$_4$ together are sulfur or C—Cl, Y$_5$ is nitrogen or methine, Y$_6$ is methyl, difluoromethoxy, trifluoromethyl or methoxy, Y$_7$ is methoxy or difluoromethoxy and R$_{74}$ is CONMe$_2$, COOMe, COOC$_2$H$_5$, trifluoromethyl, CH$_2$—CH$_2$CF$_3$ or SO$_2$CH$_2$CH$_3$, or a sodium salt thereof ("Me" being in each case the methyl group);
and the compound of formula 2.13.c

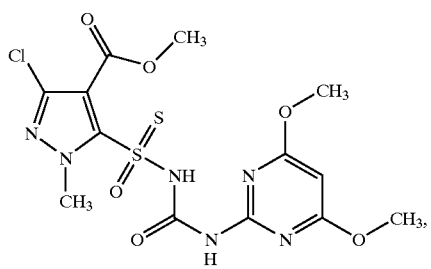
(2.13.c)

and the compound of formula 2.14

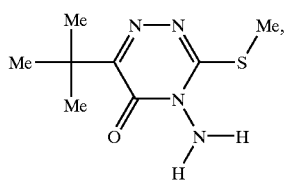
(2.14)

and the compound of formula 2.15

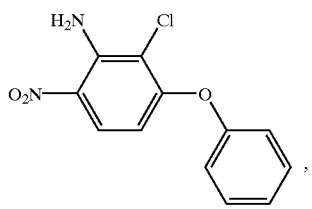
(2.15)

and the compound of formula 2.16

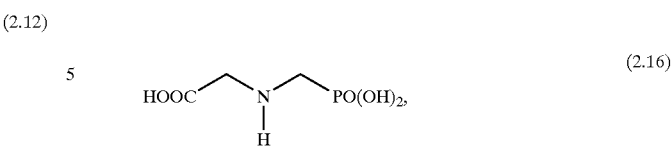
(2.16)

and the compound of formula 2.17

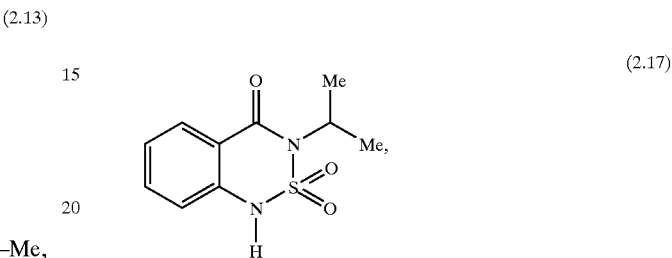
(2.17)

and the compound of formula 2.18

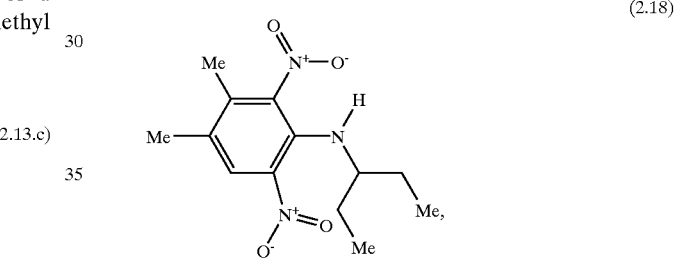
(2.18)

and the compound of formula 2.19

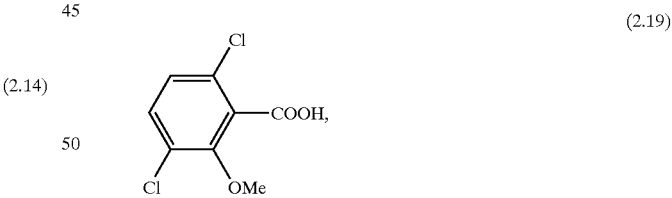
(2.19)

and the compound of formula 2.20

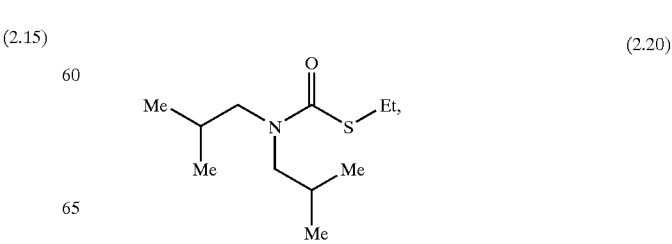
(2.20)

and the compound of formula 2.21
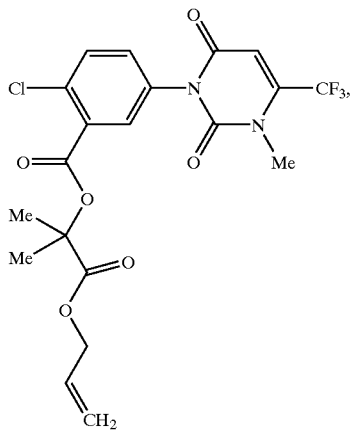
(2.21)
and the compound of formula 2.22
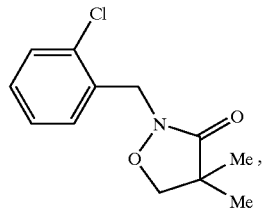
(2.22)
and the compound of formula 2.23
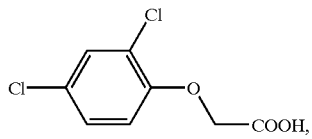
(2.23)
and the compound of formula 2.24
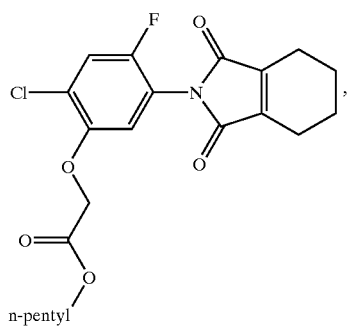
(2.24)
and the compound of formula 2.25
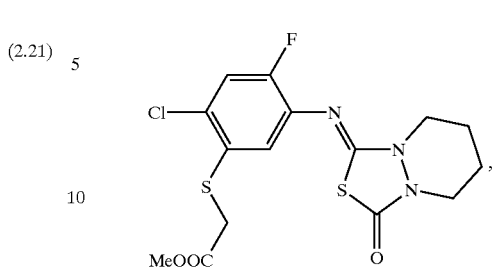
(2.25)
and the compound of formula 2.26
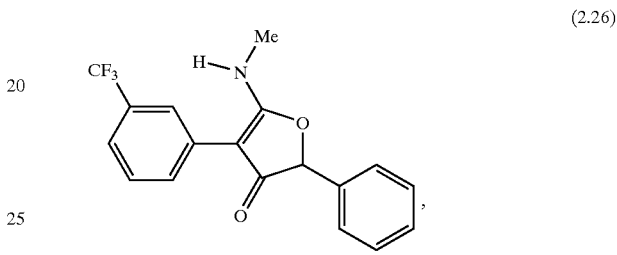
(2.26)
and the compound of formula 2.27
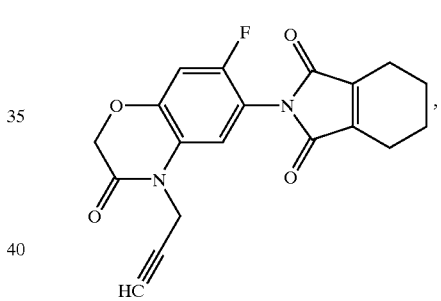
(2.27)
and the compound of formula 2.28
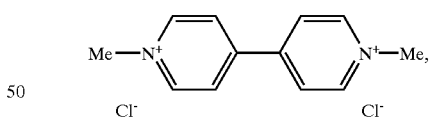
(2.28)
and the compound of formula 2.29
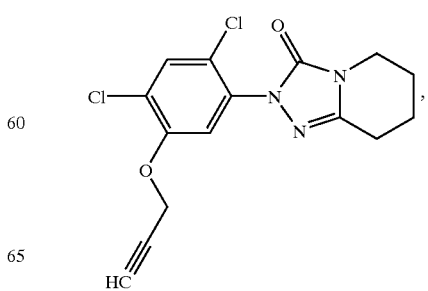
(2.29)

and the compound of formula 2.30
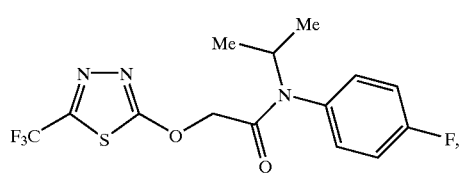
(2.30)
and the compound of formula 2.36
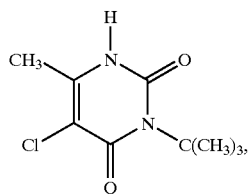
(2.36)
and the compound of formula 2.31
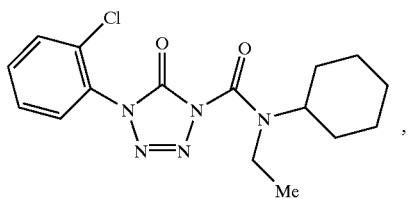
(2.31)
and the compound of formula 2.37
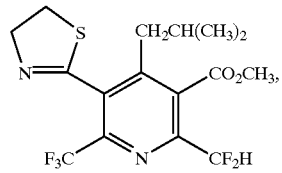
(2.37)
and the compound of formula 2.32
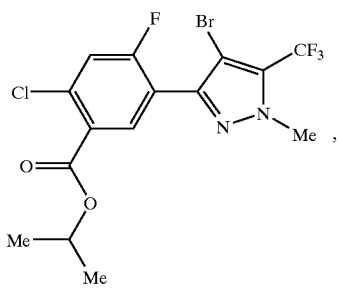
(2.32)
and the compound of formula 2.38
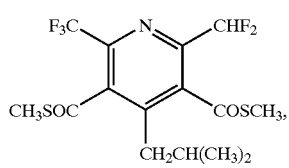
(2.38)
and the compound of formula 2.33
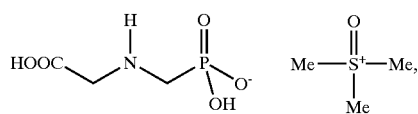
(2.33)
and the compound of formula 2.39
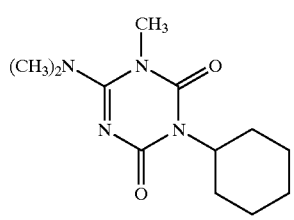
(2.39)
and the compound of formula 2.34
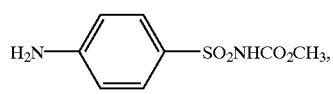
(2.34)
and the compound of formula 2.40
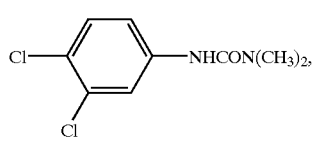
(2.40)
and the compound of formula 2.35
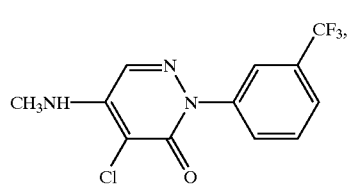
(2.35)
and the compound of formula 2.41
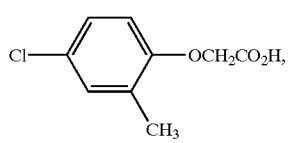
(2.41)

and the compound of formula 2.42

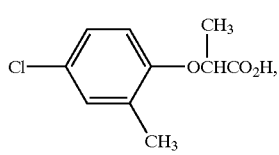

and the compound of formula 2.43

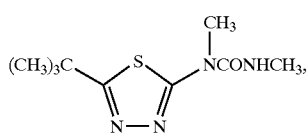

and the compound of formula 2.44

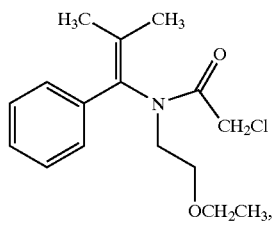

and the compound of formula 2.45

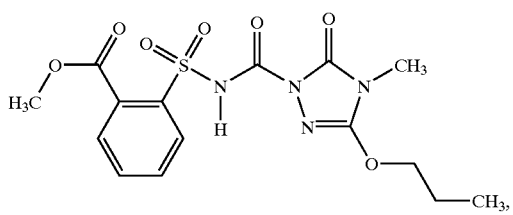

and the compound of formula 2.46

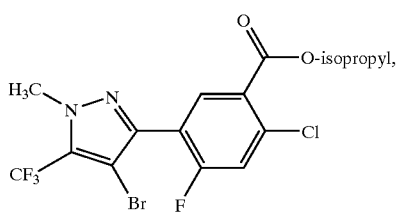

and the compound of formula 2.47

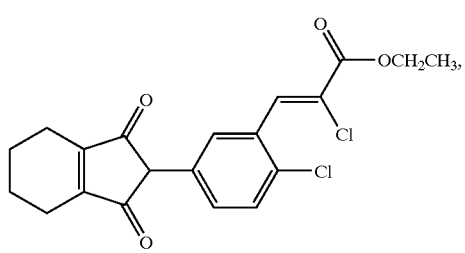

and the compound of formula 2.48

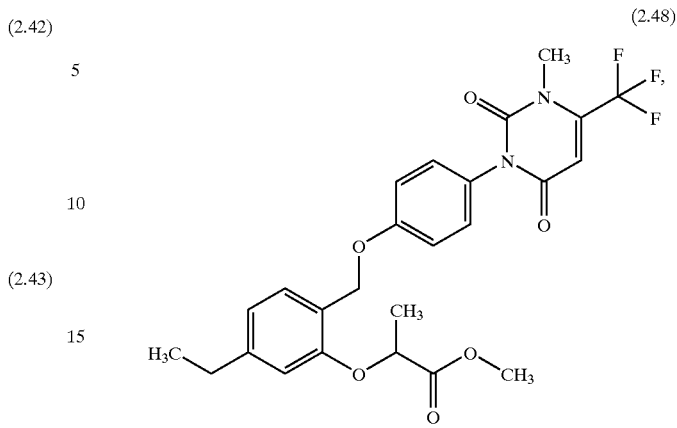

and the compound of formula 2.49

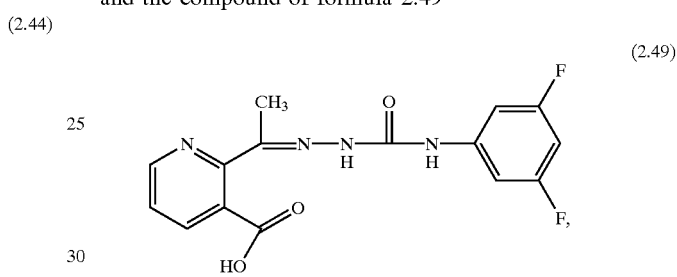

and the compound of formula 2.50

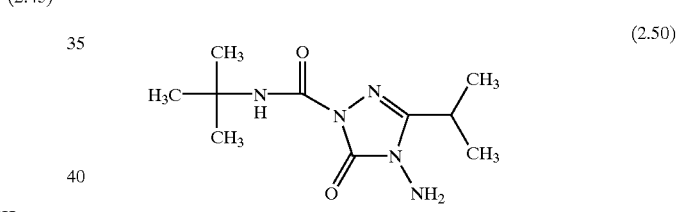

and the compound of formula 2.51

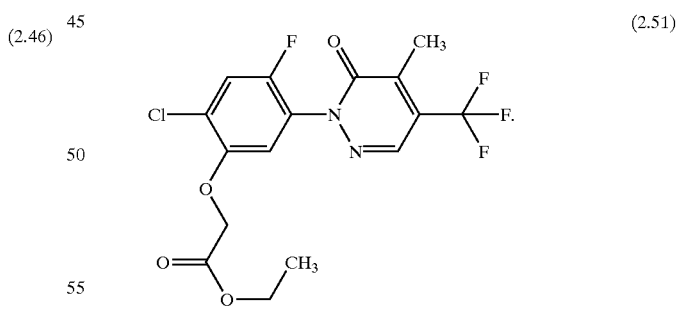

In the above formulae, "Me" is a methyl group. The alkyl groups appearing in the substituent definitions may be straight-chained or branched and are, for example, methyl, ethyl, n-propyl, isopropyl, n-butyl, sec-butyl, isobutyl, tert-butyl, pentyl, hexyl, heptyl, octyl, nonyl, decyl, undecyl and dodecyl and also branched isomers thereof. Alkoxy, alkenyl and alkynyl radicals are derived from the mentioned alkyl radicals. The alkenyl and alkynyl groups may be unsaturated once or more than once.

An alkylene group may be substituted by one or more methyl groups; preferably, such alkylene groups are unsubstituted in each case. The same also applies to all $C_3$–$C_5$cycloalkyl-, $C_3$–$C_5$oxacycloalkyl-, $C_3$–$C_5$thiacycloalkyl-, $C_3$–$C_4$dioxacycloalkyl-, $C_3$–$C_4$dithiacycloalkyl-, $C_3$–$C_4$oxathiacycloalkyl- and N(CH$_2$)-containing groups.

Halogen is, generally, fluorine, chlorine, bromine or iodine. The same correspondingly applies to halogen in the context of other definitions, such as haloalkyl or halophenyl.

Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, pentafluoroethyl, heptafluoro-n-propyl, perfluoro-n-hexyl; haloalkyl groups in the definitions of $R_2$, $R_3$ and especially $R_5$ are preferably trichloromethyl, dichlorofluoromethyl, difluorochloromethyl, difluoromethyl, trifluoromethyl, pentafluoroethyl or heptafluoro-n-propyl.

Suitable haloalkenyl radicals include alkenyl groups substituted one or more times by halogen, halogen being fluorine, chlorine, bromine or iodine and especially fluorine or chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl. Preferred $C_2$–$C_{12}$alkenyl radicals substituted once, twice or three times by halogen are those having a chain length of from 2 to 5 carbon atoms. Suitable haloalkynyl radicals include, for example, alkynyl groups substituted one or more times by halogen, halogen being bromine or iodine and, especially, fluorine or chlorine, for example 3-fluoropropynyl, 3-chloropropynyl, 3-bromopropynyl, 3,3,3-trifluoropropynyl and 4,4,4-trifluoro-but-2-yn-1-yl. Preferred alkynyl groups substituted one or more times by halogen are those having a chain length of from 2 to 5 carbon atoms.

Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy or a pentyloxy or hexyloxy isomer, preferably methoxy and ethoxy. Alkylcarbonyl is preferably acetyl or propionyl. Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl, preferably methoxycarbonyl, ethoxycarbonyl or tert-butoxycarbonyl. Haloalkoxy groups preferably have a chain length of from 1 to 8 carbon atoms.

Haloalkoxy is, for example, fluoromethoxy, difluoromethoxy, trifluoromethoxy, 2,2,2-trifluoro-ethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy. Alkylthio groups preferably have a chain length of from 1 to 8 carbon atoms. Alkylthio is, for example, methylthio, ethylthio, propylthio, isopropylthio, n-butylthio, isobutylthio, sec-butylthio or tert-butylthio, preferably methylthio or ethylthio. Alkylsulfinyl is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

Alkylsulfonyl is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

Alkylamino is, for example, methylamino, ethylamino, n-propylamino, isopropylamino or a butylamine isomer. Dialkylamino is, for example, dimethylamino, methylethylamino, diethyl-amino, n-propylmethylamino, dibutylamino or diisopropylamino. Preference is given to alkylamino groups having a chain length of from 1 to 4 carbon atoms. Alkoxyalkyl groups preferably have from 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl. Alkylthioalkyl groups preferably have from 1 to 6 carbon atoms. Alkylthioalkyl is, for example, methylthiomethyl, methylthioethyl, ethylthiomethyl, ethylthioethyl, n-propylthiomethyl, n-propylthioethyl, isopropylthiomethyl, isopropylthioethyl, butylthiomethyl, butylthioethyl or butylthiobutyl.

The cycloalkyl groups preferably have from 3 to 6 ring carbon atoms and may be substituted by one or more methyl groups; they are preferably unsubstituted, for example cyclopropyl, cyclobutyl, cyclopentyl or cyclohexyl. Phenyl, including phenyl as part of a substituent such as phenoxy, benzyl, benzyloxy, benzoyl, phenylthio, phenylalkyl, phenoxyalkyl or tosyl, may be in mono- or poly-substituted form, in which case the substituents may, as desired, be in the ortho-, meta- and/or para-position(s).

The invention also includes the salts that the compounds of formula I may form with amines, alkali metal and alkaline earth metal bases or quaternary ammonium bases. Among the alkali metal and alkaline earth metal hydroxides used as salt formers, emphasis is to be given to the hydroxides of lithium, sodium, potassium, magnesium and calcium, but especially those of sodium and potassium.

Examples of suitable amines for ammonium salt formation that come into consideration are ammonia as well as primary, secondary and tertiary $C_1$–$C_{18}$alkylamines, $C_1$–$C_4$hydroxyalkyl-amines and $C_2$–$C_4$alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methyl-ethylamine, methyl-isopropylamine, methyl-hexylamine, methyl-nonylamine, methyl-pentadecylamine, methyl-octadecylamine, ethyl-butylamine, ethyl-heptylamine, ethyl-octylamine, hexyl-heptylamine, hexyl-octylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butyl-ethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary aryl amines for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

It is extremely surprising that the combination of the active ingredient of formula I with one or more active ingredients selected from formulae 2.1 to 2.51 exceeds the additive effect on the weeds to be controlled that is to be expected in principle, and thus broadens the range of action of the individual active ingredients especially in two respects: Firstly, the rates of application of the individual compounds of formulae 1 and 2.1 to 2.51 are reduced while a good level of action is maintained and, secondly, the composition according to the invention achieves a high level of weed control also in those cases where the individual substances, in the range of low rates of application, have become unusable from the agronomic standpoint. The result is a considerable broadening of the spectrum of weeds and an additional increase in selectivity in respect of the crops of useful plants, as is necessary and desirable in the event of an unintentional overdose of active ingredient. The composition according to the invention, while retaining excellent control of weeds in crops of useful plants, also enables greater flexibility in succeeding crops.

The composition according to the invention can be used against a large number of agronomically important weeds, such as Stellaria, Nasturtium, Agrostis, Digitaria, Avena, Setaria, Sinapis, Lolium, Solanum, Phaseolus, Echinochloa, Scirpus, Monochoria, Sagittaria, Bromus, Alopecurus, Sorghum halepense, Rottboellia, Cyperus, Abutilon, Sida, Xanthium, Amaranthus, Chenopodium, Ipomoea, Chrysanthemum, Galium, Viola and Veronica. The composition according to the invention is suitable for all methods of application conventionally used in agriculture, e.g. pre-emergence application, post-emergence application and seed dressing. The composition according to the invention is suitable especially for controlling weeds in crops of useful plants, such as cereals, rape, sugar beet, sugar cane, plantation crops, rice, maize and soybeans, and also for non-selective weed control.

"Crops" are to be understood to mean also those crops which have been made tolerant to herbicides or classes of herbicides as a result of conventional methods of breeding or genetic engineering.

Preferred compositions according to the invention comprise compounds of formula I wherein each R is independently hydrogen, $C_1$–$C_6$alkyl, $C_2$–$C_6$alkenyl, $C_2$–$C_6$haloalkenyl, $C_2$–$C_6$alkynyl, $C_2$–$C_6$haloalkynyl, $C_3$–$C_6$cycloalkyl, $C_1$–$C_6$alkoxy, $C_1$–$C_6$haloalkoxy, $C_1$–$C_6$alkylthio, $C_1$–$C_6$alkylsulfinyl, $C_1$–$C_6$alkylsulfonyl, $C_1$–$C_6$haloalkyl, $C_1$–$C_6$haloalkylthio, $C_1$–$C_6$haloalkylsulfinyl, $C_1$–$C_6$haloalkylsulfonyl, $C_1$–$C_6$alkoxycarbonyl, $C_1$–$C_6$alkylcarbonyl, $C_1$–$C_6$alkylamino, di($C_1$–$C_6$alkyl)-amino, $C_1$–$C_6$alkylaminosulfonyl, di($C_1$–$C_6$alkyl)aminosulfonyl, —N($R_1$)—S—$R_2$, —N($R_3$)—SO—$R_4$, —N($R_5$)—$SO_2$—$R_6$, nitro, cyano, halogen, hydroxy, amino, benzylthio, benzylsulfinyl, -benzylsulfonyl, phenyl, phenoxy, phenylthio, phenylsulfinyl or phenylsulfonyl; wherein the phenyl group may itself be mono-, di- or tri-substituted by $C_1$–$C_6$alkyl, $C_1$–$C_6$haloalkyl, $C_3$–$C_6$alkenyl, $C_3$–$C_6$haloalkenyl, $C_6$alkynyl, $C_3$–$C_6$haloalkynyl, $C_1$–$C_6$alkoxy, $C_1$–$C_6$haloalkoxy, $C_3$–$C_6$alkenyloxy, $C_3$–$C_6$alkynyloxy, mercapto, $C_1$–$C_6$alkylthio, $C_1$–$C_6$haloalkylthio, $C_3$–$C_6$alkenylthio, $C_3$–$C_6$haloalkenylthio, $C_3$–$C_6$alkynylthio, $C_2$–$C_5$alkoxyalkylthio, $C_3$–$C_5$acetylalkylthio, $C_3$–$C_6$alkoxycarbonylalkylthio, $C_2$–$C_4$cyanoalkylthio, $C_1$–$C_6$alkylsulfinyl, $C_1$–$C_6$haloalkylsulfinyl, $C_1$–$C_6$alkylsulfonyl, $C_1$–$C_6$haloalkylsulfonyl, aminosulfonyl, $C_1$–$C_2$alkylaminosulfonyl, $C_2$–$C_4$dialkylaminosulfonyl, $C_1$–$C_3$alkylene-$R_{45}$, $NR_{46}R_{47}$, halogen, cyano, nitro, phenyl or by benzylthio, wherein the latter phenyl and benzylthio groups may themselves be substituted on the phenyl ring by $C_1$–$C_3$alkyl, $C_1$–$C_3$haloalkyl, $C_1$–$C_3$alkoxy, $C_1$–$C_3$haloalkoxy, halogen, cyano or by nitro;

or each R is independently a monocyclic or fused bicyclic ring system having from 5 to 10 members, which may be aromatic or partially saturated and may contain from 1 to 4 hetero atoms selected from nitrogen, oxygen and sulfur; wherein the ring system either is bound directly to the pyridine ring or is bound to the pyridine ring via a $C_1$–$C_4$alkylene group, and each ring system may not contain more than two oxygen atoms and may not contain more than two sulfur atoms, and the ring system may itself be mono-, di- or tri-substituted by $C_1$–$C_6$alkyl, $C_1$–$C_6$haloalkyl, $C_3$–$C_6$alkenyl, $C_3$–$C_6$haloalkenyl, $C_3$–$C_6$alkynyl, $C_3$–$C_6$haloalkynyl, $C_1$–$C_6$alkoxy, $C_1$–$C_6$haloalkoxy, $C_3$–$C_6$alkenyloxy, $C_3$–$C_6$alkynyloxy, mercapto, $C_1$–$C_6$alkylthio, $C_1$–$C_6$haloalkylthio, $C_3$–$C_6$alkenylthio, $C_3$–$C_6$haloalkenylthio, $C_3$–$C_6$alkynylthio, $C_2$–$C_5$alkoxyalkylthio, $C_3$–$C_5$acetylalkylthio, $C_3$–$C_6$alkoxycarbonylalkylthio, $C_2$–$C_4$cyanoalkylthio, $C_1$–$C_6$alkylsulfinyl, $C_1$–$C_6$haloalkylsulfinyl, $C_1$–$C_6$alkylsulfonyl, $C_1$–$C_6$haloalkylsulfonyl, aminosulfonyl, $C_1$–$C_2$alkylaminosulfonyl, $C_2$–$C_4$dialkylaminosulfonyl, $C_1$–$C_3$alkylene-$R_7$, $NR_8R_9$, halogen, cyano, nitro, phenyl or by benzylthio, wherein phenyl and benzylthio may themselves be substituted on the phenyl ring by $C_1$–$C_3$alkyl, $C_1$–$C_3$haloalkyl, $C_1$–$C_3$alkoxy, $C_1$–$C_3$haloalkoxy, halogen, cyano or by nitro, $R_1$, $R_2$, $R_3$, $R_4$, $R_5$, $R_6$, $R_7$, $R_8$, $R_9$, $R_{45}$, $R_{46}$ and $R_{47}$ have the meanings as defined above and wherein the substituents on the nitrogen in the heterocyclic ring are other than halogen.

Compositions according to the invention that are also preferred comprise, as compound of formula I, a compound of formula Ia

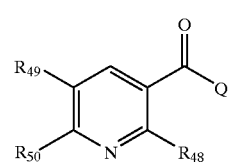

(Ia)

wherein $R_{48}$ is $C_1$–$C_6$alkyl, $C_2$–$C_6$alkenyl, $C_2$–$C_6$haloalkenyl, $C_2$–$C_6$alkynyl, $C_2$–$C_6$haloalkynyl, $C_3$–$C_6$cyclo-alkyl, $C_1$–$C_6$haloalkyl, or a monocyclic or fused bicyclic ring system having from 5 to 10 members, which may be aromatic or partially saturated and may contain from 1 to 4 hetero atoms selected from nitrogen, oxygen and sulfur, wherein the ring system either is bound directly to the pyridine ring or is bound to the pyridine ring via a $C_1$–$C_4$alkylene group, and each ring system may not contain more than two oxygen atoms and may not contain more than two sulfur atoms, and the ring system may itself be mono-, di- or tri-substituted by $C_1$–$C_6$alkyl, $C_1$–$C_6$haloalkyl, $C_3$–$C_6$alkenyl, $C_3$–$C_6$haloalkenyl, $C_3$–$C_6$alkynyl, $C_3$–$C_6$haloalkynyl, $C_1$–$C_6$alkoxy, $C_1$–$C_6$haloalkoxy, $C_3$–$C_6$alkenyloxy, $C_3$–$C_6$alkynyloxy, mercapto, $C_1$–$C_6$alkylthio, $C_1$–$C_6$haloalkylthio, $C_3$–$C_6$alkenylthio, $C_3$–$C_6$haloalkenylthio, $C_3$–$C_6$alkynylthio, $C_2$–$C_5$alkoxyalkylthio, $C_3$–$C_5$acetylalkylthio, $C_3$–$C_6$alkoxycarbonylalkylthio, $C_2$–$C_4$cyanoalkylthio, $C_1$–$C_6$alkylsulfinyl, $C_1$–$C_6$haloalkylsulfinyl, $C_1$–$C_6$alkylsulfonyl, $C_1$–$C_6$haloalkylsulfonyl, aminosulfonyl, $C_1$–$C_2$alkylaminosulfonyl, $C_2$–$C_4$dialkylaminosulfonyl, $C_1$–$C_3$alkylene-$R_7$, $NR_8R_9$, halogen, cyano, nitro, phenyl or by benzylthio, wherein phenyl and benzylthio may themselves be substituted on the phenyl ring by $C_1$–$C_3$alkyl, $C_1$–$C_3$haloalkyl, $C_1$–$C_3$alkoxy, $C_1$–$C_3$haloalkoxy, halogen, cyano or by nitro, and wherein the substituents on the nitrogen in the heterocyclic ring are other than halogen;

$R_{49}$ is hydrogen, $C_1$–$C_6$alkyl, $C_1$–$C_6$haloalkyl, halogen, or phenyl which may be substituted by $C_1$–$C_3$alkyl, $C_1$–$C_3$haloalkyl, $C_1$–$C_3$alkoxy, $C_1$–$C_3$haloalkoxy, halogen, cyano or by nitro, $R_{50}$ is $C_1$–$C_6$haloalkyl and $R_7$, $R_8$, $R_9$ and Q have the meanings as defined above.

Among that group of compounds preference is given to those wherein $R_{48}$ is $C_1$–$C_6$alkyl, $C_2$–$C_6$alkenyl, $C_2$–$C_6$haloalkenyl, $C_2$–$C_6$alkynyl, $C_2$–$C_6$haloalkynyl, $C_3$–$C_6$cycloalkyl or $C_1$–$C_6$-haloalkyl.

Preference is given also to compositions wherein, in formula I, Q is the group $Q_2$ or $Q_3$, wherein, especially, in the group $Q_2$ $R_{23}$ is hydroxy and in the group $Q_3$ $R_{40}$ is hydroxy. Among that group emphasis is to be given to those compounds wherein m is 2 and one substituent R is $C_1$–$C_4$alkoxy-$C_1$–$C_4$alkyl or $C_1$–$C_4$alkoxy-$C_1$–$C_4$alkoxy-$C_1$–$C_4$alkyl.

Further preferred synergistic mixtures according to the invention comprise as active ingredients a compound of formula I and either a compound of formula 2.2.a

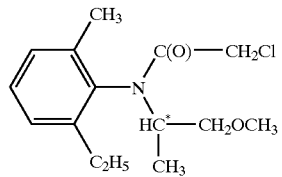

(2.2.a, aRS, 1'S(-)N-(1'-methyl-2'-methoxyethyl)-N-chloroacetyl-2-ethyl-6-methylaniline), or a compound of formula 2.2.b

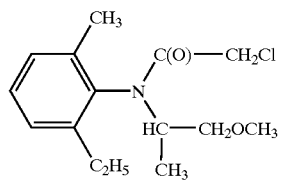

(2.2.b)

or a compound of formula 2.2 wherein $R_3$ is ethyl, $R_4$ is methyl and $R_5$ is ethoxymethyl, or a compound of formula 2.2 wherein $R_3$ is ethyl, $R_4$ is ethyl and $R_5$ is methoxymethyl, or a compound 2.3, or a compound of formula 2.30, or a compound of formula 2.4, or a compound of formula 2.13, or a compound of formula 2.14, or a compound of formula 2.6 wherein $R_{12}$ is hydrogen, Z is methine, $R_{13}$ is methyl, Y is nitrogen, $R_{14}$ is fluorine, $R_{15}$ is hydrogen and $R_{16}$ is fluorine, or $R_{12}$ is methoxy, Z is methine, $R_{13}$ is methoxy, Y is methine, $R_{14}$ is chlorine, $R_{15}$ is methyl and $R_{16}$ is chlorine, or a compound of formula 2.7 wherein $R_{17}$ is —C(O)—S-n-octyl, or a compound of formula 2.12, or a compound of formula 2.18, or a compound of formula 2.19, or a compound of formula 2.21, or a compound of formula 2.25, or a compound of formula 2.33, or a compound of formula 2.45, or a compound of formula 2.1.

Especially preferred synergistic mixtures according to the invention comprise as active ingredients a compound of formula I and either a compound of formula 2.2.a

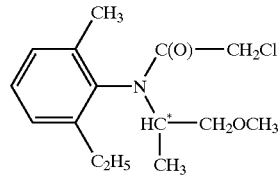

(2.2.a, aRS, 1'S(-)N-(1'-methyl-2'-methoxyethyl)-N-chloroacetyl-2-ethyl-6-methylaniline), or a compound of formula 2.2.b

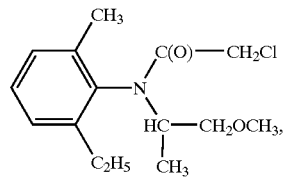

(2.2.b)

or a compound of formula 2.2 wherein $R_3$ is ethyl, $R_4$ is methyl and $R_5$ is ethoxymethyl, or a compound of formula 2.2 wherein $R_3$ is ethyl, $R_4$ is ethyl and $R_5$ is methoxymethyl, or a compound of formula 2.3, or a compound of formula 2.30.

Further preferred synergistic mixtures include mixtures of metolachlor (S) and (R) isomers wherein the ratio of (S)-2-chloro-N-(2-ethyl-6-methylphenyl)-N-(2-methoxy-1-methylethyl)acetamide to (R)-2-chloro-N-(2-ethyl-6-methylphenyl)-N-(2-methoxy-1-methylethyl)acetamide is in the range of from 50–100% to 50–0%, preferably 70–100% to 30–0% and more preferably 80–100% to 20–0%.

Combinations of the compounds of formula I with the compound of formula 2.2a

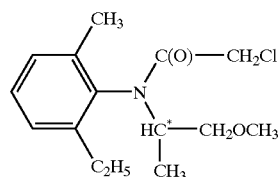

(2.2a, aRS, 1'S(-)N-(1'-methyl-2'-methoxyethyl)-N-chloroacetyl-2-ethyl-6-methylaniline) have been found to be especially effective, the compound 1.001 indicated hereinbelow under Table 1 being especially preferred as the compound of formula I.

The compounds of formula I can be prepared in a manner analogous to the processes described in WO 97/46530, by
a) reacting a compound of formula II

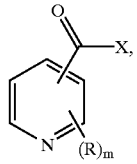
(II)

wherein R and m are as defined for formula I and X is a leaving group, e.g. halogen, in an inert, organic solvent in the presence of a base, with compounds of formula III, IV, V or VI

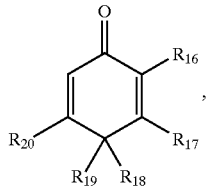
(III)

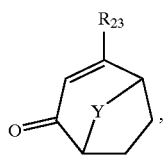
(IV)

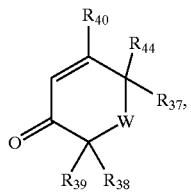
(V)

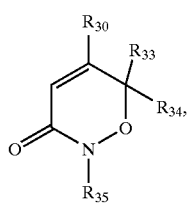
(VI)

wherein $R_{20}$, $R_{23}$, $R_{30}$ and $R_{40}$ are hydroxy and the other substituents are as defined for formula I, to form the compounds of formula VII, VIII, IX or X

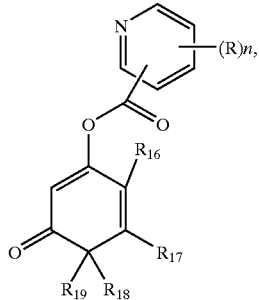
(VII)

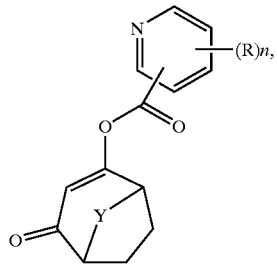
(VIII)

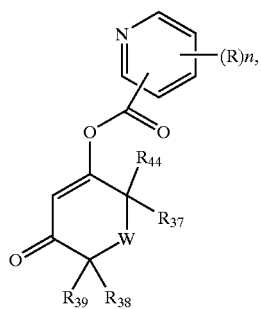
(IX)

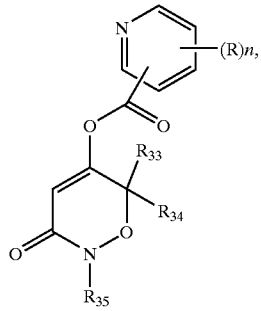
(X)

and then isomerising those compounds, for example in the presence of a base and a catalytic amount of dimethylaminopyridine (DMAP) or a cyanide source; or b) reacting a compound of formula XI

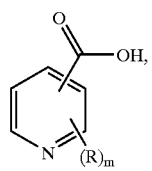
(XI)

wherein R and m are as defined for formula I, with compounds of formula III, IV, V or VI in an inert, organic solvent in the presence of a base and a coupling agent, to form the compound of formula VII, VIII, IX or X, and then isomerising that compound, for example in the manner described under route a).

Compounds of formula I wherein Q is a group $Q_5$

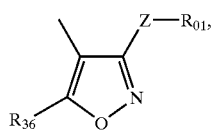
($Q_5$)

wherein Z is sulfur and $R_{36}$ and $R_{01}$ are as defined for formula I, can be prepared in a manner analogous to known processes (e.g. those described in WO 97/43270), by either a) converting a compound of formula XII

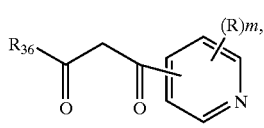
(XII)

wherein $R_{36}$, R and m are as defined, in the presence of a base, carbon disulfide and an alkylating reagent of formula XIII $$R_{01}-X_1, \quad (XIII)$$

wherein $R_{01}$ is as defined for formula I and $X_1$ is a leaving group, e.g. halogen or sulfonate, into the compound of formula XIV

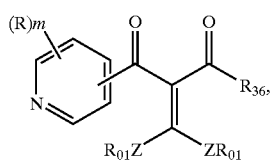
(XIV)

wherein Z is sulfur and R, $R_{01}$, $R_{36}$ and m are as defined, and then cyclising that compound with hydroxylamine hydrochloride, optionally in a solvent, in the presence of a base, to form the compound of formula Ie

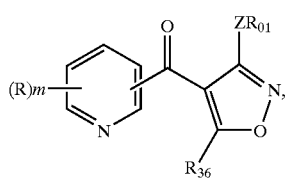
(Ie)

wherein Z is sulfur and R, $R_{36}$, $R_{01}$ and m are as defined, and then oxidising that compound with an oxidising agent, e.g. meta-chloroperbenzoic acid (m-CPBA).

Preparation of the compounds of formula I is illustrated in greater detail in the following Reaction Schemes 1 and 2.

Reaction Scheme 1 route a):

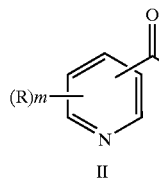 + III, IV, V or VI $\xrightarrow[\text{solvent, e.g. CH}_2\text{Cl}_2,]{\text{base, e.g. (C}_2\text{H}_5)_3\text{N},}$ 0–110° C.

II

VII, VIII, IX, or X isomerisation: $\xrightarrow[\text{KCN cat.}]{\text{base, e.g. (C}_2\text{H}_5)_3\text{N},}$

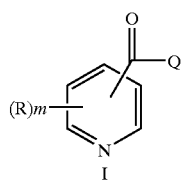
I route b):

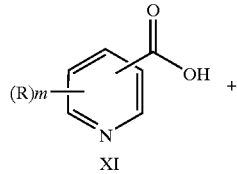 +

XI

III, IV, V or VI $\xrightarrow[\text{reagent, e.g.}]{\text{base, e.g. (C}_2\text{H}_5)_3\text{N, coupling}}$

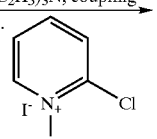

solvent, e.g. CH$_2$Cl$_2$, 0–110° C.

VII, VIII, IX, or X isomerisation: $\xrightarrow[\text{KCN cat.}]{\text{base, e.g. (C}_2\text{H}_5)_3\text{N},}$

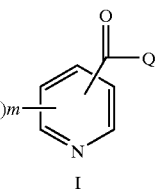
I

The compounds of formula I containing the groups $Q_1$, $Q_2$, $Q_3$ and $Q_4$ wherein $R_{20}$, $R_{23}$, $R_{30}$ and $R_{40}$ are hydroxy can especially be prepared according to the above Reaction Scheme.

Reaction Scheme 2

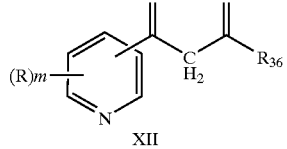

XII $\xrightarrow{\begin{array}{c}\text{K}_2\text{CO}_3/\text{CS}_2,\\ \text{R}_{01}-\text{X}_1,\\ \text{XIII}\\ \text{solvent, e.g. DMF, or}\\ \text{KF/Al/CS}_2,\\ \text{R}_{01}-\text{X}_1\\ \text{XIII}\\ \text{solvent, e.g. CH}_3\text{CN, or}\\ \text{NaH/CS}_2,\\ \text{R}_{01}-\text{X}_1\\ \text{XIII}\\ \text{solvent, e.g. DMSO}\end{array}}$

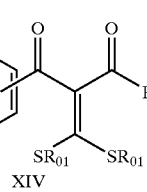 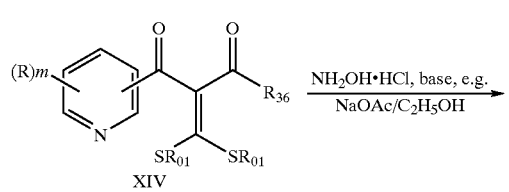 $\xrightarrow[\text{NaOAc/C}_2\text{H}_5\text{OH}]{\text{NH}_2\text{OH}\cdot\text{HCl, base, e.g.}}$

XIV

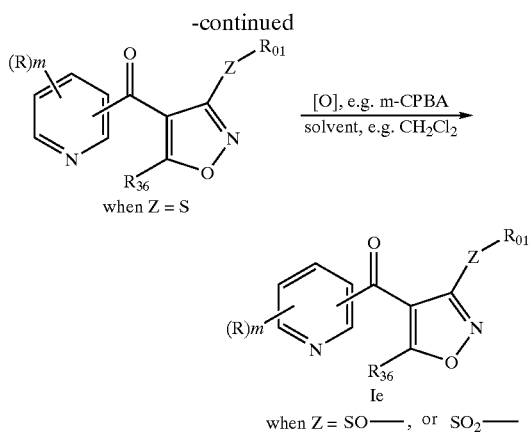

when Z = S when Z = SO——, or SO$_2$——

For preparation of the compounds of formula I wherein Q is a group Q$_1$ to Q$_4$ and R$_{20}$, R$_{23}$, R$_{30}$ and R$_{40}$ are hydroxy, there are used as starting materials, in accordance with Reaction Scheme 1, route a), the carboxylic acid derivatives of formula II wherein X is a leaving group, for example halogen, e.g. iodine, bromine or especially chlorine, N-oxyphthalimide or N,O-dimethylhydroxylamino or a moiety of an activated ester, for example

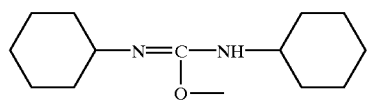

(formed from dicyclohexylcarbodiimide (DCC) and the appropriate carboxylic acid) or

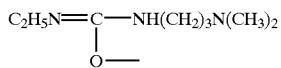

(formed from N-ethyl-N'-(3-dimethylaminopropyl) carbodiimide (EDC) and the appropriate carboxylic acid). Those compounds are reacted in an inert, organic solvent, for example a halogenated hydrocarbon, e.g. dichloromethane, a nitrile, e.g. acetonitrile, or an aromatic hydrocarbon, e.g. toluene, and in the presence of a base, for example an alkylamine, e.g. triethylamine, an aromatic amine, e.g. pyridine or 4-dimethylaminopyridine (DMAP), with the dione derivatives of formula III, IV, V or VI to form the isomeric enol ethers of formula VII, VIII, IX and X. The esterification occurs at temperatures of from 0° C. to 110° C.

The isomerisation of the ester derivatives of formulae VII, VIII, IX and X to form the dione derivatives of formula I (wherein R$_{20}$, R$_{23}$, R$_{30}$ and R$_{40}$ are hydroxy) can be carried out, for example, analogously to EP 369 803 in the presence of a base, for example an alkylamine, e.g. triethylamine, a carbonate, e.g. potassium carbonate, and a catalytic amount of DMAP or a cyanide source, for example acetone cyanohydrin or potassium cyanide.

According to Reaction Scheme 1, route b), the desired diones of formula I (wherein R$_{20}$, R$_{23}$, R$_{30}$ and R$_{40}$ are hydroxy) can be obtained, for example, analogously to Chem. Lett. 1975, 1045 by means of esterification of the carboxylic acids of formula XI with the dione derivatives of formula III, IV, V or VI in an inert solvent, for example a halogenated hydrocarbon, e.g. dichloromethane, a nitrile, e.g. acetonitrile, or an aromatic hydrocarbon, e.g. toluene, in the presence of a base, for example an alkylamine, e.g. triethylamine, and a coupling agent, for example 2-chloro-1-methyl-pyridinium iodide. The esterification occurs, depending on the solvent used, at temperatures of from 0° C. to 110° C. and yields first, as described under route a), the isomeric ester of formula I, which can be isomerised, as described under route a), for example in the presence of a base and a catalytic amount of DMAP, or a cyanide source to form the desired dione derivatives of formula I (wherein R$_{20}$, R$_{23}$, R$_{30}$ and R$_{40}$ are hydroxy).

Preparation of the compounds of formula I wherein Q is the group Q5 can be carried out in accordance with Reaction Scheme 2, by reacting the b-diketone derivative of formula XII, for example analogously to Synthesis 1991, 301; ibid. 1988, 793; or Tetrahedron 32, 3055 (1976), with carbon disulfide in the presence of a base, for example a carbonate, e.g. potassium carbonate, a metal hydride, e.g. sodium hydride, or potassium fluoride on aluminium, and an alkylating reagent of formula XIII, wherein X$_1$ is a leaving group, for example halogen, e.g. iodine, bromine or especially chlorine, R$_{25}$OSO$_2$O—, CH$_3$SO$_2$O— or

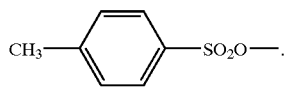

The reaction is preferably carried out in a solvent, for example an amide, e.g. N,N-dimethylformamide (DMF), a sulfoxide, e.g. dimethyl sulfoxide (DMSO), or a nitrile, e.g. acetonitrile. The ketene thioacetal of formula XIV formed is cyclised using hydroxylamine hydrochloride in the presence of a base, for example sodium acetate, in a solvent, for example an alcohol, e.g. ethanol, or an ether, e.g. tetrahydrofuran, to form the compound of formula Ie wherein Z is S—. The cyclisation reaction is carried out at temperatures of from 0° C. to 100° C. The compound of formula Ie (Z═S) may optionally be oxidised in a manner analogous to standard procedures, for example using peracids, e.g. meta-chloroperbenzoic acid (m-CPBA) or peracetic acid, to form the corresponding sulfones and sulfoxides of formula Ie (Z═SO— or SO$_2$—), wherein the degree of oxidation at the sulfur atom (Z═SO— or SO$_2$—) can be controlled by the amount of oxidising agent.

Oxidation to the compound of formula Ie (Z═SO— or SO$_2$—) is carried out as described, for example, in H. O. House, "Modern Synthetic Reactions" W. A. Benjamin, Inc., Menlo Park, Calif., 1972, pages 334–335 and 353–354.

The activated carboxylic acid derivatives of formula II in Reaction Scheme 1 (route a), wherein X is a leaving group, for example halogen, e.g. bromine, iodine or especially chlorine, can be prepared in accordance with known standard procedures, for example as described in C. Ferri "Reaktionen der organischen Synthese", Georg Thieme Verlag, Stuttgart, 1978, page 461 ff and as shown in the following Reaction Scheme 3.

Reaction Scheme 3

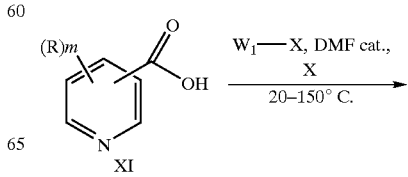

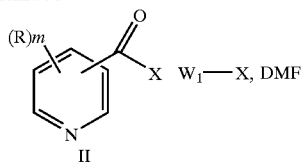

According to Reaction Scheme 3, preparation of the compounds of formula II (X=leaving group) or 11 (X=halogen) is carried out, for example, by using a halogenating agent, for example a thionyl halide, e.g. thionyl chloride or bromide; a phosphorus halide or phosphorus oxyhalide, e.g. phosphorus pentachloride or phosphorus oxychloride or phosphorus pentabromide or phosphoryl bromide; or an oxalyl halide, e.g. oxalyl chloride, or by using a reagent for the formation of an activated ester for example N,N'-dicyclohexylcarbodiimide (DCC) or N-ethyl-N'-(3-dimethylaminopropyl)carbodiimide (EDC) of formula X. In the compound of formula X, as a halogenating agent, X, for example, is a leaving group, for example halogen, e.g. fluorine, bromine or iodine and especially chlorine, and $W_1$ is, for example, $PCl_2$, SOCl, SOBr or ClCOCO.

The procedure is optionally carried out in an inert, organic solvent, for example in an aliphatic, halogenated aliphatic, aromatic or halogenated aromatic hydrocarbon, e.g. n-hexane, benzene, toluene, xylenes, dichloromethane, 1,2-dichloroethane or chlorobenzene, at reaction temperatures in the range from −20° C. to the reflux temperature of the reaction mixture, preferably at from 40 to 150° C., and in the presence of a catalytic amount of N,N-dimethylformamide. Such reactions are generally known and described in the literature in a number of variants with respect to the leaving group X.

The compounds of formulae III, IV, V and VI are known and can be prepared in an analogous manner to that described, for example, in WO 92/07837, DE 3 818 958, EP 338 992 and DE 3 902 818.

The compounds of formula XII in Reaction Scheme 2 can be obtained by standard procedures, for example from the corresponding compounds of formula II

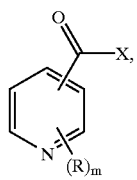

(II)

wherein R and m are as defined for formula I and X is a leaving group, for example halogen, for example via Claisen condensation, or from the compounds of formula II by reaction with a ketocarboxylic acid salt of formula XV

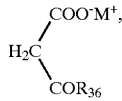

(XV)

wherein $R_{36}$ is as defined for formula I and M⁺ is an alkali metal ion (cf., for example, WO 96/26192).

The compounds of formulae II and XI are known and can be prepared in an analogous manner to that described, for example, in WO 97/46530, Heterocycles, 48, 779 (1998), Heterocycles, 46, 129 (1997) or Tetrahedron Letters, 1749 (1998).

For the preparation of all further compounds of formula I functionalised according to the definition of $(R)_m$, a large number of known standard procedures, for example alkylation, halogenation, acylation, amidation, oximation, oxidation and reduction, are available, the choice of a suitable preparation procedure being governed by the properties (reactivities) of the substituents in the respective intermediates. Examples of such reactions are given in WO 97/46353.

All further compounds falling within the scope of formula I can be prepared by simple means, taking into account the chemical properties of the pyridyl and Q moieties.

The end products of formula I can be isolated in customary manner by concentration or evaporation of the solvent and can be purified by recrystallisation or trituration of the solid residue in solvents in which they are not readily soluble, such as ethers, aromatic hydrocarbons or chlorinated hydrocarbons, by distillation or by means of column chromatography and a suitable eluant.

Furthermore, the person skilled in the art will be familiar with the sequence in which certain reactions should advantageously be performed in order to avoid possible subsidiary reactions. Where synthesis is not directed at the isolation of pure isomers, the product may be in the form of a mixture of two or more isomers. The isomers can be separated according to methods known per se.

PREPARATION EXAMPLES

Example P1

Preparation of 4-hydroxy-3-(2-methyl-6-trifluoromethyl-pyridine-3-carbonyl)-bicyclo[3.2.1]oct-3-en-2-one 6.68 g (0.0305 mol) of 2-methyl-6-trifluoromethyl-nicotinic acid methyl ester (prepared in the manner described in Heterocycles, 46, 129 (1997)) are dissolved in 250 ml of methanol/water (3:1 mixture) and 1.92 g (0.046 mol) of lithium hydroxide hydrate are added in portions at 22° C. After 4 hours at 22° C., the reaction mixture is added to ethyl acetate and 2N hydrochloric acid; the organic phase is washed three times with water, dried with sodium sulfate and concentrated by evaporation, and the residue is triturated with a small amount of hexane. After filtering, 5.69 g (90% of theory) of the expected 2-methyl-6-trifluoromethyl-nicotinic acid having a melting point of 147–149° C. are obtained.

The 2-methyl-6-trifluoromethyl-nicotinic acid (2.0 g, 0.0098 mol) obtained is dissolved in 20 ml of oxalyl chloride. Three drops of dimethylformamide are added and the mixture is refluxed for 1 hour. The mixture is then concentrated using a rotary evaporator and the residue (2-methyl-6-trifluoromethyl-nicotinoyl chloride) is taken up in 30 ml of methylene chloride. At 0° C., 2.7 ml (0.0196 mol) of triethylamine and 0.12 g (0.00098 mol) of dimethylaminopyridine are added, and then 1.49 g (0.0108 mol) of bicyclo[3.2.1]oct-2,4-dione, dissolved in 20 ml of methylene chloride, are added dropwise. After 3 hours at 22° C., the reaction mixture is extracted by shaking with 2N hydrochloric acid. The separated methylene chloride phase is washed with water and then extracted by shaking with 10% aqueous sodium bicarbonate solution, dried over sodium sulfate and concentrated by evaporation. 3.18 g (100% of theory) of 2-methyl-6-trifluoromethyl-nicotinic acid 4-oxo-bicyclo[3.2.1]oct-2-en-2-yl ester are obtained in the form of an oil, which can be used further without purification.

3.02 g (0.0093 mol) of methyl-6-trifluoromethyl-nicotinic acid 4-oxo-bicyclo[3.2.1]oct-2-en-2-yl ester and 1.9 ml (0.0136 mol) of triethylamine are dissolved in 45 ml of acetonitrile. At 22° C., 0.01 ml of acetone cyanohydrin is added. After 18 hours at 22° C., the reaction mixture is poured onto a mixture of water and 2N hydrochloric acid and extracted by shaking with ethyl acetate. The ethyl acetate phase is washed with water and then with brine, dried over sodium sulfate and concentrated by evaporation, and the residue is dissolved in a small amount of warm acetone. On being left to stand, the product crystallises out. After filtering, 0.99 g (33% of theory) of the expected 4-hydroxy-3-(2-methyl-6-trifluoromethyl-pyridine-3-carbonyl)-bicyclo[3.2.1]oct-3-en-2-one is obtained in the form of white crystals (m.p. 75–77° C.).

Example P2

(5-Cyclopropyl-3-methylsulfanyl-isoxazol-4-yl)-(2-methyl-6-trifluoromethyl-pyridin-3-yl)-methanone 14.8 g (0.080 mol) of 3-cyclopropyl-3-oxo-propionic acid tert-butyl ester are dissolved in 25 ml of MeOH and 1.93 g (0.080 mol) of magnesium are added. 7 ml of carbon tetrachloride are added dropwise while cooling in an ice bath and the reaction mixture is stirred at 22° C. for 1 hour to complete the reaction. After concentrating by evaporation, the residue is suspended in 100 ml of acetonitrile and, at 22° C., 16.31 g (0.073 mol) of 2-methyl-6-trifluoromethyl-nicotinoyl chloride (prepared in the manner described in Example P1), dissolved in 50 ml of acetonitrile, are added dropwise. After 6 hours, the reaction mixture is taken up in ethyl acetate and washed with saturated sodium bicarbonate solution. The separated ethyl acetate phase is washed with water, dried over sodium sulfate and concentrated by evaporation. The residue is dissolved in 160 ml of methylene chloride and 10 ml of trifluoroacetic acid are added dropwise at 22° C. After 18 hours, the reaction mixture is poured into water and extracted with methylene chloride. The methylene chloride phase is washed with water and then with brine, dried over sodium sulfate and concentrated by evaporation. 17.3 g (88% of theory) of 1-cyclopropyl-3-(2-methyl-6-trifluoromethyl-pyridin-3-yl)-propane-1,3-dione are obtained in the form of an oil, which can be used further without purification.

The 1-cyclopropyl-3-(2-methyl-6-trifluoromethyl-pyridin-3-yl)-propane-1,3-dione (15.0 g, 0.055 mol) obtained is dissolved in 150 ml of dimethylformamide and 50 g of potassium fluoride on an aluminium oxide support (Alox) (0.0055 mol/g, 0.276 mol) are added in portions at 0° C. After 5 minutes, 6.7 g (0.088 mol) of carbon disulfide are added. After 2 hours, 23.6 g (0.166 mol) of methyl iodide are added dropwise and the reaction mixture is heated at 22° C. After 2 hours the Alox is filtered off, the filtrate is poured into water and extracted by shaking with ethyl acetate. The ethyl acetate phase is washed with water and then with brine, dried over sodium sulfate and concentrated by evaporation. The residue is chromatographed on silica gel (eluant: ethyl acetate/hexane 15/1). 12.0 g (60% of theory) of 2-(bis-methylsulfanyl-methylene)-1-cyclopropyl-3-(2-methyl-6-trifluoromethyl-pyridin-3-yl)-propane-1,3-dione are obtained in the form of a solid substance.

12.0 g (0.033 mol) of the product obtained are suspended in 120 ml of ethanol together with 5.4 g (0.066 mol) of anhydrous sodium acetate. 4.6 g (0.066 mol) of hydroxylamine hydrochloride are added and the batch is reacted at 22° C. for 5 hours. A further 2.7 g of anhydrous sodium acetate and 2.3 g of hydroxylamine hydrochloride are then added. After 18 hours, the reaction mixture is diluted with water and extracted with ethyl acetate. The ethyl acetate phase is washed with water and then with brine, dried over sodium sulfate and concentrated by evaporation. On triturating with a small amount of ethyl acetate, 9.0 g (79.5%) of the desired product are obtained in the form of white crystals (m.p. 103–104° C.).

Example P3

(5-Cyclopropyl-3-methylsulfinyl-isoxazol-4-yl)-(2-methyl-6-trifluoromethyl-pyridin-3-yl)-methanone 1.50 g (0.0043 mol) of (5-cyclopropyl-3-methylsulfanyi-isoxazol-4-yl)-(2-methyl-6-trifluoromethyl-pyridin-3-yl)-methanone are dissolved in 30 ml of acetone/water (2:1 mixture) and 1.02 g (0.0048 mol) of sodium metaperiodate are added in portions at 22° C. After 5 hours, the reaction mixture is concentrated by evaporation using a rotary evaporator. The residue is taken up in water and ethyl acetate. The ethyl acetate phase is dried over sodium sulfate and concentrated by evaporation. The residue is chromatographed on silica gel (eluant: ethyl acetate/hexane 3/1). 0.8 g (51%) of the desired product is obtained in the form of white crystals (m.p. 96–97° C.).

Example P4

Preparation of 3-hydroxy-4,4-dimethyl-2-(2-methyl-6-trifluoromethyl-pyridine-3-carbonyl)-cyclohex-2-enone (A2–B24)

6.68 g (0.0305 mol) of 2-methyl-6-trifluoromethyl-nicotinic acid methyl ester (prepared in the manner described in Heterocycles, 46, 129 (1997)) are dissolved in 250 ml of methanol/water (3:1 mixture) and 1.92 g (0.046 mol) of lithium hydroxide hydrate are added in portions at a temperature of 22° C. After 4 hours at 22° C., the reaction mixture is added to ethyl acetate and 2N hydrochloric acid; the organic phase is washed three times with water, dried over sodium sulfate and concentrated by evaporation, and the residue is triturated with a small amount of hexane. After filtering, 5.69 g (90% of theory) of the expected 2-methyl-6-trifluoromethyl-nicotinic acid having a melting point of 147–149° C. are obtained.

The 2-methyl-6-trifluoromethyl-nicotinic acid (1.026 g, 0.005 mol) obtained is dissolved in 20 ml of oxalyl chloride. Three drops of dimethylformamide are added and the mixture is refluxed for 1 hour. The mixture is then concentrated by evaporation using a rotary evaporator and the residue (2-methyl-6-trifluoromethyl-nicotinoyl chloride) is taken up in 100 ml of methylene-chloride. At a temperature of 0° C., 1.6 ml (0.0115 mol) of triethylamine and 0.7 g (0.005 mol) 4,4-dimethyl-cyclohexane-1,3-dione are added. After 2 hours at a temperature of 22° C., the solvent is removed using a vacuum rotary evaporator, the residue that remains is dissolved in 55 ml of acetonitrile and, for rearrangement of the intermediate, 0.15 ml (0.0016 mol) of acetone cyanohydrin and 0.79 ml (0.0057 mol) of triethylamine are added. After stirring for four hours at room temperature, the reaction solution is concentrated by evaporation. The syrup that remains is chromatographed on silica gel. The light-yellow, viscous oil obtained by eluting with a mixture of toluene, ethyl alcohol, dioxane, triethylamine and water (100:40:20:20:5 parts by volume) (Rf=0.39 based on the said mixture as mobile phase) is dissolved in dichloromethane and washed with 75 ml of hydrochloric acid 5% and 75 ml of water in succession. After drying the organic solution with $Na_2SO_4$, concentration by evaporation yields 1.05 g (63%) of pure title compound.

$^1$H NMR (d$_6$-DMSO, δ in ppm): 1.342, s, 6H: 2.088, t, J 9 Hz, 2H: 2.685, s, 3H: 2.982, t, J 9 Hz, 2H: 8.030, d, J 8.1 Hz, 1H: 8.094, d, J 8.1 Hz, 1H.

Example P5

Preparation of 5-methyl-5-trifluoromethyl-cyclohexane-1,3-dione (Example B1066)

0.64 g of sodium is introduced into 40 ml of ethanol, 3.23 ml of acetic acid methyl ester and 4.9 g of 4,4,4-trifluoro-3-methyl-but-2-enoic acid isopropyl ester are incorporated and the mixture is heated at boiling temperature for 18 hours. After extraction with dilute hydrochloric acid against ethyl acetate, concentration by evaporation is carried out. The non-purified 2-methyl-4,6-dioxo-2-trifluoromethyl-cyclohexanecarboxylic acid methyl ester that remains behind is esterified in the presence of 9.1 g of sodium hydroxide in a mixture of methanol and water at boiling temperature. The mixture is then acidified with hydrochloric acid and extracted with fresh ethyl acetate. After recrystallisation (ethyl acetate), pure 5-methyl-5-trifluoromethyl-cyclohexane-1,3-dione having a melting point of 150–152° C. is obtained.

Example P6

Preparation of 2-hydroxy-1-methoxy-5-methyl-4-oxo-cyclohex-2-enecarboxylic acid methyl ester (B1069)

A 30% solution of 35.8 g of sodium methanolate is made up in 65 ml of dimethyl sulfoxide and, over a period of 20 minutes, is treated at a temperature of from 30 to 35° C. with a mixture of 16.7 g of 3-methyl-3-buten-2-one and 32.4 g of methoxymalonic acid dimethyl ester. The mixture is stirred for 1 hour at a temperature of 35° C., acidified with hydrochloric acid and then extracted several times with dichloromethane. The organic phases are washed with water, dried and concentrated. By crystallising from hot ethyl acetate and hexane, pure 2-hydroxy-1-methoxy-5-methyl-4-oxo-cyclohex-2-enecarboxylic acid methyl ester having a melting point of 117–117.5° C. is obtained.

Example P7

Preparation of 2-hydroxy-1-methoxy-5-methyl-3-(2-methyl-6-trifluoromethyl-pyridine-3-carbonyl)-4-oxo-cyclohex-2-ene-carboxylic acid methyl ester (A2–B1069)

2.23 g of fresh 2-methyl-6-trifluoromethyl-nicotinoyl chloride are added to a mixture of 2.14 g of 2-hydroxy-1-methoxy-5-methyl-4-oxo-cyclohex-2-ene-carboxylic acid methyl ester and 2.02 g of triethylamine in 30 ml of acetonitrile. After about 30 minutes, 0.065 g of potassium cyanide is added and the batch is stirred for 18 hours. The batch is then extracted at pH 2 with water against ethyl acetate, dried over magnesium sulfate and concentrated by evaporation. By filtering over silica gel (mobile phase: ethyl acetate/methanol/triethylamine 85:10:5), pure 2-hydroxy-1-methoxy-5-methyl-3-(2-methyl-6-trifluoromethyl-pyridine-3-carbonyl)-4-oxo-cyclohex-2-enecarboxylic acid methyl ester is obtained in the form of a viscous oil.

Example P8

Preparation of 3-hydroxy-4-methoxy-6-methyl-2-(2-methyl-6-trifluoromethyl-pyridine-3-carbonyl)-cyclohex-2-enone (A2–B1070)

0.586 g of potassium hydroxide is added to 1.4 g of 2-hydroxy-1-methoxy-5-methyl-3-(2-methyl-6-trifluoromethyl-pyridine-3-carbonyl)-4-oxo-cyclohex-2-enecarboxylic acid methyl ester in dioxane/water (5:3) and the batch is stirred for 3 hours. The batch is then acidified (pH 3) and extracted with fresh ethyl acetate. The crude product is purified by chromatography analogously to Example P7. 3-Hydroxy-4-methoxy-6-methyl-2-(2-methyl-6-trifluoromethyl-pyridine-3-carbonyl)-cyclohex-2-enone is obtained in the form of a viscous oil (as a mixture of 3 tautomeric forms, according to $^1$H-NMR).

The compounds listed in the following Tables can also be prepared in an analogous manner and using methods described in the general Reaction Schemes 1 and 2 and in the references mentioned therein. In the following Tables Ph is the phenyl group and CC is an ethyne group.

TABLE 1

Compounds of formula Ib:

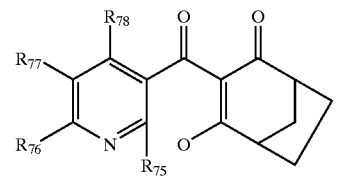

(Ib)

| Compd. no. | $R_{75}$ | $R_{76}$ | $R_{77}$ | $R_{78}$ | m.p. (° C.) |
|---|---|---|---|---|---|
| 1.001 | $CH_3$ | $CF_3$ | H | H | 75–77 |
| 1.002 | $CH_3CH_2$ | $CF_3$ | H | H | |
| 1.003 | $(CH_3)_2CH$ | $CF_3$ | H | H | 111–112 |
| 1.004 | $CH_3(CH_2)_3$ | $CF_3$ | H | H | |
| 1.005 | Ph | $CF_3$ | H | H | oil |
| 1.006 | $CH_2Br$ | $CF_3$ | H | H | |
| 1.007 | $CH_2OCH_3$ | $CF_3$ | H | H | 124–126 |
| 1.008 | $CH_2SMe$ | $CF_3$ | H | H | oil |
| 1.009 | $CH_2SO_2Me$ | $CF_3$ | H | H | 55–55 |
| 1.010 | $SCH_3$ | $CF_3$ | H | H | |
| 1.011 | $SOCH_3$ | $CF_3$ | H | H | |
| 1.012 | $SO_2CH_3$ | $CF_3$ | H | H | |
| 1.013 | SPh | $CF_3$ | H | H | |
| 1.014 | SOPh | $CF_3$ | H | H | |
| 1.015 | $SO_2Ph$ | $CF_3$ | H | H | |
| 1.016 | $CH_3$ | $CF_3CF_2$ | H | H | |
| 1.017 | $CH_3CH_2$ | $CF_3CF_2$ | H | H | |
| 1.018 | $(CH_3)_2CH$ | $CF_3CF_2$ | H | H | |
| 1.019 | $CH_3(CH_2)_3$ | $CF_3CF_2$ | H | H | |
| 1.020 | Ph | $CF_3CF_2$ | H | H | |
| 1.021 | $CH_2Br$ | $CF_3CF_2$ | H | H | |
| 1.022 | $CH_2OCH_3$ | $CF_3CF_2$ | H | H | |
| 1.023 | $CH_2SMe$ | $CF_3CF_2$ | H | H | |
| 1.024 | $CH_2SO_2Me$ | $CF_3CF_2$ | H | H | |
| 1.025 | $SCH_3$ | $CF_3CF_2$ | H | H | |
| 1.026 | $SOCH_3$ | $CF_3CF_2$ | H | H | |
| 1.027 | $SO_2CH_3$ | $CF_3CF_2$ | H | H | |
| 1.028 | SPh | $CF_3CF_2$ | H | H | |
| 1.029 | SOPh | $CF_3CF_2$ | H | H | |
| 1.030 | $SO_2Ph$ | $CF_3CF_2$ | H | H | |
| 1.031 | $CH_3$ | $CHF_2$ | H | H | |
| 1.032 | $CH_3CH_2$ | $CHF_2$ | H | H | |
| 1.033 | $(CH_3)_2CH$ | $CHF_2$ | H | H | |
| 1.034 | $CH_3(CH_2)_3$ | $CHF_2$ | H | H | |
| 1.035 | Ph | $CHF_2$ | H | H | |
| 1.036 | $CH_2Br$ | $CHF_2$ | H | H | |
| 1.037 | $CH_2OCH_3$ | $CHF_2$ | H | H | |
| 1.038 | $CH_2SMe$ | $CHF_2$ | H | H | |
| 1.039 | $CH_2SO_2Me$ | $CHF_2$ | H | H | |
| 1.040 | $SCH_3$ | $CHF_2$ | H | H | |
| 1.041 | $SOCH_3$ | $CHF_2$ | H | H | |
| 1.042 | $SO_2CH_3$ | $CHF_2$ | H | H | |
| 1.043 | SPh | $CHF_2$ | H | H | |
| 1.044 | SOPh | $CHF_2$ | H | H | |
| 1.045 | $SO_2Ph$ | $CHF_2$ | H | H | |

TABLE 1-continued

Compounds of formula Ib:

(Ib)

| Compd. no. | R$_{75}$ | R$_{76}$ | R$_{77}$ | R$_{78}$ | m.p. (° C.) |
|---|---|---|---|---|---|
| 1.046 | CH$_3$ | CF$_3$ | CH$_3$ | H | |
| 1.047 | CH$_3$CH$_2$ | CF$_3$ | CH$_3$ | H | |
| 1.048 | (CH$_3$)$_2$CH | CF$_3$ | CH$_3$ | H | |
| 1.049 | CH$_3$(CH$_2$)$_3$ | CF$_3$ | CH$_3$ | H | |
| 1.050 | Ph | CF$_3$ | CH$_3$ | H | |
| 1.051 | CH$_2$Br | CF$_3$ | CH$_3$ | H | |
| 1.052 | CH$_2$OCH$_3$ | CF$_3$ | CH$_3$ | H | |
| 1.053 | CH$_2$SMe | CF$_3$ | CH$_3$ | H | |
| 1.054 | CH$_2$SO$_2$Me | CF$_3$ | CH$_3$ | H | |
| 1.055 | SCH$_3$ | CF$_3$ | CH$_3$ | H | |
| 1.056 | SOCH$_3$ | CF$_3$ | CH$_3$ | H | |
| 1.057 | SO$_2$CH$_3$ | CF$_3$ | CH$_3$ | H | |
| 1.058 | SPh | CF$_3$ | CH$_3$ | H | |
| 1.059 | SOPh | CF$_3$ | CH$_3$ | H | |
| 1.060 | SO$_2$Ph | CF$_3$ | CH$_3$ | H | |
| 1.061 | CH$_3$ | CF$_3$CF$_2$ | CH$_3$ | H | |
| 1.062 | CH$_3$CH$_2$ | CF$_3$CF$_2$ | CH$_3$ | H | |
| 1.063 | (CH$_3$)$_2$CH | CF$_3$CF$_2$ | CH$_3$ | H | |
| 1.064 | CH$_3$(CH$_2$)$_3$ | CF$_3$CF$_2$ | CH$_3$ | H | |
| 1.065 | Ph | CF$_3$CF$_2$ | CH$_3$ | H | |
| 1.066 | CH$_2$Br | CF$_3$CF$_2$ | CH$_3$ | H | |
| 1.067 | CH$_2$OCH$_3$ | CF$_3$CF$_2$ | CH$_3$ | H | |
| 1.068 | CH$_2$SMe | CF$_3$CF$_2$ | CH$_3$ | H | |
| 1.069 | CH$_2$SO$_2$Me | CF$_3$CF$_2$ | CH$_3$ | H | |
| 1.070 | SCH$_3$ | CF$_3$CF$_2$ | CH$_3$ | H | |
| 1.071 | SOCH$_3$ | CF$_3$CF$_2$ | CH$_3$ | H | |
| 1.072 | SO$_2$CH$_3$ | CF$_3$CF$_2$ | CH$_3$ | H | |
| 1.073 | SPh | CF$_3$CF$_2$ | CH$_3$ | H | |
| 1.074 | SOPh | CF$_3$CF$_2$ | CH$_3$ | H | |
| 1.075 | SO$_2$Ph | CF$_3$CF$_2$ | CH$_3$ | H | |
| 1.076 | CH$_3$ | CHF$_2$ | CH$_3$ | H | |
| 1.077 | CH$_3$CH$_2$ | CHF$_2$ | CH$_3$ | H | |
| 1.078 | (CH$_3$)$_2$CH | CHF$_2$ | CH$_3$ | H | |
| 1.079 | CH$_3$(CH$_2$)$_3$ | CHF$_2$ | CH$_3$ | H | |
| 1.080 | Ph | CHF$_2$ | CH$_3$ | H | |
| 1.081 | CH$_2$Br | CHF$_2$ | CH$_3$ | H | |
| 1.082 | CH$_2$OCH$_3$ | CHF$_2$ | CH$_3$ | H | |
| 1.083 | CH$_2$SMe | CHF$_2$ | CH$_3$ | H | |
| 1.084 | CH$_2$SO$_2$Me | CHF$_2$ | CH$_3$ | H | |
| 1.085 | SCH$_3$ | CHF$_2$ | CH$_3$ | H | |
| 1.086 | SOCH$_3$ | CHF$_2$ | CH$_3$ | H | |
| 1.087 | SO$_2$CH$_3$ | CHF$_2$ | CH$_3$ | H | |
| 1.088 | SPh | CHF$_2$ | CH$_3$ | H | |
| 1.089 | SOPh | CHF$_2$ | CH$_3$ | H | |
| 1.090 | SO$_2$Ph | CHF$_2$ | CH$_3$ | H | |
| 1.091 | CH$_3$ | CF$_3$ | H | CH$_3$ | 92–94 |
| 1.092 | CH$_3$CH$_2$ | CF$_3$ | H | CH$_3$ | |
| 1.093 | (CH$_3$)$_2$CH | CF$_3$ | H | CH$_3$ | |
| 1.094 | CH$_3$(CH$_2$)$_3$ | CF$_3$ | H | CH$_3$ | |
| 1.095 | Ph | CF$_3$ | H | CH$_3$ | |
| 1.096 | CH$_2$Br | CF$_3$ | H | CH$_3$ | |
| 1.097 | CH$_2$OCH$_3$ | CF$_3$ | H | CH$_3$ | |
| 1.098 | CH$_2$SMe | CF$_3$ | H | CH$_3$ | |
| 1.099 | CH$_2$SO$_2$Me | CF$_3$ | H | CH$_3$ | |
| 1.100 | SCH$_3$ | CF$_3$ | H | CH$_3$ | |
| 1.101 | SOCH$_3$ | CF$_3$ | H | CH$_3$ | |
| 1.102 | SO$_2$CH$_3$ | CF$_3$ | H | CH$_3$ | |
| 1.103 | SPh | CF$_3$ | H | CH$_3$ | |
| 1.104 | SOPh | CF$_3$ | H | CH$_3$ | |
| 1.105 | SO$_2$Ph | CF$_3$ | H | CH$_3$ | |

TABLE 2

Compounds of formula Ic:

(Ic)

| Compd. no. | R$_{75}$ | R$_{76}$ | R$_{77}$ | R$_{78}$ | m.p. (° C.) |
|---|---|---|---|---|---|
| 2.001 | CH$_3$ | CF$_3$ | H | H | 107–109 |
| 2.002 | CH$_3$CH$_2$ | CF$_3$ | H | H | oil |
| 2.003 | (CH$_3$)$_2$CH | CF$_3$ | H | H | oil |
| 2.004 | CH$_3$(CH$_2$)$_3$ | CF$_3$ | H | H | |
| 2.005 | Ph | CF$_3$ | H | H | oil |
| 2.006 | CH$_2$Br | CF$_3$ | H | H | |
| 2.007 | CH$_2$OCH$_3$ | CF$_3$ | H | H | |
| 2.008 | CH$_2$SMe | CF$_3$ | H | H | |
| 2.009 | CH$_2$SO$_2$Me | CF$_3$ | H | H | |
| 2.010 | SCH$_3$ | CF$_3$ | H | H | |
| 2.011 | SOCH$_3$ | CF$_3$ | H | H | |
| 2.012 | SO$_2$CH$_3$ | CF$_3$ | H | H | |
| 2.013 | SPh | CF$_3$ | H | H | |
| 2.014 | SOPh | CF$_3$ | H | H | |
| 2.015 | SO$_2$Ph | CF$_3$ | H | H | |
| 2.016 | CH$_3$ | CF$_3$CF$_2$ | H | H | |
| 2.017 | CH$_3$CH$_2$ | CF$_3$CF$_2$ | H | H | |
| 2.018 | (CH$_3$)$_2$CH | CF$_3$CF$_2$ | H | H | |
| 2.019 | CH$_3$(CH$_2$)$_3$ | CF$_3$CF$_2$ | H | H | |
| 2.020 | Ph | CF$_3$CF$_2$ | H | H | |
| 2.021 | CH$_2$Br | CF$_3$CF$_2$ | H | H | |
| 2.022 | CH$_2$OCH$_3$ | CF$_3$CF$_2$ | H | H | |
| 2.023 | CH$_2$SMe | CF$_3$CF$_2$ | H | H | |
| 2.024 | CH$_2$SO$_2$Me | CF$_3$CF$_2$ | H | H | |
| 2.025 | SCH$_3$ | CF$_3$CF$_2$ | H | H | |
| 2.026 | SOCH$_3$ | CF$_3$CF$_2$ | H | H | |
| 2.027 | SO$_2$CH$_3$ | CF$_3$CF$_2$ | H | H | |
| 2.028 | SPh | CF$_3$CF$_2$ | H | H | |
| 2.029 | SOPh | CF$_3$CF$_2$ | H | H | |
| 2.030 | SO$_2$Ph | CF$_3$CF$_2$ | H | H | |
| 2.031 | CH$_3$ | CHF$_2$ | H | H | |
| 2.032 | CH$_3$CH$_2$ | CHF$_2$ | H | H | |
| 2.033 | (CH$_3$)$_2$CH | CHF$_2$ | H | H | |
| 2.034 | CH$_3$(CH$_2$)$_3$ | CHF$_2$ | H | H | |
| 2.035 | Ph | CHF$_2$ | H | H | |
| 2.036 | CH$_2$Br | CHF$_2$ | H | H | |
| 2.037 | CH$_2$OCH$_3$ | CHF$_2$ | H | H | |
| 2.038 | CH$_2$SMe | CHF$_2$ | H | H | |
| 2.039 | CH$_2$SO$_2$Me | CHF$_2$ | H | H | |
| 2.040 | SCH$_3$ | CHF$_2$ | H | H | |
| 2.041 | SOCH$_3$ | CHF$_2$ | H | H | |
| 2.042 | SO$_2$CH$_3$ | CHF$_2$ | H | H | |
| 2.043 | SPh | CHF$_2$ | H | H | |
| 2.044 | SOPh | CHF$_2$ | H | H | |
| 2.045 | SO$_2$Ph | CHF$_2$ | H | H | |
| 2.046 | CH$_3$ | CF$_3$ | CH$_3$ | H | |
| 2.047 | CH$_3$CH$_2$ | CF$_3$ | CH$_3$ | H | |
| 2.048 | (CH$_3$)$_2$CH | CF$_3$ | CH$_3$ | H | |
| 2.049 | CH$_3$(CH$_2$)$_3$ | CF$_3$ | CH$_3$ | H | |
| 2.050 | Ph | CF$_3$ | CH$_3$ | H | |
| 2.051 | CH$_2$Br | CF$_3$ | CH$_3$ | H | |
| 2.052 | CH$_2$OCH$_3$ | CF$_3$ | CH$_3$ | H | |
| 2.053 | CH$_2$SMe | CF$_3$ | CH$_3$ | H | |
| 2.054 | CH$_2$SO$_2$Me | CF$_3$ | CH$_3$ | H | |
| 2.055 | SCH$_3$ | CF$_3$ | CH$_3$ | H | |
| 2.056 | SOCH$_3$ | CF$_3$ | CH$_3$ | H | |
| 2.057 | SO$_2$CH$_3$ | CF$_3$ | CH$_3$ | H | |
| 2.058 | SPh | CF$_3$ | CH$_3$ | H | |
| 2.059 | SOPh | CF$_3$ | CH$_3$ | H | |
| 2.060 | SO$_2$Ph | CF$_3$ | CH$_3$ | H | |
| 2.061 | CH$_3$ | CF$_3$CF$_2$ | CH$_3$ | H | |
| 2.062 | CH$_3$CH$_2$ | CF$_3$CF$_2$ | CH$_3$ | H | |

TABLE 2-continued

Compounds of formula Ic:

(Ic)

| Compd. no. | $R_{75}$ | $R_{76}$ | $R_{77}$ | $R_{78}$ | m.p. (° C.) |
|---|---|---|---|---|---|
| 2.063 | $(CH_3)_2CH$ | $CF_3CF_2$ | $CH_3$ | H | |
| 2.064 | $CH_3(CH_2)_3$ | $CF_3CF_2$ | $CH_3$ | H | |
| 2.065 | Ph | $CF_3CF_2$ | $CH_3$ | H | |
| 2.066 | $CH_2Br$ | $CF_3CF_2$ | $CH_3$ | H | |
| 2.067 | $CH_2OCH_3$ | $CF_3CF_2$ | $CH_3$ | H | |
| 2.068 | $CH_2SMe$ | $CF_3CF_2$ | $CH_3$ | H | |
| 2.069 | $CH_2SO_2Me$ | $CF_3CF_2$ | $CH_3$ | H | |
| 2.070 | $SCH_3$ | $CF_3CF_2$ | $CH_3$ | H | |
| 2.071 | $SOCH_3$ | $CF_3CF_2$ | $CH_3$ | H | |
| 2.072 | $SO_2CH_3$ | $CF_3CF_2$ | $CH_3$ | H | |
| 2.073 | SPh | $CF_3CF_2$ | $CH_3$ | H | |
| 2.074 | SOPh | $CF_3CF_2$ | $CH_3$ | H | |
| 2.075 | $SO_2Ph$ | $CF_3CF_2$ | $CH_3$ | H | |
| 2.076 | $CH_3$ | $CHF_2$ | $CH_3$ | H | |
| 2.077 | $CH_3CH_2$ | $CHF_2$ | $CH_3$ | H | |
| 2.078 | $(CH_3)_2CH$ | $CHF_2$ | $CH_3$ | H | |
| 2.079 | $CH_3(CH_2)_3$ | $CHF_2$ | $CH_3$ | H | |
| 2.080 | Ph | $CHF_2$ | $CH_3$ | H | |
| 2.081 | $CH_2Br$ | $CHF_2$ | $CH_3$ | H | |
| 2.082 | $CH_2OCH_3$ | $CHF_2$ | $CH_3$ | H | |
| 2.083 | $CH_2SMe$ | $CHF_2$ | $CH_3$ | H | |
| 2.084 | $CH_2SO_2Me$ | $CHF_2$ | $CH_3$ | H | |
| 2.085 | $SCH_3$ | $CHF_2$ | $CH_3$ | H | |
| 2.086 | $SOCH_3$ | $CHF_2$ | $CH_3$ | H | |
| 2.087 | $SO_2CH_3$ | $CHF_2$ | $CH_3$ | H | |
| 2.088 | SPh | $CHF_2$ | $CH_3$ | H | |
| 2.089 | SOPh | $CHF_2$ | $CH_3$ | H | |
| 2.090 | $SO_2Ph$ | $CHF_2$ | $CH_3$ | H | |
| 2.091 | $CH_3$ | $CF_3$ | H | $CH_3$ | |
| 2.092 | $CH_3CH_2$ | $CF_3$ | H | $CH_3$ | |
| 2.093 | $(CH_3)_2CH$ | $CF_3$ | H | $CH_3$ | |
| 2.094 | $CH_3(CH_2)_3$ | $CF_3$ | H | $CH_3$ | |
| 2.095 | Ph | $CF_3$ | H | $CH_3$ | |
| 2.096 | $CH_2Br$ | $CF_3$ | H | $CH_3$ | |
| 2.097 | $CH_2OCH_3$ | $CF_3$ | H | $CH_3$ | |
| 2.098 | $CH_2SMe$ | $CF_3$ | H | $CH_3$ | |
| 2.099 | $CH_2SO_2Me$ | $CF_3$ | H | $CH_3$ | |
| 2.100 | $SCH_3$ | $CF_3$ | H | $CH_3$ | |
| 2.101 | $SOCH_3$ | $CF_3$ | H | $CH_3$ | |
| 2.102 | $SO_2CH_3$ | $CF_3$ | H | $CH_3$ | |
| 2.103 | SPh | $CF_3$ | H | $CH_3$ | |
| 2.104 | SOPh | $CF_3$ | H | $CH_3$ | |
| 2.105 | $SO_2Ph$ | $CF_3$ | H | $CH_3$ | |

TABLE 3

Compounds of formula Id:

(Id)

| Compd. no. | $R_{75}$ | $R_{76}$ | $R_{77}$ | $R_{78}$ | m.p. (° C.) |
|---|---|---|---|---|---|
| 3.001 | $CH_3$ | $CF_3$ | H | H | |
| 3.002 | $CH_3CH_2$ | $CF_3$ | H | H | |
| 3.003 | $(CH_3)_2CH$ | $CF_3$ | H | H | |
| 3.004 | $CH_3(CH_2)_3$ | $CF_3$ | H | H | |
| 3.005 | Ph | $CF_3$ | H | H | |
| 3.006 | $CH_2Br$ | $CF_3$ | H | H | |
| 3.007 | $CH_2OCH_3$ | $CF_3$ | H | H | |
| 3.008 | $CH_2SMe$ | $CF_3$ | H | H | |
| 3.009 | $CH_2SO_2Me$ | $CF_3$ | H | H | |
| 3.010 | $SCH_3$ | $CF_3$ | H | H | |
| 3.011 | $SOCH_3$ | $CF_3$ | H | H | |
| 3.012 | $SO_2CH_3$ | $CF_3$ | H | H | |
| 3.013 | SPh | $CF_3$ | H | H | |
| 3.014 | SOPh | $CF_3$ | H | H | |
| 3.015 | $SO_2Ph$ | $CF_3$ | H | H | |
| 3.016 | $CH_3$ | $CF_3CF_2$ | H | H | |
| 3.017 | $CH_3CH_2$ | $CF_3CF_2$ | H | H | |
| 3.018 | $(CH_3)_2CH$ | $CF_3CF_2$ | H | H | |
| 3.019 | $CH_3(CH_2)_3$ | $CF_3CF_2$ | H | H | |
| 3.020 | Ph | $CF_3CF_2$ | H | H | |
| 3.021 | $CH_2Br$ | $CF_3CF_2$ | H | H | |
| 3.022 | $CH_2OCH_3$ | $CF_3CF_2$ | H | H | |
| 3.023 | $CH_2SMe$ | $CF_3CF_2$ | H | H | |
| 3.024 | $CH_2SO_2Me$ | $CF_3CF_2$ | H | H | |
| 3.025 | $SCH_3$ | $CF_3CF_2$ | H | H | |
| 3.026 | $SOCH_3$ | $CF_3CF_2$ | H | H | |
| 3.027 | $SO_2CH_3$ | $CF_3CF_2$ | H | H | |
| 3.028 | SPh | $CF_3CF_2$ | H | H | |
| 3.029 | SOPh | $CF_3CF_2$ | H | H | |
| 3.030 | $SO_2Ph$ | $CF_3CF_2$ | H | H | |
| 3.031 | $CH_3$ | $CHF_2$ | H | H | |
| 3.032 | $CH_3CH_2$ | $CHF_2$ | H | H | |
| 3.033 | $(CH_3)_2CH$ | $CHF_2$ | H | H | |
| 3.034 | $CH_3(CH_2)_3$ | $CHF_2$ | H | H | |
| 3.035 | Ph | $CHF_2$ | H | H | |
| 3.036 | $CH_2Br$ | $CHF_2$ | H | H | |
| 3.037 | $CH_2OCH_3$ | $CHF_2$ | H | H | |
| 3.038 | $CH_2SMe$ | $CHF_2$ | H | H | |
| 3.039 | $CH_2SO_2Me$ | $CHF_2$ | H | H | |
| 3.040 | $SCH_3$ | $CHF_2$ | H | H | |
| 3.041 | $SOCH_3$ | $CHF_2$ | H | H | |
| 3.042 | $SO_2CH_3$ | $CHF_2$ | H | H | |
| 3.043 | SPh | $CHF_2$ | H | H | |
| 3.044 | SOPh | $CHF_2$ | H | H | |
| 3.045 | $SO_2Ph$ | $CHF_2$ | H | H | |
| 3.046 | $CH_3$ | $CF_3$ | $CH_3$ | H | |
| 3.047 | $CH_3CH_2$ | $CF_3$ | $CH_3$ | H | |

TABLE 3-continued

Compounds of formula Id:

(Id)

| Compd. no. | R$_{75}$ | R$_{76}$ | R$_{77}$ | R$_{78}$ | m.p. (° C.) |
|---|---|---|---|---|---|
| 3.048 | (CH$_3$)$_2$CH | CF$_3$ | CH$_3$ | H | |
| 3.049 | CH$_3$(CH$_2$)$_3$ | CF$_3$ | CH$_3$ | H | |
| 3.050 | Ph | CF$_3$ | CH$_3$ | H | |
| 3.051 | CH$_2$Br | CF$_3$ | CH$_3$ | H | |
| 3.052 | CH$_2$OCH$_3$ | CF$_3$ | CH$_3$ | H | |
| 3.053 | CH$_2$SMe | CF$_3$ | CH$_3$ | H | |
| 3.054 | CH$_2$SO$_2$Me | CF$_3$ | CH$_3$ | H | |
| 3.055 | SCH$_3$ | CF$_3$ | CH$_3$ | H | |
| 3.056 | SOCH$_3$ | CF$_3$ | CH$_3$ | H | |
| 3.057 | SO$_2$CH$_3$ | CF$_3$ | CH$_3$ | H | |
| 3.058 | SPh | CF$_3$ | CH$_3$ | H | |
| 3.059 | SOPh | CF$_3$ | CH$_3$ | H | |
| 3.060 | SO$_2$Ph | CF$_3$ | CH$_3$ | H | |
| 3.061 | CH$_3$ | CF$_3$CF$_2$ | CH$_3$ | H | |
| 3.062 | CH$_3$CH$_2$ | CF$_3$CF$_2$ | CH$_3$ | H | |
| 3.063 | (CH$_3$)$_2$CH | CF$_3$CF$_2$ | CH$_3$ | H | |
| 3.064 | CH$_3$(CH$_2$)$_3$ | CF$_3$CF$_2$ | CH$_3$ | H | |
| 3.065 | Ph | CF$_3$CF$_2$ | CH$_3$ | H | |
| 3.066 | CH$_2$Br | CF$_3$CF$_2$ | CH$_3$ | H | |
| 3.067 | CH$_2$OCH$_3$ | CF$_3$CF$_2$ | CH$_3$ | H | |
| 3.068 | CH$_2$SMe | CF$_3$CF$_2$ | CH$_3$ | H | |
| 3.069 | CH$_2$SO$_2$Me | CF$_3$CF$_2$ | CH$_3$ | H | |
| 3.070 | SCH$_3$ | CF$_3$CF$_2$ | CH$_3$ | H | |
| 3.071 | SOCH$_3$ | CF$_3$CF$_2$ | CH$_3$ | H | |
| 3.072 | SO$_2$CH$_3$ | CF$_3$CF$_2$ | CH$_3$ | H | |
| 3.073 | SPh | CF$_3$CF$_2$ | CH$_3$ | H | |
| 3.074 | SOPh | CF$_3$CF$_2$ | CH$_3$ | H | |
| 3.075 | SO$_2$Ph | CF$_3$CF$_2$ | CH$_3$ | H | |
| 3.076 | CH$_3$ | CHF$_2$ | CH$_3$ | H | |
| 3.077 | CH$_3$CH$_2$ | CHF$_2$ | CH$_3$ | H | |
| 3.078 | (CH$_3$)$_2$CH | CHF$_2$ | CH$_3$ | H | |
| 3.079 | CH$_3$(CH$_2$)$_3$ | CHF$_2$ | CH$_3$ | H | |
| 3.080 | Ph | CHF$_2$ | CH$_3$ | H | |
| 3.081 | CH$_2$Br | CHF$_2$ | CH$_3$ | H | |
| 3.082 | CH$_2$OCH$_3$ | CHF$_2$ | CH$_3$ | H | |
| 3.083 | CH$_2$SMe | CHF$_2$ | CH$_3$ | H | |
| 3.084 | CH$_2$SO$_2$Me | CHF$_2$ | CH$_3$ | H | |
| 3.085 | SCH$_3$ | CHF$_2$ | CH$_3$ | H | |
| 3.086 | SOCH$_3$ | CHF$_2$ | CH$_3$ | H | |
| 3.087 | SO$_2$CH$_3$ | CHF$_2$ | CH$_3$ | H | |
| 3.088 | SPh | CHF$_2$ | CH$_3$ | H | |
| 3.089 | SOPh | CHF$_2$ | CH$_3$ | H | |
| 3.090 | SO$_2$Ph | CHF$_2$ | CH$_3$ | H | |
| 3.091 | CH$_3$ | CF$_3$ | H | CH$_3$ | |
| 3.092 | CH$_3$CH$_2$ | CF$_3$ | H | CH$_3$ | |
| 3.093 | (CH$_3$)$_2$CH | CF$_3$ | H | CH$_3$ | |
| 3.094 | CH$_3$(CH$_2$)$_3$ | CF$_3$ | H | CH$_3$ | |
| 3.095 | Ph | CF$_3$ | H | CH$_3$ | |
| 3.096 | CH$_2$Br | CF$_3$ | H | CH$_3$ | |
| 3.097 | CH$_2$OCH$_3$ | CF$_3$ | H | CH$_3$ | |
| 3.098 | CH$_2$SMe | CF$_3$ | H | CH$_3$ | |
| 3.099 | CH$_2$SO$_2$Me | CF$_3$ | H | CH$_3$ | |
| 3.100 | SCH$_3$ | CF$_3$ | H | CH$_3$ | |
| 3.101 | SOCH$_3$ | CF$_3$ | H | CH$_3$ | |
| 3.102 | SO$_2$CH$_3$ | CF$_3$ | H | CH$_3$ | |
| 3.103 | SPh | CF$_3$ | H | CH$_3$ | |
| 3.104 | SOPh | CF$_3$ | H | CH$_3$ | |
| 3.105 | SO$_2$Ph | CF$_3$ | H | CH$_3$ | |

TABLE 4

Compounds of formula Ie:

(Ie)

| Compd. no. | R$_{75}$ | R$_{76}$ | R$_{77}$ | R$_{78}$ | Z | m.p. (° C.) |
|---|---|---|---|---|---|---|
| 4.001 | CH$_3$ | CF$_3$ | H | H | S | 103–104 |
| 4.002 | CH$_3$CH$_2$ | CF$_3$ | H | H | S | |
| 4.003 | (CH$_3$)$_2$CH | CF$_3$ | H | H | S | |
| 4.004 | CH$_3$(CH$_2$)$_3$ | CF$_3$ | H | H | S | |
| 4.005 | Ph | CF$_3$ | H | H | S | |
| 4.006 | CH$_2$Br | CF$_3$ | H | H | S | |
| 4.007 | CH$_2$OCH$_3$ | CF$_3$ | H | H | S | |
| 4.008 | CH$_2$SMe | CF$_3$ | H | H | S | |
| 4.009 | CH$_2$SO$_2$Me | CF$_3$ | H | H | S | |
| 4.010 | SCH$_3$ | CF$_3$ | H | H | S | |
| 4.011 | SOCH$_3$ | CF$_3$ | H | H | S | |
| 4.012 | SO$_2$CH$_3$ | CF$_3$ | H | H | S | |
| 4.013 | SPh | CF$_3$ | H | H | S | |
| 4.014 | SOPh | CF$_3$ | H | H | S | |
| 4.015 | SO$_2$Ph | CF$_3$ | H | H | S | |
| 4.016 | CH$_3$ | CF$_3$CF$_2$ | H | H | S | |
| 4.017 | CH$_3$CH$_2$ | CF$_3$CF$_2$ | H | H | S | |
| 4.018 | (CH$_3$)$_2$CH | CF$_3$CF$_2$ | H | H | S | |
| 4.019 | CH$_3$(CH$_2$)$_3$ | CF$_3$CF$_2$ | H | H | S | |
| 4.020 | Ph | CF$_3$CF$_2$ | H | H | S | |
| 4.021 | CH$_2$Br | CF$_3$CF$_2$ | H | H | S | |
| 4.022 | CH$_2$OCH$_3$ | CF$_3$CF$_2$ | H | H | S | |
| 4.023 | CH$_2$SMe | CF$_3$CF$_2$ | H | H | S | |
| 4.024 | CH$_2$SO$_2$Me | CF$_3$CF$_2$ | H | H | S | |
| 4.025 | SCH$_3$ | CF$_3$CF$_2$ | H | H | S | |
| 4.026 | SOCH$_3$ | CF$_3$CF$_2$ | H | H | S | |
| 4.027 | SO$_2$CH$_3$ | CF$_3$CF$_2$ | H | H | S | |
| 4.028 | SPh | CF$_3$CF$_2$ | H | H | S | |
| 4.029 | SOPh | CF$_3$CF$_2$ | H | H | S | |
| 4.030 | SO$_2$Ph | CF$_3$CF$_2$ | H | H | S | |
| 4.031 | CH$_3$ | CHF$_2$ | H | H | S | |
| 4.032 | CH$_3$CH$_2$ | CHF$_2$ | H | H | S | |
| 4.033 | (CH$_3$)$_2$CH | CHF$_2$ | H | H | S | |
| 4.034 | CH$_3$(CH$_2$)$_3$ | CHF$_2$ | H | H | S | |
| 4.035 | Ph | CHF$_2$ | H | H | S | |
| 4.036 | CH$_2$Br | CHF$_2$ | H | H | S | |
| 4.037 | CH$_2$OCH$_3$ | CHF$_2$ | H | H | S | |
| 4.038 | CH$_2$SMe | CHF$_2$ | H | H | S | |
| 4.039 | CH$_2$SO$_2$Me | CHF$_2$ | H | H | S | |
| 4.040 | SCH$_3$ | CHF$_2$ | H | H | S | |
| 4.041 | SOCH$_3$ | CHF$_2$ | H | H | S | |
| 4.042 | SO$_2$CH$_3$ | CHF$_2$ | H | H | S | |
| 4.043 | SPh | CHF$_2$ | H | H | S | |
| 4.044 | SOPh | CHF$_2$ | H | H | S | |
| 4.045 | SO$_2$Ph | CHF$_2$ | H | H | S | |
| 4.046 | CH$_3$ | CF$_3$ | CH$_3$ | H | | |
| 4.047 | CH$_3$CH$_2$ | CF$_3$ | CH$_3$ | H | | |
| 4.048 | (CH$_3$)$_2$CH | CF$_3$ | CH$_3$ | H | | |
| 4.049 | CH$_3$(CH$_2$)$_3$ | CF$_3$ | CH$_3$ | H | | |
| 4.050 | Ph | CF$_3$ | CH$_3$ | H | | |
| 4.051 | CH$_2$Br | CF$_3$ | CH$_3$ | H | | |
| 4.052 | CH$_2$OCH$_3$ | CF$_3$ | CH$_3$ | H | | |
| 4.053 | CH$_2$SMe | CF$_3$ | CH$_3$ | H | | |
| 4.054 | CH$_2$SO$_2$Me | CF$_3$ | CH$_3$ | H | | |
| 4.055 | SCH$_3$ | CF$_3$ | CH$_3$ | H | | |
| 4.056 | SOCH$_3$ | CF$_3$ | CH$_3$ | H | | |
| 4.057 | SO$_2$CH$_3$ | CF$_3$ | CH$_3$ | H | | |
| 4.058 | SPh | CF$_3$ | CH$_3$ | H | | |
| 4.059 | SOPh | CF$_3$ | CH$_3$ | H | | |
| 4.060 | SO$_2$Ph | CF$_3$ | CH$_3$ | H | | |
| 4.061 | CH$_3$ | CF$_3$CF$_2$ | CH$_3$ | H | S | |

TABLE 4-continued

Compounds of formula Ie:

(Ie)

[Structure: pyridine ring with R76, R77, R78 substituents and R75 at position next to N; connected via C(=O) to isoxazole ring bearing CH3-Z group and cyclopropyl]

| Compd. no. | R75 | R76 | R77 | R78 | Z | m.p. (°C.) |
|---|---|---|---|---|---|---|
| 4.062 | CH$_3$CH$_2$ | CF$_3$CF$_2$ | CH$_3$ | H | S | |
| 4.063 | (CH$_3$)$_2$CH | CF$_3$CF$_2$ | CH$_3$ | H | S | |
| 4.064 | CH$_3$(CH$_2$)$_3$ | CF$_3$CF$_2$ | CH$_3$ | H | S | |
| 4.065 | Ph | CF$_3$CF$_2$ | CH$_3$ | H | S | |
| 4.066 | CH$_2$Br | CF$_3$CF$_2$ | CH$_3$ | H | S | |
| 4.067 | CH$_2$OCH$_3$ | CF$_3$CF$_2$ | CH$_3$ | H | S | |
| 4.068 | CH$_2$SMe | CF$_3$CF$_2$ | CH$_3$ | H | S | |
| 4.069 | CH$_2$SO$_2$Me | CF$_3$CF$_2$ | CH$_3$ | H | S | |
| 4.070 | SCH$_3$ | CF$_3$CF$_2$ | CH$_3$ | H | S | |
| 4.071 | SOCH$_3$ | CF$_3$CF$_2$ | CH$_3$ | H | S | |
| 4.072 | SO$_2$CH$_3$ | CF$_3$CF$_2$ | CH$_3$ | H | S | |
| 4.073 | SPh | CF$_3$CF$_2$ | CH$_3$ | H | S | |
| 4.074 | SOPh | CF$_3$CF$_2$ | CH$_3$ | H | S | |
| 4.075 | SO$_2$Ph | CF$_3$CF$_2$ | CH$_3$ | H | S | |
| 4.076 | CH$_3$ | CHF$_2$ | CH$_3$ | H | S | |
| 4.077 | CH$_3$CH$_2$ | CHF$_2$ | CH$_3$ | H | S | |
| 4.078 | (CH$_3$)$_2$CH | CHF$_2$ | CH$_3$ | H | S | |
| 4.079 | CH$_3$(CH$_2$)$_3$ | CHF$_2$ | CH$_3$ | H | S | |
| 4.080 | Ph | CHF$_2$ | CH$_3$ | H | S | |
| 4.081 | CH$_2$Br | CHF$_2$ | CH$_3$ | H | S | |
| 4.082 | CH$_2$OCH$_3$ | CHF$_2$ | CH$_3$ | H | S | |
| 4.083 | CH$_2$SMe | CHF$_2$ | CH$_3$ | H | S | |
| 4.084 | CH$_2$SO$_2$Me | CHF$_2$ | CH$_3$ | H | S | |
| 4.085 | SCH$_3$ | CHF$_2$ | CH$_3$ | H | S | |
| 4.086 | SOCH$_3$ | CHF$_2$ | CH$_3$ | H | S | |
| 4.087 | SO$_2$CH$_3$ | CHF$_2$ | CH$_3$ | H | S | |
| 4.088 | SPh | CHF$_2$ | CH$_3$ | H | S | |
| 4.089 | SOPh | CHF$_2$ | CH$_3$ | H | S | |
| 4.090 | SO$_2$Ph | CHF$_2$ | CH$_3$ | H | S | |
| 4.091 | CH$_3$ | CF$_3$ | H | CH$_3$ | S | |
| 4.092 | CH$_3$CH$_2$ | CF$_3$ | H | CH$_3$ | S | |
| 4.093 | (CH$_3$)$_2$CH | CF$_3$ | H | CH$_3$ | S | |
| 4.094 | CH$_3$(CH$_2$)$_3$ | CF$_3$ | H | CH$_3$ | S | |
| 4.095 | Ph | CF$_3$ | H | CH$_3$ | S | |
| 4.096 | CH$_2$Br | CF$_3$ | H | CH$_3$ | S | |
| 4.097 | CH$_2$OCH$_3$ | CF$_3$ | H | CH$_3$ | S | |
| 4.098 | CH$_2$SMe | CF$_3$ | H | CH$_3$ | S | |
| 4.099 | CH$_2$SO$_2$Me | CF$_3$ | H | CH$_3$ | S | |
| 4.100 | SCH$_3$ | CF$_3$ | H | CH$_3$ | S | |
| 4.101 | SOCH$_3$ | CF$_3$ | H | CH$_3$ | S | |
| 4.102 | SO$_2$CH$_3$ | CF$_3$ | H | CH$_3$ | S | |
| 4.103 | SPh | CF$_3$ | H | CH$_3$ | S | |
| 4.104 | SOPh | CF$_3$ | H | CH$_3$ | S | |
| 4.105 | SO$_2$Ph | CF$_3$ | H | CH$_3$ | S | |
| 4.106 | CH$_3$ | CF$_3$ | H | H | SO | 96–97 |
| 4.107 | CH$_3$CH$_2$ | CF$_3$ | H | H | SO | |
| 4.108 | (CH$_3$)$_2$CH | CF$_3$ | H | H | SO | |
| 4.109 | CH$_3$(CH$_2$)$_3$ | CF$_3$ | H | H | SO | |
| 4.110 | Ph | CF$_3$ | H | H | SO | |
| 4.111 | CH$_2$Br | CF$_3$ | H | H | SO | |
| 4.112 | CH$_2$OCH$_3$ | CF$_3$ | H | H | SO | |
| 4.113 | CH$_2$SMe | CF$_3$ | H | H | SO | |
| 4.114 | CH$_2$SO$_2$Me | CF$_3$ | H | H | SO | |
| 4.115 | SCH$_3$ | CF$_3$ | H | H | SO | |
| 4.116 | SOCH$_3$ | CF$_3$ | H | H | SO | |
| 4.117 | SO$_2$CH$_3$ | CF$_3$ | H | H | SO | |
| 4.118 | SPh | CF$_3$ | H | H | SO | |
| 4.119 | SOPh | CF$_3$ | H | H | SO | |
| 4.120 | SO$_2$Ph | CF$_3$ | H | H | SO | |
| 4.121 | CH$_3$ | CF$_3$CF$_2$ | H | H | SO | |
| 4.122 | CH$_3$CH$_2$ | CF$_3$CF$_2$ | H | H | SO | |
| 4.123 | (CH$_3$)$_2$CH | CF$_3$CF$_2$ | H | H | SO | |
| 4.124 | CH$_3$(CH$_2$)$_3$ | CF$_3$CF$_2$ | H | H | SO | |
| 4.125 | Ph | CF$_3$CF$_2$ | H | H | SO | |
| 4.126 | CH$_2$Br | CF$_3$CF$_2$ | H | H | SO | |
| 4.127 | CH$_2$OCH$_3$ | CF$_3$CF$_2$ | H | H | SO | |
| 4.128 | CH$_2$SMe | CF$_3$CF$_2$ | H | H | SO | |
| 4.129 | CH$_2$SO$_2$Me | CF$_3$CF$_2$ | H | H | SO | |
| 4.130 | SCH$_3$ | CF$_3$CF$_2$ | H | H | SO | |
| 4.131 | SOCH$_3$ | CF$_3$CF$_2$ | H | H | SO | |
| 4.132 | SO$_2$CH$_3$ | CF$_3$CF$_2$ | H | H | SO | |
| 4.133 | SPh | CF$_3$CF$_2$ | H | H | SO | |
| 4.134 | SOPh | CF$_3$CF$_2$ | H | H | SO | |
| 4.135 | SO$_2$Ph | CF$_3$CF$_2$ | H | H | SO | |
| 4.136 | CH$_3$ | CHF$_2$ | H | H | SO | |
| 4.137 | CH$_3$CH$_2$ | CHF$_2$ | H | H | SO | |
| 4.138 | (CH$_3$)$_2$CH | CHF$_2$ | H | H | SO | |
| 4.139 | CH$_3$(CH$_2$)$_3$ | CHF$_2$ | H | H | SO | |
| 4.140 | Ph | CHF$_2$ | H | H | SO | |
| 4.141 | CH$_2$Br | CHF$_2$ | H | H | SO | |
| 4.142 | CH$_2$OCH$_3$ | CHF$_2$ | H | H | SO | |
| 4.143 | CH$_2$SMe | CHF$_2$ | H | H | SO | |
| 4.144 | CH$_2$SO$_2$Me | CHF$_2$ | H | H | SO | |
| 4.145 | SCH$_3$ | CHF$_2$ | H | H | SO | |
| 4.146 | SOCH$_3$ | CHF$_2$ | H | H | SO | |
| 4.147 | SO$_2$CH$_3$ | CHF$_2$ | H | H | SO | |
| 4.148 | SPh | CHF$_2$ | H | H | SO | |
| 4.149 | SOPh | CHF$_2$ | H | H | SO | |
| 4.150 | SO$_2$Ph | CHF$_2$ | H | H | SO | |
| 4.151 | CH$_3$ | CF$_3$ | CH$_3$ | H | SO | |
| 4.152 | CH$_3$CH$_2$ | CF$_3$ | CH$_3$ | H | SO | |
| 4.153 | (CH$_3$)$_2$CH | CF$_3$ | CH$_3$ | H | SO | |
| 4.154 | CH$_3$(CH$_2$)$_3$ | CF$_3$ | CH$_3$ | H | SO | |
| 4.155 | Ph | CF$_3$ | CH$_3$ | H | SO | |
| 4.156 | CH$_2$Br | CF$_3$ | CH$_3$ | H | SO | |
| 4.157 | CH$_2$OCH$_3$ | CF$_3$ | CH$_3$ | H | SO | |
| 4.158 | CH$_2$SMe | CF$_3$ | CH$_3$ | H | SO | |
| 4.159 | CH$_2$SO$_2$Me | CF$_3$ | CH$_3$ | H | SO | |
| 4.160 | SCH$_3$ | CF$_3$ | CH$_3$ | H | SO | |
| 4.161 | SOCH$_3$ | CF$_3$ | CH$_3$ | H | SO | |
| 4.162 | SO$_2$CH$_3$ | CF$_3$ | CH$_3$ | H | SO | |
| 4.163 | SPh | CF$_3$ | CH$_3$ | H | SO | |
| 4.164 | SOPh | CF$_3$ | CH$_3$ | H | SO | |
| 4.165 | SO$_2$Ph | CF$_3$ | CH$_3$ | H | SO | |
| 4.166 | CH$_3$ | CF$_3$CF$_2$ | CH$_3$ | H | SO | |
| 4.167 | CH$_3$CH$_2$ | CF$_3$CF$_2$ | CH$_3$ | H | SO | |
| 4.168 | (CH$_3$)$_2$CH | CF$_3$CF$_2$ | CH$_3$ | H | SO | |
| 4.169 | CH$_3$(CH$_2$)$_3$ | CF$_3$CF$_2$ | CH$_3$ | H | SO | |
| 4.170 | Ph | CF$_3$CF$_2$ | CH$_3$ | H | SO | |
| 4.171 | CH$_2$Br | CF$_3$CF$_2$ | CH$_3$ | H | SO | |
| 4.172 | CH$_2$OCH$_3$ | CF$_3$CF$_2$ | CH$_3$ | H | SO | |
| 4.173 | CH$_2$SMe | CF$_3$CF$_2$ | CH$_3$ | H | SO | |
| 4.174 | CH$_2$SO$_2$Me | CF$_3$CF$_2$ | CH$_3$ | H | SO | |
| 4.175 | SCH$_3$ | CF$_3$CF$_2$ | CH$_3$ | H | SO | |
| 4.176 | SOCH$_3$ | CF$_3$CF$_2$ | CH$_3$ | H | SO | |
| 4.177 | SO$_2$CH$_3$ | CF$_3$CF$_2$ | CH$_3$ | H | SO | |
| 4.178 | SPh | CF$_3$CF$_2$ | CH$_3$ | H | SO | |
| 4.179 | SOPh | CF$_3$CF$_2$ | CH$_3$ | H | SO | |
| 4.180 | SO$_2$Ph | CF$_3$CF$_2$ | CH$_3$ | H | SO | |
| 4.181 | CH$_3$ | CHF$_2$ | CH$_3$ | H | SO | |
| 4.182 | CH$_3$CH$_2$ | CHF$_2$ | CH$_3$ | H | SO | |
| 4.183 | (CH$_3$)$_2$CH | CHF$_2$ | CH$_3$ | H | SO | |

TABLE 4-continued

Compounds of formula Ie:

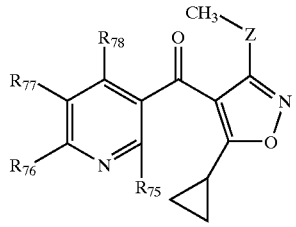

| Compd. no. | $R_{75}$ | $R_{76}$ | $R_{77}$ | $R_{78}$ | Z | m.p. (° C.) |
|---|---|---|---|---|---|---|
| 4.184 | $CH_3(CH_2)_3$ | $CHF_2$ | $CH_3$ | H | SO | |
| 4.185 | Ph | $CHF_2$ | $CH_3$ | H | SO | |
| 4.186 | $CH_2Br$ | $CHF_2$ | $CH_3$ | H | SO | |
| 4.187 | $CH_2OCH_3$ | $CHF_2$ | $CH_3$ | H | SO | |
| 4.188 | $CH_2SMe$ | $CHF_2$ | $CH_3$ | H | SO | |
| 4.189 | $CH_2SO_2Me$ | $CHF_2$ | $CH_3$ | H | SO | |
| 4.190 | $SCH_3$ | $CHF_2$ | $CH_3$ | H | SO | |
| 4.191 | $SOCH_3$ | $CHF_2$ | $CH_3$ | H | SO | |
| 4.192 | $SO_2CH_3$ | $CHF_2$ | $CH_3$ | H | SO | |
| 4.193 | SPh | $CHF_2$ | $CH_3$ | H | SO | |
| 4.194 | SOPh | $CHF_2$ | $CH_3$ | H | SO | |
| 4.195 | $SO_2Ph$ | $CHF_2$ | $CH_3$ | H | SO | |
| 4.196 | $CH_3$ | $CF_3$ | H | $CH_3$ | SO | |
| 4.197 | $CH_3CH_2$ | $CF_3$ | H | $CH_3$ | SO | |
| 4.198 | $(CH_3)_2CH$ | $CF_3$ | H | $CH_3$ | SO | |
| 4.199 | $CH_3(CH_2)_3$ | $CF_3$ | H | $CH_3$ | SO | |
| 4.200 | Ph | $CF_3$ | H | $CH_3$ | SO | |
| 4.201 | $CH_2Br$ | $CF_3$ | H | $CH_3$ | SO | |
| 4.202 | $CH_2OCH_3$ | $CF_3$ | H | $CH_3$ | SO | |
| 4.203 | $CH_2SMe$ | $CF_3$ | H | $CH_3$ | SO | |
| 4.204 | $CH_2SO_2Me$ | $CF_3$ | H | $CH_3$ | SO | |
| 4.205 | $SCH_3$ | $CF_3$ | H | $CH_3$ | SO | |
| 4.206 | $SOCH_3$ | $CF_3$ | H | $CH_3$ | SO | |
| 4.207 | $SO_2CH_3$ | $CF_3$ | H | $CH_3$ | SO | |
| 4.208 | SPh | $CF_3$ | H | $CH_3$ | SO | |
| 4.209 | SOPh | $CF_3$ | H | $CH_3$ | SO | |
| 4.210 | $SO_2Ph$ | $CF_3$ | H | $CH_3$ | SO | |
| 4.211 | $CH_3$ | $CF_3$ | H | H | $SO_2$ | amorphous |
| 4.212 | $CH_3CH_2$ | $CF_3$ | H | H | $SO_2$ | |
| 4.213 | $(CH_3)_2CH$ | $CF_3$ | H | H | $SO_2$ | |
| 4.214 | $CH_3(CH_2)_3$ | $CF_3$ | H | H | $SO_2$ | |
| 4.215 | Ph | $CF_3$ | H | H | $SO_2$ | |
| 4.216 | $CH_2Br$ | $CF_3$ | H | H | $SO_2$ | |
| 4.217 | $CH_2OCH_3$ | $CF_3$ | H | H | $SO_2$ | |
| 4.218 | $CH_2SMe$ | $CF_3$ | H | H | $SO_2$ | |
| 4.219 | $CH_2SO_2Me$ | $CF_3$ | H | H | $SO_2$ | |
| 4.220 | $SCH_3$ | $CF_3$ | H | H | $SO_2$ | |
| 4.221 | $SOCH_3$ | $CF_3$ | H | H | $SO_2$ | |
| 4.222 | $SO_2CH_3$ | $CF_3$ | H | H | $SO_2$ | |
| 4.223 | SPh | $CF_3$ | H | H | $SO_2$ | |
| 4.224 | SOPh | $CF_3$ | H | H | $SO_2$ | |
| 4.225 | $SO_2Ph$ | $CF_3$ | H | H | $SO_2$ | |
| 4.226 | $CH_3$ | $CF_3CF_2$ | H | H | $SO_2$ | |
| 4.227 | $CH_3CH_2$ | $CF_3CF_2$ | H | H | $SO_2$ | |
| 4.228 | $(CH_3)_2CH$ | $CF_3CF_2$ | H | H | $SO_2$ | |
| 4.229 | $CH_3(CH_2)_3$ | $CF_3CF_2$ | H | H | $SO_2$ | |
| 4.230 | Ph | $CF_3CF_2$ | H | H | $SO_2$ | |
| 4.231 | $CH_2Br$ | $CF_3CF_2$ | H | H | $SO_2$ | |
| 4.232 | $CH_2OCH_3$ | $CF_3CF_2$ | H | H | $SO_2$ | |
| 4.233 | $CH_2SMe$ | $CF_3CF_2$ | H | H | $SO_2$ | |
| 4.234 | $CH_2SO_2Me$ | $CF_3CF_2$ | H | H | $SO_2$ | |
| 4.235 | $SCH_3$ | $CF_3CF_2$ | H | H | $SO_2$ | |
| 4.236 | $SOCH_3$ | $CF_3CF_2$ | H | H | $SO_2$ | |
| 4.237 | $SO_2CH_3$ | $CF_3CF_2$ | H | H | $SO_2$ | |
| 4.238 | SPh | $CF_3CF_2$ | H | H | $SO_2$ | |
| 4.239 | SOPh | $CF_3CF_2$ | H | H | $SO_2$ | |
| 4.240 | $SO_2Ph$ | $CF_3CF_2$ | H | H | $SO_2$ | |
| 4.241 | $CH_3$ | $CHF_2$ | H | H | $SO_2$ | |
| 4.242 | $CH_3CH_2$ | $CHF_2$ | H | H | $SO_2$ | |
| 4.243 | $(CH_3)_2CH$ | $CHF_2$ | H | H | $SO_2$ | |
| 4.244 | $CH_3(CH_2)_3$ | $CHF_2$ | H | H | $SO_2$ | |
| 4.245 | Ph | $CHF_2$ | H | H | $SO_2$ | |
| 4.246 | $CH_2Br$ | $CHF_2$ | H | H | $SO_2$ | |
| 4.247 | $CH_2OCH_3$ | $CHF_2$ | H | H | $SO_2$ | |
| 4.248 | $CH_2SMe$ | $CHF_2$ | H | H | $SO_2$ | |
| 4.249 | $CH_2SO_2Me$ | $CHF_2$ | H | H | $SO_2$ | |
| 4.250 | $SCH_3$ | $CHF_2$ | H | H | $SO_2$ | |
| 4.251 | $SOCH_3$ | $CHF_2$ | H | H | $SO_2$ | |
| 4.252 | $SO_2CH_3$ | $CHF_2$ | H | H | $SO_2$ | |
| 4.253 | SPh | $CHF_2$ | H | H | $SO_2$ | |
| 4.254 | SOPh | $CHF_2$ | H | H | $SO_2$ | |
| 4.255 | $SO_2Ph$ | $CHF_2$ | H | H | $SO_2$ | |
| 4.256 | $CH_3$ | $CF_3$ | $CH_3$ | H | $SO_2$ | |
| 4.257 | $CH_3CH_2$ | $CF_3$ | $CH_3$ | H | $SO_2$ | |
| 4.258 | $(CH_3)_2CH$ | $CF_3$ | $CH_3$ | H | $SO_2$ | |
| 4.259 | $CH_3(CH_2)_3$ | $CF_3$ | $CH_3$ | H | $SO_2$ | |
| 4.260 | Ph | $CF_3$ | $CH_3$ | H | $SO_2$ | |
| 4.261 | $CH_2Br$ | $CF_3$ | $CH_3$ | H | $SO_2$ | |
| 4.262 | $CH_2OCH_3$ | $CF_3$ | $CH_3$ | H | $SO_2$ | |
| 4.263 | $CH_2SMe$ | $CF_3$ | $CH_3$ | H | $SO_2$ | |
| 4.264 | $CH_2SO_2Me$ | $CF_3$ | $CH_3$ | H | $SO_2$ | |
| 4.265 | $SCH_3$ | $CF_3$ | $CH_3$ | H | $SO_2$ | |
| 4.266 | $SOCH_3$ | $CF_3$ | $CH_3$ | H | $SO_2$ | |
| 4.267 | $SO_2CH_3$ | $CF_3$ | $CH_3$ | H | $SO_2$ | |
| 4.268 | SPh | $CF_3$ | $CH_3$ | H | $SO_2$ | |
| 4.269 | SOPh | $CF_3$ | $CH_3$ | H | $SO_2$ | |
| 4.270 | $SO_2Ph$ | $CF_3$ | $CH_3$ | H | $SO_2$ | |
| 4.271 | $CH_3$ | $CF_3CF_2$ | $CH_3$ | H | $SO_2$ | |
| 4.272 | $CH_3CH_2$ | $CF_3CF_2$ | $CH_3$ | H | $SO_2$ | |
| 4.273 | $(CH_3)_2CH$ | $CF_3CF_2$ | $CH_3$ | H | $SO_2$ | |
| 4.274 | $CH_3(CH_2)_3$ | $CF_3CF_2$ | $CH_3$ | H | $SO_2$ | |
| 4.275 | Ph | $CF_3CF_2$ | $CH_3$ | H | $SO_2$ | |
| 4.276 | $CH_2Br$ | $CF_3CF_2$ | $CH_3$ | H | $SO_2$ | |
| 4.277 | $CH_2OCH_3$ | $CF_3CF_2$ | $CH_3$ | H | $SO_2$ | |
| 4.278 | $CH_2SMe$ | $CF_3CF_2$ | $CH_3$ | H | $SO_2$ | |
| 4.279 | $CH_2SO_2Me$ | $CF_3CF_2$ | $CH_3$ | H | $SO_2$ | |
| 4.280 | $SCH_3$ | $CF_3CF_2$ | $CH_3$ | H | $SO_2$ | |
| 4.281 | $SOCH_3$ | $CF_3CF_2$ | $CH_3$ | H | $SO_2$ | |
| 4.282 | $SO_2CH_3$ | $CF_3CF_2$ | $CH_3$ | H | $SO_2$ | |
| 4.283 | SPh | $CF_3CF_2$ | $CH_3$ | H | $SO_2$ | |
| 4.284 | SOPh | $CF_3CF_2$ | $CH_3$ | H | $SO_2$ | |
| 4.285 | $SO_2Ph$ | $CF_3CF_2$ | $CH_3$ | H | $SO_2$ | |
| 4.286 | $CH_3$ | $CHF_2$ | $CH_3$ | H | $SO_2$ | |
| 4.287 | $CH_3CH_2$ | $CHF_2$ | $CH_3$ | H | $SO_2$ | |
| 4.288 | $(CH_3)_2CH$ | $CHF_2$ | $CH_3$ | H | $SO_2$ | |
| 4.289 | $CH_3(CH_2)_3$ | $CHF_2$ | $CH_3$ | H | $SO_2$ | |
| 4.290 | Ph | $CHF_2$ | $CH_3$ | H | $SO_2$ | |
| 4.291 | $CH_2Br$ | $CHF_2$ | $CH_3$ | H | $SO_2$ | |
| 4.292 | $CH_2OCH_3$ | $CHF_2$ | $CH_3$ | H | $SO_2$ | |
| 4.293 | $CH_2SMe$ | $CHF_2$ | $CH_3$ | H | $SO_2$ | |
| 4.294 | $CH_2SO_2Me$ | $CHF_2$ | $CH_3$ | H | $SO_2$ | |
| 4.295 | $SCH_3$ | $CHF_2$ | $CH_3$ | H | $SO_2$ | |
| 4.296 | $SOCH_3$ | $CHF_2$ | $CH_3$ | H | $SO_2$ | |
| 4.297 | $SO_2CH_3$ | $CHF_2$ | $CH_3$ | H | $SO_2$ | |
| 4.298 | SPh | $CHF_2$ | $CH_3$ | H | $SO_2$ | |
| 4.299 | SOPh | $CHF_2$ | $CH_3$ | H | $SO_2$ | |
| 4.300 | $SO_2Ph$ | $CHF_2$ | $CH_3$ | H | $SO_2$ | |
| 4.301 | $CH_3$ | $CF_3$ | H | $CH_3$ | $SO_2$ | |
| 4.302 | $CH_3CH_2$ | $CF_3$ | H | $CH_3$ | $SO_2$ | |
| 4.303 | $(CH_3)_2CH$ | $CF_3$ | H | $CH_3$ | $SO_2$ | |
| 4.304 | $CH_3(CH_2)_3$ | $CF_3$ | H | $CH_3$ | $SO_2$ | |

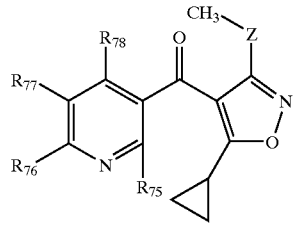

TABLE 4-continued

Compounds of formula Ie:

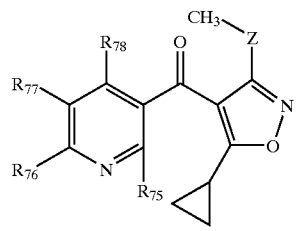

(Ie)

| Compd. no. | $R_{75}$ | $R_{76}$ | $R_{77}$ | $R_{78}$ | Z | m.p. (°C.) |
|---|---|---|---|---|---|---|
| 4.305 | Ph | $CF_3$ | H | $CH_3$ | $SO_2$ | |
| 4.306 | $CH_2Br$ | $CF_3$ | H | $CH_3$ | $SO_2$ | |
| 4.307 | $CH_2OCH_3$ | $CF_3$ | H | $CH_3$ | $SO_2$ | |
| 4.308 | $CH_2SMe$ | $CF_3$ | H | $CH_3$ | $SO_2$ | |
| 4.309 | $CH_2SO_2Me$ | $CF_3$ | H | $CH_3$ | $SO_2$ | |
| 4.310 | $SCH_3$ | $CF_3$ | H | $CH_3$ | $SO_2$ | |

TABLE 4-continued

Compounds of formula Ie:

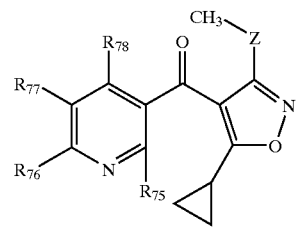

(Ie)

| Compd. no. | $R_{75}$ | $R_{76}$ | $R_{77}$ | $R_{78}$ | Z | m.p. (°C.) |
|---|---|---|---|---|---|---|
| 4.311 | $SOCH_3$ | $CF_3$ | H | $CH_3$ | $SO_2$ | |
| 4.312 | $SO_2CH_3$ | $CF_3$ | H | $CH_3$ | $SO_2$ | |
| 4.313 | SPh | $CF_3$ | H | $CH_3$ | $SO_2$ | |
| 4.314 | SOPh | $CF_3$ | H | $CH_3$ | $SO_2$ | |
| 4.315 | $SO_2Ph$ | $CF_3$ | H | $CH_3$ | $SO_2$ | |

TABLE 5

Compounds of formula XVI:

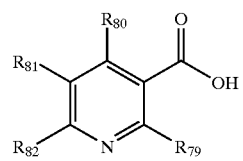

(XVI)

| Compd. no. | $R_{79}$ | $R_{80}$ | $R_{81}$ | $R_{82}$ |
|---|---|---|---|---|
| A1 | H | H | H | $CF_3$ |
| A2 | $CH_3$ | H | H | $CF_3$ |
| A3 | $CH_3CH_2$ | H | H | $CF_3$ |
| A4 | $(CH_3)_2CH$ | H | H | $CF_3$ |
| A5 | $(CH_3)_3C$ | H | H | $CF_3$ |
| A6 | cyclopropyl | H | H | $CF_3$ |
| A7 | $CH_3(CH_2)_2$ | H | H | $CF_3$ |
| A8 | $CH_3OCH_2$ | H | H | $CF_3$ |
| A9 | $CH_3O(CH_2)_2$ | H | H | $CF_3$ |
| A10 | Ph | H | H | $CF_3$ |
| A11 | PhO | H | H | $CF_3$ |
| A12 | PhS | H | H | $CF_3$ |
| A13 | PhSO | H | H | $CF_3$ |
| A14 | $PhSO_2$ | H | H | $CF_3$ |
| A15 | $CH_3S$ | H | H | $CF_3$ |
| A16 | $CH_3SO$ | H | H | $CF_3$ |
| A17 | $CF_3$ | H | H | $CF_3$ |
| A18 | $F_2CH$ | H | H | $CF_3$ |
| A19 | HCC | H | H | $CF_3$ |
| A20 | $CH_3CC$ | H | H | $CF_3$ |
| A21 | $CH_2=CH$ | H | H | $CF_3$ |
| A22 | $CH_2=CHCH_2$ | H | H | $CF_3$ |
| A23 | $CH_3SO_2N(CH_3)$ | H | H | $CF_3$ |
| A24 | $(CH_3)_2N$ | H | H | $CF_3$ |
| A25 | $(CH_3)_2NSO_2$ | H | H | $CF_3$ |
| A26 | $ClCH_2$ | H | H | $CF_3$ |
| A27 | $CH_3SCH_2$ | H | H | $CF_3$ |
| A28 | $CH_3SOCH_2$ | H | H | $CF_3$ |

TABLE 5-continued

Compounds of formula XVI:

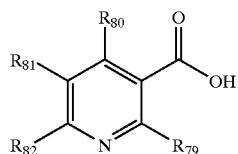

(XVI)

| Compd. no. | $R_{79}$ | $R_{80}$ | $R_{81}$ | $R_{82}$ |
|---|---|---|---|---|
| A29 | $CH_3SO_2CH_2$ | H | H | $CF_3$ |
| A30 | [1,2,4]-triazol-1-yl-methyl | H | H | $CF_3$ |
| A31 | $CH_3$ | $CF_3$ | H | $CH_3$ |
| A32 | $CH_3$ | $CH_3$ | H | $CF_3$ |
| A33 | H | H | H | $CF_3CF_2$ |
| A34 | $CH_3$ | H | H | $CF_3CF_2$ |
| A35 | $CH_3CH_2$ | H | H | $CF_3CF_2$ |
| A36 | cyclopropyl | H | H | $CF_3CF_2$ |
| A37 | $(CH_3)_3C$ | H | H | $CF_3CF_2$ |
| A38 | $(CH_3)_2CH$ | H | H | $CF_3CF_2$ |
| A39 | $CH_3(CH_2)_2$ | H | H | $CF_3CF_2$ |
| A40 | $CH_3OCH_2$ | H | H | $CF_3CF_2$ |
| A41 | $CH_3O(CH_2)_2$ | H | H | $CF_3CF_2$ |
| A42 | Ph | H | H | $CF_3CF_2$ |
| A43 | PhO | H | H | $CF_3CF_2$ |
| A44 | PhS | H | H | $CF_3CF_2$ |
| A45 | PhSO | H | H | $CF_3CF_2$ |
| A46 | $PhSO_2$ | H | H | $CF_3CF_2$ |
| A47 | $CH_3S$ | H | H | $CF_3CF_2$ |
| A48 | $CH_3SO$ | H | H | $CF_3CF_2$ |
| A49 | $CF_3$ | H | H | $CF_3CF_2$ |
| A50 | $F_2CH$ | H | H | $CF_3CF_2$ |
| A51 | HCC | H | H | $CF_3CF_2$ |
| A52 | $CH_3CC$ | H | H | $CF_3CF_2$ |
| A53 | $CH_2=CH$ | H | H | $CF_3CF_2$ |
| A54 | $CH_2=CHCH_2$ | H | H | $CF_3CF_2$ |
| A55 | $CH_3SO_2N(CH_3)$ | H | H | $CF_3CF_2$ |
| A56 | $(CH_3)_2N$ | H | H | $CF_3CF_2$ |
| A57 | $(CH_3)_2NSO_2$ | H | H | $CF_3CF_2$ |
| A58 | $ClCH_2$ | H | H | $CF_3CF_2$ |
| A59 | $CH_3SCH_2$ | H | H | $CF_3CF_2$ |
| A60 | $CH_3SOCH_2$ | H | H | $CF_3CF_2$ |
| A61 | $CH_3SO_2CH_2$ | H | H | $CF_3CF_2$ |
| A62 | [1,2,4]-triazol-1-yl-methyl | H | H | $CF_3CF_2$ |
| A63 | H | H | H | $CF_3CF_2CF_2$ |
| A64 | $CH_3$ | H | H | $CF_3CF_2CF_2$ |
| A65 | $CH_3CH_2$ | H | H | $CF_3CF_2CF_2$ |
| A66 | cyclopropyl | H | H | $CF_3CF_2CF_2$ |
| A67 | $(CH_3)_3C$ | H | H | $CF_3CF_2CF_2$ |
| A68 | $(CH_3)_2CH$ | H | H | $CF_3CF_2CF_2$ |
| A69 | $CH_3(CH_2)_2$ | H | H | $CF_3CF_2CF_2$ |
| A70 | $CH_3OCH_2$ | H | H | $CF_3CF_2CF_2$ |
| A71 | $CH_3O(CH_2)_2$ | H | H | $CF_3CF_2CF_2$ |
| A72 | Ph | H | H | $CF_3CF_2CF_2$ |
| A73 | PhO | H | H | $CF_3CF_2CF_2$ |
| A74 | PhS | H | H | $CF_3CF_2CF_2$ |
| A75 | PhSO | H | H | $CF_3CF_2CF_2$ |
| A76 | $PhSO_2$ | H | H | $CF_3CF_2CF_2$ |
| A77 | $CH_3S$ | H | H | $CF_3CF_2CF_2$ |
| A78 | $CH_3SO$ | H | H | $CF_3CF_2CF_2$ |
| A79 | $CF_3$ | H | H | $CF_3CF_2CF_2$ |
| A80 | $F_2CH$ | H | H | $CF_3CF_2CF_2$ |
| A81 | HCC | H | H | $CF_3CF_2CF_2$ |
| A82 | $CH_3CC$ | H | H | $CF_3CF_2CF_2$ |
| A83 | $CH_2=CH$ | H | H | $CF_3CF_2CF_2$ |
| A84 | $CH_2=CHCH_2$ | H | H | $CF_3CF_2CF_2$ |
| A85 | $CH_3SO_2N(CH_3)$ | H | H | $CF_3CF_2CF_2$ |
| A86 | $(CH_3)_2N$ | H | H | $CF_3CF_2CF_2$ |
| A87 | $(CH_3)_2NSO_2$ | H | H | $CF_3CF_2CF_2$ |
| A88 | $ClCH_2$ | H | H | $CF_3CF_2CF_2$ |
| A89 | $CH_3SCH_2$ | H | H | $CF_3CF_2CF_2$ |
| A90 | $CH_3SOCH_2$ | H | H | $CF_3CF_2CF_2$ |
| A91 | $CH_3SO_2CH_2$ | H | H | $CF_3CF_2CF_2$ |
| A92 | [1,2,4]-triazol-1-yl-methyl | H | H | $CF_3CF_2CF_2$ |
| A93 | H | H | H | $CF_2Cl$ |

TABLE 5-continued

Compounds of formula XVI:

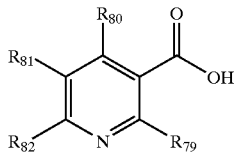

(XVI)

| Compd. no. | $R_{79}$ | $R_{80}$ | $R_{81}$ | $R_{82}$ |
| --- | --- | --- | --- | --- |
| A94 | $CH_3$ | H | H | $CF_2Cl$ |
| A95 | $CH_3CH_2$ | H | H | $CF_2Cl$ |
| A96 | cyclopropyl | H | H | $CF_2Cl$ |
| A97 | $(CH_3)_3C$ | H | H | $CF_2Cl$ |
| A98 | $(CH_3)_2CH$ | H | H | $CF_2Cl$ |
| A99 | $CH_3(CH_2)_2$ | H | H | $CF_2Cl$ |
| A100 | $CH_3OCH_2$ | H | H | $CF_2Cl$ |
| A101 | $CH_3O(CH_2)_2$ | H | H | $CF_2Cl$ |
| A102 | Ph | H | H | $CF_2Cl$ |
| A103 | PhO | H | H | $CF_2Cl$ |
| A104 | PhS | H | H | $CF_2Cl$ |
| A105 | PhSO | H | H | $CF_2Cl$ |
| A106 | $PhSO_2$ | H | H | $CF_2Cl$ |
| A107 | $CH_3S$ | H | H | $CF_2Cl$ |
| A108 | $CH_3SO$ | H | H | $CF_2Cl$ |
| A109 | $CF_3$ | H | H | $CF_2Cl$ |
| A110 | $F_2CH$ | H | H | $CF_2Cl$ |
| A111 | HCC | H | H | $CF_2Cl$ |
| A112 | $CH_3CC$ | H | H | $CF_2Cl$ |
| A113 | $CH_2$=CH | H | H | $CF_2Cl$ |
| A114 | $CH_2$=$CHCH_2$ | H | H | $CF_2Cl$ |
| A115 | $CH_3SO_2N(CH_3)$ | H | H | $CF_2Cl$ |
| A116 | $(CH_3)_2N$ | H | H | $CF_2Cl$ |
| A117 | $(CH_3)_2NSO_2$ | H | H | $CF_2Cl$ |
| A118 | $ClCH_2$ | H | H | $CF_2Cl$ |
| A119 | $CH_3SCH_2$ | H | H | $CF_2Cl$ |
| A120 | $CH_3SOCH_2$ | H | H | $CF_2Cl$ |
| A121 | $CH_3SO_2CH_2$ | H | H | $CF_2Cl$ |
| A122 | [1,2,4]-triazol-1-yl-methyl | H | H | $CF_2Cl$ |
| A123 | H | H | H | $CHF_2$ |
| A124 | $CH_3$ | H | H | $CHF_2$ |
| A125 | $CH_3CH_2$ | H | H | $CHF_2$ |
| A126 | cyclopropyl | H | H | $CHF_2$ |
| A127 | $(CH_3)_3C$ | H | H | $CHF_2$ |
| A128 | $(CH_3)_2CH$ | H | H | $CHF_2$ |
| A129 | $CH_3(CH_2)_2$ | H | H | $CHF_2$ |
| A130 | $CH_3OCH_2$ | H | H | $CHF_2$ |
| A131 | $CH_3O(CH_2)_2$ | H | H | $CHF_2$ |
| A132 | Ph | H | H | $CHF_2$ |
| A133 | PhO | H | H | $CHF_2$ |
| A134 | PhS | H | H | $CHF_2$ |
| A135 | PhSO | H | H | $CHF_2$ |
| A136 | $PhSO_2$ | H | H | $CHF_2$ |
| A137 | $CH_3S$ | H | H | $CHF_2$ |
| A138 | $CH_3SO$ | H | H | $CHF_2$ |
| A139 | $CF_3$ | H | H | $CHF_2$ |
| A140 | $F_2CH$ | H | H | $CHF_2$ |
| A141 | HCC | H | H | $CHF_2$ |
| A142 | $CH_3CC$ | H | H | $CHF_2$ |
| A143 | $CH_2$=CH | H | H | $CHF_2$ |
| A144 | $CH_2$=$CHCH_2$ | H | H | $CHF_2$ |
| A145 | $CH_3SO_2N(CH_3)$ | H | H | $CHF_2$ |
| A146 | $(CH_3)_2N$ | H | H | $CHF_2$ |
| A147 | $(CH_3)_2NSO_2$ | H | H | $CHF_2$ |
| A148 | $ClCH_2$ | H | H | $CHF_2$ |
| A149 | $CH_3SCH_2$ | H | H | $CHF_2$ |
| A150 | $CH_3SOCH_2$ | H | H | $CHF_2$ |
| A151 | $CH_3SO_2CH_2$ | H | H | $CHF_2$ |
| A152 | [1,2,4]-triazol-1-yl-methyl | H | H | $CHF_2$ |
| A153 | H | H | H | $CCl_3$ |
| A154 | $CH_3$ | H | H | $CCl_3$ |
| A155 | $CH_3CH_2$ | H | H | $CCl_3$ |
| A156 | cyclopropyl | H | H | $CCl_3$ |
| A157 | $(CH_3)_3C$ | H | H | $CCl_3$ |
| A158 | $(CH_3)_2CH$ | H | H | $CCl_3$ |

TABLE 5-continued

Compounds of formula XVI:

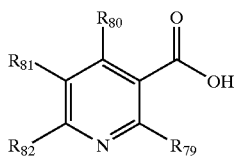

(XVI)

| Compd. no. | $R_{79}$ | $R_{80}$ | $R_{81}$ | $R_{82}$ |
|---|---|---|---|---|
| A159 | $CH_3(CH_2)_2$ | H | H | $CCl_3$ |
| A160 | $CH_3OCH_2$ | H | H | $CCl_3$ |
| A161 | $CH_3O(CH_2)_2$ | H | H | $CCl_3$ |
| A162 | Ph | H | H | $CCl_3$ |
| A163 | PhO | H | H | $CCl_3$ |
| A164 | PhS | H | H | $CCl_3$ |
| A165 | PhSO | H | H | $CCl_3$ |
| A166 | $PhSO_2$ | H | H | $CCl_3$ |
| A167 | $CH_3S$ | H | H | $CCl_3$ |
| A168 | $CH_3SO$ | H | H | $CCl_3$ |
| A169 | $CF_3$ | H | H | $CCl_3$ |
| A170 | $F_2CH$ | H | H | $CCl_3$ |
| A171 | HCC | H | H | $CCl_3$ |
| A172 | $CH_3CC$ | H | H | $CCl_3$ |
| A173 | $CH_2=CH$ | H | H | $CCl_3$ |
| A174 | $CH_2=CHCH_2$ | H | H | $CCl_3$ |
| A175 | $CH_3SO_2N(CH_3)$ | H | H | $CCl_3$ |
| A176 | $(CH_3)_2N$ | H | H | $CCl_3$ |
| A177 | $(CH_3)_2NSO_2$ | H | H | $CCl_3$ |
| A178 | $ClCH_2$ | H | H | $CCl_3$ |
| A179 | $CH_3SCH_2$ | H | H | $CCl_3$ |
| A180 | $CH_3SOCH_2$ | H | H | $CCl_3$ |
| A181 | $CH_3SO_2CH_2$ | H | H | $CCl_3$ |
| A182 | [1,2,4]-triazol-1-yl-methyl | H | H | $CCl_3$ |
| A183 | H | H | $CH_3$ | $CF_3$ |
| A184 | $CH_3$ | H | $CH_3$ | $CF_3$ |
| A185 | $CH_3CH_2$ | H | $CH_3$ | $CF_3$ |
| A186 | cyclopropyl | H | $CH_3$ | $CF_3$ |
| A187 | $(CH_3)_3C$ | H | $CH_3$ | $CF_3$ |
| A188 | $(CH_3)_2CH$ | H | $CH_3$ | $CF_3$ |
| A189 | $CH_3(CH_2)_2$ | H | $CH_3$ | $CF_3$ |
| A190 | $CH_3OCH_2$ | H | $CH_3$ | $CF_3$ |
| A191 | $CH_3O(CH_2)_2$ | H | $CH_3$ | $CF_3$ |
| A192 | Ph | H | $CH_3$ | $CF_3$ |
| A193 | PhO | H | $CH_3$ | $CF_3$ |
| A194 | PhS | H | $CH_3$ | $CF_3$ |
| A195 | PhSO | H | $CH_3$ | $CF_3$ |
| A196 | $PhSO_2$ | H | $CH_3$ | $CF_3$ |
| A197 | $CH_3S$ | H | $CH_3$ | $CF_3$ |
| A198 | $CH_3SO$ | H | $CH_3$ | $CF_3$ |
| A199 | $CF_3$ | H | $CH_3$ | $CF_3$ |
| A200 | $F_2CH$ | H | $CH_3$ | $CF_3$ |
| A201 | HCC | H | $CH_3$ | $CF_3$ |
| A202 | $CH_3CC$ | H | $CH_3$ | $CF_3$ |
| A203 | $CH_2=CH$ | H | $CH_3$ | $CF_3$ |
| A204 | $CH_2=CHCH_2$ | H | $CH_3$ | $CF_3$ |
| A205 | $CH_3SO_2N(CH_3)$ | H | $CH_3$ | $CF_3$ |
| A206 | $(CH_3)_2N$ | H | $CH_3$ | $CF_3$ |
| A207 | $(CH_3)_2NSO_2$ | H | $CH_3$ | $CF_3$ |
| A208 | $ClCH_2$ | H | $CH_3$ | $CF_3$ |
| A209 | $CH_3SCH_2$ | H | $CH_3$ | $CF_3$ |
| A210 | $CH_3SOCH_2$ | H | $CH_3$ | $CF_3$ |
| A211 | $CH_3SO_2CH_2$ | H | $CH_3$ | $CF_3$ |
| A212 | H | H | $CH_3$ | $CF_3CF_2$ |
| A213 | $CH_3$ | H | $CH_3$ | $CF_3CF_2$ |
| A214 | $CH_3CH_2$ | H | $CH_3$ | $CF_3CF_2$ |
| A215 | cyclopropyl | H | $CH_3$ | $CF_3CF_2$ |
| A216 | $(CH_3)_3C$ | H | $CH_3$ | $CF_3CF_2$ |
| A217 | $(CH_3)_2CH$ | H | $CH_3$ | $CF_3CF_2$ |
| A218 | $CH_3(CH_2)_2$ | H | $CH_3$ | $CF_3CF_2$ |
| A219 | $CH_3OCH_2$ | H | $CH_3$ | $CF_3CF_2$ |
| A220 | $CH_3O(CH_2)_2$ | H | $CH_3$ | $CF_3CF_2$ |
| A221 | Ph | H | $CH_3$ | $CF_3CF_2$ |
| A222 | PhO | H | $CH_3$ | $CF_3CF_2$ |
| A223 | PhS | H | $CH_3$ | $CF_3CF_2$ |

TABLE 5-continued

Compounds of formula XVI:

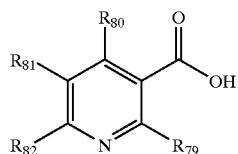

(XVI)

| Compd. no. | $R_{79}$ | $R_{80}$ | $R_{81}$ | $R_{82}$ |
|---|---|---|---|---|
| A224 | PhSO | H | $CH_3$ | $CF_3CF_2$ |
| A225 | $PhSO_2$ | H | $CH_3$ | $CF_3CF_2$ |
| A226 | $CH_3S$ | H | $CH_3$ | $CF_3CF_2$ |
| A227 | $CH_3SO$ | H | $CH_3$ | $CF_3CF_2$ |
| A228 | $CF_3$ | H | $CH_3$ | $CF_3CF_2$ |
| A229 | $F_2CH$ | H | $CH_3$ | $CF_3CF_2$ |
| A230 | HCC | H | $CH_3$ | $CF_3CF_2$ |
| A231 | $CH_3CC$ | H | $CH_3$ | $CF_3CF_2$ |
| A232 | $CH_2{=}CH$ | H | $CH_3$ | $CF_3CF_2$ |
| A233 | $CH_2{=}CHCH_2$ | H | $CH_3$ | $CF_3CF_2$ |
| A234 | $CH_3SO_2N(CH_3)$ | H | $CH_3$ | $CF_3CF_2$ |
| A235 | $(CH_3)_2N$ | H | $CH_3$ | $CF_3CF_2$ |
| A236 | $(CH_3)_2NSO_2$ | H | $CH_3$ | $CF_3CF_2$ |
| A237 | $ClCH_2$ | H | $CH_3$ | $CF_3CF_2$ |
| A238 | $CH_3SCH_2$ | H | $CH_3$ | $CF_3CF_2$ |
| A239 | $CH_3SOCH_2$ | H | $CH_3$ | $CF_3CF_2$ |
| A240 | $CH_3SO_2CH_2$ | H | $CH_3$ | $CF_3CF_2$ |
| A241 | H | H | $CH_3$ | $CF_3CF_2CF_2$ |
| A242 | $CH_3$ | H | $CH_3$ | $CF_3CF_2CF_2$ |
| A243 | $CH_3CH_2$ | H | $CH_3$ | $CF_3CF_2CF_2$ |
| A244 | cyclopropyl | H | $CH_3$ | $CF_3CF_2CF_2$ |
| A245 | $(CH_3)_3C$ | H | $CH_3$ | $CF_3CF_2CF_2$ |
| A246 | $(CH_3)_2CH$ | H | $CH_3$ | $CF_3CF_2CF_2$ |
| A247 | $CH_3(CH_2)_2$ | H | $CH_3$ | $CF_3CF_2CF_2$ |
| A248 | $CH_3OCH_2$ | H | $CH_3$ | $CF_3CF_2CF_2$ |
| A249 | $CH_3O(CH_2)_2$ | H | $CH_3$ | $CF_3CF_2CF_2$ |
| A250 | Ph | H | $CH_3$ | $CF_3CF_2CF_2$ |
| A251 | PhO | H | $CH_3$ | $CF_3CF_2CF_2$ |
| A252 | PhS | H | $CH_3$ | $CF_3CF_2CF_2$ |
| A253 | PhSO | H | $CH_3$ | $CF_3CF_2CF_2$ |
| A254 | $PhSO_2$ | H | $CH_3$ | $CF_3CF_2CF_2$ |
| A255 | $CH_3S$ | H | $CH_3$ | $CF_3CF_2CF_2$ |
| A256 | $CH_3SO$ | H | $CH_3$ | $CF_3CF_2CF_2$ |
| A257 | $CF_3$ | H | $CH_3$ | $CF_3CF_2CF_2$ |
| A258 | $F_2CH$ | H | $CH_3$ | $CF_3CF_2CF_2$ |
| A259 | HCC | H | $CH_3$ | $CF_3CF_2CF_2$ |
| A260 | $CH_3CC$ | H | $CH_3$ | $CF_3CF_2CF_2$ |
| A261 | $CH_2{=}CH$ | H | $CH_3$ | $CF_3CF_2CF_2$ |
| A262 | $CH_2{=}CHCH_2$ | H | $CH_3$ | $CF_3CF_2CF_2$ |
| A263 | $CH_3SO_2N(CH_3)$ | H | $CH_3$ | $CF_3CF_2CF_2$ |
| A264 | $(CH_3)_2N$ | H | $CH_3$ | $CF_3CF_2CF_2$ |
| A265 | $(CH_3)_2NSO_2$ | H | $CH_3$ | $CF_3CF_2CF_2$ |
| A266 | $ClCH_2$ | H | $CH_3$ | $CF_3CF_2CF_2$ |
| A267 | $CH_3SCH_2$ | H | $CH_3$ | $CF_3CF_2CF_2$ |
| A268 | $CH_3SOCH_2$ | H | $CH_3$ | $CF_3CF_2CF_2$ |
| A269 | $CH_3SO_2CH_2$ | H | $CH_3$ | $CF_3CF_2CF_2$ |
| A270 | H | H | $CH_3$ | $CF_2Cl$ |
| A271 | $CH_3$ | H | $CH_3$ | $CF_2Cl$ |
| A272 | $CH_3CH_2$ | H | $CH_3$ | $CF_2Cl$ |
| A273 | cyclopropyl | H | $CH_3$ | $CF_2Cl$ |
| A274 | $(CH_3)_3C$ | H | $CH_3$ | $CF_2Cl$ |
| A275 | $(CH_3)_2CH$ | H | $CH_3$ | $CF_2Cl$ |
| A276 | $CH_3(CH_2)_2$ | H | $CH_3$ | $CF_2Cl$ |
| A277 | $CH_3OCH_2$ | H | $CH_3$ | $CF_2Cl$ |
| A278 | $CH_3O(CH_2)_2$ | H | $CH_3$ | $CF_2Cl$ |
| A279 | Ph | H | $CH_3$ | $CF_2Cl$ |
| A280 | PhO | H | $CH_3$ | $CF_2Cl$ |
| A281 | PhS | H | $CH_3$ | $CF_2Cl$ |
| A282 | PhSO | H | $CH_3$ | $CF_2Cl$ |
| A283 | $PhSO_2$ | H | $CH_3$ | $CF_2Cl$ |
| A284 | $CH_3S$ | H | $CH_3$ | $CF_2Cl$ |
| A285 | $CH_3SO$ | H | $CH_3$ | $CF_2Cl$ |
| A286 | $CF_3$ | H | $CH_3$ | $CF_2Cl$ |
| A287 | $F_2CH$ | H | $CH_3$ | $CF_2Cl$ |
| A288 | HCC | H | $CH_3$ | $CF_2Cl$ |

TABLE 5-continued

Compounds of formula XVI:

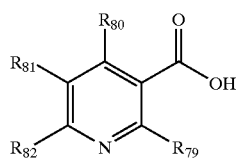

(XVI)

| Compd. no. | $R_{79}$ | $R_{80}$ | $R_{81}$ | $R_{82}$ |
|---|---|---|---|---|
| A289 | $CH_3CC$ | H | $CH_3$ | $CF_2Cl$ |
| A290 | $CH_2=CH$ | H | $CH_3$ | $CF_2Cl$ |
| A291 | $CH_2=CHCH_2$ | H | $CH_3$ | $CF_2Cl$ |
| A292 | $CH_3SO_2N(CH_3)$ | H | $CH_3$ | $CF_2Cl$ |
| A293 | $(CH_3)_2N$ | H | $CH_3$ | $CF_2Cl$ |
| A294 | $(CH_3)_2NSO_2$ | H | $CH_3$ | $CF_2Cl$ |
| A295 | $ClCH_2$ | H | $CH_3$ | $CF_2Cl$ |
| A296 | $CH_3SCH_2$ | H | $CH_3$ | $CF_2Cl$ |
| A297 | $CH_3SOCH_2$ | H | $CH_3$ | $CF_2Cl$ |
| A298 | $CH_3SO_2CH_2$ | H | $CH_3$ | $CF_2Cl$ |
| A299 | H | H | $CH_3$ | $CHF_2$ |
| A300 | $CH_3$ | H | $CH_3$ | $CHF_2$ |
| A301 | $CH_3CH_2$ | H | $CH_3$ | $CHF_2$ |
| A302 | cyclopropyl | H | $CH_3$ | $CHF_2$ |
| A303 | $(CH_3)_3C$ | H | $CH_3$ | $CHF_2$ |
| A304 | $(CH_3)_2CH$ | H | $CH_3$ | $CHF_2$ |
| A305 | $CH_3(CH_2)_2$ | H | $CH_3$ | $CHF_2$ |
| A306 | $CH_3OCH_2$ | H | $CH_3$ | $CHF_2$ |
| A307 | $CH_3O(CH_2)_2$ | H | $CH_3$ | $CHF_2$ |
| A308 | Ph | H | $CH_3$ | $CHF_2$ |
| A309 | PhO | H | $CH_3$ | $CHF_2$ |
| A310 | PhS | H | $CH_3$ | $CHF_2$ |
| A311 | PhSO | H | $CH_3$ | $CHF_2$ |
| A312 | $PhSO_2$ | H | $CH_3$ | $CHF_2$ |
| A313 | $CH_3S$ | H | $CH_3$ | $CHF_2$ |
| A314 | $CH_3SO$ | H | $CH_3$ | $CHF_2$ |
| A315 | $CF_3$ | H | $CH_3$ | $CHF_2$ |
| A316 | $F_2CH$ | H | $CH_3$ | $CHF_2$ |
| A317 | HCC | H | $CH_3$ | $CHF_2$ |
| A318 | $CH_3CC$ | H | $CH_3$ | $CHF_2$ |
| A319 | $CH_2=CH$ | H | $CH_3$ | $CHF_2$ |
| A320 | $CH_2=CHCH_2$ | H | $CH_3$ | $CHF_2$ |
| A321 | $CH_3SO_2N(CH_3)$ | H | $CH_3$ | $CHF_2$ |
| A322 | $(CH_3)_2N$ | H | $CH_3$ | $CHF_2$ |
| A323 | $(CH_3)_2NSO_2$ | H | $CH_3$ | $CHF_2$ |
| A324 | $ClCH_2$ | H | $CH_3$ | $CHF_2$ |
| A325 | $CH_3SCH_2$ | H | $CH_3$ | $CHF_2$ |
| A326 | $CH_3SOCH_2$ | H | $CH_3$ | $CHF_2$ |
| A327 | $CH_3SO_2CH_2$ | H | $CH_3$ | $CHF_2$ |
| A328 | H | H | $CH_3$ | $CCl_3$ |
| A329 | $CH_3$ | H | $CH_3$ | $CCl_3$ |
| A330 | $CH_3CH_2$ | H | $CH_3$ | $CCl_3$ |
| A331 | $(CH_3)_3C$ | H | $CH_3$ | $CCl_3$ |
| A332 | $(CH_3)_2CH$ | H | $CH_3$ | $CCl_3$ |
| A333 | cyclopropyl | H | $CH_3$ | $CCl_3$ |
| A334 | $CH_3(CH_2)_2$ | H | $CH_3$ | $CCl_3$ |
| A335 | $CH_3OCH_2$ | H | $CH_3$ | $CCl_3$ |
| A336 | $CH_3O(CH_2)_2$ | H | $CH_3$ | $CCl_3$ |
| A337 | Ph | H | $CH_3$ | $CCl_3$ |
| A338 | PhO | H | $CH_3$ | $CCl_3$ |
| A339 | PhS | H | $CH_3$ | $CCl_3$ |
| A340 | PhSO | H | $CH_3$ | $CCl_3$ |
| A341 | $PhSO_2$ | H | $CH_3$ | $CCl_3$ |
| A342 | $CH_3S$ | H | $CH_3$ | $CCl_3$ |
| A343 | $CH_3SO$ | H | $CH_3$ | $CCl_3$ |
| A344 | $CF_3$ | H | $CH_3$ | $CCl_3$ |
| A345 | $F_2CH$ | H | $CH_3$ | $CCl_3$ |
| A346 | HCC | H | $CH_3$ | $CCl_3$ |
| A347 | $CH_3CC$ | H | $CH_3$ | $CCl_3$ |
| A348 | $CH_2=CH$ | H | $CH_3$ | $CCl_3$ |
| A349 | $CH_2=CHCH_2$ | H | $CH_3$ | $CCl_3$ |
| A350 | $CH_3SO_2N(CH_3)$ | H | $CH_3$ | $CCl_3$ |
| A351 | $(CH_3)_2N$ | H | $CH_3$ | $CCl_3$ |
| A352 | $(CH_3)_2NSO_2$ | H | $CH_3$ | $CCl_3$ |
| A353 | $ClCH_2$ | H | $CH_3$ | $CCl_3$ |

TABLE 5-continued

Compounds of formula XVI:

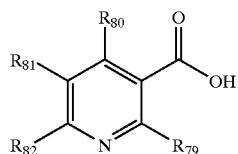

(XVI)

| Compd. no. | $R_{79}$ | $R_{80}$ | $R_{81}$ | $R_{82}$ |
| --- | --- | --- | --- | --- |
| A354 | $CH_3SCH_2$ | H | $CH_3$ | $CCl_3$ |
| A355 | $CH_3SOCH_2$ | H | $CH_3$ | $CCl_3$ |
| A356 | $CH_3SO_2CH_2$ | H | $CH_3$ | $CCl_3$ |
| A357 | H | H | Ph | $CF_3$ |
| A358 | $CH_3$ | H | Ph | $CF_3$ |
| A359 | $CH_3CH_2$ | H | Ph | $CF_3$ |
| A360 | cyclopropyl | H | Ph | $CF_3$ |
| A361 | $(CH_3)_3C$ | H | Ph | $CF_3$ |
| A362 | $(CH_3)_2CH$ | H | Ph | $CF_3$ |
| A363 | $CH_3(CH_2)_2$ | H | Ph | $CF_3$ |
| A364 | $CH_3OCH_2$ | H | Ph | $CF_3$ |
| A365 | $CH_3O(CH_2)_2$ | H | Ph | $CF_3$ |
| A366 | Ph | H | Ph | $CF_3$ |
| A367 | PhO | H | Ph | $CF_3$ |
| A368 | PhS | H | Ph | $CF_3$ |
| A369 | PhSO | H | Ph | $CF_3$ |
| A370 | $PhSO_2$ | H | Ph | $CF_3$ |
| A371 | $CH_3S$ | H | Ph | $CF_3$ |
| A372 | $CH_3SO$ | H | Ph | $CF_3$ |
| A373 | $CF_3$ | H | Ph | $CF_3$ |
| A374 | $F_2CH$ | H | Ph | $CF_3$ |
| A375 | HCC | H | Ph | $CF_3$ |
| A376 | $CH_3CC$ | H | Ph | $CF_3$ |
| A377 | $CH_2=CH$ | H | Ph | $CF_3$ |
| A378 | $CH_2=CHCH_2$ | H | Ph | $CF_3$ |
| A379 | $CH_3SO_2N(CH_3)$ | H | Ph | $CF_3$ |
| A380 | $(CH_3)_2N$ | H | Ph | $CF_3$ |
| A381 | $(CH_3)_2NSO_2$ | H | Ph | $CF_3$ |
| A382 | $ClCH_2$ | H | Ph | $CF_3$ |
| A383 | $CH_3SCH_2$ | H | Ph | $CF_3$ |
| A384 | $CH_3SOCH_2$ | H | Ph | $CF_3$ |
| A385 | $CH_3SO_2CH_2$ | H | Ph | $CF_3$ |
| A386 | H | H | Ph | $CF_3CF_2$ |
| A387 | $CH_3$ | H | Ph | $CF_3CF_2$ |
| A388 | $CH_3CH_2$ | H | Ph | $CF_3CF_2$ |
| A389 | cyclopropyl | H | Ph | $CF_3CF_2$ |
| A390 | $(CH_3)_3C$ | H | Ph | $CF_3CF_2$ |
| A391 | $(CH_3)_2CH$ | H | Ph | $CF_3CF_2$ |
| A392 | $CH_3(CH_2)_2$ | H | Ph | $CF_3CF_2$ |
| A393 | $CH_3OCH_2$ | H | Ph | $CF_3CF_2$ |
| A394 | $CH_3O(CH_2)_2$ | H | Ph | $CF_3CF_2$ |
| A395 | Ph | H | Ph | $CF_3CF_2$ |
| A396 | PhO | H | Ph | $CF_3CF_2$ |
| A397 | PhS | H | Ph | $CF_3CF_2$ |
| A398 | PhSO | H | Ph | $CF_3CF_2$ |
| A399 | $PhSO_2$ | H | Ph | $CF_3CF_2$ |
| A400 | $CH_3S$ | H | Ph | $CF_3CF_2$ |
| A401 | $CH_3SO$ | H | Ph | $CF_3CF_2$ |
| A402 | $CF_3$ | H | Ph | $CF_3CF_2$ |
| A403 | $F_2CH$ | H | Ph | $CF_3CF_2$ |
| A404 | HCC | H | Ph | $CF_3CF_2$ |
| A405 | $CH_3CC$ | H | Ph | $CF_3CF_2$ |
| A406 | $CH_2=CH$ | H | Ph | $CF_3CF_2$ |
| A407 | $CH_2=CHCH_2$ | H | Ph | $CF_3CF_2$ |
| A408 | $CH_3SO_2N(CH_3)$ | H | Ph | $CF_3CF_2$ |
| A409 | $(CH_3)_2N$ | H | Ph | $CF_3CF_2$ |
| A410 | $(CH_3)_2NSO_2$ | H | Ph | $CF_3CF_2$ |
| A411 | $ClCH_2$ | H | Ph | $CF_3CF_2$ |
| A412 | $CH_3SCH_2$ | H | Ph | $CF_3CF_2$ |
| A413 | $CH_3SOCH_2$ | H | Ph | $CF_3CF_2$ |
| A414 | $CH_3SO_2CH_2$ | H | Ph | $CF_3CF_2$ |
| A415 | H | H | Ph | $CF_3CF_2CF_2$ |
| A416 | $CH_3$ | H | Ph | $CF_3CF_2CF_2$ |
| A417 | $CH_3CH_2$ | H | Ph | $CF_3CF_2CF_2$ |
| A418 | cyclopropyl | H | Ph | $CF_3CF_2CF_2$ |

TABLE 5-continued

Compounds of formula XVI:

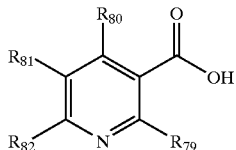

(XVI)

| Compd. no. | $R_{79}$ | $R_{80}$ | $R_{81}$ | $R_{82}$ |
|---|---|---|---|---|
| A419 | $(CH_3)_3C$ | H | Ph | $CF_3CF_2CF_2$ |
| A420 | $(CH_3)_2CH$ | H | Ph | $CF_3CF_2CF_2$ |
| A421 | $CH_3(CH_2)_2$ | H | Ph | $CF_3CF_2CF_2$ |
| A422 | $CH_3OCH_2$ | H | Ph | $CF_3CF_2CF_2$ |
| A423 | $CH_3O(CH_2)_2$ | H | Ph | $CF_3CF_2CF_2$ |
| A424 | Ph | H | Ph | $CF_3CF_2CF_2$ |
| A425 | PhO | H | Ph | $CF_3CF_2CF_2$ |
| A426 | PhS | H | Ph | $CF_3CF_2CF_2$ |
| A427 | PhSO | H | Ph | $CF_3CF_2CF_2$ |
| A428 | $PhSO_2$ | H | Ph | $CF_3CF_2CF_2$ |
| A429 | $CH_3S$ | H | Ph | $CF_3CF_2CF_2$ |
| A430 | $CH_3SO$ | H | Ph | $CF_3CF_2CF_2$ |
| A431 | $CF_3$ | H | Ph | $CF_3CF_2CF_2$ |
| A432 | $F_2CH$ | H | Ph | $CF_3CF_2CF_2$ |
| A433 | HCC | H | Ph | $CF_3CF_2CF_2$ |
| A434 | $CH_3CC$ | H | Ph | $CF_3CF_2CF_2$ |
| A435 | $CH_2=CH$ | H | Ph | $CF_3CF_2CF_2$ |
| A436 | $CH_2=CHCH_2$ | H | Ph | $CF_3CF_2CF_2$ |
| A437 | $CH_3SO_2N(CH_3)$ | H | Ph | $CF_3CF_2CF_2$ |
| A438 | $(CH_3)_2N$ | H | Ph | $CF_3CF_2CF_2$ |
| A439 | $(CH_3)_2NSO_2$ | H | Ph | $CF_3CF_2CF_2$ |
| A440 | $ClCH_2$ | H | Ph | $CF_3CF_2CF_2$ |
| A441 | $CH_3SCH_2$ | H | Ph | $CF_3CF_2CF_2$ |
| A442 | $CH_3SOCH_2$ | H | Ph | $CF_3CF_2CF_2$ |
| A443 | $CH_3SO_2CH_2$ | H | Ph | $CF_3CF_2CF_2$ |
| A444 | H | H | Ph | $CF_2Cl$ |
| A445 | $CH_3$ | H | Ph | $CF_2Cl$ |
| A446 | $CH_3CH_2$ | H | Ph | $CF_2Cl$ |
| A447 | cyclopropyl | H | Ph | $CF_2Cl$ |
| A448 | $(CH_3)_3C$ | H | Ph | $CF_2Cl$ |
| A449 | $(CH_3)_2CH$ | H | Ph | $CF_2Cl$ |
| A450 | $CH_3(CH_2)_2$ | H | Ph | $CF_2Cl$ |
| A451 | $CH_3OCH_2$ | H | Ph | $CF_2Cl$ |
| A452 | $CH_3O(CH_2)_2$ | H | Ph | $CF_2Cl$ |
| A453 | Ph | H | Ph | $CF_2Cl$ |
| A454 | PhO | H | Ph | $CF_2Cl$ |
| A455 | PhS | H | Ph | $CF_2Cl$ |
| A456 | PhSO | H | Ph | $CF_2Cl$ |
| A457 | $PhSO_2$ | H | Ph | $CF_2Cl$ |
| A458 | $CH_3S$ | H | Ph | $CF_2Cl$ |
| A459 | $CH_3SO$ | H | Ph | $CF_2Cl$ |
| A460 | $CF_3$ | H | Ph | $CF_2Cl$ |
| A461 | $F_2CH$ | H | Ph | $CF_2Cl$ |
| A462 | HCC | H | Ph | $CF_2Cl$ |
| A463 | $CH_3CC$ | H | Ph | $CF_2Cl$ |
| A464 | $CH_2=CH$ | H | Ph | $CF_2Cl$ |
| A465 | $CH_2=CHCH_2$ | H | Ph | $CF_2Cl$ |
| A466 | $CH_3SO_2N(CH_3)$ | H | Ph | $CF_2Cl$ |
| A467 | $(CH_3)_2N$ | H | Ph | $CF_2Cl$ |
| A468 | $(CH_3)_2NSO_2$ | H | Ph | $CF_2Cl$ |
| A469 | $ClCH_2$ | H | Ph | $CF_2Cl$ |
| A470 | $CH_3SCH_2$ | H | Ph | $CF_2Cl$ |
| A471 | $CH_3SOCH_2$ | H | Ph | $CF_2Cl$ |
| A472 | $CH_3SO_2CH_2$ | H | Ph | $CF_2Cl$ |
| A473 | H | H | Ph | $CHF_2$ |
| A474 | $CH_3$ | H | Ph | $CHF_2$ |
| A475 | $CH_3CH_2$ | H | Ph | $CHF_2$ |
| A476 | cyclopropyl | H | Ph | $CHF_2$ |
| A477 | $(CH_3)_3C$ | H | Ph | $CHF_2$ |
| A478 | $(CH_3)_2CH$ | H | Ph | $CHF_2$ |
| A479 | $CH_3(CH_2)_2$ | H | Ph | $CHF_2$ |
| A480 | $CH_3OCH_2$ | H | Ph | $CHF_2$ |
| A481 | $CH_3O(CH_2)_2$ | H | Ph | $CHF_2$ |
| A482 | Ph | H | Ph | $CHF_2$ |
| A483 | PhO | H | Ph | $CHF_2$ |

TABLE 5-continued

Compounds of formula XVI:

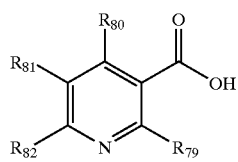

(XVI)

| Compd. no. | $R_{79}$ | $R_{80}$ | $R_{81}$ | $R_{82}$ |
|---|---|---|---|---|
| A484 | PhS | H | Ph | $CHF_2$ |
| A485 | PhSO | H | Ph | $CHF_2$ |
| A486 | $PhSO_2$ | H | Ph | $CHF_2$ |
| A487 | $CH_3S$ | H | Ph | $CHF_2$ |
| A488 | $CH_3SO$ | H | Ph | $CHF_2$ |
| A489 | $CF_3$ | H | Ph | $CHF_2$ |
| A490 | $F_2CH$ | H | Ph | $CHF_2$ |
| A491 | HCC | H | Ph | $CHF_2$ |
| A492 | $CH_3CC$ | H | Ph | $CHF_2$ |
| A493 | $CH_2=CH$ | H | Ph | $CHF_2$ |
| A494 | $CH_2=CHCH_2$ | H | Ph | $CHF_2$ |
| A495 | $CH_3SO_2N(CH_3)$ | H | Ph | $CHF_2$ |
| A496 | $(CH_3)_2N$ | H | Ph | $CHF_2$ |
| A497 | $(CH_3)_2NSO_2$ | H | Ph | $CHF_2$ |
| A498 | $ClCH_2$ | H | Ph | $CHF_2$ |
| A499 | $CH_3SCH_2$ | H | Ph | $CHF_2$ |
| A500 | $CH_3SOCH_2$ | H | Ph | $CHF_2$ |
| A501 | $CH_3SO_2CH_2$ | H | Ph | $CHF_2$ |
| A502 | H | H | Ph | $CCl_3$ |
| A503 | $CH_3$ | H | Ph | $CCl_3$ |
| A504 | $CH_3CH_2$ | H | Ph | $CCl_3$ |
| A505 | cyclopropyl | H | Ph | $CCl_3$ |
| A506 | $(CH_3)_3C$ | H | Ph | $CCl_3$ |
| A507 | $(CH_3)_2CH$ | H | Ph | $CCl_3$ |
| A508 | $CH_3(CH_2)_2$ | H | Ph | $CCl_3$ |
| A509 | $CH_3OCH_2$ | H | Ph | $CCl_3$ |
| A510 | $CH_3O(CH_2)_2$ | H | Ph | $CCl_3$ |
| A511 | Ph | H | Ph | $CCl_3$ |
| A512 | PhO | H | Ph | $CCl_3$ |
| A513 | PhS | H | Ph | $CCl_3$ |
| A514 | PhSO | H | Ph | $CCl_3$ |
| A515 | $PhSO_2$ | H | Ph | $CCl_3$ |
| A516 | $CH_3S$ | H | Ph | $CCl_3$ |
| A517 | $CH_3SO$ | H | Ph | $CCl_3$ |
| A518 | $CF_3$ | H | Ph | $CCl_3$ |
| A519 | $F_2CH$ | H | Ph | $CCl_3$ |
| A520 | HCC | H | Ph | $CCl_3$ |
| A521 | $CH_3CC$ | H | Ph | $CCl_3$ |
| A522 | $CH_2=CH$ | H | Ph | $CCl_3$ |
| A523 | $CH_2=CHCH_2$ | H | Ph | $CCl_3$ |
| A524 | $CH_3SO_2N(CH_3)$ | H | Ph | $CCl_3$ |
| A525 | $(CH_3)_2N$ | H | Ph | $CCl_3$ |
| A526 | $(CH_3)_2NSO_2$ | H | Ph | $CCl_3$ |
| A527 | $ClCH_2$ | H | Ph | $CCl_3$ |
| A528 | $CH_3SCH_2$ | H | Ph | $CCl_3$ |
| A529 | $CH_3SOCH_2$ | H | Ph | $CCl_3$ |
| A530 | $CH_3SO_2CH_2$ | H | Ph | $CCl_3$ |
| A531 | H | $CH_3$ | H | $CF_3$ |
| A532 | H | $CH_3CH_2$ | H | $CF_3$ |
| A533 | H | cyclopropyl | H | $CF_3$ |
| A534 | H | $(CH_3)_3CH$ | H | $CF_3$ |
| A535 | H | $(CH_3)_2CH$ | H | $CF_3$ |
| A536 | H | $CH_3(CH_2)_2$ | H | $CF_3$ |
| A537 | H | $CH_3OCH_2$ | H | $CF_3$ |
| A538 | H | $CH_3O(CH_2)_2$ | H | $CF_3$ |
| A539 | H | Ph | H | $CF_3$ |
| A540 | H | PhO | H | $CF_3$ |
| A541 | H | PhS | H | $CF_3$ |
| A542 | H | PhSO | H | $CF_3$ |
| A543 | H | $PhSO_2$ | H | $CF_3$ |
| A544 | H | $CH_3S$ | H | $CF_3$ |
| A545 | H | $CH_3SO$ | H | $CF_3$ |
| A546 | H | $CF_3$ | H | $CF_3$ |
| A547 | H | $F_2CH$ | H | $CF_3$ |
| A548 | H | HCC | H | $CF_3$ |

TABLE 5-continued

Compounds of formula XVI:

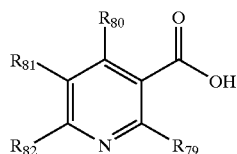

(XVI)

| Compd. no. | $R_{79}$ | $R_{80}$ | $R_{81}$ | $R_{82}$ |
|---|---|---|---|---|
| A549 | H | $CH_3CC$ | H | $CF_3$ |
| A550 | H | $CH_2=CH$ | H | $CF_3$ |
| A551 | H | $CH_2=CHCH_2$ | H | $CF_3$ |
| A552 | H | $CH_3SO_2N(CH_3)$ | H | $CF_3$ |
| A553 | H | $(CH_3)_2N$ | H | $CF_3$ |
| A554 | H | $(CH_3)_2NSO_2$ | H | $CF_3$ |
| A555 | H | $CH_3SCH_2$ | H | $CF_3$ |
| A556 | H | $CH_3SOCH_2$ | H | $CF_3$ |
| A557 | H | $CH_3SO_2CH_2$ | H | $CF_3$ |
| A558 | H | $CH_3$ | H | $CF_3CF_2$ |
| A559 | H | $CH_3CH_2$ | H | $CF_3CF_2$ |
| A560 | H | cyclopropyl | H | $CF_3CF_2$ |
| A561 | H | $(CH_3)_3C$ | H | $CF_3CF_2$ |
| A562 | H | $(CH_3)_2CH$ | H | $CF_3CF_2$ |
| A563 | H | $CH_3(CH_2)_2$ | H | $CF_3CF_2$ |
| A564 | H | $CH_3OCH_2$ | H | $CF_3CF_2$ |
| A565 | H | $CH_3O(CH_2)_2$ | H | $CF_3CF_2$ |
| A566 | H | Ph | H | $CF_3CF_2$ |
| A567 | H | PhO | H | $CF_3CF_2$ |
| A568 | H | PhS | H | $CF_3CF_2$ |
| A569 | H | PhSO | H | $CF_3CF_2$ |
| A570 | H | $PhSO_2$ | H | $CF_3CF_2$ |
| A571 | H | $CH_3S$ | H | $CF_3CF_2$ |
| A572 | H | $CH_3SO$ | H | $CF_3CF_2$ |
| A573 | H | $CF_3$ | H | $CF_3CF_2$ |
| A574 | H | $F_2CH$ | H | $CF_3CF_2$ |
| A575 | H | HCC | H | $CF_3CF_2$ |
| A576 | H | $CH_3CC$ | H | $CF_3CF_2$ |
| A577 | H | $CH_2=CH$ | H | $CF_3CF_2$ |
| A578 | H | $CH_2=CHCH_2$ | H | $CF_3CF_2$ |
| A579 | H | $CH_3SO_2N(CH_3)$ | H | $CF_3CF_2$ |
| A580 | H | $(CH_3)_2N$ | H | $CF_3CF_2$ |
| A581 | H | $(CH_3)_2NSO_2$ | H | $CF_3CF_2$ |
| A582 | H | $CH_3SCH_2$ | H | $CF_3CF_2$ |
| A583 | H | $CH_3SOCH_2$ | H | $CF_3CF_2$ |
| A584 | H | $CH_3SO_2CH_2$ | H | $CF_3CF_2$ |
| A585 | H | $CH_3$ | H | $CF_3CF_2CF_2$ |
| A586 | H | $CH_3CH_2$ | H | $CF_3CF_2CF_2$ |
| A587 | H | cyclopropyl | H | $CF_3CF_2CF_2$ |
| A588 | H | $(CH_3)_3C$ | H | $CF_3CF_2CF_2$ |
| A589 | H | $(CH_3)_2CH$ | H | $CF_3CF_2CF_2$ |
| A590 | H | $CH_3(CH_2)_2$ | H | $CF_3CF_2CF_2$ |
| A591 | H | $CH_3OCH_2$ | H | $CF_3CF_2CF_2$ |
| A592 | H | $CH_3O(CH_2)_2$ | H | $CF_3CF_2CF_2$ |
| A593 | H | Ph | H | $CF_3CF_2CF_2$ |
| A594 | H | PhO | H | $CF_3CF_2CF_2$ |
| A595 | H | PhS | H | $CF_3CF_2CF_2$ |
| A596 | H | PhSO | H | $CF_3CF_2CF_2$ |
| A597 | H | $PhSO_2$ | H | $CF_3CF_2CF_2$ |
| A598 | H | $CH_3S$ | H | $CF_3CF_2CF_2$ |
| A599 | H | $CH_3SO$ | H | $CF_3CF_2CF_2$ |
| A600 | H | $CF_3$ | H | $CF_3CF_2CF_2$ |
| A601 | H | $F_2CH$ | H | $CF_3CF_2CF_2$ |
| A602 | H | HCC | H | $CF_3CF_2CF_2$ |
| A603 | H | $CH_3CC$ | H | $CF_3CF_2CF_2$ |
| A604 | H | $CH_2=CH$ | H | $CF_3CF_2CF_2$ |
| A605 | H | $CH_2=CHCH_2$ | H | $CF_3CF_2CF_2$ |
| A606 | H | $CH_3SO_2N(CH_3)$ | H | $CF_3CF_2CF_2$ |
| A607 | H | $(CH_3)_2N$ | H | $CF_3CF_2CF_2$ |
| A608 | H | $(CH_3)_2NSO_2$ | H | $CF_3CF_2CF_2$ |
| A609 | H | $CH_3SCH_2$ | H | $CF_3CF_2CF_2$ |
| A610 | H | $CH_3SOCH_2$ | H | $CF_3CF_2CF_2$ |
| A611 | H | $CH_3SO_2CH_2$ | H | $CF_3CF_2CF_2$ |
| A612 | H | $CH_3$ | H | $CF_2Cl$ |
| A613 | H | $CH_3CH_2$ | H | $CF_2Cl$ |

TABLE 5-continued

Compounds of formula XVI:

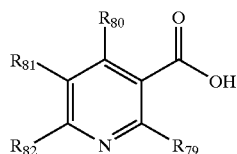

(XVI)

| Compd. no. | $R_{79}$ | $R_{80}$ | $R_{81}$ | $R_{82}$ |
|---|---|---|---|---|
| A614 | H | cyclopropyl | H | $CF_2Cl$ |
| A615 | H | $(CH_3)_3C$ | H | $CF_2Cl$ |
| A616 | H | $(CH_3)_2CH$ | H | $CF_2Cl$ |
| A617 | H | $CH_3(CH_2)_2$ | H | $CF_2Cl$ |
| A618 | H | $CH_3OCH_2$ | H | $CF_2Cl$ |
| A619 | H | $CH_3O(CH_2)_2$ | H | $CF_2Cl$ |
| A620 | H | Ph | H | $CF_2Cl$ |
| A621 | H | PhO | H | $CF_2Cl$ |
| A622 | H | PhS | H | $CF_2Cl$ |
| A623 | H | PhSO | H | $CF_2Cl$ |
| A624 | H | $PhSO_2$ | H | $CF_2Cl$ |
| A625 | H | $CH_3S$ | H | $CF_2Cl$ |
| A626 | H | $CH_3SO$ | H | $CF_2Cl$ |
| A627 | H | $CF_3$ | H | $CF_2Cl$ |
| A628 | H | $F_2CH$ | H | $CF_2Cl$ |
| A629 | H | HCC | H | $CF_2Cl$ |
| A630 | H | $CH_3CC$ | H | $CF_2Cl$ |
| A631 | H | $CH_2=CH$ | H | $CF_2Cl$ |
| A632 | H | $CH_2=CHCH_2$ | H | $CF_2Cl$ |
| A633 | H | $CH_3SO_2N(CH_3)$ | H | $CF_2Cl$ |
| A634 | H | $(CH_3)_2N$ | H | $CF_2Cl$ |
| A635 | H | $(CH_3)_2NSO_2$ | H | $CF_2Cl$ |
| A636 | H | $CH_3SCH_2$ | H | $CF_2Cl$ |
| A637 | H | $CH_3SOCH_2$ | H | $CF_2Cl$ |
| A638 | H | $CH_3SO_2CH_2$ | H | $CF_2Cl$ |
| A639 | H | $CH_3$ | H | $CHF_2$ |
| A640 | H | $CH_3CH_2$ | H | $CHF_2$ |
| A641 | H | cyclopropyl | H | $CHF_2$ |
| A642 | H | $(CH_3)_3C$ | H | $CHF_2$ |
| A643 | H | $(CH_3)_2CH$ | H | $CHF_2$ |
| A644 | H | $CH_3(CH_2)_2$ | H | $CHF_2$ |
| A645 | H | $CH_3OCH_2$ | H | $CHF_2$ |
| A646 | H | $CH_3O(CH_2)_2$ | H | $CHF_2$ |
| A647 | H | Ph | H | $CHF_2$ |
| A648 | H | PhO | H | $CHF_2$ |
| A649 | H | PhS | H | $CHF_2$ |
| A650 | H | PhSO | H | $CHF_2$ |
| A651 | H | $PhSO_2$ | H | $CHF_2$ |
| A652 | H | $CH_3S$ | H | $CHF_2$ |
| A653 | H | $CH_3SO$ | H | $CHF_2$ |
| A654 | H | $CF_3$ | H | $CHF_2$ |
| A655 | H | $F_2CH$ | H | $CHF_2$ |
| A656 | H | HCC | H | $CHF_2$ |
| A657 | H | $CH_3CC$ | H | $CHF_2$ |
| A658 | H | $CH_2=CH$ | H | $CHF_2$ |
| A659 | H | $CH_2=CHCH_2$ | H | $CHF_2$ |
| A660 | H | $CH_3SO_2N(CH_3)$ | H | $CHF_2$ |
| A661 | H | $(CH_3)_2N$ | H | $CHF_2$ |
| A662 | H | $(CH_3)_2NSO_2$ | H | $CHF_2$ |
| A663 | H | $CH_3SCH_2$ | H | $CHF_2$ |
| A664 | H | $CH_3SOCH_2$ | H | $CHF_2$ |
| A665 | H | $CH_3SO_2CH_2$ | H | $CHF_2$ |
| A666 | H | $CH_3$ | H | $CCl_3$ |
| A667 | H | $CH_3CH_2$ | H | $CCl_3$ |
| A668 | H | cyclopropyl | H | $CCl_3$ |
| A669 | H | $(CH_3)_3C$ | H | $CCl_3$ |
| A670 | H | $(CH_3)_2CH$ | H | $CCl_3$ |
| A671 | H | $CH_3(CH_2)_2$ | H | $CCl_3$ |
| A672 | H | $CH_3OCH_2$ | H | $CCl_3$ |
| A673 | H | $CH_3O(CH_2)_2$ | H | $CCl_3$ |
| A674 | H | Ph | H | $CCl_3$ |
| A675 | H | PhO | H | $CCl_3$ |
| A676 | H | PhS | H | $CCl_3$ |
| A677 | H | PhSO | H | $CCl_3$ |
| A678 | H | $PhSO_2$ | H | $CCl_3$ |

TABLE 5-continued

Compounds of formula XVI:

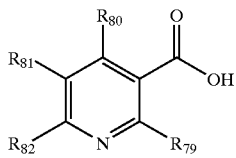

(XVI)

| Compd. no. | $R_{79}$ | $R_{80}$ | $R_{81}$ | $R_{82}$ |
|---|---|---|---|---|
| A679 | H | $CH_3S$ | H | $CCl_3$ |
| A680 | H | $CH_3SO$ | H | $CCl_3$ |
| A681 | H | $CF_3$ | H | $CCl_3$ |
| A682 | H | $F_2CH$ | H | $CCl_3$ |
| A683 | H | HCC | H | $CCl_3$ |
| A684 | H | $CH_3CC$ | H | $CCl_3$ |
| A685 | H | $CH_2=CH$ | H | $CCl_3$ |
| A686 | H | $CH_2=CHCH_2$ | H | $CCl_3$ |
| A687 | H | $CH_3SO_2N(CH_3)$ | H | $CCl_3$ |
| A688 | H | $(CH_3)_2N$ | H | $CCl_3$ |
| A689 | H | $(CH_3)_2NSO_2$ | H | $CCl_3$ |
| A690 | H | $CH_3SCH_2$ | H | $CCl_3$ |
| A691 | H | $CH_3SOCH_2$ | H | $CCl_3$ |
| A692 | H | $CH_3SO_2CH_2$ | H | $CCl_3$ |
| A693 | H | $CH_3$ | $CH_3$ | $CF_3$ |
| A694 | H | $CH_3CH_2$ | $CH_3$ | $CF_3$ |
| A695 | H | cyclopropyl | $CH_3$ | $CF_3$ |
| A696 | H | $(CH_3)_3C$ | $CH_3$ | $CF_3$ |
| A697 | H | $(CH_3)_2CH$ | $CH_3$ | $CF_3$ |
| A698 | H | $CH_3(CH_2)_2$ | $CH_3$ | $CF_3$ |
| A699 | H | $CH_3OCH_2$ | $CH_3$ | $CF_3$ |
| A700 | H | $CH_3O(CH_2)_2$ | $CH_3$ | $CF_3$ |
| A701 | H | Ph | $CH_3$ | $CF_3$ |
| A702 | H | PhO | $CH_3$ | $CF_3$ |
| A703 | H | PhS | $CH_3$ | $CF_3$ |
| A704 | H | PhSO | $CH_3$ | $CF_3$ |
| A705 | H | $PhSO_2$ | $CH_3$ | $CF_3$ |
| A706 | H | $CH_3S$ | $CH_3$ | $CF_3$ |
| A707 | H | $CH_3SO$ | $CH_3$ | $CF_3$ |
| A708 | H | $CF_3$ | $CH_3$ | $CF_3$ |
| A709 | H | $F_2CH$ | $CH_3$ | $CF_3$ |
| A710 | H | HCC | $CH_3$ | $CF_3$ |
| A711 | H | $CH_3CC$ | $CH_3$ | $CF_3$ |
| A712 | H | $CH_2=CH$ | $CH_3$ | $CF_3$ |
| A713 | H | $CH_2=CHCH_2$ | $CH_3$ | $CF_3$ |
| A714 | H | $CH_3SO_2N(CH_3)$ | $CH_3$ | $CF_3$ |
| A715 | H | $(CH_3)_2N$ | $CH_3$ | $CF_3$ |
| A716 | H | $(CH_3)_2NSO_2$ | $CH_3$ | $CF_3$ |
| A717 | H | $CH_3SCH_2$ | $CH_3$ | $CF_3$ |
| A718 | H | $CH_3SOCH_2$ | $CH_3$ | $CF_3$ |
| A719 | H | $CH_3SO_2CH_2$ | $CH_3$ | $CF_3$ |
| A720 | H | $CH_3$ | $CH_3$ | $CF_3CF_2$ |
| A721 | H | $CH_3CH_2$ | $CH_3$ | $CF_3CF_2$ |
| A722 | H | cyclopropyl | $CH_3$ | $CF_3CF_2$ |
| A723 | H | $(CH_3)_3C$ | $CH_3$ | $CF_3CF_2$ |
| A724 | H | $(CH_3)_2CH$ | $CH_3$ | $CF_3CF_2$ |
| A725 | H | $CH_3(CH_2)_2$ | $CH_3$ | $CF_3CF_2$ |
| A726 | H | $CH_3OCH_2$ | $CH_3$ | $CF_3CF_2$ |
| A727 | H | $CH_3O(CH_2)_2$ | $CH_3$ | $CF_3CF_2$ |
| A728 | H | Ph | $CH_3$ | $CF_3CF_2$ |
| A729 | H | PhO | $CH_3$ | $CF_3CF_2$ |
| A730 | H | PhS | $CH_3$ | $CF_3CF_2$ |
| A731 | H | PhSO | $CH_3$ | $CF_3CF_2$ |
| A732 | H | $PhSO_2$ | $CH_3$ | $CF_3CF_2$ |
| A733 | H | $CH_3S$ | $CH_3$ | $CF_3CF_2$ |
| A734 | H | $CH_3SO$ | $CH_3$ | $CF_3CF_2$ |
| A735 | H | $CF_3$ | $CH_3$ | $CF_3CF_2$ |
| A736 | H | $F_2CH$ | $CH_3$ | $CF_3CF_2$ |
| A737 | H | HCC | $CH_3$ | $CF_3CF_2$ |
| A738 | H | $CH_3CC$ | $CH_3$ | $CF_3CF_2$ |
| A739 | H | $CH_2=CH$ | $CH_3$ | $CF_3CF_2$ |
| A740 | H | $CH_2=CHCH_2$ | $CH_3$ | $CF_3CF_2$ |
| A741 | H | $CH_3SO_2N(CH_3)$ | $CH_3$ | $CF_3CF_2$ |
| A742 | H | $(CH_3)_2N$ | $CH_3$ | $CF_3CF_2$ |
| A743 | H | $(CH_3)_2NSO_2$ | $CH_3$ | $CF_3CF_2$ |

TABLE 5-continued

Compounds of formula XVI:

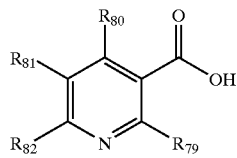

(XVI)

| Compd. no. | $R_{79}$ | $R_{80}$ | $R_{81}$ | $R_{82}$ |
|---|---|---|---|---|
| A744 | H | $CH_3SCH_2$ | $CH_3$ | $CF_3CF_2$ |
| A745 | H | $CH_3SOCH_2$ | $CH_3$ | $CF_3CF_2$ |
| A746 | H | $CH_3SO_2CH_2$ | $CH_3$ | $CF_3CF_2$ |
| A747 | H | $CH_3$ | $CH_3$ | $CF_3CF_2CF_2$ |
| A748 | H | $CH_3CH_2$ | $CH_3$ | $CF_3CF_2CF_2$ |
| A749 | H | cyclopropyl | $CH_3$ | $CF_3CF_2CF_2$ |
| A750 | H | $(CH_3)_3C$ | $CH_3$ | $CF_3CF_2CF_2$ |
| A751 | H | $(CH_3)_2CH$ | $CH_3$ | $CF_3CF_2CF_2$ |
| A752 | H | $CH_3(CH_2)_2$ | $CH_3$ | $CF_3CF_2CF_2$ |
| A753 | H | $CH_3OCH_2$ | $CH_3$ | $CF_3CF_2CF_2$ |
| A754 | H | $CH_3O(CH_2)_2$ | $CH_3$ | $CF_3CF_2CF_2$ |
| A755 | H | Ph | $CH_3$ | $CF_3CF_2CF_2$ |
| A756 | H | PhO | $CH_3$ | $CF_3CF_2CF_2$ |
| A757 | H | PhS | $CH_3$ | $CF_3CF_2CF_2$ |
| A758 | H | PhSO | $CH_3$ | $CF_3CF_2CF_2$ |
| A759 | H | $PhSO_2$ | $CH_3$ | $CF_3CF_2CF_2$ |
| A760 | H | $CH_3S$ | $CH_3$ | $CF_3CF_2CF_2$ |
| A761 | H | $CH_3SO$ | $CH_3$ | $CF_3CF_2CF_2$ |
| A762 | H | $CF_3$ | $CH_3$ | $CF_3CF_2CF_2$ |
| A763 | H | $F_2CH$ | $CH_3$ | $CF_3CF_2CF_2$ |
| A764 | H | HCC | $CH_3$ | $CF_3CF_2CF_2$ |
| A765 | H | $CH_3CC$ | $CH_3$ | $CF_3CF_2CF_2$ |
| A766 | H | $CH_2=CH$ | $CH_3$ | $CF_3CF_2CF_2$ |
| A767 | H | $CH_2=CHCH_2$ | $CH_3$ | $CF_3CF_2CF_2$ |
| A768 | H | $CH_3SO_2N(CH_3)$ | $CH_3$ | $CF_3CF_2CF_2$ |
| A769 | H | $(CH_3)_2N$ | $CH_3$ | $CF_3CF_2CF_2$ |
| A770 | H | $(CH_3)_2NSO_2$ | $CH_3$ | $CF_3CF_2CF_2$ |
| A771 | H | $CH_3SCH_2$ | $CH_3$ | $CF_3CF_2CF_2$ |
| A772 | H | $CH_3SOCH_2$ | $CH_3$ | $CF_3CF_2CF_2$ |
| A773 | H | $CH_3SO_2CH_2$ | $CH_3$ | $CF_3CF_2CF_2$ |
| A774 | H | $CH_3$ | $CH_3$ | $CF_2Cl$ |
| A775 | H | $CH_3CH_2$ | $CH_3$ | $CF_2Cl$ |
| A776 | H | cyclopropyl | $CH_3$ | $CF_2Cl$ |
| A777 | H | $(CH_3)_3C$ | $CH_3$ | $CF_2Cl$ |
| A778 | H | $(CH_3)_2CH$ | $CH_3$ | $CF_2Cl$ |
| A779 | H | $CH_3(CH_2)_2$ | $CH_3$ | $CF_2Cl$ |
| A780 | H | $CH_3OCH_2$ | $CH_3$ | $CF_2Cl$ |
| A781 | H | $CH_3O(CH_2)_2$ | $CH_3$ | $CF_2Cl$ |
| A782 | H | Ph | $CH_3$ | $CF_2Cl$ |
| A783 | H | PhO | $CH_3$ | $CF_2Cl$ |
| A784 | H | PhS | $CH_3$ | $CF_2Cl$ |
| A785 | H | PhSO | $CH_3$ | $CF_2Cl$ |
| A786 | H | $PhSO_2$ | $CH_3$ | $CF_2Cl$ |
| A787 | H | $CH_3S$ | $CH_3$ | $CF_2Cl$ |
| A788 | H | $CH_3SO$ | $CH_3$ | $CF_2Cl$ |
| A789 | H | $CF_3$ | $CH_3$ | $CF_2Cl$ |
| A790 | H | $F_2CH$ | $CH_3$ | $CF_2Cl$ |
| A791 | H | HCC | $CH_3$ | $CF_2Cl$ |
| A792 | H | $CH_3CC$ | $CH_3$ | $CF_2Cl$ |
| A793 | H | $CH_2=CH$ | $CH_3$ | $CF_2Cl$ |
| A794 | H | $CH_2=CHCH_2$ | $CH_3$ | $CF_2Cl$ |
| A795 | H | $CH_3SO_2N(CH_3)$ | $CH_3$ | $CF_2Cl$ |
| A796 | H | $(CH_3)_2N$ | $CH_3$ | $CF_2Cl$ |
| A797 | H | $(CH_3)_2NSO_2$ | $CH_3$ | $CF_2Cl$ |
| A798 | H | $CH_3SCH_2$ | $CH_3$ | $CF_2Cl$ |
| A799 | H | $CH_3SOCH_2$ | $CH_3$ | $CF_2Cl$ |
| A800 | H | $CH_3SO_2CH_2$ | $CH_3$ | $CF_2Cl$ |
| A801 | H | $CH_3$ | $CH_3$ | $CHF_2$ |
| A802 | H | $CH_3CH_2$ | $CH_3$ | $CHF_2$ |
| A803 | H | cyclopropyl | $CH_3$ | $CHF_2$ |
| A804 | H | $(CH_3)_3C$ | $CH_3$ | $CHF_2$ |
| A805 | H | $(CH_3)_2CH$ | $CH_3$ | $CHF_2$ |
| A806 | H | $CH_3(CH_2)_2$ | $CH_3$ | $CHF_2$ |
| A807 | H | $CH_3OCH_2$ | $CH_3$ | $CHF_2$ |
| A808 | H | $CH_3O(CH_2)_2$ | $CH_3$ | $CHF_2$ |

TABLE 5-continued

Compounds of formula XVI:

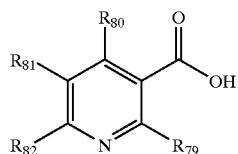

(XVI)

| Compd. no. | $R_{79}$ | $R_{80}$ | $R_{81}$ | $R_{82}$ |
|---|---|---|---|---|
| A809 | H | Ph | $CH_3$ | $CHF_2$ |
| A810 | H | PhO | $CH_3$ | $CHF_2$ |
| A811 | H | PhS | $CH_3$ | $CHF_2$ |
| A812 | H | PhSO | $CH_3$ | $CHF_2$ |
| A813 | H | $PhSO_2$ | $CH_3$ | $CHF_2$ |
| A814 | H | $CH_3S$ | $CH_3$ | $CHF_2$ |
| A815 | H | $CH_3SO$ | $CH_3$ | $CHF_2$ |
| A816 | H | $CF_3$ | $CH_3$ | $CHF_2$ |
| A817 | H | $F_2CH$ | $CH_3$ | $CHF_2$ |
| A818 | H | HCC | $CH_3$ | $CHF_2$ |
| A819 | H | $CH_3CC$ | $CH_3$ | $CHF_2$ |
| A820 | H | $CH_2=CH$ | $CH_3$ | $CHF_2$ |
| A821 | H | $CH_2=CHCH_2$ | $CH_3$ | $CHF_2$ |
| A822 | H | $CH_3SO_2N(CH_3)$ | $CH_3$ | $CHF_2$ |
| A823 | H | $(CH_3)_2N$ | $CH_3$ | $CHF_2$ |
| A824 | H | $(CH_3)_2NSO_2$ | $CH_3$ | $CHF_2$ |
| A825 | H | $CH_3SCH_2$ | $CH_3$ | $CHF_2$ |
| A826 | H | $CH_3SOCH_2$ | $CH_3$ | $CHF_2$ |
| A827 | H | $CH_3SO_2CH_2$ | $CH_3$ | $CHF_2$ |
| A828 | H | $CH_3$ | $CH_3$ | $CCl_3$ |
| A829 | H | $CH_3CH_2$ | $CH_3$ | $CCl_3$ |
| A830 | H | cyclopropyl | $CH_3$ | $CCl_3$ |
| A831 | H | $(CH_3)_3C$ | $CH_3$ | $CCl_3$ |
| A832 | H | $(CH_3)_2CH$ | $CH_3$ | $CCl_3$ |
| A833 | H | $CH_3(CH_2)_2$ | $CH_3$ | $CCl_3$ |
| A834 | H | $CH_3OCH_2$ | $CH_3$ | $CCl_3$ |
| A835 | H | $CH_3O(CH_2)_2$ | $CH_3$ | $CCl_3$ |
| A836 | H | Ph | $CH_3$ | $CCl_3$ |
| A837 | H | PhO | $CH_3$ | $CCl_3$ |
| A838 | H | PhS | $CH_3$ | $CCl_3$ |
| A839 | H | PhSO | $CH_3$ | $CCl_3$ |
| A840 | H | $PhSO_2$ | $CH_3$ | $CCl_3$ |
| A841 | H | $CH_3S$ | $CH_3$ | $CCl_3$ |
| A842 | H | $CH_3SO$ | $CH_3$ | $CCl_3$ |
| A843 | H | $CF_3$ | $CH_3$ | $CCl_3$ |
| A844 | H | $F_2CH$ | $CH_3$ | $CCl_3$ |
| A845 | H | HCC | $CH_3$ | $CCl_3$ |
| A846 | H | $CH_3CC$ | $CH_3$ | $CCl_3$ |
| A847 | H | $CH_2=CH$ | $CH_3$ | $CCl_3$ |
| A848 | H | $CH_2=CHCH_2$ | $CH_3$ | $CCl_3$ |
| A849 | H | $CH_3SO_2N(CH_3)$ | $CH_3$ | $CCl_3$ |
| A850 | H | $(CH_3)_2N$ | $CH_3$ | $CCl_3$ |
| A851 | H | $(CH_3)_2NSO_2$ | $CH_3$ | $CCl_3$ |
| A852 | H | $CH_3SCH_2$ | $CH_3$ | $CCl_3$ |
| A853 | H | $CH_3SOCH_2$ | $CH_3$ | $CCl_3$ |
| A854 | H | $CH_3SO_2CH_2$ | $CH_3$ | $CCl_3$ |
| A855 | H | $CH_3$ | Ph | $CF_3$ |
| A856 | H | $CH_3CH_2$ | Ph | $CF_3$ |
| A857 | H | $(CH_3)_2CH$ | Ph | $CF_3$ |
| A858 | H | $(CH_3)_2CH$ | Ph | $CF_3$ |
| A859 | H | cyclopropyl | Ph | $CF_3$ |
| A860 | H | $CH_3(CH_2)_2$ | Ph | $CF_3$ |
| A861 | H | $CH_3OCH_2$ | Ph | $CF_3$ |
| A862 | H | $CH_3O(CH_2)_2$ | Ph | $CF_3$ |
| A863 | H | Ph | Ph | $CF_3$ |
| A864 | H | PhO | Ph | $CF_3$ |
| A865 | H | PhS | Ph | $CF_3$ |
| A866 | H | PhSO | Ph | $CF_3$ |
| A867 | H | $PhSO_2$ | Ph | $CF_3$ |
| A868 | H | $CH_3S$ | Ph | $CF_3$ |
| A869 | H | $CH_3SO$ | Ph | $CF_3$ |
| A870 | H | $CF_3$ | Ph | $CF_3$ |
| A871 | H | $F_2CH$ | Ph | $CF_3$ |
| A872 | H | HCC | Ph | $CF_3$ |
| A873 | H | $CH_3CC$ | Ph | $CF_3$ |

TABLE 5-continued

Compounds of formula XVI:

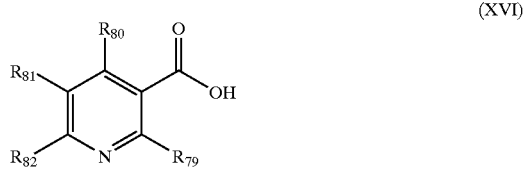

(XVI)

| Compd. no. | $R_{79}$ | $R_{80}$ | $R_{81}$ | $R_{82}$ |
|---|---|---|---|---|
| A874 | H | $CH_2=CH$ | Ph | $CF_3$ |
| A875 | H | $CH_2=CHCH_2$ | Ph | $CF_3$ |
| A876 | H | $CH_3SO_2N(CH_3)$ | Ph | $CF_3$ |
| A877 | H | $(CH_3)_2N$ | Ph | $CF_3$ |
| A878 | H | $(CH_3)_2NSO_2$ | Ph | $CF_3$ |
| A879 | H | $CH_3SCH_2$ | Ph | $CF_3$ |
| A880 | H | $CH_3SOCH_2$ | Ph | $CF_3$ |
| A881 | H | $CH_3SO_2CH_2$ | Ph | $CF_3$ |
| A882 | H | $CH_3$ | Ph | $CF_3CF_2$ |
| A883 | H | $CH_3CH_2$ | Ph | $CF_3CF_2$ |
| A884 | H | cyclopropyl | Ph | $CF_3CF_2$ |
| A885 | H | $(CH_3)_3C$ | Ph | $CF_3CF_2$ |
| A886 | H | $(CH_3)_2CH$ | Ph | $CF_3CF_2$ |
| A887 | H | $CH_3(CH_2)_2$ | Ph | $CF_3CF_2$ |
| A888 | H | $CH_3OCH_2$ | Ph | $CF_3CF_2$ |
| A889 | H | $CH_3O(CH_2)_2$ | Ph | $CF_3CF_2$ |
| A890 | H | Ph | Ph | $CF_3CF_2$ |
| A891 | H | PhO | Ph | $CF_3CF_2$ |
| A892 | H | PhS | Ph | $CF_3CF_2$ |
| A893 | H | PhSO | Ph | $CF_3CF_2$ |
| A894 | H | $PhSO_2$ | Ph | $CF_3CF_2$ |
| A895 | H | $CH_3S$ | Ph | $CF_3CF_2$ |
| A896 | H | $CH_3SO$ | Ph | $CF_3CF_2$ |
| A897 | H | $CF_3$ | Ph | $CF_3CF_2$ |
| A898 | H | $F_2CH$ | Ph | $CF_3CF_2$ |
| A899 | H | HCC | Ph | $CF_3CF_2$ |
| A900 | H | $CH_3CC$ | Ph | $CF_3CF_2$ |
| A901 | H | $CH_2=CH$ | Ph | $CF_3CF_2$ |
| A902 | H | $CH_2=CHCH_2$ | Ph | $CF_3CF_2$ |
| A903 | H | $CH_3SO_2N(CH_3)$ | Ph | $CF_3CF_2$ |
| A904 | H | $(CH_3)_2N$ | Ph | $CF_3CF_2$ |
| A905 | H | $(CH_3)_2NSO_2$ | Ph | $CF_3CF_2$ |
| A906 | H | $CH_3SCH_2$ | Ph | $CF_3CF_2$ |
| A907 | H | $CH_3SOCH_2$ | Ph | $CF_3CF_2$ |
| A908 | H | $CH_3SO_2CH_2$ | Ph | $CF_3CF_2$ |
| A909 | H | $CH_3$ | Ph | $CF_3CF_2CF_2$ |
| A910 | H | $CH_3CH_2$ | Ph | $CF_3CF_2CF_2$ |
| A911 | H | cyclopropyl | Ph | $CF_3CF_2CF_2$ |
| A912 | H | $(CH_3)_3C$ | Ph | $CF_3CF_2CF_2$ |
| A913 | H | $(CH_3)_2CH$ | Ph | $CF_3CF_2CF_2$ |
| A914 | H | $CH_3(CH_2)_2$ | Ph | $CF_3CF_2CF_2$ |
| A915 | H | $CH_3OCH_2$ | Ph | $CF_3CF_2CF_2$ |
| A916 | H | $CH_3O(CH_2)_2$ | Ph | $CF_3CF_2CF_2$ |
| A917 | H | Ph | Ph | $CF_3CF_2CF_2$ |
| A918 | H | PhO | Ph | $CF_3CF_2CF_2$ |
| A919 | H | PhS | Ph | $CF_3CF_2CF_2$ |
| A920 | H | PhSO | Ph | $CF_3CF_2CF_2$ |
| A921 | H | $PhSO_2$ | Ph | $CF_3CF_2CF_2$ |
| A922 | H | $CH_3S$ | Ph | $CF_3CF_2CF_2$ |
| A923 | H | $CH_3SO$ | Ph | $CF_3CF_2CF_2$ |
| A924 | H | $CF_3$ | Ph | $CF_3CF_2CF_2$ |
| A925 | H | $F_2CH$ | Ph | $CF_3CF_2CF_2$ |
| A926 | H | HCC | Ph | $CF_3CF_2CF_2$ |
| A927 | H | $CH_3CC$ | Ph | $CF_3CF_2CF_2$ |
| A928 | H | $CH_2=CH$ | Ph | $CF_3CF_2CF_2$ |
| A929 | H | $CH_2=CHCH_2$ | Ph | $CF_3CF_2CF_2$ |
| A930 | H | $CH_3SO_2N(CH_3)$ | Ph | $CF_3CF_2CF_2$ |
| A931 | H | $(CH_3)_2N$ | Ph | $CF_3CF_2CF_2$ |
| A932 | H | $(CH_3)_2NSO_2$ | Ph | $CF_3CF_2CF_2$ |
| A933 | H | $CH_3SCH_2$ | Ph | $CF_3CF_2CF_2$ |
| A934 | H | $CH_3SOCH_2$ | Ph | $CF_3CF_2CF_2$ |
| A935 | H | $CH_3SO_2CH_2$ | Ph | $CF_3CF_2CF_2$ |
| A936 | H | $CH_3$ | Ph | $CF_2Cl$ |
| A937 | H | $CH_3CH_2$ | Ph | $CF_2Cl$ |
| A938 | H | cyclopropyl | Ph | $CF_2Cl$ |

TABLE 5-continued

Compounds of formula XVI:

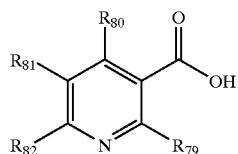

(XVI)

| Compd. no. | $R_{79}$ | $R_{80}$ | $R_{81}$ | $R_{82}$ |
|---|---|---|---|---|
| A939 | H | $(CH_3)_3C$ | Ph | $CF_2Cl$ |
| A940 | H | $(CH_3)_2CH$ | Ph | $CF_2Cl$ |
| A941 | H | $CH_3(CH_2)_2$ | Ph | $CF_2Cl$ |
| A942 | H | $CH_3OCH_2$ | Ph | $CF_2Cl$ |
| A943 | H | $CH_3O(CH_2)_2$ | Ph | $CF_2Cl$ |
| A944 | H | Ph | Ph | $CF_2Cl$ |
| A945 | H | PhO | Ph | $CF_2Cl$ |
| A946 | H | PhS | Ph | $CF_2Cl$ |
| A947 | H | PhSO | Ph | $CF_2Cl$ |
| A948 | H | $PhSO_2$ | Ph | $CF_2Cl$ |
| A949 | H | $CH_3S$ | Ph | $CF_2Cl$ |
| A950 | H | $CH_3SO$ | Ph | $CF_2Cl$ |
| A951 | H | $CF_3$ | Ph | $CF_2Cl$ |
| A952 | H | $F_2CH$ | Ph | $CF_2Cl$ |
| A953 | H | HCC | Ph | $CF_2Cl$ |
| A954 | H | $CH_3CC$ | Ph | $CF_2Cl$ |
| A955 | H | $CH_2\!=\!CH$ | Ph | $CF_2Cl$ |
| A956 | H | $CH_2\!=\!CHCH_2$ | Ph | $CF_2Cl$ |
| A957 | H | $CH_3SO_2N(CH_3)$ | Ph | $CF_2Cl$ |
| A958 | H | $(CH_3)_2N$ | Ph | $CF_2Cl$ |
| A959 | H | $(CH_3)_2NSO_2$ | Ph | $CF_2Cl$ |
| A960 | H | $CH_3SCH_2$ | Ph | $CF_2Cl$ |
| A961 | H | $CH_3SOCH_2$ | Ph | $CF_2Cl$ |
| A962 | H | $CH_3SO_2CH_2$ | Ph | $CF_2Cl$ |
| A963 | H | $CH_3$ | Ph | $CHF_2$ |
| A964 | H | $CH_3CH_2$ | Ph | $CHF_2$ |
| A965 | H | $(CH_3)_3C$ | Ph | $CHF_2$ |
| A966 | H | $(CH_3)_2CH$ | Ph | $CHF_2$ |
| A967 | H | cyclopropyl | Ph | $CHF_2$ |
| A968 | H | $CH_3(CH_2)_2$ | Ph | $CHF_2$ |
| A969 | H | $CH_3OCH_2$ | Ph | $CHF_2$ |
| A970 | H | $CH_3O(CH_2)_2$ | Ph | $CHF_2$ |
| A971 | H | Ph | Ph | $CHF_2$ |
| A972 | H | PhO | Ph | $CHF_2$ |
| A973 | H | PhS | Ph | $CHF_2$ |
| A974 | H | PhSO | Ph | $CHF_2$ |
| A975 | H | $PhSO_2$ | Ph | $CHF_2$ |
| A976 | H | $CH_3S$ | Ph | $CHF_2$ |
| A977 | H | $CH_3SO$ | Ph | $CHF_2$ |
| A978 | H | $CF_3$ | Ph | $CHF_2$ |
| A979 | H | $F_2CH$ | Ph | $CHF_2$ |
| A980 | H | HCC | Ph | $CHF_2$ |
| A981 | H | $CH_3CC$ | Ph | $CHF_2$ |
| A982 | H | $CH_2\!=\!CH$ | Ph | $CHF_2$ |
| A983 | H | $CH_2\!=\!CHCH_2$ | Ph | $CHF_2$ |
| A984 | H | $CH_3SO_2N(CH_3)$ | Ph | $CHF_2$ |
| A985 | H | $(CH_3)_2N$ | Ph | $CHF_2$ |
| A986 | H | $(CH_3)_2NSO_2$ | Ph | $CHF_2$ |
| A987 | H | $CH_3SCH_2$ | Ph | $CHF_2$ |
| A988 | H | $CH_3SOCH_2$ | Ph | $CHF_2$ |
| A989 | H | $CH_3SO_2CH_2$ | Ph | $CHF_2$ |
| A990 | H | $CH_3$ | Ph | $CCl_3$ |
| A991 | H | $CH_3CH_2$ | Ph | $CCl_3$ |
| A992 | H | $(CH_3)_3C$ | Ph | $CCl_3$ |
| A993 | H | $(CH_3)_2CH$ | Ph | $CCl_3$ |
| A994 | H | cyclopropyl | Ph | $CCl_3$ |
| A995 | H | $CH_3(CH_2)_2$ | Ph | $CCl_3$ |
| A996 | H | $CH_3OCH_2$ | Ph | $CCl_3$ |
| A997 | H | $CH_3O(CH_2)_2$ | Ph | $CCl_3$ |
| A998 | H | Ph | Ph | $CCl_3$ |
| A999 | H | PhO | Ph | $CCl_3$ |
| A1000 | H | PhS | Ph | $CCl_3$ |
| A1001 | H | PhSO | Ph | $CCl_3$ |
| A1002 | H | $PhSO_2$ | Ph | $CCl_3$ |
| A1003 | H | $CH_3S$ | Ph | $CCl_3$ |

TABLE 5-continued

Compounds of formula XVI:

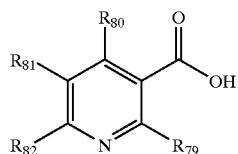

(XVI)

| Compd. no. | $R_{79}$ | $R_{80}$ | $R_{81}$ | $R_{82}$ |
|---|---|---|---|---|
| A1004 | H | $CH_3SO$ | Ph | $CCl_3$ |
| A1005 | H | $CF_3$ | Ph | $CCl_3$ |
| A1006 | H | $F_2CH$ | Ph | $CCl_3$ |
| A1007 | H | HCC | Ph | $CCl_3$ |
| A1008 | H | $CH_3CC$ | Ph | $CCl_3$ |
| A1009 | H | $CH_2=CH$ | Ph | $CCl_3$ |
| A1010 | H | $CH_2=CHCH_2$ | Ph | $CCl_3$ |
| A1011 | H | $CH_3SO_2N(CH_3)$ | Ph | $CCl_3$ |
| A1012 | H | $(CH_3)_2N$ | Ph | $CCl_3$ |
| A1013 | H | $(CH_3)_2NSO_2$ | Ph | $CCl_3$ |
| A1014 | H | $CH_3SCH_2$ | Ph | $CCl_3$ |
| A1015 | H | $CH_3SOCH_2$ | Ph | $CCl_3$ |
| A1016 | H | $CH_3SO_2CH_2$ | Ph | $CCl_3$ |
| A1017 | F | H | H | $CF_3$ |
| A1018 | Cl | H | H | $CF_3$ |
| A1019 | Br | H | H | $CF_3$ |
| A1020 | CN | H | H | $CF_3$ |
| A1021 | $CH_3SO_2O$ | H | H | $CF_3$ |
| A1022 | $CH_3O$ | H | H | $CF_3$ |
| A1023 | $CH_2CH_3O$ | H | H | $CF_3$ |
| A1024 | $CH_2CH=CH_2O$ | H | H | $CF_3$ |
| A1025 | $HCCCH_2O$ | H | H | $CF_3$ |
| A1026 | S-benzyl | H | H | $CF_3$ |
| A1027 | $SO_2$-benzyl | H | H | $CF_3$ |
| A1028 | $ClCH_2$ | H | H | $CF_3$ |
| A1029 | $BrCH_2$ | H | H | $CF_3$ |
| A1030 | $FCH_2$ | H | H | $CF_3$ |
| A1031 | $CHF_2CH_2$ | H | H | $CF_3$ |
| A1032 | $CF_3CH_2$ | H | H | $CF_3$ |
| A1033 | triazolylmethyl | H | H | $CF_3$ |
| A1034 | $CHCl_2CH_2$ | H | H | $CF_3$ |
| A1035 | $ClCH=CH$ | H | H | $CF_3$ |
| A1036 | $Cl_2C=CH$ | H | H | $CF_3$ |
| A1037 | $CF_3CH=CH$ | H | H | $CF_3$ |
| A1038 | ClCC | H | H | $CF_3$ |
| A1039 | Ph | H | H | $CF_3$ |
| A1040 | $CH_3$ | $CH_3$ | H | $CF_3$ |
| A1041 | $CH_3$ | OH | H | $CF_3$ |
| A1042 | $CH_3$ | F | H | $CF_3$ |
| A1043 | $CH_3$ | Cl | H | $CF_3$ |
| A1044 | F | $CH_3$ | H | $CF_3$ |
| A1045 | Cl | $CH_3$ | H | $CF_3$ |
| A1046 | H | F | H | $CF_3$ |
| A1047 | H | Cl | H | $CF_3$ |
| A1048 | H | Br | H | $CF_3$ |
| A1049 | H | OH | H | $CF_3$ |
| A1050 | H | $OCH_3$ | H | $CF_3$ |
| A1051 | H | $OCHF_2$ | H | $CF_3$ |
| A1052 | H | $OSO_2CH_3$ | H | $CF_3$ |
| A1053 | H | $OSO_2CF_3$ | H | $CF_3$ |
| A1054 | H | $ClCH_2$ | H | $CF_3$ |
| A1055 | H | $BrCH_2$ | H | $CF_3$ |
| A1056 | H | $FCH_2$ | H | $CF_3$ |
| A1057 | H | $CHF_2CH_2$ | H | $CF_3$ |
| A1058 | H | $CF_3CH_2$ | H | $CF_3$ |
| A1059 | H | triazolylmethyl | H | $CF_3$ |
| A1060 | H | $CHCl_2CH_2$ | H | $CF_3$ |
| A1061 | H | $ClCH=CH$ | H | $CF_3$ |
| A1062 | H | $Cl_2C=CH$ | H | $CF_3$ |
| A1063 | H | $CF_3CH=CH$ | H | $CF_3$ |
| A1064 | H | ClCC | H | $CF_3$ |
| A1065 | H | $CH_3C(O)$ | H | $CF_3$ |
| A1066 | H | phenyl | H | $CF_3$ |
| A1067 | H | $SO_2CH_3$ | H | $CF_3$ |
| A1068 | H | $SO_2CF_3$ | H | $CF_3$ |

TABLE 5-continued

Compounds of formula XVI:

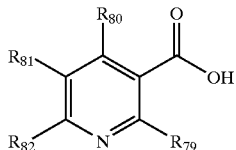

(XVI)

| Compd. no. | $R_{79}$ | $R_{80}$ | $R_{81}$ | $R_{82}$ |
|---|---|---|---|---|
| A1069 | H | CN | H | $CF_3$ |
| A1070 | H | $NO_2$ | H | $CF_3$ |
| A1071 | $CH_3$ | H | F | $CF_3$ |
| A1072 | $CH_3$ | H | Cl | $CF_3$ |
| A1073 | $CH_3$ | H | Br | $CF_3$ |
| A1074 | $CH_3$ | H | CN | $CF_3$ |
| A1075 | $CH_3$ | H | $CH_3O$ | $CF_3$ |
| A1076 | $CH_3$ | H | $CH_3S$ | $CF_3$ |
| A1077 | $CH_3$ | H | $CH_3SO$ | $CF_3$ |
| A1078 | $CH_3$ | H | $CH_3SO_2$ | $CF_3$ |

In the following Table 6 0 is $Q_3$

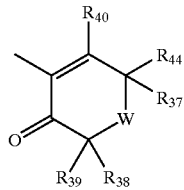

($Q_3$)

and $Q_3$ represents the following radicals B:

TABLE 6

Radicals B:

| Radical | $R_{44}$ | $R_{37}$ | $R_{38}$ | $R_{39}$ | $R_{40}$ | W |
|---|---|---|---|---|---|---|
| B1 | H | H | H | H | OH | $CH_2$ |
| B2 | $CH_3$ | H | H | H | OH | $CH_2$ |
| B3 | $CH_3CH_2$ | H | H | H | OH | $CH_2$ |
| B4 | $CH_3CH_2CH_2$ | H | H | H | OH | $CH_2$ |
| B5 | $(CH_3)_2CH$ | H | H | H | OH | $CH_2$ |
| B6 | $(CH_3)_3C$ | H | H | H | OH | $CH_2$ |
| B7 | $CH_3S$ | H | H | H | OH | $CH_2$ |
| B8 | $CH_3SO$ | H | H | H | OH | $CH_2$ |
| B9 | $CH_3SO_2$ | H | H | H | OH | $CH_2$ |
| B10 | Ph | H | H | H | OH | $CH_2$ |
| B11 | $CH_3O$ | H | H | H | OH | $CH_2$ |
| B12 | $CH_3CO_2$ | H | H | H | OH | $CH_2$ |
| B13 | $CH_3CH_2CO_2$ | H | H | H | OH | $CH_2$ |
| B14 | $CH_2=CHCH_2$ | H | H | H | OH | $CH_2$ |
| B15 | $HCCCH_2$ | H | H | H | OH | $CH_2$ |
| B16 | $CF_3$ | H | H | H | OH | $CH_2$ |
| B17 | $(CH_3)_2NSO_2$ | H | H | H | OH | $CH_2$ |
| B18 | $(CH_3)_2N$ | H | H | H | OH | $CH_2$ |
| B19 | PhO | H | H | H | OH | $CH_2$ |
| B20 | PhS | H | H | H | OH | $CH_2$ |
| B21 | PhSO | H | H | H | OH | $CH_2$ |
| B22 | $PhSO_2$ | H | H | H | OH | $CH_2$ |
| B23 | CN | H | H | H | OH | $CH_2$ |
| B24 | $CH_3$ | $CH_3$ | H | H | OH | $CH_2$ |
| B25 | $CH_3CH_2$ | $CH_3$ | H | H | OH | $CH_2$ |
| B26 | $CH_3CH_2CH_2$ | $CH_3$ | H | H | OH | $CH_2$ |
| B27 | $(CH_3)_2CH$ | $CH_3$ | H | H | OH | $CH_2$ |
| B28 | $(CH_3)_3C$ | $CH_3$ | H | H | OH | $CH_2$ |
| B29 | $CH_3S$ | $CH_3$ | H | H | OH | $CH_2$ |

TABLE 6-continued

Radicals B:

| Radical | $R_{44}$ | $R_{37}$ | $R_{38}$ | $R_{39}$ | $R_{40}$ | W |
|---|---|---|---|---|---|---|
| B30 | $CH_3SO$ | $CH_3$ | H | H | OH | $CH_2$ |
| B31 | $CH_3SO_2$ | $CH_3$ | H | H | OH | $CH_2$ |
| B32 | Ph | $CH_3$ | H | H | OH | $CH_2$ |
| B33 | $CH_3O$ | $CH_3$ | H | H | OH | $CH_2$ |
| B34 | $CH_3CO_2$ | $CH_3$ | H | H | OH | $CH_2$ |
| B35 | $CH_3CH_2CO_2$ | $CH_3$ | H | H | OH | $CH_2$ |
| B36 | $CH_2=CHCH_2$ | $CH_3$ | H | H | OH | $CH_2$ |
| B37 | $HCCCH_2$ | $CH_3$ | H | H | OH | $CH_2$ |
| B38 | $CF_3$ | $CH_3$ | H | H | OH | $CH_2$ |
| B39 | $(CH_3)_2NSO_2$ | $CH_3$ | H | H | OH | $CH_2$ |
| B40 | $(CH_3)_2N$ | $CH_3$ | H | H | OH | $CH_2$ |
| B41 | PhO | $CH_3$ | H | H | OH | $CH_2$ |
| B42 | PhS | $CH_3$ | H | H | OH | $CH_2$ |
| B43 | PhSO | $CH_3$ | H | H | OH | $CH_2$ |
| B44 | $PhSO_2$ | $CH_3$ | H | H | OH | $CH_2$ |
| B45 | CN | $CH_3$ | H | H | OH | $CH_2$ |
| B46 | $CH_3$ | H | $CH_3$ | H | OH | $CH_2$ |
| B47 | $CH_3CH_2$ | H | $CH_3$ | H | OH | $CH_2$ |
| B48 | $CH_3CH_2CH_2$ | H | $CH_3$ | H | OH | $CH_2$ |
| B49 | $(CH_3)_2CH$ | H | $CH_3$ | H | OH | $CH_2$ |
| B50 | $(CH_3)_3C$ | H | $CH_3$ | H | OH | $CH_2$ |
| B51 | $CH_3S$ | H | $CH_3$ | H | OH | $CH_2$ |
| B52 | $CH_3SO$ | H | $CH_3$ | H | OH | $CH_2$ |
| B53 | $CH_3SO_2$ | H | $CH_3$ | H | OH | $CH_2$ |
| B54 | Ph | H | $CH_3$ | H | OH | $CH_2$ |
| B55 | $CH_3O$ | H | $CH_3$ | H | OH | $CH_2$ |
| B56 | $CH_3CO_2$ | H | $CH_3$ | H | OH | $CH_2$ |
| B57 | $CH_3CH_2CO_2$ | H | $CH_3$ | H | OH | $CH_2$ |
| B58 | $CH_2=CHCH_2$ | H | $CH_3$ | H | OH | $CH_2$ |
| B59 | $HCCCH_2$ | H | $CH_3$ | H | OH | $CH_2$ |
| B60 | $CF_3$ | H | $CH_3$ | H | OH | $CH_2$ |
| B61 | $(CH_3)_2NSO_2$ | H | $CH_3$ | H | OH | $CH_2$ |
| B62 | $(CH_3)_2N$ | H | $CH_3$ | H | OH | $CH_2$ |
| B63 | PhO | H | $CH_3$ | H | OH | $CH_2$ |
| B64 | PhS | H | $CH_3$ | H | OH | $CH_2$ |
| B65 | PhSO | H | $CH_3$ | H | OH | $CH_2$ |
| B66 | $PhSO_2$ | H | $CH_3$ | H | OH | $CH_2$ |
| B67 | CN | H | $CH_3$ | H | OH | $CH_2$ |
| B68 | $CH_3$ | $CH_3$ | $CH_3$ | H | OH | $CH_2$ |
| B69 | $CH_3CH_2$ | $CH_3$ | $CH_3$ | H | OH | $CH_2$ |
| B70 | $CH_3CH_2CH_2$ | $CH_3$ | $CH_3$ | H | OH | $CH_2$ |
| B71 | $(CH_3)_2CH$ | $CH_3$ | $CH_3$ | H | OH | $CH_2$ |
| B72 | $(CH_3)_3C$ | $CH_3$ | $CH_3$ | H | OH | $CH_2$ |
| B73 | $CH_3S$ | $CH_3$ | $CH_3$ | H | OH | $CH_2$ |
| B74 | $CH_3SO$ | $CH_3$ | $CH_3$ | H | OH | $CH_2$ |
| B75 | $CH_3SO_2$ | $CH_3$ | $CH_3$ | H | OH | $CH_2$ |
| B76 | Ph | $CH_3$ | $CH_3$ | H | OH | $CH_2$ |
| B77 | $CH_3O$ | $CH_3$ | $CH_3$ | H | OH | $CH_2$ |
| B78 | $CH_3CO_2$ | $CH_3$ | $CH_3$ | H | OH | $CH_2$ |
| B79 | $CH_3CH_2CO_2$ | $CH_3$ | $CH_3$ | H | OH | $CH_2$ |
| B80 | $CH_2=CHCH_2$ | $CH_3$ | $CH_3$ | H | OH | $CH_2$ |
| B81 | $HCCCH_2$ | $CH_3$ | $CH_3$ | H | OH | $CH_2$ |
| B82 | $CF_3$ | $CH_3$ | $CH_3$ | H | OH | $CH_2$ |
| B83 | $(CH_3)_2NSO_2$ | $CH_3$ | $CH_3$ | H | OH | $CH_2$ |
| B84 | $(CH_3)_2N$ | $CH_3$ | $CH_3$ | H | OH | $CH_2$ |
| B85 | PhO | $CH_3$ | $CH_3$ | H | OH | $CH_2$ |
| B86 | PhS | $CH_3$ | $CH_3$ | H | OH | $CH_2$ |
| B87 | PhSO | $CH_3$ | $CH_3$ | H | OH | $CH_2$ |
| B88 | $PhSO_2$ | $CH_3$ | $CH_3$ | H | OH | $CH_2$ |
| B89 | CN | $CH_3$ | $CH_3$ | H | OH | $CH_2$ |
| B90 | $CH_3$ | $CH_3$ | $CH_3$ | $CH_3$ | OH | $CH_2$ |
| B91 | $CH_3CH_2$ | $CH_3$ | $CH_3$ | $CH_3$ | OH | $CH_2$ |
| B92 | $CH_3CH_2CH_2$ | $CH_3$ | $CH_3$ | $CH_3$ | OH | $CH_2$ |
| B93 | $(CH_3)_2CH$ | $CH_3$ | $CH_3$ | $CH_3$ | OH | $CH_2$ |
| B94 | $(CH_3)_3C$ | $CH_3$ | $CH_3$ | $CH_3$ | OH | $CH_2$ |
| B95 | $CH_3S$ | $CH_3$ | $CH_3$ | $CH_3$ | OH | $CH_2$ |
| B96 | $CH_3SO$ | $CH_3$ | $CH_3$ | $CH_3$ | OH | $CH_2$ |
| B97 | $CH_3SO_2$ | $CH_3$ | $CH_3$ | $CH_3$ | OH | $CH_2$ |
| B98 | Ph | $CH_3$ | $CH_3$ | $CH_3$ | OH | $CH_2$ |
| B99 | $CH_3O$ | $CH_3$ | $CH_3$ | $CH_3$ | OH | $CH_2$ |
| B100 | $CH_3CO_2$ | $CH_3$ | $CH_3$ | $CH_3$ | OH | $CH_2$ |
| B101 | $CH_3CH_2CO_2$ | $CH_3$ | $CH_3$ | $CH_3$ | OH | $CH_2$ |
| B102 | $CH_2=CHCH_2$ | $CH_3$ | $CH_3$ | $CH_3$ | OH | $CH_2$ |
| B103 | $HCCCH_2$ | $CH_3$ | $CH_3$ | $CH_3$ | OH | $CH_2$ |
| B104 | $CF_3$ | $CH_3$ | $CH_3$ | $CH_3$ | OH | $CH_2$ |

TABLE 6-continued

Radicals B:

| Radical | R$_{44}$ | R$_{37}$ | R$_{38}$ | R$_{39}$ | R$_{40}$ | W |
|---|---|---|---|---|---|---|
| B105 | (CH$_3$)$_2$NSO$_2$ | CH$_3$ | CH$_3$ | CH$_3$ | OH | CH$_2$ |
| B106 | (CH$_3$)$_2$N | CH$_3$ | CH$_3$ | CH$_3$ | OH | CH$_2$ |
| B107 | PhO | CH$_3$ | CH$_3$ | CH$_3$ | OH | CH$_2$ |
| B108 | PhS | CH$_3$ | CH$_3$ | CH$_3$ | OH | CH$_2$ |
| B109 | PhSO | CH$_3$ | CH$_3$ | CH$_3$ | OH | CH$_2$ |
| B110 | PhSO$_2$ | CH$_3$ | CH$_3$ | CH$_3$ | OH | CH$_2$ |
| B111 | CN | CH$_3$ | CH$_3$ | CH$_3$ | OH | CH$_2$ |
| B112 | CH$_3$CH$_2$ | CH$_3$CH$_2$ | H | H | OH | CH$_2$ |
| B113 | CH$_3$CH$_2$CH$_2$ | CH$_3$CH$_2$ | H | H | OH | CH$_2$ |
| B114 | (CH$_3$)$_2$CH | CH$_3$CH$_2$ | H | H | OH | CH$_2$ |
| B115 | (CH$_3$)$_3$C | CH$_3$CH$_2$ | H | H | OH | CH$_2$ |
| B116 | CH$_3$S | CH$_3$CH$_2$ | H | H | OH | CH$_2$ |
| B117 | CH$_3$SO | CH$_3$CH$_2$ | H | H | OH | CH$_2$ |
| B118 | CH$_3$SO$_2$ | CH$_3$CH$_2$ | H | H | OH | CH$_2$ |
| B119 | Ph | CH$_3$CH$_2$ | H | H | OH | CH$_2$ |
| B120 | CH$_3$O | CH$_3$CH$_2$ | H | H | OH | CH$_2$ |
| B121 | CH$_3$CO$_2$ | CH$_3$CH$_2$ | H | H | OH | CH$_2$ |
| B122 | CH$_3$CH$_2$CO$_2$ | CH$_3$CH$_2$ | H | H | OH | CH$_2$ |
| B123 | CH$_2$=CHCH$_2$ | CH$_3$CH$_2$ | H | H | OH | CH$_2$ |
| B124 | HCCCH$_2$ | CH$_3$CH$_2$ | H | H | OH | CH$_2$ |
| B125 | CF$_3$ | CH$_3$CH$_2$ | H | H | OH | CH$_2$ |
| B126 | (CH$_3$)$_2$NSO$_2$ | CH$_3$CH$_2$ | H | H | OH | CH$_2$ |
| B127 | (CH$_3$)$_2$N | CH$_3$CH$_2$ | H | H | OH | CH$_2$ |
| B128 | PhO | CH$_3$CH$_2$ | H | H | OH | CH$_2$ |
| B129 | PhS | CH$_3$CH$_2$ | H | H | OH | CH$_2$ |
| B130 | PhSO | CH$_3$CH$_2$ | H | H | OH | CH$_2$ |
| B131 | PhSO$_2$ | CH$_3$CH$_2$ | H | H | OH | CH$_2$ |
| B132 | CN | CH$_3$CH$_2$ | H | H | OH | CH$_2$ |
| B133 | H | H | H | H | OH | CHCH$_3$ |
| B134 | CH$_3$ | H | H | H | OH | CHCH$_3$ |
| B135 | CH$_3$CH$_2$ | H | H | H | OH | CHCH$_3$ |
| B136 | CH$_3$CH$_2$CH$_2$ | H | H | H | OH | CHCH$_3$ |
| B137 | (CH$_3$)$_2$CH | H | H | H | OH | CHCH$_3$ |
| B138 | (CH$_3$)$_3$C | H | H | H | OH | CHCH$_3$ |
| B139 | CH$_3$S | H | H | H | OH | CHCH$_3$ |
| B140 | CH$_3$SO | H | H | H | OH | CHCH$_3$ |
| B141 | CH$_3$SO$_2$ | H | H | H | OH | CHCH$_3$ |
| B142 | Ph | H | H | H | OH | CHCH$_3$ |
| B143 | CH$_3$O | H | H | H | OH | CHCH$_3$ |
| B144 | CH$_3$CO$_2$ | H | H | H | OH | CHCH$_3$ |
| B145 | CH$_3$CH$_2$CO$_2$ | H | H | H | OH | CHCH$_3$ |
| B146 | CH$_2$=CHCH$_2$ | H | H | H | OH | CHCH$_3$ |
| B147 | HCCCH$_2$ | H | H | H | OH | CHCH$_3$ |
| B148 | CF$_3$ | H | H | H | OH | CHCH$_3$ |
| B149 | (CH$_3$)$_2$NSO$_2$ | H | H | H | OH | CHCH$_3$ |
| B150 | (CH$_3$)$_2$N | H | H | H | OH | CHCH$_3$ |
| B151 | PhO | H | H | H | OH | CHCH$_3$ |
| B152 | PhS | H | H | H | OH | CHCH$_3$ |
| B153 | PhSO | H | H | H | OH | CHCH$_3$ |
| B154 | PhSO$_2$ | H | H | H | OH | CHCH$_3$ |
| B155 | CN | H | H | H | OH | CHCH$_3$ |
| B156 | CH$_3$ | CH$_3$ | H | H | OH | CHCH$_3$ |
| B157 | CH$_3$CH$_2$ | CH$_3$ | H | H | OH | CHCH$_3$ |
| B158 | CH$_3$CH$_2$CH$_2$ | CH$_3$ | H | H | OH | CHCH$_3$ |
| B159 | (CH$_3$)$_2$CH | CH$_3$ | H | H | OH | CHCH$_3$ |
| B160 | (CH$_3$)$_3$C | CH$_3$ | H | H | OH | CHCH$_3$ |
| B161 | CH$_3$S | CH$_3$ | H | H | OH | CHCH$_3$ |
| B162 | CH$_3$SO | CH$_3$ | H | H | OH | CHCH$_3$ |
| B163 | CH$_3$SO$_2$ | CH$_3$ | H | H | OH | CHCH$_3$ |
| B164 | Ph | CH$_3$ | H | H | OH | CHCH$_3$ |
| B165 | CH$_3$O | CH$_3$ | H | H | OH | CHCH$_3$ |
| B166 | CH$_3$CO$_2$ | CH$_3$ | H | H | OH | CHCH$_3$ |
| B167 | CH$_3$CH$_2$CO$_2$ | CH$_3$ | H | H | OH | CHCH$_3$ |
| B168 | CH$_2$=CHCH$_2$ | CH$_3$ | H | H | OH | CHCH$_3$ |
| B169 | HCCCH$_2$ | CH$_3$ | H | H | OH | CHCH$_3$ |
| B170 | CF$_3$ | CH$_3$ | H | H | OH | CHCH$_3$ |
| B171 | (CH$_3$)$_2$NSO$_2$ | CH$_3$ | H | H | OH | CHCH$_3$ |
| B172 | (CH$_3$)$_2$N | CH$_3$ | H | H | OH | CHCH$_3$ |
| B173 | PhO | CH$_3$ | H | H | OH | CHCH$_3$ |
| B174 | PhS | CH$_3$ | H | H | OH | CHCH$_3$ |
| B175 | PhSO | CH$_3$ | H | H | OH | CHCH$_3$ |
| B176 | PhSO$_2$ | CH$_3$ | H | H | OH | CHCH$_3$ |
| B177 | CN | CH$_3$ | H | H | OH | CHCH$_3$ |
| B178 | CH$_3$ | H | CH$_3$ | H | OH | CHCH$_3$ |
| B179 | CH$_3$CH$_2$ | H | CH$_3$ | H | OH | CHCH$_3$ |

TABLE 6-continued

Radicals B:

| Radical | $R_{44}$ | $R_{37}$ | $R_{38}$ | $R_{39}$ | $R_{40}$ | W |
|---|---|---|---|---|---|---|
| B180 | $CH_3CH_2CH_2$ | H | $CH_3$ | H | OH | $CHCH_3$ |
| B181 | $(CH_3)_2CH$ | H | $CH_3$ | H | OH | $CHCH_3$ |
| B182 | $(CH_3)_3C$ | H | $CH_3$ | H | OH | $CHCH_3$ |
| B183 | $CH_3S$ | H | $CH_3$ | H | OH | $CHCH_3$ |
| B184 | $CH_3SO$ | H | $CH_3$ | H | OH | $CHCH_3$ |
| B185 | $CH_3SO_2$ | H | $CH_3$ | H | OH | $CHCH_3$ |
| B186 | Ph | H | $CH_3$ | H | OH | $CHCH_3$ |
| B187 | $CH_3O$ | H | $CH_3$ | H | OH | $CHCH_3$ |
| B188 | $CH_3CO_2$ | H | $CH_3$ | H | OH | $CHCH_3$ |
| B189 | $CH_3CH_2CO_2$ | H | $CH_3$ | H | OH | $CHCH_3$ |
| B190 | $CH_2{=}CHCH_2$ | H | $CH_3$ | H | OH | $CHCH_3$ |
| B191 | $HCCCH_2$ | H | $CH_3$ | H | OH | $CHCH_3$ |
| B192 | $CF_3$ | H | $CH_3$ | H | OH | $CHCH_3$ |
| B193 | $(CH_3)_2NSO_2$ | H | $CH_3$ | H | OH | $CHCH_3$ |
| B194 | $(CH_3)_2N$ | H | $CH_3$ | H | OH | $CHCH_3$ |
| B195 | PhO | H | $CH_3$ | H | OH | $CHCH_3$ |
| B196 | PhS | H | $CH_3$ | H | OH | $CHCH_3$ |
| B197 | PhSO | H | $CH_3$ | H | OH | $CHCH_3$ |
| B198 | $PhSO_2$ | H | $CH_3$ | H | OH | $CHCH_3$ |
| B199 | CN | H | $CH_3$ | H | OH | $CHCH_3$ |
| B200 | $CH_3$ | $CH_3$ | $CH_3$ | H | OH | $CHCH_3$ |
| B201 | $CH_3CH_2$ | $CH_3$ | $CH_3$ | H | OH | $CHCH_3$ |
| B202 | $CH_3CH_2CH_2$ | $CH_3$ | $CH_3$ | H | OH | $CHCH_3$ |
| B203 | $(CH_3)_2CH$ | $CH_3$ | $CH_3$ | H | OH | $CHCH_3$ |
| B204 | $(CH_3)_3C$ | $CH_3$ | $CH_3$ | H | OH | $CHCH_3$ |
| B205 | $CH_3S$ | $CH_3$ | $CH_3$ | H | OH | $CHCH_3$ |
| B206 | $CH_3SO$ | $CH_3$ | $CH_3$ | H | OH | $CHCH_3$ |
| B207 | $CH_3SO_2$ | $CH_3$ | $CH_3$ | H | OH | $CHCH_3$ |
| B208 | Ph | $CH_3$ | $CH_3$ | H | OH | $CHCH_3$ |
| B209 | $CH_3O$ | $CH_3$ | $CH_3$ | H | OH | $CHCH_3$ |
| B210 | $CH_3CO_2$ | $CH_3$ | $CH_3$ | H | OH | $CHCH_3$ |
| B211 | $CH_3CH_2CO_2$ | $CH_3$ | $CH_3$ | H | OH | $CHCH_3$ |
| B212 | $CH_2{=}CHCH_2$ | $CH_3$ | $CH_3$ | H | OH | $CHCH_3$ |
| B213 | $HCCCH_2$ | $CH_3$ | $CH_3$ | H | OH | $CHCH_3$ |
| B214 | $CF_3$ | $CH_3$ | $CH_3$ | H | OH | $CHCH_3$ |
| B215 | $(CH_3)_2NSO_2$ | $CH_3$ | $CH_3$ | H | OH | $CHCH_3$ |
| B216 | $(CH_3)_2N$ | $CH_3$ | $CH_3$ | H | OH | $CHCH_3$ |
| B217 | PhO | $CH_3$ | $CH_3$ | H | OH | $CHCH_3$ |
| B218 | PhS | $CH_3$ | $CH_3$ | H | OH | $CHCH_3$ |
| B219 | PhSO | $CH_3$ | $CH_3$ | H | OH | $CHCH_3$ |
| B220 | $PhSO_2$ | $CH_3$ | $CH_3$ | H | OH | $CHCH_3$ |
| B221 | CN | $CH_3$ | $CH_3$ | H | OH | $CHCH_3$ |
| B222 | $CH_3$ | $CH_3$ | $CH_3$ | $CH_3$ | OH | $CHCH_3$ |
| B223 | $CH_3CH_2$ | $CH_3$ | $CH_3$ | $CH_3$ | OH | $CHCH_3$ |
| B224 | $CH_3CH_2CH_2$ | $CH_3$ | $CH_3$ | $CH_3$ | OH | $CHCH_3$ |
| B225 | $(CH_3)_2CH$ | $CH_3$ | $CH_3$ | $CH_3$ | OH | $CHCH_3$ |
| B226 | $(CH_3)_3C$ | $CH_3$ | $CH_3$ | $CH_3$ | OH | $CHCH_3$ |
| B227 | $CH_3S$ | $CH_3$ | $CH_3$ | $CH_3$ | OH | $CHCH_3$ |
| B228 | $CH_3SO$ | $CH_3$ | $CH_3$ | $CH_3$ | OH | $CHCH_3$ |
| B229 | $CH_3SO_2$ | $CH_3$ | $CH_3$ | $CH_3$ | OH | $CHCH_3$ |
| B230 | Ph | $CH_3$ | $CH_3$ | $CH_3$ | OH | $CHCH_3$ |
| B231 | $CH_3O$ | $CH_3$ | $CH_3$ | $CH_3$ | OH | $CHCH_3$ |
| B232 | $CH_3CO_2$ | $CH_3$ | $CH_3$ | $CH_3$ | OH | $CHCH_3$ |
| B233 | $CH_3CH_2CO_2$ | $CH_3$ | $CH_3$ | $CH_3$ | OH | $CHCH_3$ |
| B234 | $CH_2{=}CHCH_2$ | $CH_3$ | $CH_3$ | $CH_3$ | OH | $CHCH_3$ |
| B235 | $HCCCH_2$ | $CH_3$ | $CH_3$ | $CH_3$ | OH | $CHCH_3$ |
| B236 | $CF_3$ | $CH_3$ | $CH_3$ | $CH_3$ | OH | $CHCH_3$ |
| B237 | $(CH_3)_2NSO_2$ | $CH_3$ | $CH_3$ | $CH_3$ | OH | $CHCH_3$ |
| B238 | $(CH_3)_2N$ | $CH_3$ | $CH_3$ | $CH_3$ | OH | $CHCH_3$ |
| B239 | PhO | $CH_3$ | $CH_3$ | $CH_3$ | OH | $CHCH_3$ |
| B240 | PhS | $CH_3$ | $CH_3$ | $CH_3$ | OH | $CHCH_3$ |
| B241 | PhSO | $CH_3$ | $CH_3$ | $CH_3$ | OH | $CHCH_3$ |
| B242 | $PhSO_2$ | $CH_3$ | $CH_3$ | $CH_3$ | OH | $CHCH_3$ |
| B243 | CN | $CH_3$ | $CH_3$ | $CH_3$ | OH | $CHCH_3$ |
| B244 | $CH_3CH_2$ | $CH_3CH_2$ | H | H | OH | $CHCH_3$ |
| B245 | $CH_3CH_2CH_2$ | $CH_3CH_2$ | H | H | OH | $CHCH_3$ |
| B246 | $(CH_3)_2CH$ | $CH_3CH_2$ | H | H | OH | $CHCH_3$ |
| B247 | $(CH_3)_3C$ | $CH_3CH_2$ | H | H | OH | $CHCH_3$ |
| B248 | $CH_3S$ | $CH_3CH_2$ | H | H | OH | $CHCH_3$ |
| B249 | $CH_3SO$ | $CH_3CH_2$ | H | H | OH | $CHCH_3$ |
| B250 | $CH_3SO_2$ | $CH_3CH_2$ | H | H | OH | $CHCH_3$ |
| B251 | Ph | $CH_3CH_2$ | H | H | OH | $CHCH_3$ |
| B252 | $CH_3O$ | $CH_3CH_2$ | H | H | OH | $CHCH_3$ |
| B253 | $CH_3CO_2$ | $CH_3CH_2$ | H | H | OH | $CHCH_3$ |
| B254 | $CH_3CH_2CO_2$ | $CH_3CH_2$ | H | H | OH | $CHCH_3$ |

TABLE 6-continued

Radicals B:

| Radical | $R_{44}$ | $R_{37}$ | $R_{38}$ | $R_{39}$ | $R_{40}$ | W |
|---|---|---|---|---|---|---|
| B255 | CH$_2$=CHCH$_2$ | CH$_3$CH$_2$ | H | H | OH | CHCH$_3$ |
| B256 | HCCCH$_2$ | CH$_3$CH$_2$ | H | H | OH | CHCH$_3$ |
| B257 | CF$_3$ | CH$_3$CH$_2$ | H | H | OH | CHCH$_3$ |
| B258 | (CH$_3$)$_2$NSO$_2$ | CH$_3$CH$_2$ | H | H | OH | CHCH$_3$ |
| B259 | (CH$_3$)$_2$N | CH$_3$CH$_2$ | H | H | OH | CHCH$_3$ |
| B260 | PhO | CH$_3$CH$_2$ | H | H | OH | CHCH$_3$ |
| B261 | PhS | CH$_3$CH$_2$ | H | H | OH | CHCH$_3$ |
| B262 | PhSO | CH$_3$CH$_2$ | H | H | OH | CHCH$_3$ |
| B263 | PhSO$_2$ | CH$_3$CH$_2$ | H | H | OH | CHCH$_3$ |
| B264 | CN | CH$_3$CH$_2$ | H | H | OH | CHCH$_3$ |
| B265 | H | H | H | H | OH | C=O |
| B266 | CH$_3$ | H | H | H | OH | C=O |
| B267 | CH$_3$CH$_2$ | H | H | H | OH | C=O |
| B268 | CH$_3$CH$_2$CH$_2$ | H | H | H | OH | C=O |
| B269 | (CH$_3$)$_2$CH | H | H | H | OH | C=O |
| B270 | (CH$_3$)$_3$C | H | H | H | OH | C=O |
| B271 | CH$_3$S | H | H | H | OH | C=O |
| B272 | CH$_3$SO | H | H | H | OH | C=O |
| B273 | CH$_3$SO$_2$ | H | H | H | OH | C=O |
| B274 | Ph | H | H | H | OH | C=O |
| B275 | CH$_3$O | H | H | H | OH | C=O |
| B276 | CH$_3$CO$_2$ | H | H | H | OH | C=O |
| B277 | CH$_3$CH$_2$CO$_2$ | H | H | H | OH | C=O |
| B278 | CH$_2$=CHCH$_2$ | H | H | H | OH | C=O |
| B279 | HCCCH$_2$ | H | H | H | OH | C=O |
| B280 | CF$_3$ | H | H | H | OH | C=O |
| B281 | (CH$_3$)$_2$NSO$_2$ | H | H | H | OH | C=O |
| B282 | (CH$_3$)$_2$N | H | H | H | OH | C=O |
| B283 | PhO | H | H | H | OH | C=O |
| B284 | PhS | H | H | H | OH | C=O |
| B285 | PhSO | H | H | H | OH | C=O |
| B286 | PhSO$_2$ | H | H | H | OH | C=O |
| B287 | CN | H | H | H | OH | C=O |
| B288 | CH$_3$ | CH$_3$ | H | H | OH | C=O |
| B289 | CH$_3$CH$_2$ | CH$_3$ | H | H | OH | C=O |
| B290 | CH$_3$CH$_2$CH$_2$ | CH$_3$ | H | H | OH | C=O |
| B291 | (CH$_3$)$_2$CH | CH$_3$ | H | H | OH | C=O |
| B292 | (CH$_3$)$_3$C | CH$_3$ | H | H | OH | C=O |
| B293 | CH$_3$S | CH$_3$ | H | H | OH | C=O |
| B294 | CH$_3$SO | CH$_3$ | H | H | OH | C=O |
| B295 | CH$_3$SO$_2$ | CH$_3$ | H | H | OH | C=O |
| B296 | Ph | CH$_3$ | H | H | OH | C=O |
| B297 | CH$_3$O | CH$_3$ | H | H | OH | C=O |
| B298 | CH$_3$CO$_2$ | CH$_3$ | H | H | OH | C=O |
| B299 | CH$_3$CH$_2$CO$_2$ | CH$_3$ | H | H | OH | C=O |
| B300 | CH$_2$=CHCH$_2$ | CH$_3$ | H | H | OH | C=O |
| B301 | HCCCH$_2$ | CH$_3$ | H | H | OH | C=O |
| B302 | CF$_3$ | CH$_3$ | H | H | OH | C=O |
| B303 | (CH$_3$)$_2$NSO$_2$ | CH$_3$ | H | H | OH | C=O |
| B304 | (CH$_3$)$_2$N | CH$_3$ | H | H | OH | C=O |
| B305 | PhO | CH$_3$ | H | H | OH | C=O |
| B306 | PhS | CH$_3$ | H | H | OH | C=O |
| B307 | PhSO | CH$_3$ | H | H | OH | C=O |
| B308 | PhSO$_2$ | CH$_3$ | H | H | OH | C=O |
| B309 | CN | CH$_3$ | H | H | OH | C=O |
| B310 | CH$_3$ | H | CH$_3$ | H | OH | C=O |
| B311 | CH$_3$CH$_2$ | H | CH$_3$ | H | OH | C=O |
| B312 | CH$_3$CH$_2$CH$_2$ | H | CH$_3$ | H | OH | C=O |
| B313 | (CH$_3$)$_2$CH | H | CH$_3$ | H | OH | C=O |
| B314 | (CH$_3$)$_3$C | H | CH$_3$ | H | OH | C=O |
| B315 | CH$_3$S | H | CH$_3$ | H | OH | C=O |
| B316 | CH$_3$SO | H | CH$_3$ | H | OH | C=O |
| B317 | CH$_3$SO$_2$ | H | CH$_3$ | H | OH | C=O |
| B318 | Ph | H | CH$_3$ | H | OH | C=O |
| B319 | CH$_3$O | H | CH$_3$ | H | OH | C=O |
| B320 | CH$_3$CO$_2$ | H | CH$_3$ | H | OH | C=O |
| B321 | CH$_3$CH$_2$CO$_2$ | H | CH$_3$ | H | OH | C=O |
| B322 | CH$_2$=CHCH$_2$ | H | CH$_3$ | H | OH | C=O |
| B323 | HCCCH$_2$ | H | CH$_3$ | H | OH | C=O |
| B324 | CF$_3$ | H | CH$_3$ | H | OH | C=O |
| B325 | (CH$_3$)$_2$NSO$_2$ | H | CH$_3$ | H | OH | C=O |
| B326 | (CH$_3$)$_2$N | H | CH$_3$ | H | OH | C=O |
| B327 | PhO | H | CH$_3$ | H | OH | C=O |
| B328 | PhS | H | CH$_3$ | H | OH | C=O |
| B329 | PhSO | H | CH$_3$ | H | OH | C=O |

TABLE 6-continued

Radicals B:

| Radical | $R_{44}$ | $R_{37}$ | $R_{38}$ | $R_{39}$ | $R_{40}$ | W |
|---|---|---|---|---|---|---|
| B330 | $PhSO_2$ | H | $CH_3$ | H | OH | C=O |
| B331 | CN | H | $CH_3$ | H | OH | C=O |
| B332 | $CH_3$ | $CH_3$ | $CH_3$ | H | OH | C=O |
| B333 | $CH_3CH_2$ | $CH_3$ | $CH_3$ | H | OH | C=O |
| B334 | $CH_3CH_2CH_2$ | $CH_3$ | $CH_3$ | H | OH | C=O |
| B335 | $(CH_3)_2CH$ | $CH_3$ | $CH_3$ | H | OH | C=O |
| B336 | $(CH_3)_3C$ | $CH_3$ | $CH_3$ | H | OH | C=O |
| B337 | $CH_3S$ | $CH_3$ | $CH_3$ | H | OH | C=O |
| B338 | $CH_3SO$ | $CH_3$ | $CH_3$ | H | OH | C=O |
| B339 | $CH_3SO_2$ | $CH_3$ | $CH_3$ | H | OH | C=O |
| B340 | Ph | $CH_3$ | $CH_3$ | H | OH | C=O |
| B341 | $CH_3O$ | $CH_3$ | $CH_3$ | H | OH | C=O |
| B342 | $CH_3CO_2$ | $CH_3$ | $CH_3$ | H | OH | C=O |
| B343 | $CH_3CH_2CO_2$ | $CH_3$ | $CH_3$ | H | OH | C=O |
| B344 | $CH_2=CHCH_2$ | $CH_3$ | $CH_3$ | H | OH | C=O |
| B345 | $HCCCH_2$ | $CH_3$ | $CH_3$ | H | OH | C=O |
| B346 | $CF_3$ | $CH_3$ | $CH_3$ | H | OH | C=O |
| B347 | $(CH_3)_2NSO_2$ | $CH_3$ | $CH_3$ | H | OH | C=O |
| B348 | $(CH_3)_2N$ | $CH_3$ | $CH_3$ | H | OH | C=O |
| B349 | PhO | $CH_3$ | $CH_3$ | H | OH | C=O |
| B350 | PhS | $CH_3$ | $CH_3$ | H | OH | C=O |
| B351 | PhSO | $CH_3$ | $CH_3$ | H | OH | C=O |
| B352 | $PhSO_2$ | $CH_3$ | $CH_3$ | H | OH | C=O |
| B353 | CN | $CH_3$ | $CH_3$ | H | OH | C=O |
| B354 | $CH_3$ | $CH_3$ | $CH_3$ | $CH_3$ | OH | C=O |
| B355 | $CH_3CH_2$ | $CH_3$ | $CH_3$ | $CH_3$ | OH | C=O |
| B356 | $CH_3CH_2CH_2$ | $CH_3$ | $CH_3$ | $CH_3$ | OH | C=O |
| B357 | $(CH_3)_2CH$ | $CH_3$ | $CH_3$ | $CH_3$ | OH | C=O |
| B358 | $(CH_3)_3C$ | $CH_3$ | $CH_3$ | $CH_3$ | OH | C=O |
| B359 | $CH_3S$ | $CH_3$ | $CH_3$ | $CH_3$ | OH | C=O |
| B360 | $CH_3SO$ | $CH_3$ | $CH_3$ | $CH_3$ | OH | C=O |
| B361 | $CH_3SO_2$ | $CH_3$ | $CH_3$ | $CH_3$ | OH | C=O |
| B362 | Ph | $CH_3$ | $CH_3$ | $CH_3$ | OH | C=O |
| B363 | $CH_3O$ | $CH_3$ | $CH_3$ | $CH_3$ | OH | C=O |
| B364 | $CH_3CO_2$ | $CH_3$ | $CH_3$ | $CH_3$ | OH | C=O |
| B365 | $CH_3CH_2CO_2$ | $CH_3$ | $CH_3$ | $CH_3$ | OH | C=O |
| B366 | $CH_2=CHCH_2$ | $CH_3$ | $CH_3$ | $CH_3$ | OH | C=O |
| B367 | $HCCCH_2$ | $CH_3$ | $CH_3$ | $CH_3$ | OH | C=O |
| B368 | $CF_3$ | $CH_3$ | $CH_3$ | $CH_3$ | OH | C=O |
| B369 | $(CH_3)_2NSO_2$ | $CH_3$ | $CH_3$ | $CH_3$ | OH | C=O |
| B370 | $(CH_3)_2N$ | $CH_3$ | $CH_3$ | $CH_3$ | OH | C=O |
| B371 | PhO | $CH_3$ | $CH_3$ | $CH_3$ | OH | C=O |
| B372 | PhS | $CH_3$ | $CH_3$ | $CH_3$ | OH | C=O |
| B373 | PhSO | $CH_3$ | $CH_3$ | $CH_3$ | OH | C=O |
| B374 | $PhSO_2$ | $CH_3$ | $CH_3$ | $CH_3$ | OH | C=O |
| B375 | CN | $CH_3$ | $CH_3$ | $CH_3$ | OH | C=O |
| B376 | $CH_3CH_2$ | $CH_3CH_2$ | H | H | OH | C=O |
| B377 | $CH_3CH_2CH_2$ | $CH_3CH_2$ | H | H | OH | C=O |
| B378 | $(CH_3)_2CH$ | $CH_3CH_2$ | H | H | OH | C=O |
| B379 | $(CH_3)_3C$ | $CH_3CH_2$ | H | H | OH | C=O |
| B380 | $CH_3S$ | $CH_3CH_2$ | H | H | OH | C=O |
| B381 | $CH_3SO$ | $CH_3CH_2$ | H | H | OH | C=O |
| B382 | $CH_3SO_2$ | $CH_3CH_2$ | H | H | OH | C=O |
| B383 | Ph | $CH_3CH_2$ | H | H | OH | C=O |
| B384 | $CH_3O$ | $CH_3CH_2$ | H | H | OH | C=O |
| B385 | $CH_3CO_2$ | $CH_3CH_2$ | H | H | OH | C=O |
| B386 | $CH_3CH_2CO_2$ | $CH_3CH_2$ | H | H | OH | C=O |
| B387 | $CH_2=CHCH_2$ | $CH_3CH_2$ | H | H | OH | C=O |
| B388 | $HCCCH_2$ | $CH_3CH_2$ | H | H | OH | C=O |
| B389 | $CF_3$ | $CH_3CH_2$ | H | H | OH | C=O |
| B390 | $(CH_3)_2NSO_2$ | $CH_3CH_2$ | H | H | OH | C=O |
| B391 | $(CH_3)_2N$ | $CH_3CH_2$ | H | H | OH | C=O |
| B392 | PhO | $CH_3CH_2$ | H | H | OH | C=O |
| B393 | PhS | $CH_3CH_2$ | H | H | OH | C=O |
| B394 | PhSO | $CH_3CH_2$ | H | H | OH | C=O |
| B395 | $PhSO_2$ | $CH_3CH_2$ | H | H | OH | C=O |
| B396 | CN | $CH_3CH_2$ | H | H | OH | C=O |
| B397 | H | H | H | H | OH | N—$CH_3$ |
| B398 | $CH_3$ | H | H | H | OH | N—$CH_3$ |
| B399 | $CH_3CH_2$ | H | H | H | OH | N—$CH_3$ |
| B400 | $CH_3CH_2CH_2$ | H | H | H | OH | N—$CH_3$ |
| B401 | $(CH_3)_2CH$ | H | H | H | OH | N—$CH_3$ |
| B402 | $(CH_3)_3C$ | H | H | H | OH | N—$CH_3$ |
| B403 | $CH_3S$ | H | H | H | OH | N—$CH_3$ |
| B404 | $CH_3SO$ | H | H | H | OH | N—$CH_3$ |

TABLE 6-continued

Radicals B:

| Radical | $R_{44}$ | $R_{37}$ | $R_{38}$ | $R_{39}$ | $R_{40}$ | W |
|---|---|---|---|---|---|---|
| B405 | $CH_3SO_2$ | H | H | H | OH | N—$CH_3$ |
| B406 | Ph | H | H | H | OH | N—$CH_3$ |
| B407 | $CH_3O$ | H | H | H | OH | N—$CH_3$ |
| B408 | $CH_3CO_2$ | H | H | H | OH | N—$CH_3$ |
| B409 | $CH_3CH_2CO_2$ | H | H | H | OH | N—$CH_3$ |
| B410 | $CH_2$=$CHCH_2$ | H | H | H | OH | N—$CH_3$ |
| B411 | $HCCCH_2$ | H | H | H | OH | N—$CH_3$ |
| B412 | $CF_3$ | H | H | H | OH | N—$CH_3$ |
| B413 | $(CH_3)_2NSO_2$ | H | H | H | OH | N—$CH_3$ |
| B414 | $(CH_3)_2N$ | H | H | H | OH | N—$CH_3$ |
| B415 | PhO | H | H | H | OH | N—$CH_3$ |
| B416 | PhS | H | H | H | OH | N—$CH_3$ |
| B417 | PhSO | H | H | H | OH | N—$CH_3$ |
| B418 | $PhSO_2$ | H | H | H | OH | N—$CH_3$ |
| B419 | CN | H | H | H | OH | N—$CH_3$ |
| B420 | $CH_3$ | $CH_3$ | H | H | OH | N—$CH_3$ |
| B421 | $CH_3CH_2$ | $CH_3$ | H | H | OH | N—$CH_3$ |
| B422 | $CH_3CH_2CH_2$ | $CH_3$ | H | H | OH | N—$CH_3$ |
| B423 | $(CH_3)_2CH$ | $CH_3$ | H | H | OH | N—$CH_3$ |
| B424 | $(CH_3)_3C$ | $CH_3$ | H | H | OH | N—$CH_3$ |
| B425 | $CH_3S$ | $CH_3$ | H | H | OH | N—$CH_3$ |
| B426 | $CH_3SO$ | $CH_3$ | H | H | OH | N—$CH_3$ |
| B427 | $CH_3SO_2$ | $CH_3$ | H | H | OH | N—$CH_3$ |
| B428 | Ph | $CH_3$ | H | H | OH | N—$CH_3$ |
| B429 | $CH_3O$ | $CH_3$ | H | H | OH | N—$CH_3$ |
| B430 | $CH_3CO_2$ | $CH_3$ | H | H | OH | N—$CH_3$ |
| B431 | $CH_3CH_2CO_2$ | $CH_3$ | H | H | OH | N—$CH_3$ |
| B432 | $CH_2$=$CHCH_2$ | $CH_3$ | H | H | OH | N—$CH_3$ |
| B433 | $HCCCH_2$ | $CH_3$ | H | H | OH | N—$CH_3$ |
| B434 | $CF_3$ | $CH_3$ | H | H | OH | N—$CH_3$ |
| B435 | $(CH_3)_2NSO_2$ | $CH_3$ | H | H | OH | N—$CH_3$ |
| B436 | $(CH_3)_2N$ | $CH_3$ | H | H | OH | N—$CH_3$ |
| B437 | PhO | $CH_3$ | H | H | OH | N—$CH_3$ |
| B438 | PhS | $CH_3$ | H | H | OH | N—$CH_3$ |
| B439 | PhSO | $CH_3$ | H | H | OH | N—$CH_3$ |
| B440 | $PhSO_2$ | $CH_3$ | H | H | OH | N—$CH_3$ |
| B441 | CN | $CH_3$ | H | H | OH | N—$CH_3$ |
| B442 | $CH_3$ | H | $CH_3$ | H | OH | N—$CH_3$ |
| B443 | $CH_3CH_2$ | H | $CH_3$ | H | OH | N—$CH_3$ |
| B444 | $CH_3CH_2CH_2$ | H | $CH_3$ | H | OH | N—$CH_3$ |
| B445 | $(CH_3)_2CH$ | H | $CH_3$ | H | OH | N—$CH_3$ |
| B446 | $(CH_3)_3C$ | H | $CH_3$ | H | OH | N—$CH_3$ |
| B447 | $CH_3S$ | H | $CH_3$ | H | OH | N—$CH_3$ |
| B448 | $CH_3SO$ | H | $CH_3$ | H | OH | N—$CH_3$ |
| B449 | $CH_3SO_2$ | H | $CH_3$ | H | OH | N—$CH_3$ |
| B450 | Ph | H | $CH_3$ | H | OH | N—$CH_3$ |
| B451 | $CH_3O$ | H | $CH_3$ | H | OH | N—$CH_3$ |
| B452 | $CH_3CO_2$ | H | $CH_3$ | H | OH | N—$CH_3$ |
| B453 | $CH_3CH_2CO_2$ | H | $CH_3$ | H | OH | N—$CH_3$ |
| B454 | $CH_2$=$CHCH_2$ | H | $CH_3$ | H | OH | N—$CH_3$ |
| B455 | $HCCCH_2$ | H | $CH_3$ | H | OH | N—$CH_3$ |
| B456 | $CF_3$ | H | $CH_3$ | H | OH | N—$CH_3$ |
| B457 | $(CH_3)_2NSO_2$ | H | $CH_3$ | H | OH | N—$CH_3$ |
| B458 | $(CH_3)_2N$ | H | $CH_3$ | H | OH | N—$CH_3$ |
| B459 | PhO | H | $CH_3$ | H | OH | N—$CH_3$ |
| B460 | PhS | H | $CH_3$ | H | OH | N—$CH_3$ |
| B461 | PhSO | H | $CH_3$ | H | OH | N—$CH_3$ |
| B462 | $PhSO_2$ | H | $CH_3$ | H | OH | N—$CH_3$ |
| B463 | CN | H | $CH_3$ | H | OH | N—$CH_3$ |
| B464 | $CH_3$ | $CH_3$ | $CH_3$ | H | OH | N—$CH_3$ |
| B465 | $CH_3CH_2$ | $CH_3$ | $CH_3$ | H | OH | N—$CH_3$ |
| B466 | $CH_3CH_2CH_2$ | $CH_3$ | $CH_3$ | H | OH | N—$CH_3$ |
| B467 | $(CH_3)_2CH$ | $CH_3$ | $CH_3$ | H | OH | N—$CH_3$ |
| B468 | $(CH_3)_3C$ | $CH_3$ | $CH_3$ | H | OH | N—$CH_3$ |
| B469 | $CH_3S$ | $CH_3$ | $CH_3$ | H | OH | N—$CH_3$ |
| B470 | $CH_3SO$ | $CH_3$ | $CH_3$ | H | OH | N—$CH_3$ |
| B471 | $CH_3SO_2$ | $CH_3$ | $CH_3$ | H | OH | N—$CH_3$ |
| B472 | Ph | $CH_3$ | $CH_3$ | H | OH | N—$CH_3$ |
| B473 | $CH_3O$ | $CH_3$ | $CH_3$ | H | OH | N—$CH_3$ |
| B474 | $CH_3CO_2$ | $CH_3$ | $CH_3$ | H | OH | N—$CH_3$ |
| B475 | $CH_3CH_2CO_2$ | $CH_3$ | $CH_3$ | H | OH | N—$CH_3$ |
| B476 | $CH_2$=$CHCH_2$ | $CH_3$ | $CH_3$ | H | OH | N—$CH_3$ |
| B477 | $HCCCH_2$ | $CH_3$ | $CH_3$ | H | OH | N—$CH_3$ |
| B478 | $CF_3$ | $CH_3$ | $CH_3$ | H | OH | N—$CH_3$ |
| B479 | $(CH_3)_2NSO_2$ | $CH_3$ | $CH_3$ | H | OH | N—$CH_3$ |

TABLE 6-continued

Radicals B:

| Radical | $R_{44}$ | $R_{37}$ | $R_{38}$ | $R_{39}$ | $R_{40}$ | W |
|---|---|---|---|---|---|---|
| B480 | $(CH_3)_2N$ | $CH_3$ | $CH_3$ | H | OH | $N-CH_3$ |
| B481 | PhO | $CH_3$ | $CH_3$ | H | OH | $N-CH_3$ |
| B482 | PhS | $CH_3$ | $CH_3$ | H | OH | $N-CH_3$ |
| B483 | PhSO | $CH_3$ | $CH_3$ | H | OH | $N-CH_3$ |
| B484 | $PhSO_2$ | $CH_3$ | $CH_3$ | H | OH | $N-CH_3$ |
| B485 | CN | $CH_3$ | $CH_3$ | H | OH | $N-CH_3$ |
| B486 | $CH_3$ | $CH_3$ | $CH_3$ | $CH_3$ | OH | $N-CH_3$ |
| B487 | $CH_3CH_2$ | $CH_3$ | $CH_3$ | $CH_3$ | OH | $N-CH_3$ |
| B488 | $CH_3CH_2CH_2$ | $CH_3$ | $CH_3$ | $CH_3$ | OH | $N-CH_3$ |
| B489 | $(CH_3)_2CH$ | $CH_3$ | $CH_3$ | $CH_3$ | OH | $N-CH_3$ |
| B490 | $(CH_3)_3C$ | $CH_3$ | $CH_3$ | $CH_3$ | OH | $N-CH_3$ |
| B491 | $CH_3S$ | $CH_3$ | $CH_3$ | $CH_3$ | OH | $N-CH_3$ |
| B492 | $CH_3SO$ | $CH_3$ | $CH_3$ | $CH_3$ | OH | $N-CH_3$ |
| B493 | $CH_3SO_2$ | $CH_3$ | $CH_3$ | $CH_3$ | OH | $N-CH_3$ |
| B494 | Ph | $CH_3$ | $CH_3$ | $CH_3$ | OH | $N-CH_3$ |
| B495 | $CH_3O$ | $CH_3$ | $CH_3$ | $CH_3$ | OH | $N-CH_3$ |
| B496 | $CH_3CO_2$ | $CH_3$ | $CH_3$ | $CH_3$ | OH | $N-CH_3$ |
| B497 | $CH_3CH_2CO_2$ | $CH_3$ | $CH_3$ | $CH_3$ | OH | $N-CH_3$ |
| B498 | $CH_2=CHCH_2$ | $CH_3$ | $CH_3$ | $CH_3$ | OH | $N-CH_3$ |
| B499 | $HCCCH_2$ | $CH_3$ | $CH_3$ | $CH_3$ | OH | $N-CH_3$ |
| B500 | $CF_3$ | $CH_3$ | $CH_3$ | $CH_3$ | OH | $N-CH_3$ |
| B501 | $(CH_3)_2NSO_2$ | $CH_3$ | $CH_3$ | $CH_3$ | OH | $N-CH_3$ |
| B502 | $(CH_3)_2N$ | $CH_3$ | $CH_3$ | $CH_3$ | OH | $N-CH_3$ |
| B503 | PhO | $CH_3$ | $CH_3$ | $CH_3$ | OH | $N-CH_3$ |
| B504 | PhS | $CH_3$ | $CH_3$ | $CH_3$ | OH | $N-CH_3$ |
| B505 | PhSO | $CH_3$ | $CH_3$ | $CH_3$ | OH | $N-CH_3$ |
| B506 | $PhSO_2$ | $CH_3$ | $CH_3$ | $CH_3$ | OH | $N-CH_3$ |
| B507 | CN | $CH_3$ | $CH_3$ | $CH_3$ | OH | $N-CH_3$ |
| B508 | $CH_3CH_2$ | $CH_3CH_2$ | H | H | OH | $N-CH_3$ |
| B509 | $CH_3CH_2CH_2$ | $CH_3CH_2$ | H | H | OH | $N-CH_3$ |
| B510 | $(CH_3)_2CH$ | $CH_3CH_2$ | H | H | OH | $N-CH_3$ |
| B511 | $(CH_3)_3C$ | $CH_3CH_2$ | H | H | OH | $N-CH_3$ |
| B512 | $CH_3S$ | $CH_3CH_2$ | H | H | OH | $N-CH_3$ |
| B513 | $CH_3SO$ | $CH_3CH_2$ | H | H | OH | $N-CH_3$ |
| B514 | $CH_3SO_2$ | $CH_3CH_2$ | H | H | OH | $N-CH_3$ |
| B515 | Ph | $CH_3CH_2$ | H | H | OH | $N-CH_3$ |
| B516 | $CH_3O$ | $CH_3CH_2$ | H | H | OH | $N-CH_3$ |
| B517 | $CH_3CO_2$ | $CH_3CH_2$ | H | H | OH | $N-CH_3$ |
| B518 | $CH_3CH_2CO_2$ | $CH_3CH_2$ | H | H | OH | $N-CH_3$ |
| B519 | $CH_2=CHCH_2$ | $CH_3CH_2$ | H | H | OH | $N-CH_3$ |
| B520 | $HCCCH_2$ | $CH_3CH_2$ | H | H | OH | $N-CH_3$ |
| B521 | $CF_3$ | $CH_3CH_2$ | H | H | OH | $N-CH_3$ |
| B522 | $(CH_3)_2NSO_2$ | $CH_3CH_2$ | H | H | OH | $N-CH_3$ |
| B523 | $(CH_3)_2N$ | $CH_3CH_2$ | H | H | OH | $N-CH_3$ |
| B524 | PhO | $CH_3CH_2$ | H | H | OH | $N-CH_3$ |
| B525 | PhS | $CH_3CH_2$ | H | H | OH | $N-CH_3$ |
| B526 | PhSO | $CH_3CH_2$ | H | H | OH | $N-CH_3$ |
| B527 | $PhSO_2$ | $CH_3CH_2$ | H | H | OH | $N-CH_3$ |
| B528 | CN | $CH_3CH_2$ | H | H | OH | $N-CH_3$ |
| B529 | H | H | H | H | OH | O |
| B530 | $CH_3$ | H | H | H | OH | O |
| B531 | $CH_3CH_2$ | H | H | H | OH | O |
| B532 | $CH_3CH_2CH_2$ | H | H | H | OH | O |
| B533 | $(CH_3)_2CH$ | H | H | H | OH | O |
| B534 | $(CH_3)_3C$ | H | H | H | OH | O |
| B535 | $CH_3S$ | H | H | H | OH | O |
| B536 | $CH_3SO$ | H | H | H | OH | O |
| B537 | $CH_3SO_2$ | H | H | H | OH | O |
| B538 | Ph | H | H | H | OH | O |
| B539 | $CH_3O$ | H | H | H | OH | O |
| B540 | $CH_3CO_2$ | H | H | H | OH | O |
| B541 | $CH_3CH_2CO_2$ | H | H | H | OH | O |
| B542 | $CH_2=CHCH_2$ | H | H | H | OH | O |
| B543 | $HCCCH_2$ | H | H | H | OH | O |
| B544 | $CF_3$ | H | H | H | OH | O |
| B545 | $(CH_3)_2NSO_2$ | H | H | H | OH | O |
| B546 | $(CH_3)_2N$ | H | H | H | OH | O |
| B547 | PhO | H | H | H | OH | O |
| B548 | PhS | H | H | H | OH | O |
| B549 | PhSO | H | H | H | OH | O |
| B550 | $PhSO_2$ | H | H | H | OH | O |
| B551 | CN | H | H | H | OH | O |
| B552 | $CH_3$ | $CH_3$ | H | H | OH | O |
| B553 | $CH_3CH_2$ | $CH_3$ | H | H | OH | O |
| B554 | $CH_3CH_2CH_2$ | $CH_3$ | H | H | OH | O |

TABLE 6-continued

Radicals B:

| Radical | $R_{44}$ | $R_{37}$ | $R_{38}$ | $R_{39}$ | $R_{40}$ | W |
|---|---|---|---|---|---|---|
| B555 | $(CH_3)_2CH$ | $CH_3$ | H | H | OH | O |
| B556 | $(CH_3)_3C$ | $CH_3$ | H | H | OH | O |
| B557 | $CH_3S$ | $CH_3$ | H | H | OH | O |
| B558 | $CH_3SO$ | $CH_3$ | H | H | OH | O |
| B559 | $CH_3SO_2$ | $CH_3$ | H | H | OH | O |
| B560 | Ph | $CH_3$ | H | H | OH | O |
| B561 | $CH_3O$ | $CH_3$ | H | H | OH | O |
| B562 | $CH_3CO_2$ | $CH_3$ | H | H | OH | O |
| B563 | $CH_3CH_2CO_2$ | $CH_3$ | H | H | OH | O |
| B564 | $CH_2=CHCH_2$ | $CH_3$ | H | H | OH | O |
| B565 | $HCCCH_2$ | $CH_3$ | H | H | OH | O |
| B566 | $CF_3$ | $CH_3$ | H | H | OH | O |
| B567 | $(CH_3)_2NSO_2$ | $CH_3$ | H | H | OH | O |
| B568 | $(CH_3)_2N$ | $CH_3$ | H | H | OH | O |
| B569 | PhO | $CH_3$ | H | H | OH | O |
| B570 | PhS | $CH_3$ | H | H | OH | O |
| B571 | PhSO | $CH_3$ | H | H | OH | O |
| B572 | $PhSO_2$ | $CH_3$ | H | H | OH | O |
| B573 | CN | $CH_3$ | H | H | OH | O |
| B574 | $CH_3$ | H | $CH_3$ | H | OH | O |
| B575 | $CH_3CH_2$ | H | $CH_3$ | H | OH | O |
| B576 | $CH_3CH_2CH_2$ | H | $CH_3$ | H | OH | O |
| B577 | $(CH_3)_2CH$ | H | $CH_3$ | H | OH | O |
| B578 | $(CH_3)_3C$ | H | $CH_3$ | H | OH | O |
| B579 | $CH_3S$ | H | $CH_3$ | H | OH | O |
| B580 | $CH_3SO$ | H | $CH_3$ | H | OH | O |
| B581 | $CH_3SO_2$ | H | $CH_3$ | H | OH | O |
| B582 | Ph | H | $CH_3$ | H | OH | O |
| B583 | $CH_3O$ | H | $CH_3$ | H | OH | O |
| B584 | $CH_3CO_2$ | H | $CH_3$ | H | OH | O |
| B585 | $CH_3CH_2CO_2$ | H | $CH_3$ | H | OH | O |
| B586 | $CH_2=CHCH_2$ | H | $CH_3$ | H | OH | O |
| B587 | $HCCCH_2$ | H | $CH_3$ | H | OH | O |
| B588 | $CF_3$ | H | $CH_3$ | H | OH | O |
| B589 | $(CH_3)_2NSO_2$ | H | $CH_3$ | H | OH | O |
| B590 | $(CH_3)_2N$ | H | $CH_3$ | H | OH | O |
| B591 | PhO | H | $CH_3$ | H | OH | O |
| B592 | PhS | H | $CH_3$ | H | OH | O |
| B593 | PhSO | H | $CH_3$ | H | OH | O |
| B594 | $PhSO_2$ | H | $CH_3$ | H | OH | O |
| B595 | CN | H | $CH_3$ | H | OH | O |
| B596 | $CH_3$ | $CH_3$ | $CH_3$ | H | OH | O |
| B597 | $CH_3CH_2$ | $CH_3$ | $CH_3$ | H | OH | O |
| B598 | $CH_3CH_2CH_2$ | $CH_3$ | $CH_3$ | H | OH | O |
| B599 | $(CH_3)_2CH$ | $CH_3$ | $CH_3$ | H | OH | O |
| B600 | $(CH_3)_3C$ | $CH_3$ | $CH_3$ | H | OH | O |
| B601 | $CH_3S$ | $CH_3$ | $CH_3$ | H | OH | O |
| B602 | $CH_3SO$ | $CH_3$ | $CH_3$ | H | OH | O |
| B603 | $CH_3SO_2$ | $CH_3$ | $CH_3$ | H | OH | O |
| B604 | Ph | $CH_3$ | $CH_3$ | H | OH | O |
| B605 | $CH_3O$ | $CH_3$ | $CH_3$ | H | OH | O |
| B606 | $CH_3CO_2$ | $CH_3$ | $CH_3$ | H | OH | O |
| B607 | $CH_3CH_2CO_2$ | $CH_3$ | $CH_3$ | H | OH | O |
| B608 | $CH_2=CHCH_2$ | $CH_3$ | $CH_3$ | H | OH | O |
| B609 | $HCCCH_2$ | $CH_3$ | $CH_3$ | H | OH | O |
| B610 | $CF_3$ | $CH_3$ | $CH_3$ | H | OH | O |
| B611 | $(CH_3)_2NSO_2$ | $CH_3$ | $CH_3$ | H | OH | O |
| B612 | $(CH_3)_2N$ | $CH_3$ | $CH_3$ | H | OH | O |
| B613 | PhO | $CH_3$ | $CH_3$ | H | OH | O |
| B614 | PhS | $CH_3$ | $CH_3$ | H | OH | O |
| B615 | PhSO | $CH_3$ | $CH_3$ | H | OH | O |
| B616 | $PhSO_2$ | $CH_3$ | $CH_3$ | H | OH | O |
| B617 | CN | $CH_3$ | $CH_3$ | H | OH | O |
| B618 | $CH_3$ | $CH_3$ | $CH_3$ | $CH_3$ | OH | O |
| B619 | $CH_3CH_2$ | $CH_3$ | $CH_3$ | $CH_3$ | OH | O |
| B620 | $CH_3CH_2CH_2$ | $CH_3$ | $CH_3$ | $CH_3$ | OH | O |
| B621 | $(CH_3)_2CH$ | $CH_3$ | $CH_3$ | $CH_3$ | OH | O |
| B622 | $(CH_3)_3C$ | $CH_3$ | $CH_3$ | $CH_3$ | OH | O |
| B623 | $CH_3S$ | $CH_3$ | $CH_3$ | $CH_3$ | OH | O |
| B624 | $CH_3SO$ | $CH_3$ | $CH_3$ | $CH_3$ | OH | O |
| B625 | $CH_3SO_2$ | $CH_3$ | $CH_3$ | $CH_3$ | OH | O |
| B626 | Ph | $CH_3$ | $CH_3$ | $CH_3$ | OH | O |
| B627 | $CH_3O$ | $CH_3$ | $CH_3$ | $CH_3$ | OH | O |
| B628 | $CH_3CO_2$ | $CH_3$ | $CH_3$ | $CH_3$ | OH | O |
| B629 | $CH_3CH_2CO_2$ | $CH_3$ | $CH_3$ | $CH_3$ | OH | O |

TABLE 6-continued

Radicals B:

| Radical | $R_{44}$ | $R_{37}$ | $R_{38}$ | $R_{39}$ | $R_{40}$ | W |
|---|---|---|---|---|---|---|
| B630 | $CH_2$=$CHCH_2$ | $CH_3$ | $CH_3$ | $CH_3$ | OH | O |
| B631 | $HCCCH_2$ | $CH_3$ | $CH_3$ | $CH_3$ | OH | O |
| B632 | $CF_3$ | $CH_3$ | $CH_3$ | $CH_3$ | OH | O |
| B633 | $(CH_3)_2NSO_2$ | $CH_3$ | $CH_3$ | $CH_3$ | OH | O |
| B634 | $(CH_3)_2N$ | $CH_3$ | $CH_3$ | $CH_3$ | OH | O |
| B635 | PhO | $CH_3$ | $CH_3$ | $CH_3$ | OH | O |
| B636 | PhS | $CH_3$ | $CH_3$ | $CH_3$ | OH | O |
| B637 | PhSO | $CH_3$ | $CH_3$ | $CH_3$ | OH | O |
| B638 | $PhSO_2$ | $CH_3$ | $CH_3$ | $CH_3$ | OH | O |
| B639 | CN | $CH_3$ | $CH_3$ | $CH_3$ | OH | O |
| B640 | $CH_3CH_2$ | $CH_3CH_2$ | H | H | OH | O |
| B641 | $CH_3CH_2CH_2$ | $CH_3CH_2$ | H | H | OH | O |
| B642 | $(CH_3)_2CH$ | $CH_3CH_2$ | H | H | OH | O |
| B643 | $(CH_3)_3C$ | $CH_3CH_2$ | H | H | OH | O |
| B644 | $CH_3S$ | $CH_3CH_2$ | H | H | OH | O |
| B645 | $CH_3SO$ | $CH_3CH_2$ | H | H | OH | O |
| B646 | $CH_3SO_2$ | $CH_3CH_2$ | H | H | OH | O |
| B647 | Ph | $CH_3CH_2$ | H | H | OH | O |
| B648 | $CH_3O$ | $CH_3CH_2$ | H | H | OH | O |
| B649 | $CH_3CO_2$ | $CH_3CH_2$ | H | H | OH | O |
| B650 | $CH_3CH_2CO_2$ | $CH_3CH_2$ | H | H | OH | O |
| B651 | $CH_2$=$CHCH_2$ | $CH_3CH_2$ | H | H | OH | O |
| B652 | $HCCCH_2$ | $CH_3CH_2$ | H | H | OH | O |
| B653 | $CF_3$ | $CH_3CH_2$ | H | H | OH | O |
| B654 | $(CH_3)_2NSO_2$ | $CH_3CH_2$ | H | H | OH | O |
| B655 | $(CH_3)_2N$ | $CH_3CH_2$ | H | H | OH | O |
| B656 | PhO | $CH_3CH_2$ | H | H | OH | O |
| B657 | PhS | $CH_3CH_2$ | H | H | OH | O |
| B658 | PhSO | $CH_3CH_2$ | H | H | OH | O |
| B659 | $PhSO_2$ | $CH_3CH_2$ | H | H | OH | O |
| B660 | CN | $CH_3CH_2$ | H | H | OH | O |
| B661 | H | H | H | H | OH | S |
| B662 | $CH_3$ | H | H | H | OH | S |
| B663 | $CH_3CH_2$ | H | H | H | OH | S |
| B664 | $CH_3CH_2CH_2$ | H | H | H | OH | S |
| B665 | $(CH_3)_2CH$ | H | H | H | OH | S |
| B666 | $(CH_3)_3C$ | H | H | H | OH | S |
| B667 | $CH_3S$ | H | H | H | OH | S |
| B668 | $CH_3SO$ | H | H | H | OH | S |
| B669 | $CH_3SO_2$ | H | H | H | OH | S |
| B670 | Ph | H | H | H | OH | S |
| B671 | $CH_3O$ | H | H | H | OH | S |
| B672 | $CH_3CO_2$ | H | H | H | OH | S |
| B673 | $CH_3CH_2CO_2$ | H | H | H | OH | S |
| B674 | $CH_2$=$CHCH_2$ | H | H | H | OH | S |
| B675 | $HCCCH_2$ | H | H | H | OH | S |
| B676 | $CF_3$ | H | H | H | OH | S |
| B677 | $(CH_3)_2NSO_2$ | H | H | H | OH | S |
| B678 | $(CH_3)_2N$ | H | H | H | OH | S |
| B679 | PhO | H | H | H | OH | S |
| B680 | PhS | H | H | H | OH | S |
| B681 | PhSO | H | H | H | OH | S |
| B682 | $PhSO_2$ | H | H | H | OH | S |
| B683 | CN | H | H | H | OH | S |
| B684 | $CH_3$ | $CH_3$ | H | H | OH | S |
| B685 | $CH_3CH_2$ | $CH_3$ | H | H | OH | S |
| B686 | $CH_3CH_2CH_2$ | $CH_3$ | H | H | OH | S |
| B687 | $(CH_3)_2CH$ | $CH_3$ | H | H | OH | S |
| B688 | $(CH_3)_3C$ | $CH_3$ | H | H | OH | S |
| B689 | $CH_3S$ | $CH_3$ | H | H | OH | S |
| B690 | $CH_3SO$ | $CH_3$ | H | H | OH | S |
| B691 | $CH_3SO_2$ | $CH_3$ | H | H | OH | S |
| B692 | Ph | $CH_3$ | H | H | OH | S |
| B693 | $CH_3O$ | $CH_3$ | H | H | OH | S |
| B694 | $CH_3CO_2$ | $CH_3$ | H | H | OH | S |
| B695 | $CH_3CH_2CO_2$ | $CH_3$ | H | H | OH | S |
| B696 | $CH_2$=$CHCH_2$ | $CH_3$ | H | H | OH | S |
| B697 | $HCCCH_2$ | $CH_3$ | H | H | OH | S |
| B698 | $CF_3$ | $CH_3$ | H | H | OH | S |
| B699 | $(CH_3)_2NSO_2$ | $CH_3$ | H | H | OH | S |
| B700 | $(CH_3)_2N$ | $CH_3$ | H | H | OH | S |
| B701 | PhO | $CH_3$ | H | H | OH | S |
| B702 | PhS | $CH_3$ | H | H | OH | S |
| B703 | PhSO | $CH_3$ | H | H | OH | S |
| B704 | $PhSO_2$ | $CH_3$ | H | H | OH | S |

TABLE 6-continued

Radicals B:

| Radical | $R_{44}$ | $R_{37}$ | $R_{38}$ | $R_{39}$ | $R_{40}$ | W |
|---|---|---|---|---|---|---|
| B705 | CN | $CH_3$ | H | H | OH | S |
| B706 | $CH_3$ | H | $CH_3$ | H | OH | S |
| B707 | $CH_3CH_2$ | H | $CH_3$ | H | OH | S |
| B708 | $CH_3CH_2CH_2$ | H | $CH_3$ | H | OH | S |
| B709 | $(CH_3)_2CH$ | H | $CH_3$ | H | OH | S |
| B710 | $(CH_3)_3C$ | H | $CH_3$ | H | OH | S |
| B711 | $CH_3S$ | H | $CH_3$ | H | OH | S |
| B712 | $CH_3SO$ | H | $CH_3$ | H | OH | S |
| B713 | $CH_3SO_2$ | H | $CH_3$ | H | OH | S |
| B714 | Ph | H | $CH_3$ | H | OH | S |
| B715 | $CH_3O$ | H | $CH_3$ | H | OH | S |
| B716 | $CH_3CO_2$ | H | $CH_3$ | H | OH | S |
| B717 | $CH_3CH_2CO_2$ | H | $CH_3$ | H | OH | S |
| B718 | $CH_2\!\!=\!\!CHCH_2$ | H | $CH_3$ | H | OH | S |
| B719 | $HCCCH_2$ | H | $CH_3$ | H | OH | S |
| B720 | $CF_3$ | H | $CH_3$ | H | OH | S |
| B721 | $(CH_3)_2NSO_2$ | H | $CH_3$ | H | OH | S |
| B722 | $(CH_3)_2N$ | H | $CH_3$ | H | OH | S |
| B723 | PhO | H | $CH_3$ | H | OH | S |
| B724 | PhS | H | $CH_3$ | H | OH | S |
| B725 | PhSO | H | $CH_3$ | H | OH | S |
| B726 | $PhSO_2$ | H | $CH_3$ | H | OH | S |
| B727 | CN | H | $CH_3$ | H | OH | S |
| B728 | $CH_3$ | $CH_3$ | $CH_3$ | H | OH | S |
| B729 | $CH_3CH_2$ | $CH_3$ | $CH_3$ | H | OH | S |
| B730 | $CH_3CH_2CH_2$ | $CH_3$ | $CH_3$ | H | OH | S |
| B731 | $(CH_3)_2CH$ | $CH_3$ | $CH_3$ | H | OH | S |
| B732 | $(CH_3)_3C$ | $CH_3$ | $CH_3$ | H | OH | S |
| B733 | $CH_3S$ | $CH_3$ | $CH_3$ | H | OH | S |
| B734 | $CH_3SO$ | $CH_3$ | $CH_3$ | H | OH | S |
| B735 | $CH_3SO_2$ | $CH_3$ | $CH_3$ | H | OH | S |
| B736 | Ph | $CH_3$ | $CH_3$ | H | OH | S |
| B737 | $CH_3O$ | $CH_3$ | $CH_3$ | H | OH | S |
| B738 | $CH_3CO_2$ | $CH_3$ | $CH_3$ | H | OH | S |
| B739 | $CH_3CH_2CO_2$ | $CH_3$ | $CH_3$ | H | OH | S |
| B740 | $CH_2\!\!=\!\!CHCH_2$ | $CH_3$ | $CH_3$ | H | OH | S |
| B741 | $HCCCH_2$ | $CH_3$ | $CH_3$ | H | OH | S |
| B742 | $CF_3$ | $CH_3$ | $CH_3$ | H | OH | S |
| B743 | $(CH_3)_2NSO_2$ | $CH_3$ | $CH_3$ | H | OH | S |
| B744 | $(CH_3)_2N$ | $CH_3$ | $CH_3$ | H | OH | S |
| B745 | PhO | $CH_3$ | $CH_3$ | H | OH | S |
| B746 | PhS | $CH_3$ | $CH_3$ | H | OH | S |
| B747 | PhSO | $CH_3$ | $CH_3$ | H | OH | S |
| B748 | $PhSO_2$ | $CH_3$ | $CH_3$ | H | OH | S |
| B749 | CN | $CH_3$ | $CH_3$ | H | OH | S |
| B750 | $CH_3$ | $CH_3$ | $CH_3$ | $CH_3$ | OH | S |
| B751 | $CH_3CH_2$ | $CH_3$ | $CH_3$ | $CH_3$ | OH | S |
| B752 | $CH_3CH_2CH_2$ | $CH_3$ | $CH_3$ | $CH_3$ | OH | S |
| B753 | $(CH_3)_2CH$ | $CH_3$ | $CH_3$ | $CH_3$ | OH | S |
| B754 | $(CH_3)_3C$ | $CH_3$ | $CH_3$ | $CH_3$ | OH | S |
| B755 | $CH_3S$ | $CH_3$ | $CH_3$ | $CH_3$ | OH | S |
| B756 | $CH_3SO$ | $CH_3$ | $CH_3$ | $CH_3$ | OH | S |
| B757 | $CH_3SO_2$ | $CH_3$ | $CH_3$ | $CH_3$ | OH | S |
| B758 | Ph | $CH_3$ | $CH_3$ | $CH_3$ | OH | S |
| B759 | $CH_3O$ | $CH_3$ | $CH_3$ | $CH_3$ | OH | S |
| B760 | $CH_3CO_2$ | $CH_3$ | $CH_3$ | $CH_3$ | OH | S |
| B761 | $CH_3CH_2CO_2$ | $CH_3$ | $CH_3$ | $CH_3$ | OH | S |
| B762 | $CH_2\!\!=\!\!CHCH_2$ | $CH_3$ | $CH_3$ | $CH_3$ | OH | S |
| B763 | $HCCCH_2$ | $CH_3$ | $CH_3$ | $CH_3$ | OH | S |
| B764 | $CF_3$ | $CH_3$ | $CH_3$ | $CH_3$ | OH | S |
| B765 | $(CH_3)_2NSO_2$ | $CH_3$ | $CH_3$ | $CH_3$ | OH | S |
| B766 | $(CH_3)_2N$ | $CH_3$ | $CH_3$ | $CH_3$ | OH | S |
| B767 | PhO | $CH_3$ | $CH_3$ | $CH_3$ | OH | S |
| B768 | PhS | $CH_3$ | $CH_3$ | $CH_3$ | OH | S |
| B769 | PhSO | $CH_3$ | $CH_3$ | $CH_3$ | OH | S |
| B770 | $PhSO_2$ | $CH_3$ | $CH_3$ | $CH_3$ | OH | S |
| B771 | CN | $CH_3$ | $CH_3$ | $CH_3$ | OH | S |
| B772 | $CH_3CH_2$ | $CH_3CH_2$ | H | H | OH | S |
| B773 | $CH_3CH_2CH_2$ | $CH_3CH_2$ | H | H | OH | S |
| B774 | $(CH_3)_2CH$ | $CH_3CH_2$ | H | H | OH | S |
| B775 | $(CH_3)_3C$ | $CH_3CH_2$ | H | H | OH | S |
| B776 | $CH_3S$ | $CH_3CH_2$ | H | H | OH | S |
| B777 | $CH_3SO$ | $CH_3CH_2$ | H | H | OH | S |
| B778 | $CH_3SO_2$ | $CH_3CH_2$ | H | H | OH | S |
| B779 | Ph | $CH_3CH_2$ | H | H | OH | S |

TABLE 6-continued

Radicals B:

| Radical | $R_{44}$ | $R_{37}$ | $R_{38}$ | $R_{39}$ | $R_{40}$ | W |
|---|---|---|---|---|---|---|
| B780 | $CH_3O$ | $CH_3CH_2$ | H | H | OH | S |
| B781 | $CH_3CO_2$ | $CH_3CH_2$ | H | H | OH | S |
| B782 | $CH_3CH_2CO_2$ | $CH_3CH_2$ | H | H | OH | S |
| B783 | $CH_2=CHCH_2$ | $CH_3CH_2$ | H | H | OH | S |
| B784 | $HCCCH_2$ | $CH_3CH_2$ | H | H | OH | S |
| B785 | $CF_3$ | $CH_3CH_2$ | H | H | OH | S |
| B786 | $(CH_3)_2NSO_2$ | $CH_3CH_2$ | H | H | OH | S |
| B787 | $(CH_3)_2N$ | $CH_3CH_2$ | H | H | OH | S |
| B788 | PhO | $CH_3CH_2$ | H | H | OH | S |
| B789 | PhS | $CH_3CH_2$ | H | H | OH | S |
| B790 | PhSO | $CH_3CH_2$ | H | H | OH | S |
| B791 | $PhSO_2$ | $CH_3CH_2$ | H | H | OH | S |
| B792 | CN | $CH_3CH_2$ | H | H | OH | S |
| B793 | H | H | H | H | OH | $SO_2$ |
| B794 | $CH_3$ | H | H | H | OH | $SO_2$ |
| B795 | $CH_3CH_2$ | H | H | H | OH | $SO_2$ |
| B796 | $CH_3CH_2CH_2$ | H | H | H | OH | $SO_2$ |
| B797 | $(CH_3)_2CH$ | H | H | H | OH | $SO_2$ |
| B798 | $(CH_3)_3C$ | H | H | H | OH | $SO_2$ |
| B799 | $CH_3S$ | H | H | H | OH | $SO_2$ |
| B800 | $CH_3SO$ | H | H | H | OH | $SO_2$ |
| B801 | $CH_3SO_2$ | H | H | H | OH | $SO_2$ |
| B802 | Ph | H | H | H | OH | $SO_2$ |
| B803 | $CH_3O$ | H | H | H | OH | $SO_2$ |
| B804 | $CH_3CO_2$ | H | H | H | OH | $SO_2$ |
| B805 | $CH_3CH_2CO_2$ | H | H | H | OH | $SO_2$ |
| B806 | $CH_2=CHCH_2$ | H | H | H | OH | $SO_2$ |
| B807 | $HCCCH_2$ | H | H | H | OH | $SO_2$ |
| B808 | $CF_3$ | H | H | H | OH | $SO_2$ |
| B809 | $(CH_3)_2NSO_2$ | H | H | H | OH | $SO_2$ |
| B810 | $(CH_3)_2N$ | H | H | H | OH | $SO_2$ |
| B811 | PhO | H | H | H | OH | $SO_2$ |
| B812 | PhS | H | H | H | OH | $SO_2$ |
| B813 | PhSO | H | H | H | OH | $SO_2$ |
| B814 | $PhSO_2$ | H | H | H | OH | $SO_2$ |
| B815 | CN | H | H | H | OH | $SO_2$ |
| B816 | $CH_3$ | $CH_3$ | H | H | OH | $SO_2$ |
| B817 | $CH_3CH_2$ | $CH_3$ | H | H | OH | $SO_2$ |
| B818 | $CH_3CH_2CH_2$ | $CH_3$ | H | H | OH | $SO_2$ |
| B819 | $(CH_3)_2CH$ | $CH_3$ | H | H | OH | $SO_2$ |
| B820 | $(CH_3)_3C$ | $CH_3$ | H | H | OH | $SO_2$ |
| B821 | $CH_3S$ | $CH_3$ | H | H | OH | $SO_2$ |
| B822 | $CH_3SO$ | $CH_3$ | H | H | OH | $SO_2$ |
| B823 | $CH_3SO_2$ | $CH_3$ | H | H | OH | $SO_2$ |
| B824 | Ph | $CH_3$ | H | H | OH | $SO_2$ |
| B825 | $CH_3O$ | $CH_3$ | H | H | OH | $SO_2$ |
| B826 | $CH_3CO_2$ | $CH_3$ | H | H | OH | $SO_2$ |
| B827 | $CH_3CH_2CO_2$ | $CH_3$ | H | H | OH | $SO_2$ |
| B828 | $CH_2=CHCH_2$ | $CH_3$ | H | H | OH | $SO_2$ |
| B829 | $HCCCH_2$ | $CH_3$ | H | H | OH | $SO_2$ |
| B830 | $CF_3$ | $CH_3$ | H | H | OH | $SO_2$ |
| B831 | $(CH_3)_2NSO_2$ | $CH_3$ | H | H | OH | $SO_2$ |
| B832 | $(CH_3)_2N$ | $CH_3$ | H | H | OH | $SO_2$ |
| B833 | PhO | $CH_3$ | H | H | OH | $SO_2$ |
| B834 | PhS | $CH_3$ | H | H | OH | $SO_2$ |
| B835 | PhSO | $CH_3$ | H | H | OH | $SO_2$ |
| B836 | $PhSO_2$ | $CH_3$ | H | H | OH | $SO_2$ |
| B837 | CN | $CH_3$ | H | H | OH | $SO_2$ |
| B838 | $CH_3$ | H | $CH_3$ | H | OH | $SO_2$ |
| B839 | $CH_3CH_2$ | H | $CH_3$ | H | OH | $SO_2$ |
| B840 | $CH_3CH_2CH_2$ | H | $CH_3$ | H | OH | $SO_2$ |
| B841 | $(CH_3)_2CH$ | H | $CH_3$ | H | OH | $SO_2$ |
| B842 | $(CH_3)_3C$ | H | $CH_3$ | H | OH | $SO_2$ |
| B843 | $CH_3S$ | H | $CH_3$ | H | OH | $SO_2$ |
| B844 | $CH_3SO$ | H | $CH_3$ | H | OH | $SO_2$ |
| B845 | $CH_3SO_2$ | H | $CH_3$ | H | OH | $SO_2$ |
| B846 | Ph | H | $CH_3$ | H | OH | $SO_2$ |
| B847 | $CH_3O$ | H | $CH_3$ | H | OH | $SO_2$ |
| B848 | $CH_3CO_2$ | H | $CH_3$ | H | OH | $SO_2$ |
| B849 | $CH_3CH_2CO_2$ | H | $CH_3$ | H | OH | $SO_2$ |
| B850 | $CH_2=CHCH_2$ | H | $CH_3$ | H | OH | $SO_2$ |
| B851 | $HCCCH_2$ | H | $CH_3$ | H | OH | $SO_2$ |
| B852 | $CF_3$ | H | $CH_3$ | H | OH | $SO_2$ |
| B853 | $(CH_3)_2NSO_2$ | H | $CH_3$ | H | OH | $SO_2$ |
| B854 | $(CH_3)_2N$ | H | $CH_3$ | H | OH | $SO_2$ |

TABLE 6-continued

Radicals B:

| Radical | $R_{44}$ | $R_{37}$ | $R_{38}$ | $R_{39}$ | $R_{40}$ | W |
|---|---|---|---|---|---|---|
| B855 | PhO | H | $CH_3$ | H | OH | $SO_2$ |
| B856 | PhS | H | $CH_3$ | H | OH | $SO_2$ |
| B857 | PhSO | H | $CH_3$ | H | OH | $SO_2$ |
| B858 | $PhSO_2$ | H | $CH_3$ | H | OH | $SO_2$ |
| B859 | CN | H | $CH_3$ | H | OH | $SO_2$ |
| B860 | $CH_3$ | $CH_3$ | $CH_3$ | H | OH | $SO_2$ |
| B861 | $CH_3CH_2$ | $CH_3$ | $CH_3$ | H | OH | $SO_2$ |
| B862 | $CH_3CH_2CH_2$ | $CH_3$ | $CH_3$ | H | OH | $SO_2$ |
| B863 | $(CH_3)_2CH$ | $CH_3$ | $CH_3$ | H | OH | $SO_2$ |
| B864 | $(CH_3)_3C$ | $CH_3$ | $CH_3$ | H | OH | $SO_2$ |
| B865 | $CH_3S$ | $CH_3$ | $CH_3$ | H | OH | $SO_2$ |
| B866 | $CH_3SO$ | $CH_3$ | $CH_3$ | H | OH | $SO_2$ |
| B867 | $CH_3SO_2$ | $CH_3$ | $CH_3$ | H | OH | $SO_2$ |
| B868 | Ph | $CH_3$ | $CH_3$ | H | OH | $SO_2$ |
| B869 | $CH_3O$ | $CH_3$ | $CH_3$ | H | OH | $SO_2$ |
| B870 | $CH_3CO_2$ | $CH_3$ | $CH_3$ | H | OH | $SO_2$ |
| B871 | $CH_3CH_2CO_2$ | $CH_3$ | $CH_3$ | H | OH | $SO_2$ |
| B872 | $CH_2=CHCH_2$ | $CH_3$ | $CH_3$ | H | OH | $SO_2$ |
| B873 | $HCCCH_2$ | $CH_3$ | $CH_3$ | H | OH | $SO_2$ |
| B874 | $CF_3$ | $CH_3$ | $CH_3$ | H | OH | $SO_2$ |
| B875 | $(CH_3)_2NSO_2$ | $CH_3$ | $CH_3$ | H | OH | $SO_2$ |
| B876 | $(CH_3)_2N$ | $CH_3$ | $CH_3$ | H | OH | $SO_2$ |
| B877 | PhO | $CH_3$ | $CH_3$ | H | OH | $SO_2$ |
| B878 | PhS | $CH_3$ | $CH_3$ | H | OH | $SO_2$ |
| B879 | PhSO | $CH_3$ | $CH_3$ | H | OH | $SO_2$ |
| B880 | $PhSO_2$ | $CH_3$ | $CH_3$ | H | OH | $SO_2$ |
| B881 | CN | $CH_3$ | $CH_3$ | H | OH | $SO_2$ |
| B882 | $CH_3$ | $CH_3$ | $CH_3$ | $CH_3$ | OH | $SO_2$ |
| B883 | $CH_3CH_2$ | $CH_3$ | $CH_3$ | $CH_3$ | OH | $SO_2$ |
| B884 | $CH_3CH_2CH_2$ | $CH_3$ | $CH_3$ | $CH_3$ | OH | $SO_2$ |
| B885 | $(CH_3)_2CH$ | $CH_3$ | $CH_3$ | $CH_3$ | OH | $SO_2$ |
| B886 | $(CH_3)_3C$ | $CH_3$ | $CH_3$ | $CH_3$ | OH | $SO_2$ |
| B887 | $CH_3S$ | $CH_3$ | $CH_3$ | $CH_3$ | OH | $SO_2$ |
| B888 | $CH_3SO$ | $CH_3$ | $CH_3$ | $CH_3$ | OH | $SO_2$ |
| B889 | $CH_3SO_2$ | $CH_3$ | $CH_3$ | $CH_3$ | OH | $SO_2$ |
| B890 | Ph | $CH_3$ | $CH_3$ | $CH_3$ | OH | $SO_2$ |
| B891 | $CH_3O$ | $CH_3$ | $CH_3$ | $CH_3$ | OH | $SO_2$ |
| B892 | $CH_3CO_2$ | $CH_3$ | $CH_3$ | $CH_3$ | OH | $SO_2$ |
| B893 | $CH_3CH_2CO_2$ | $CH_3$ | $CH_3$ | $CH_3$ | OH | $SO_2$ |
| B894 | $CH_2=CHCH_2$ | $CH_3$ | $CH_3$ | $CH_3$ | OH | $SO_2$ |
| B895 | $HCCCH_2$ | $CH_3$ | $CH_3$ | $CH_3$ | OH | $SO_2$ |
| B896 | $CF_3$ | $CH_3$ | $CH_3$ | $CH_3$ | OH | $SO_2$ |
| B897 | $(CH_3)_2NSO_2$ | $CH_3$ | $CH_3$ | $CH_3$ | OH | $SO_2$ |
| B898 | $(CH_3)_2N$ | $CH_3$ | $CH_3$ | $CH_3$ | OH | $SO_2$ |
| B899 | PhO | $CH_3$ | $CH_3$ | $CH_3$ | OH | $SO_2$ |
| B900 | PhS | $CH_3$ | $CH_3$ | $CH_3$ | OH | $SO_2$ |
| B901 | PhSO | $CH_3$ | $CH_3$ | $CH_3$ | OH | $SO_2$ |
| B902 | $PhSO_2$ | $CH_3$ | $CH_3$ | $CH_3$ | OH | $SO_2$ |
| B903 | CN | $CH_3$ | $CH_3$ | $CH_3$ | OH | $SO_2$ |
| B904 | $CH_3CH_2$ | $CH_3CH_2$ | H | H | OH | $SO_2$ |
| B905 | $CH_3CH_2CH_2$ | $CH_3CH_2$ | H | H | OH | $SO_2$ |
| B906 | $(CH_3)_2CH$ | $CH_3CH_2$ | H | H | OH | $SO_2$ |
| B907 | $(CH_3)_3C$ | $CH_3CH_2$ | H | H | OH | $SO_2$ |
| B908 | $CH_3S$ | $CH_3CH_2$ | H | H | OH | $SO_2$ |
| B909 | $CH_3SO$ | $CH_3CH_2$ | H | H | OH | $SO_2$ |
| B910 | $CH_3SO_2$ | $CH_3CH_2$ | H | H | OH | $SO_2$ |
| B911 | Ph | $CH_3CH_2$ | H | H | OH | $SO_2$ |
| B912 | $CH_3O$ | $CH_3CH_2$ | H | H | OH | $SO_2$ |
| B913 | $CH_3CO_2$ | $CH_3CH_2$ | H | H | OH | $SO_2$ |
| B914 | $CH_3CH_2CO_2$ | $CH_3CH_2$ | H | H | OH | $SO_2$ |
| B915 | $CH_2=CHCH_2$ | $CH_3CH_2$ | H | H | OH | $SO_2$ |
| B916 | $HCCCH_2$ | $CH_3CH_2$ | H | H | OH | $SO_2$ |
| B917 | $CF_3$ | $CH_3CH_2$ | H | H | OH | $SO_2$ |
| B918 | $(CH_3)_2NSO_2$ | $CH_3CH_2$ | H | H | OH | $SO_2$ |
| B919 | $(CH_3)_2N$ | $CH_3CH_2$ | H | H | OH | $SO_2$ |
| B920 | PhO | $CH_3CH_2$ | H | H | OH | $SO_2$ |
| B921 | PhS | $CH_3CH_2$ | H | H | OH | $SO_2$ |
| B922 | PhSO | $CH_3CH_2$ | H | H | OH | $SO_2$ |
| B923 | $PhSO_2$ | $CH_3CH_2$ | H | H | OH | $SO_2$ |
| B924 | CN | $CH_3CH_2$ | H | H | OH | $SO_2$ |
| B925 | H | H | H | H | OH | $CH(CO_2CH_2CH_3)$ |
| B926 | $CH_3$ | H | H | H | OH | $CH(CO_2CH_2CH_3)$ |
| B927 | $CH_3CH_2$ | H | H | H | OH | $CH(CO_2CH_2CH_3)$ |
| B928 | $CH_3CH_2CH_2$ | H | H | H | OH | $CH(CO_2CH_2CH_3)$ |
| B929 | $(CH_3)_2CH$ | H | H | H | OH | $CH(CO_2CH_2CH_3)$ |

TABLE 6-continued

Radicals B:

| Radical | $R_{44}$ | $R_{37}$ | $R_{38}$ | $R_{39}$ | $R_{40}$ | W |
|---|---|---|---|---|---|---|
| B930 | $(CH_3)_3C$ | H | H | H | OH | $CH(CO_2CH_2CH_3)$ |
| B931 | $CH_3S$ | H | H | H | OH | $CH(CO_2CH_2CH_3)$ |
| B932 | $CH_3SO$ | H | H | H | OH | $CH(CO_2CH_2CH_3)$ |
| B933 | $CH_3SO_2$ | H | H | H | OH | $CH(CO_2CH_2CH_3)$ |
| B934 | Ph | H | H | H | OH | $CH(CO_2CH_2CH_3)$ |
| B935 | $CH_3O$ | H | H | H | OH | $CH(CO_2CH_2CH_3)$ |
| B936 | $CH_3CO_2$ | H | H | H | OH | $CH(CO_2CH_2CH_3)$ |
| B937 | $CH_3CH_2CO_2$ | H | H | H | OH | $CH(CO_2CH_2CH_3)$ |
| B938 | $CH_2=CHCH_2$ | H | H | H | OH | $CH(CO_2CH_2CH_3)$ |
| B939 | $HCCCH_2$ | H | H | H | OH | $CH(CO_2CH_2CH_3)$ |
| B940 | $CF_3$ | H | H | H | OH | $CH(CO_2CH_2CH_3)$ |
| B941 | $(CH_3)_2NSO_2$ | H | H | H | OH | $CH(CO_2CH_2CH_3)$ |
| B942 | $(CH_3)_2N$ | H | H | H | OH | $CH(CO_2CH_2CH_3)$ |
| B943 | PhO | H | H | H | OH | $CH(CO_2CH_2CH_3)$ |
| B944 | PhS | H | H | H | OH | $CH(CO_2CH_2CH_3)$ |
| B945 | PhSO | H | H | H | OH | $CH(CO_2CH_2CH_3)$ |
| B946 | $PhSO_2$ | H | H | H | OH | $CH(CO_2CH_2CH_3)$ |
| B947 | CN | H | H | H | OH | $CH(CO_2CH_2CH_3)$ |
| B948 | $CH_3$ | $CH_3$ | H | H | OH | $CH(CO_2CH_2CH_3)$ |
| B949 | $CH_3CH_2$ | $CH_3$ | H | H | OH | $CH(CO_2CH_2CH_3)$ |
| B950 | $CH_3CH_2CH_2$ | $CH_3$ | H | H | OH | $CH(CO_2CH_2CH_3)$ |
| B951 | $(CH_3)_2CH$ | $CH_3$ | H | H | OH | $CH(CO_2CH_2CH_3)$ |
| B952 | $(CH_3)_3C$ | $CH_3$ | H | H | OH | $CH(CO_2CH_2CH_3)$ |
| B953 | $CH_3S$ | $CH_3$ | H | H | OH | $CH(CO_2CH_2CH_3)$ |
| B954 | $CH_3SO$ | $CH_3$ | H | H | OH | $CH(CO_2CH_2CH_3)$ |
| B955 | $CH_3SO_2$ | $CH_3$ | H | H | OH | $CH(CO_2CH_2CH_3)$ |
| B956 | Ph | $CH_3$ | H | H | OH | $CH(CO_2CH_2CH_3)$ |
| B957 | $CH_3O$ | $CH_3$ | H | H | OH | $CH(CO_2CH_2CH_3)$ |
| B958 | $CH_3CO_2$ | $CH_3$ | H | H | OH | $CH(CO_2CH_2CH_3)$ |
| B959 | $CH_3CH_2CO_2$ | $CH_3$ | H | H | OH | $CH(CO_2CH_2CH_3)$ |
| B960 | $CH_2=CHCH_2$ | $CH_3$ | H | H | OH | $CH(CO_2CH_2CH_3)$ |
| B961 | $HCCCH_2$ | $CH_3$ | H | H | OH | $CH(CO_2CH_2CH_3)$ |
| B962 | $CF_3$ | $CH_3$ | H | H | OH | $CH(CO_2CH_2CH_3)$ |
| B963 | $(CH_3)_2NSO_2$ | $CH_3$ | H | H | OH | $CH(CO_2CH_2CH_3)$ |
| B964 | $(CH_3)_2N$ | $CH_3$ | H | H | OH | $CH(CO_2CH_2CH_3)$ |
| B965 | PhO | $CH_3$ | H | H | OH | $CH(CO_2CH_2CH_3)$ |
| B966 | PhS | $CH_3$ | H | H | OH | $CH(CO_2CH_2CH_3)$ |
| B967 | PhSO | $CH_3$ | H | H | OH | $CH(CO_2CH_2CH_3)$ |
| B968 | $PhSO_2$ | $CH_3$ | H | H | OH | $CH(CO_2CH_2CH_3)$ |
| B969 | CN | $CH_3$ | H | H | OH | $CH(CO_2CH_2CH_3)$ |
| B970 | $CH_3$ | H | $CH_3$ | H | OH | $CH(CO_2CH_2CH_3)$ |
| B971 | $CH_3CH_2$ | H | $CH_3$ | H | OH | $CH(CO_2CH_2CH_3)$ |
| B972 | $CH_3CH_2CH_2$ | H | $CH_3$ | H | OH | $CH(CO_2CH_2CH_3)$ |
| B973 | $(CH_3)_2CH$ | H | $CH_3$ | H | OH | $CH(CO_2CH_2CH_3)$ |
| B974 | $(CH_3)_3C$ | H | $CH_3$ | H | OH | $CH(CO_2CH_2CH_3)$ |
| B975 | $CH_3S$ | H | $CH_3$ | H | OH | $CH(CO_2CH_2CH_3)$ |
| B976 | $CH_3SO$ | H | $CH_3$ | H | OH | $CH(CO_2CH_2CH_3)$ |
| B977 | $CH_3SO_2$ | H | $CH_3$ | H | OH | $CH(CO_2CH_2CH_3)$ |
| B978 | Ph | H | $CH_3$ | H | OH | $CH(CO_2CH_2CH_3)$ |
| B979 | $CH_3O$ | H | $CH_3$ | H | OH | $CH(CO_2CH_2CH_3)$ |
| B980 | $CH_3CO_2$ | H | $CH_3$ | H | OH | $CH(CO_2CH_2CH_3)$ |
| B981 | $CH_3CH_2CO_2$ | H | $CH_3$ | H | OH | $CH(CO_2CH_2CH_3)$ |
| B982 | $CH_2=CHCH_2$ | H | $CH_3$ | H | OH | $CH(CO_2CH_2CH_3)$ |
| B983 | $HCCCH_2$ | H | $CH_3$ | H | OH | $CH(CO_2CH_2CH_3)$ |
| B984 | $CF_3$ | H | $CH_3$ | H | OH | $CH(CO_2CH_2CH_3)$ |
| B985 | $(CH_3)_2NSO_2$ | H | $CH_3$ | H | OH | $CH(CO_2CH_2CH_3)$ |
| B986 | $(CH_3)_2N$ | H | $CH_3$ | H | OH | $CH(CO_2CH_2CH_3)$ |
| B987 | PhO | H | $CH_3$ | H | OH | $CH(CO_2CH_2CH_3)$ |
| B988 | PhS | H | $CH_3$ | H | OH | $CH(CO_2CH_2CH_3)$ |
| B989 | PhSO | H | $CH_3$ | H | OH | $CH(CO_2CH_2CH_3)$ |
| B990 | $PhSO_2$ | H | $CH_3$ | H | OH | $CH(CO_2CH_2CH_3)$ |
| B991 | CN | H | $CH_3$ | H | OH | $CH(CO_2CH_2CH_3)$ |
| B992 | $CH_3$ | $CH_3$ | $CH_3$ | H | OH | $CH(CO_2CH_2CH_3)$ |
| B993 | $CH_3CH_2$ | $CH_3$ | $CH_3$ | H | OH | $CH(CO_2CH_2CH_3)$ |
| B994 | $CH_3CH_2CH_2$ | $CH_3$ | $CH_3$ | H | OH | $CH(CO_2CH_2CH_3)$ |
| B995 | $(CH_3)_2CH$ | $CH_3$ | $CH_3$ | H | OH | $CH(CO_2CH_2CH_3)$ |
| B996 | $(CH_3)_3C$ | $CH_3$ | $CH_3$ | H | OH | $CH(CO_2CH_2CH_3)$ |
| B997 | $CH_3S$ | $CH_3$ | $CH_3$ | H | OH | $CH(CO_2CH_2CH_3)$ |
| B998 | $CH_3SO$ | $CH_3$ | $CH_3$ | H | OH | $CH(CO_2CH_2CH_3)$ |
| B999 | $CH_3SO_2$ | $CH_3$ | $CH_3$ | H | OH | $CH(CO_2CH_2CH_3)$ |
| B1000 | Ph | $CH_3$ | $CH_3$ | H | OH | $CH(CO_2CH_2CH_3)$ |
| B1001 | $CH_3O$ | $CH_3$ | $CH_3$ | H | OH | $CH(CO_2CH_2CH_3)$ |
| B1002 | $CH_3CO_2$ | $CH_3$ | $CH_3$ | H | OH | $CH(CO_2CH_2CH_3)$ |
| B1003 | $CH_3CH_2CO_2$ | $CH_3$ | $CH_3$ | H | OH | $CH(CO_2CH_2CH_3)$ |
| B1004 | $CH_2=CHCH_2$ | $CH_3$ | $CH_3$ | H | OH | $CH(CO_2CH_2CH_3)$ |

TABLE 6-continued

Radicals B:

| Radical | R₄₄ | R₃₇ | R₃₈ | R₃₉ | R₄₀ | W |
|---|---|---|---|---|---|---|
| B1005 | HCCCH₂ | CH₃ | CH₃ | H | OH | CH(CO₂CH₂CH₃) |
| B1006 | CF₃ | CH₃ | CH₃ | H | OH | CH(CO₂CH₂CH₃) |
| B1007 | (CH₃)₂NSO₂ | CH₃ | CH₃ | H | OH | CH(CO₂CH₂CH₃) |
| B1008 | (CH₃)₂N | CH₃ | CH₃ | H | OH | CH(CO₂CH₂CH₃) |
| B1009 | PhO | CH₃ | CH₃ | H | OH | CH(CO₂CH₂CH₃) |
| B1010 | PhS | CH₃ | CH₃ | H | OH | CH(CO₂CH₂CH₃) |
| B1011 | PhSO | CH₃ | CH₃ | H | OH | CH(CO₂CH₂CH₃) |
| B1012 | PhSO₂ | CH₃ | CH₃ | H | OH | CH(CO₂CH₂CH₃) |
| B1013 | CN | CH₃ | CH₃ | H | OH | CH(CO₂CH₂CH₃) |
| B1014 | CH₃ | CH₃ | CH₃ | CH₃ | OH | CH(CO₂CH₂CH₃) |
| B1015 | CH₃CH₂ | CH₃ | CH₃ | CH₃ | OH | CH(CO₂CH₂CH₃) |
| B1016 | CH₃CH₂CH₂ | CH₃ | CH₃ | CH₃ | OH | CH(CO₂CH₂CH₃) |
| B1017 | (CH₃)₂CH | CH₃ | CH₃ | CH₃ | OH | CH(CO₂CH₂CH₃) |
| B1018 | (CH₃)₃C | CH₃ | CH₃ | CH₃ | OH | CH(CO₂CH₂CH₃) |
| B1019 | CH₃S | CH₃ | CH₃ | CH₃ | OH | CH(CO₂CH₂CH₃) |
| B1020 | CH₃SO | CH₃ | CH₃ | CH₃ | OH | CH(CO₂CH₂CH₃) |
| B1021 | CH₃SO₂ | CH₃ | CH₃ | CH₃ | OH | CH(CO₂CH₂CH₃) |
| B1022 | Ph | CH₃ | CH₃ | CH₃ | OH | CH(CO₂CH₂CH₃) |
| B1023 | CH₃O | CH₃ | CH₃ | CH₃ | OH | CH(CO₂CH₂CH₃) |
| B1024 | CH₃CO₂ | CH₃ | CH₃ | CH₃ | OH | CH(CO₂CH₂CH₃) |
| B1025 | CH₃CH₂CO₂ | CH₃ | CH₃ | CH₃ | OH | CH(CO₂CH₂CH₃) |
| B1026 | CH₂=CHCH₂ | CH₃ | CH₃ | CH₃ | OH | CH(CO₂CH₂CH₃) |
| B1027 | HCCCH₂ | CH₃ | CH₃ | CH₃ | OH | CH(CO₂CH₂CH₃) |
| B1028 | CF₃ | CH₃ | CH₃ | CH₃ | OH | CH(CO₂CH₂CH₃) |
| B1029 | (CH₃)₂NSO₂ | CH₃ | CH₃ | CH₃ | OH | CH(CO₂CH₂CH₃) |
| B1030 | (CH₃)₂N | CH₃ | CH₃ | CH₃ | OH | CH(CO₂CH₂CH₃) |
| B1031 | PhO | CH₃ | CH₃ | CH₃ | OH | CH(CO₂CH₂CH₃) |
| B1032 | PhS | CH₃ | CH₃ | CH₃ | OH | CH(CO₂CH₂CH₃) |
| B1033 | PhSO | CH₃ | CH₃ | CH₃ | OH | CH(CO₂CH₂CH₃) |
| B1034 | PhSO₂ | CH₃ | CH₃ | CH₃ | OH | CH(CO₂CH₂CH₃) |
| B1035 | CN | CH₃ | CH₃ | CH₃ | OH | CH(CO₂CH₂CH₃) |
| B1036 | CH₃CH₂ | CH₃CH₂ | H | H | OH | CH(CO₂CH₂CH₃) |
| B1037 | CH₃CH₂CH₂ | CH₃CH₂ | H | H | OH | CH(CO₂CH₂CH₃) |
| B1038 | (CH₃)₂CH | CH₃CH₂ | H | H | OH | CH(CO₂CH₂CH₃) |
| B1039 | (CH₃)₃C | CH₃CH₂ | H | H | OH | CH(CO₂CH₂CH₃) |
| B1040 | CH₃S | CH₃CH₂ | H | H | OH | CH(CO₂CH₂CH₃) |
| B1041 | CH₃SO | CH₃CH₂ | H | H | OH | CH(CO₂CH₂CH₃) |
| B1042 | CH₃SO₂ | CH₃CH₂ | H | H | OH | CH(CO₂CH₂CH₃) |
| B1043 | Ph | CH₃CH₂ | H | H | OH | CH(CO₂CH₂CH₃) |
| B1044 | CH₃O | CH₃CH₂ | H | H | OH | CH(CO₂CH₂CH₃) |
| B1045 | CH₃CO₂ | CH₃CH₂ | H | H | OH | CH(CO₂CH₂CH₃) |
| B1046 | CH₃CH₂CO₂ | CH₃CH₂ | H | H | OH | CH(CO₂CH₂CH₃) |
| B1047 | CH₂=CHCH₂ | CH₃CH₂ | H | H | OH | CH(CO₂CH₂CH₃) |
| B1048 | HCCCH₂ | CH₃CH₂ | H | H | OH | CH(CO₂CH₂CH₃) |
| B1049 | CF₃ | CH₃CH₂ | H | H | OH | CH(CO₂CH₂CH₃) |
| B1050 | (CH₃)₂NSO₂ | CH₃CH₂ | H | H | OH | CH(CO₂CH₂CH₃) |
| B1051 | (CH₃)₂N | CH₃CH₂ | H | H | OH | CH(CO₂CH₂CH₃) |
| B1052 | PhO | CH₃CH₂ | H | H | OH | CH(CO₂CH₂CH₃) |
| B1053 | PhS | CH₃CH₂ | H | H | OH | CH(CO₂CH₂CH₃) |
| B1054 | PhSO | CH₃CH₂ | H | H | OH | CH(CO₂CH₂CH₃) |
| B1055 | PhSO₂ | CH₃CH₂ | H | H | OH | CH(CO₂CH₂CH₃) |
| B1056 | CN | CH₃CH₂ | H | H | OH | CH(CO₂CH₂CH₃) |
| B1057 | CH₃OCO | H | H | H | OH | CHPh |
| B1058 | H | H | H | H | OH | CHPh |
| B1059 | H | H | H | H | OH | CH(CH₂CH₃) |
| B1060 | H | H | H | H | OH | CH(CH₂CH₂CH₃) |
| B1061 | H | H | H | H | OH | CH(CH(CH₃)₂) |
| B1062 | H | H | H | H | OH | CH(C(CH₃)₃) |
| B1063 | H | H | H | H | OH | C(CH₃)₂ |
| B1064 | H | H | H | H | OH | CH(CF₃) |
| B1065 | CH₃OCO | H | H | H | OH | C(CH₃)(CF₃) |
| B1066 | H | H | H | H | OH | C(CH₃)(CF₃) |
| B1067 | CH₃OCO | CH₃O | H | H | OH | CH₂ |
| B1068 | H | CH₃O | H | H | OH | CH₂ |
| B1069 | CH₃O | CH₃OCO | H | CH₃ | OH | CH₂ |
| B1070 | CH₃O | H | CH₃ | H | OH | CH₂ |
| B1071 | Cl | H | H | H | OH | CH₂ |
| B1072 | F | H | H | H | OH | CH₂ |
| B1073 | H | H | H | H | OH | CH(OCH₃)₂ |
| B1074 | H | H | H | H | OH | CH₂OSO₂CH₃ |
| B1075 | CH₃ | CH₃ | CH₃ | CH₃ | OH | S(O) |
| B1076 | ClCH₂CH₂ | H | H | H | OH | CH₂ |
| B1077 | HO(CH₂)₂ | H | H | H | OH | CH₂ |
| B1078 | MsO(CH₂)₂ | H | H | H | OH | CH₂ |
| B1079 | HOCH(CH₃)CH₂ | H | H | H | OH | CH₂ |

TABLE 6-continued

Radicals B:

| Radical | $R_{44}$ | $R_{37}$ | $R_{38}$ | $R_{39}$ | $R_{40}$ | W |
|---|---|---|---|---|---|---|
| B1080 | MsOCH(CH$_3$)CH$_2$ | H | H | H | OH | CH$_2$ |
| B1081 | (CH$_3$)$_2$CH | H | CH$_3$ | CH$_3$ | OH | CH$_2$ |
| B1082 | HCCCH$_2$ | H | CH$_3$ | CH$_3$ | OH | CH$_2$ |
| B1083 | H$_2$C=CCH$_2$ | H | CH$_3$ | CH$_3$ | OH | CH$_2$ |

In the following Table 7 is $Q_6$

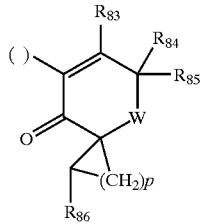

($Q_6$)

and $Q_6$ represent the following radicals C:

TABLE 7

Radicals C:

| Radical | $R_{84}$ | $R_{85}$ | $R_{86}$ | $R_{83}$ | p | W |
|---|---|---|---|---|---|---|
| C1 | H | H | H | OH | 1 | CH$_2$ |
| C2 | CH$_3$ | H | H | OH | 1 | CH$_2$ |
| C3 | CH$_3$CH$_2$ | H | H | OH | 1 | CH$_2$ |
| C4 | CH$_3$CH$_2$CH$_2$ | H | H | OH | 1 | CH$_2$ |
| C5 | (CH$_3$)$_2$CH | H | H | OH | 1 | CH$_2$ |
| C6 | (CH$_3$)$_3$C | H | H | OH | 1 | CH$_2$ |
| C7 | CH$_3$S | H | H | OH | 1 | CH$_2$ |
| C8 | CH$_3$SO | H | H | OH | 1 | CH$_2$ |
| C9 | CH$_3$SO$_2$ | H | H | OH | 1 | CH$_2$ |
| C10 | Ph | H | H | OH | 1 | CH$_2$ |
| C11 | CH$_3$O | H | H | OH | 1 | CH$_2$ |
| C12 | CH$_3$OCO$_2$ | H | H | OH | 1 | CH$_2$ |
| C13 | CH$_3$CH$_2$OCO$_2$ | H | H | OH | 1 | CH$_2$ |
| C14 | CH$_2$=CHCH$_2$ | H | H | OH | 1 | CH$_2$ |
| C15 | HCCCH$_2$ | H | H | OH | 1 | CH$_2$ |
| C16 | CF$_3$ | H | H | OH | 1 | CH$_2$ |
| C17 | (CH$_3$)$_2$NSO$_2$ | H | H | OH | 1 | CH$_2$ |
| C18 | (CH$_3$)$_2$N | H | H | OH | 1 | CH$_2$ |
| C19 | PhO | H | H | OH | 1 | CH$_2$ |
| C20 | PhS | H | H | OH | 1 | CH$_2$ |
| C21 | PhSO | H | H | OH | 1 | CH$_2$ |
| C22 | PhSO$_2$ | H | H | OH | 1 | CH$_2$ |
| C23 | CN | H | H | OH | 1 | CH$_2$ |
| C24 | CH$_3$ | CH$_3$ | H | OH | 1 | CH$_2$ |
| C25 | CH$_3$CH$_2$ | CH$_3$ | H | OH | 1 | CH$_2$ |
| C26 | CH$_3$CH$_2$CH$_2$ | CH$_3$ | H | OH | 1 | CH$_2$ |
| C27 | (CH$_3$)$_2$CH | CH$_3$ | H | OH | 1 | CH$_2$ |
| C28 | (CH$_3$)$_3$C | CH$_3$ | H | OH | 1 | CH$_2$ |
| C29 | CH$_3$S | CH$_3$ | H | OH | 1 | CH$_2$ |
| C30 | CH$_3$SO | CH$_3$ | H | OH | 1 | CH$_2$ |
| C31 | CH$_3$SO$_2$ | CH$_3$ | H | OH | 1 | CH$_2$ |
| C32 | Ph | CH$_3$ | H | OH | 1 | CH$_2$ |
| C33 | CH$_3$O | CH$_3$ | H | OH | 1 | CH$_2$ |
| C34 | CH$_3$OCO$_2$ | CH$_3$ | H | OH | 1 | CH$_2$ |
| C35 | CH$_3$CH$_2$OCO$_2$ | CH$_3$ | H | OH | 1 | CH$_2$ |
| C36 | CH$_2$=CHCH$_2$ | CH$_3$ | H | OH | 1 | CH$_2$ |
| C37 | HCCCH$_2$ | CH$_3$ | H | OH | 1 | CH$_2$ |
| C38 | CF$_3$ | CH$_3$ | H | OH | 1 | CH$_2$ |
| C39 | (CH$_3$)$_2$NSO$_2$ | CH$_3$ | H | OH | 1 | CH$_2$ |
| C40 | (CH$_3$)$_2$N | CH$_3$ | H | OH | 1 | CH$_2$ |
| C41 | PhO | CH$_3$ | H | OH | 1 | CH$_2$ |
| C42 | PhS | CH$_3$ | H | OH | 1 | CH$_2$ |
| C43 | PhSO | CH$_3$ | H | OH | 1 | CH$_2$ |
| C44 | PhSO$_2$ | CH$_3$ | H | OH | 1 | CH$_2$ |
| C45 | CN | CH$_3$ | H | OH | 1 | CH$_2$ |

TABLE 7-continued

Radicals C:

| Radical | $R_{84}$ | $R_{85}$ | $R_{86}$ | $R_{83}$ | p | W |
|---|---|---|---|---|---|---|
| C46 | H | H | H | OH | 4 | CH$_2$ |
| C47 | CH$_3$ | H | H | OH | 4 | CH$_2$ |
| C48 | CH$_3$CH$_2$ | H | H | OH | 4 | CH$_2$ |
| C49 | CH$_3$CH$_2$CH$_2$ | H | H | OH | 4 | CH$_2$ |
| C50 | (CH$_3$)$_2$CH | H | H | OH | 4 | CH$_2$ |
| C51 | (CH$_3$)$_3$C | H | H | OH | 4 | CH$_2$ |
| C52 | CH$_3$S | H | H | OH | 4 | CH$_2$ |
| C53 | CH$_3$SO | H | H | OH | 4 | CH$_2$ |
| C54 | CH$_3$SO$_2$ | H | H | OH | 4 | CH$_2$ |
| C55 | Ph | H | H | OH | 4 | CH$_2$ |
| C56 | CH$_3$O | H | H | OH | 4 | CH$_2$ |
| C57 | CH$_3$OCO$_2$ | H | H | OH | 4 | CH$_2$ |
| C58 | CH$_3$CH$_2$OCO$_2$ | H | H | OH | 4 | CH$_2$ |
| C59 | CH$_2$=CHCH$_2$ | H | H | OH | 4 | CH$_2$ |
| C60 | HCCCH$_2$ | H | H | OH | 4 | CH$_2$ |
| C61 | CF$_3$ | H | H | OH | 4 | CH$_2$ |
| C62 | (CH$_3$)$_2$NSO$_2$ | H | H | OH | 4 | CH$_2$ |
| C63 | (CH$_3$)$_2$N | H | H | OH | 4 | CH$_2$ |
| C64 | PhO | H | H | OH | 4 | CH$_2$ |
| C65 | PhS | H | H | OH | 4 | CH$_2$ |
| C66 | PhSO | H | H | OH | 4 | CH$_2$ |
| C67 | PhSO$_2$ | H | H | OH | 4 | CH$_2$ |
| C68 | CN | H | H | OH | 4 | CH$_2$ |
| C69 | CH$_3$ | CH$_3$ | H | OH | 4 | CH$_2$ |
| C70 | CH$_3$CH$_2$ | CH$_3$ | H | OH | 4 | CH$_2$ |
| C71 | CH$_3$CH$_2$CH$_2$ | CH$_3$ | H | OH | 4 | CH$_2$ |
| C72 | (CH$_3$)$_2$CH | CH$_3$ | H | OH | 4 | CH$_2$ |
| C73 | (CH$_3$)$_3$C | CH$_3$ | H | OH | 4 | CH$_2$ |
| C74 | CH$_3$S | CH$_3$ | H | OH | 4 | CH$_2$ |
| C75 | CH$_3$SO | CH$_3$ | H | OH | 4 | CH$_2$ |
| C76 | CH$_3$SO$_2$ | CH$_3$ | H | OH | 4 | CH$_2$ |
| C77 | Ph | CH$_3$ | H | OH | 4 | CH$_2$ |
| C78 | CH$_3$O | CH$_3$ | H | OH | 4 | CH$_2$ |
| C79 | CH$_3$OCO$_2$ | CH$_3$ | H | OH | 4 | CH$_2$ |
| C80 | CH$_3$CH$_2$OCO$_2$ | CH$_3$ | H | OH | 4 | CH$_2$ |
| C81 | CH$_2$=CHCH$_2$ | CH$_3$ | H | OH | 4 | CH$_2$ |
| C82 | HCCCH$_2$ | CH$_3$ | H | OH | 4 | CH$_2$ |
| C83 | CF$_3$ | CH$_3$ | H | OH | 4 | CH$_2$ |
| C84 | (CH$_3$)$_2$NSO$_2$ | CH$_3$ | H | OH | 4 | CH$_2$ |
| C85 | (CH$_3$)$_2$N | CH$_3$ | H | OH | 4 | CH$_2$ |
| C86 | PhO | CH$_3$ | H | OH | 4 | CH$_2$ |
| C87 | PhS | CH$_3$ | H | OH | 4 | CH$_2$ |
| C88 | PhSO | CH$_3$ | H | OH | 4 | CH$_2$ |
| C89 | PhSO$_2$ | CH$_3$ | H | OH | 4 | CH$_2$ |
| C90 | CN | CH$_3$ | H | OH | 4 | CH$_2$ |
| C91 | H | H | H | OH | 3 | CH$_2$ |
| C92 | CH$_3$ | H | H | OH | 3 | CH$_2$ |
| C93 | CH$_3$CH$_2$ | H | H | OH | 3 | CH$_2$ |
| C94 | CH$_3$CH$_2$CH$_2$ | H | H | OH | 3 | CH$_2$ |
| C95 | (CH$_3$)$_2$CH | H | H | OH | 3 | CH$_2$ |
| C96 | (CH$_3$)$_3$C | H | H | OH | 3 | CH$_2$ |
| C97 | CH$_3$S | H | H | OH | 3 | CH$_2$ |
| C98 | CH$_3$SO | H | H | OH | 3 | CH$_2$ |
| C99 | CH$_3$SO$_2$ | H | H | OH | 3 | CH$_2$ |
| C100 | Ph | H | H | OH | 3 | CH$_2$ |
| C101 | CH$_3$O | H | H | OH | 3 | CH$_2$ |
| C102 | CH$_3$OCO$_2$ | H | H | OH | 3 | CH$_2$ |
| C103 | CH$_3$CH$_2$OCO$_2$ | H | H | OH | 3 | CH$_2$ |
| C104 | CH$_2$=CHCH$_2$ | H | H | OH | 3 | CH$_2$ |
| C105 | HCCCH$_2$ | H | H | OH | 3 | CH$_2$ |

TABLE 7-continued

Radicals C:

| Radical | $R_{84}$ | $R_{85}$ | $R_{86}$ | $R_{83}$ | p | W |
|---|---|---|---|---|---|---|
| C106 | $CF_3$ | H | H | OH | 3 | $CH_2$ |
| C107 | $(CH_3)_2NSO_2$ | H | H | OH | 3 | $CH_2$ |
| C108 | $(CH_3)_2N$ | H | H | OH | 3 | $CH_2$ |
| C109 | PhO | H | H | OH | 3 | $CH_2$ |
| C110 | PhS | H | H | OH | 3 | $CH_2$ |
| C111 | PhSO | H | H | OH | 3 | $CH_2$ |
| C112 | $PhSO_2$ | H | H | OH | 3 | $CH_2$ |
| C113 | CN | H | H | OH | 3 | $CH_2$ |
| C114 | $CH_3$ | $CH_3$ | H | OH | 3 | $CH_2$ |
| C115 | $CH_3CH_2$ | $CH_3$ | H | OH | 3 | $CH_2$ |
| C116 | $CH_3CH_2CH_2$ | $CH_3$ | H | OH | 3 | $CH_2$ |
| C117 | $(CH_3)_2CH$ | $CH_3$ | H | OH | 3 | $CH_2$ |
| C118 | $(CH_3)_3C$ | $CH_3$ | H | OH | 3 | $CH_2$ |
| C119 | $CH_3S$ | $CH_3$ | H | OH | 3 | $CH_2$ |
| C120 | $CH_3SO$ | $CH_3$ | H | OH | 3 | $CH_2$ |
| C121 | $CH_3SO_2$ | $CH_3$ | H | OH | 3 | $CH_2$ |
| C122 | Ph | $CH_3$ | H | OH | 3 | $CH_2$ |
| C123 | $CH_3O$ | $CH_3$ | H | OH | 3 | $CH_2$ |
| C124 | $CH_3OCO_2$ | $CH_3$ | H | OH | 3 | $CH_2$ |
| C125 | $CH_3CH_2OCO_2$ | $CH_3$ | H | OH | 3 | $CH_2$ |
| C126 | $CH_2=CHCH_2$ | $CH_3$ | H | OH | 3 | $CH_2$ |
| C127 | $HCCCH_2$ | $CH_3$ | H | OH | 3 | $CH_2$ |
| C128 | $CF_3$ | $CH_3$ | H | OH | 3 | $CH_2$ |
| C129 | $(CH_3)_2NSO_2$ | $CH_3$ | H | OH | 3 | $CH_2$ |
| C130 | $(CH_3)_2N$ | $CH_3$ | H | OH | 3 | $CH_2$ |
| C131 | PhO | $CH_3$ | H | OH | 3 | $CH_2$ |
| C132 | PhS | $CH_3$ | H | OH | 3 | $CH_2$ |
| C133 | PhSO | $CH_3$ | H | OH | 3 | $CH_2$ |
| C134 | $PhSO_2$ | $CH_3$ | H | OH | 3 | $CH_2$ |
| C135 | CN | $CH_3$ | H | OH | 3 | $CH_2$ |
| C136 | $CH_3CH_2$ | $CH_3CH_2$ | H | OH | 1 | $CH_2$ |
| C137 | H | H | H | OH | 1 | $CH(CH_3)$ |
| C138 | $CH_3$ | H | H | OH | 1 | $CH(CH_3)$ |
| C139 | $CH_3$ | $CH_3$ | H | OH | 1 | $CH(CH_3)$ |
| C140 | $CH_3CH_2$ | H | H | OH | 1 | $CH(CH_3)$ |
| C141 | $CH_3CH_2$ | $CH_3$ | H | OH | 1 | $CH(CH_3)$ |
| C142 | $CH_3CH_2$ | $CH_3CH_2$ | H | OH | 1 | $CH(CH_3)$ |
| C143 | H | H | $CH_3$ | OH | 1 | $CH_2$ |
| C144 | $CH_3$ | $CH_3$ | $CH_3$ | OH | 1 | $CH_2$ |
| C145 | $CH_3CH_2$ | $CH_3CH_2$ | $CH_3$ | OH | 1 | $CH_2$ |
| C146 | H | H | H | OH | 2 | $CH_2$ |
| C147 | $CH_3$ | $CH_3$ | H | OH | 2 | $CH_2$ |
| C148 | $CH_3CH_2$ | $CH_3CH_2$ | H | OH | 2 | $CH_2$ |
| C149 | H | H | H | OH | 5 | $CH_2$ |
| C150 | $CH_3$ | $CH_3$ | H | OH | 5 | $CH_2$ |
| C151 | $CH_3CH_2$ | $CH_3CH_2$ | H | OH | 5 | $CH_2$ |

In the following Table 8 is $Q_8$

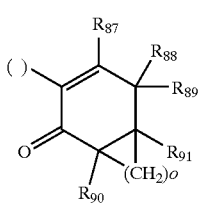

(Q8)

and $Q_8$ represent the following radicals D:

TABLE 8

Radicals D:

| Radical | $R_{88}$ | $R_{89}$ | $R_{90}$ | $R_{91}$ | $R_{87}$ | o |
|---|---|---|---|---|---|---|
| D1 | H | H | H | H | OH | 2 |
| D2 | $CH_3$ | H | H | H | OH | 2 |
| D3 | $CH_3CH_2$ | H | H | H | OH | 2 |
| D4 | $CH_3CH_2CH_2$ | H | H | H | OH | 2 |
| D5 | $(CH_3)_2CH$ | H | H | H | OH | 2 |
| D6 | $(CH_3)_3C$ | H | H | H | OH | 2 |
| D7 | $CH_3S$ | H | H | H | OH | 2 |
| D8 | $CH_3SO$ | H | H | H | OH | 2 |
| D9 | $CH_3SO_2$ | H | H | H | OH | 2 |
| D10 | Ph | H | H | H | OH | 2 |
| D11 | $CH_3O$ | H | H | H | OH | 2 |
| D12 | $CH_2=CHCH_2$ | H | H | H | OH | 2 |
| D13 | $HCCCH_2$ | H | H | H | OH | 2 |
| D14 | $CF_3$ | H | H | H | OH | 2 |
| D15 | PhO | H | H | H | OH | 2 |
| D16 | PhS | H | H | H | OH | 2 |
| D17 | PhSO | H | H | H | OH | 2 |
| D18 | $PhSO_2$ | H | H | H | OH | 2 |
| D19 | $CH_3$ | $CH_3$ | H | H | OH | 2 |
| D20 | $CH_3CH_2$ | $CH_3$ | H | H | OH | 2 |
| D21 | $CH_3CH_2CH_2$ | $CH_3$ | H | H | OH | 2 |
| D22 | $(CH_3)_2CH$ | $CH_3$ | H | H | OH | 2 |
| D23 | $(CH_3)_3C$ | $CH_3$ | H | H | OH | 2 |
| D24 | $CH_3S$ | $CH_3$ | H | H | OH | 2 |
| D25 | $CH_3SO$ | $CH_3$ | H | H | OH | 2 |
| D26 | $CH_3SO_2$ | $CH_3$ | H | H | OH | 2 |
| D27 | Ph | $CH_3$ | H | H | OH | 2 |
| D28 | $CH_3O$ | $CH_3$ | H | H | OH | 2 |
| D29 | $CH_2=CHCH_2$ | $CH_3$ | H | H | OH | 2 |
| D30 | $HCCCH_2$ | $CH_3$ | H | H | OH | 2 |
| D31 | $CF_3$ | $CH_3$ | H | H | OH | 2 |
| D32 | PhO | $CH_3$ | H | H | OH | 2 |
| D33 | PhS | $CH_3$ | H | H | OH | 2 |
| D34 | PhSO | $CH_3$ | H | H | OH | 2 |
| D35 | $PhSO_2$ | $CH_3$ | H | H | OH | 2 |
| D36 | H | H | H | H | OH | 3 |
| D37 | $CH_3$ | H | H | H | OH | 3 |
| D38 | $CH_3CH_2$ | H | H | H | OH | 3 |
| D39 | $CH_3CH_2CH_2$ | H | H | H | OH | 3 |
| D40 | $(CH_3)_2CH$ | H | H | H | OH | 3 |
| D41 | $(CH_3)_3C$ | H | H | H | OH | 3 |
| D42 | $CH_3S$ | H | H | H | OH | 3 |
| D43 | $CH_3SO$ | H | H | H | OH | 3 |
| D44 | $CH_3SO_2$ | H | H | H | OH | 3 |
| D45 | Ph | H | H | H | OH | 3 |
| D46 | $CH_3O$ | H | H | H | OH | 3 |
| D47 | $CH_2=CHCH_2$ | H | H | H | OH | 3 |
| D48 | $HCCCH_2$ | H | H | H | OH | 3 |
| D49 | $CF_3$ | H | H | H | OH | 3 |
| D50 | PhO | H | H | H | OH | 3 |
| D51 | PhS | H | H | H | OH | 3 |
| D52 | PhSO | H | H | H | OH | 3 |
| D53 | $PhSO_2$ | H | H | H | OH | 3 |
| D54 | $CH_3$ | $CH_3$ | H | H | OH | 3 |
| D55 | $CH_3CH_2$ | $CH_3$ | H | H | OH | 3 |
| D56 | $CH_3CH_2CH_2$ | $CH_3$ | H | H | OH | 3 |
| D57 | $(CH_3)_2CH$ | $CH_3$ | H | H | OH | 3 |
| D58 | $(CH_3)_3C$ | $CH_3$ | H | H | OH | 3 |
| D59 | $CH_3S$ | $CH_3$ | H | H | OH | 3 |
| D60 | $CH_3SO$ | $CH_3$ | H | H | OH | 3 |
| D61 | $CH_3SO_2$ | $CH_3$ | H | H | OH | 3 |
| D62 | Ph | $CH_3$ | H | H | OH | 3 |
| D63 | $CH_3O$ | $CH_3$ | H | H | OH | 3 |
| D64 | $CH_2=CHCH_2$ | $CH_3$ | H | H | OH | 3 |
| D65 | $HCCCH_2$ | $CH_3$ | H | H | OH | 3 |
| D66 | $CF_3$ | $CH_3$ | H | H | OH | 3 |
| D67 | PhO | $CH_3$ | H | H | OH | 3 |
| D68 | PhS | $CH_3$ | H | H | OH | 3 |
| D69 | PhSO | $CH_3$ | H | H | OH | 3 |
| D70 | $PhSO_2$ | $CH_3$ | H | H | OH | 3 |
| D71 | H | H | H | H | OH | 4 |
| D72 | $CH_3$ | H | H | H | OH | 4 |
| D73 | $CH_3CH_2$ | H | H | H | OH | 4 |
| D74 | $CH_3CH_2CH_2$ | H | H | H | OH | 4 |
| D75 | $(CH_3)_2CH$ | H | H | H | OH | 4 |
| D76 | $(CH_3)_3C$ | H | H | H | OH | 4 |
| D77 | $CH_3S$ | H | H | H | OH | 4 |
| D78 | $CH_3SO$ | H | H | H | OH | 4 |

TABLE 8-continued

Radicals D:

| Radical | $R_{88}$ | $R_{89}$ | $R_{90}$ | $R_{91}$ | $R_{87}$ | o |
|---|---|---|---|---|---|---|
| D79 | $CH_3SO_2$ | H | H | H | OH | 4 |
| D80 | Ph | H | H | H | OH | 4 |
| D81 | $CH_3O$ | H | H | H | OH | 4 |
| D82 | $CH_2=CHCH_2$ | H | H | H | OH | 4 |
| D83 | $HCCCH_2$ | H | H | H | OH | 4 |
| D84 | $CF_3$ | H | H | H | OH | 4 |
| D85 | PhO | H | H | H | OH | 4 |
| D86 | PhS | H | H | H | OH | 4 |
| D87 | PhSO | H | H | H | OH | 4 |
| D88 | $PhSO_2$ | H | H | H | OH | 4 |
| D89 | $CH_3$ | $CH_3$ | H | H | OH | 4 |
| D90 | $CH_3CH_2$ | $CH_3$ | H | H | OH | 4 |
| D91 | $CH_3CH_2CH_2$ | $CH_3$ | H | H | OH | 4 |
| D92 | $(CH_3)_2CH$ | $CH_3$ | H | H | OH | 4 |
| D93 | $(CH_3)_3C$ | $CH_3$ | H | H | OH | 4 |
| D94 | $CH_3S$ | $CH_3$ | H | H | OH | 4 |
| D95 | $CH_3SO$ | $CH_3$ | H | H | OH | 4 |
| D96 | $CH_3SO_2$ | $CH_3$ | H | H | OH | 4 |
| D97 | Ph | $CH_3$ | H | H | OH | 4 |
| D98 | $CH_3O$ | $CH_3$ | H | H | OH | 4 |
| D99 | $CH_2=CHCH_2$ | $CH_3$ | H | H | OH | 4 |
| D100 | $HCCCH_2$ | $CH_3$ | H | H | OH | 4 |
| D101 | $CF_3$ | $CH_3$ | H | H | OH | 4 |
| D102 | PhO | $CH_3$ | H | H | OH | 4 |
| D103 | PhS | $CH_3$ | H | H | OH | 4 |
| D104 | PhSO | $CH_3$ | H | H | OH | 4 |
| D105 | $PhSO_2$ | $CH_3$ | H | H | OH | 4 |
| D106 | H | H | H | $CH_3$ | OH | 4 |
| D107 | H | H | H | $CH_3$ | OH | 3 |
| D108 | H | H | H | H | OH | 1 |
| D109 | $CH_3$ | H | H | H | OH | 1 |
| D110 | $CH_3OCO$ | $CH_3$ | H | H | OH | 1 |
| D111 | $CH_3CH_2OCO$ | $CH_3$ | H | H | OH | 1 |
| D112 | $CH_3O$ | $CH_3$ | H | H | OH | 1 |
| D113 | $CH_3S$ | $CH_3$ | H | H | OH | 1 |
| D114 | $CH_3SO$ | $CH_3$ | H | H | OH | 1 |
| D115 | $CH_3SO_2$ | $CH_3$ | H | H | OH | 1 |
| D116 | $CH_3CH_2$ | H | H | H | OH | 1 |
| D117 | $CH_3OCO$ | $CH_3CH_2$ | H | H | OH | 1 |
| D118 | $CH_3CH_2OCO$ | $CH_3CH_2$ | H | H | OH | 1 |
| D119 | $CH_3O$ | $CH_3CH_2$ | H | H | OH | 1 |
| D120 | $CH_3S$ | $CH_3CH_2$ | H | H | OH | 1 |
| D121 | $CH_3SO$ | $CH_3CH_2$ | H | H | OH | 1 |
| D122 | $CH_3SO_2$ | $CH_3CH_2$ | H | H | OH | 1 |
| D123 | $CH_3CH_2S$ | $CH_3$ | H | H | OH | 1 |
| D124 | $CH_3CH_2SO$ | $CH_3$ | H | H | OH | 1 |
| D125 | $CH_3CH_2SO_2$ | $CH_3$ | H | H | OH | 1 |
| D126 | $CH_3CH_2S$ | $CH_3CH_2$ | H | H | OH | 1 |
| D127 | $CH_3CH_2SO$ | $CH_3CH_2$ | H | H | OH | 1 |
| D128 | $CH_3CH_2SO$ | $CH_3CH_2$ | H | H | OH | 1 |
| D129 | H | H | $CH_3$ | H | OH | 1 |
| D130 | $CH_3$ | H | $CH_3$ | H | OH | 1 |
| D131 | $CH_3OCO$ | $CH_3$ | $CH_3$ | H | OH | 1 |
| D132 | $CH_3CH_2OCO$ | $CH_3$ | $CH_3$ | H | OH | 1 |
| D133 | $CH_3O$ | $CH_3$ | $CH_3$ | H | OH | 1 |
| D134 | $CH_3S$ | $CH_3$ | $CH_3$ | H | OH | 1 |
| D135 | $CH_3SO$ | $CH_3$ | $CH_3$ | H | OH | 1 |
| D136 | $CH_3SO_2$ | $CH_3$ | $CH_3$ | H | OH | 1 |
| D137 | H | H | H | $CH_3$ | OH | 1 |
| D138 | $CH_3$ | H | H | $CH_3$ | OH | 1 |
| D139 | H | H | $CH_3$ | $CH_3$ | OH | 1 |
| D140 | $CH_3CH_2OCO$ | $CH_3$ | H | H | OH | 4 |

TABLE 9

Compounds of formula If:

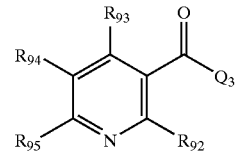

(If)

| Compd. no. | $R_{92}$ | $R_{93}$ | $R_{94}$ | $R_{95}$ | $Q_3$ |
|---|---|---|---|---|---|
| A1 | H | H | H | $CF_3$ | B24 |
| A2 | $CH_3$ | H | H | $CF_3$ | B24 |
| A3 | $CH_3CH_2$ | H | H | $CF_3$ | B24 |
| A4 | $(CH_3)_2CH$ | H | H | $CF_3$ | B24 |
| A5 | $(CH_3)_3C$ | H | H | $CF_3$ | B24 |
| A6 | cyclopropyl | H | H | $CF_3$ | B24 |
| A7 | $CH_3(CH_2)_2$ | H | H | $CF_3$ | B24 |
| A8 | $CH_3OCH_2$ | H | H | $CF_3$ | B24 |
| A9 | $CH_3O(CH_2)_2$ | H | H | $CF_3$ | B24 |
| A10 | Ph | H | H | $CF_3$ | B24 |
| A11 | PhO | H | H | $CF_3$ | B24 |
| A12 | PhS | H | H | $CF_3$ | B24 |
| A13 | PhSO | H | H | $CF_3$ | B24 |
| A14 | $PhSO_2$ | H | H | $CF_3$ | B24 |
| A15 | $CH_3S$ | H | H | $CF_3$ | B24 |

TABLE 9-continued

Compounds of formula If:

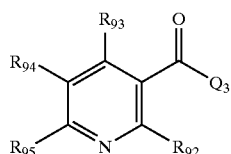

(If)

| Compd. no. | $R_{92}$ | $R_{93}$ | $R_{94}$ | $R_{95}$ | $Q_3$ |
|---|---|---|---|---|---|
| A16 | $CH_3SO$ | H | H | $CF_3$ | B24 |
| A17 | $CF_3$ | H | H | $CF_3$ | B24 |
| A18 | $F_2CH$ | H | H | $CF_3$ | B24 |
| A19 | HCC | H | H | $CF_3$ | B24 |
| A20 | $CH_3CC$ | H | H | $CF_3$ | B24 |
| A21 | $CH_2=CH$ | H | H | $CF_3$ | B24 |
| A22 | $CH_2=CHCH_2$ | H | H | $CF_3$ | B24 |
| A23 | $CH_3SO_2N(CH_3)$ | H | H | $CF_3$ | B24 |
| A24 | $(CH_3)_2N$ | H | H | $CF_3$ | B24 |
| A25 | $(CH_3)_2NSO_2$ | H | H | $CF_3$ | B24 |
| A26 | $ClCH_2$ | H | H | $CF_3$ | B24 |
| A27 | $CH_3SCH_2$ | H | H | $CF_3$ | B24 |
| A28 | $CH_3SOCH_2$ | H | H | $CF_3$ | B24 |
| A29 | $CH_3SO_2CH_2$ | H | H | $CF_3$ | B24 |
| A30 | [1,2,4]-triazol-1-yl-methyl | H | H | $CF_3$ | B24 |
| A31 | $CH_3$ | $CF_3$ | H | $CH_3$ | B24 |
| A32 | $CH_3$ | $CH_3$ | H | $CF_3$ | B24 |
| A33 | H | H | H | $CF_3CF_2$ | B24 |
| A34 | $CH_3$ | H | H | $CF_3CF_2$ | B24 |
| A35 | $CH_3CH_2$ | H | H | $CF_3CF_2$ | B24 |
| A36 | cyclopropyl | H | H | $CF_3CF_2$ | B24 |
| A37 | $(CH_3)_3C$ | H | H | $CF_3CF_2$ | B24 |
| A38 | $(CH_3)_2CH$ | H | H | $CF_3CF_2$ | B24 |
| A39 | $CH_3(CH_2)_2$ | H | H | $CF_3CF_2$ | B24 |
| A40 | $CH_3OCH_2$ | H | H | $CF_3CF_2$ | B24 |
| A41 | $CH_3O(CH_2)_2$ | H | H | $CF_3CF_2$ | B24 |
| A42 | Ph | H | H | $CF_3CF_2$ | B24 |
| A43 | PhO | H | H | $CF_3CF_2$ | B24 |
| A44 | PhS | H | H | $CF_3CF_2$ | B24 |
| A45 | PhSO | H | H | $CF_3CF_2$ | B24 |
| A46 | $PhSO_2$ | H | H | $CF_3CF_2$ | B24 |
| A47 | $CH_3S$ | H | H | $CF_3CF_2$ | B24 |
| A48 | $CH_3SO$ | H | H | $CF_3CF_2$ | B24 |
| A49 | $CF_3$ | H | H | $CF_3CF_2$ | B24 |
| A50 | $F_2CH$ | H | H | $CF_3CF_2$ | B24 |
| A51 | HCC | H | H | $CF_3CF_2$ | B24 |
| A52 | $CH_3CC$ | H | H | $CF_3CF_2$ | B24 |
| A53 | $CH_2=CH$ | H | H | $CF_3CF_2$ | B24 |
| A54 | $CH_2=CHCH_2$ | H | H | $CF_3CF_2$ | B24 |
| A55 | $CH_3SO_2N(CH_3)$ | H | H | $CF_3CF_2$ | B24 |
| A56 | $(CH_3)_2N$ | H | H | $CF_3CF_2$ | B24 |
| A57 | $(CH_3)_2NSO_2$ | H | H | $CF_3CF_2$ | B24 |
| A58 | $ClCH_2$ | H | H | $CF_3CF_2$ | B24 |
| A59 | $CH_3SCH_2$ | H | H | $CF_3CF_2$ | B24 |
| A60 | $CH_3SOCH_2$ | H | H | $CF_3CF_2$ | B24 |
| A61 | $CH_3SO_2CH_2$ | H | H | $CF_3CF_2$ | B24 |
| A62 | [1,2,4]-triazol-1-yl-methyl | H | H | $CF_3CF_2$ | B24 |
| A63 | H | H | H | $CF_3CF_2CF_2$ | B24 |
| A64 | $CH_3$ | H | H | $CF_3CF_2CF_2$ | B24 |
| A65 | $CH_3CH_2$ | H | H | $CF_3CF_2CF_2$ | B24 |
| A66 | cyclopropyl | H | H | $CF_3CF_2CF_2$ | B24 |
| A67 | $(CH_3)_3C$ | H | H | $CF_3CF_2CF_2$ | B24 |
| A68 | $(CH_3)_2CH$ | H | H | $CF_3CF_2CF_2$ | B24 |
| A69 | $CH_3(CH_2)_2$ | H | H | $CF_3CF_2CF_2$ | B24 |
| A70 | $CH_3OCH_2$ | H | H | $CF_3CF_2CF_2$ | B24 |
| A71 | $CH_3O(CH_2)_2$ | H | H | $CF_3CF_2CF_2$ | B24 |
| A72 | Ph | H | H | $CF_3CF_2CF_2$ | B24 |
| A73 | PhO | H | H | $CF_3CF_2CF_2$ | B24 |
| A74 | PhS | H | H | $CF_3CF_2CF_2$ | B24 |
| A75 | PhSO | H | H | $CF_3CF_2CF_2$ | B24 |
| A76 | $PhSO_2$ | H | H | $CF_3CF_2CF_2$ | B24 |
| A77 | $CH_3S$ | H | H | $CF_3CF_2CF_2$ | B24 |
| A78 | $CH_3SO$ | H | H | $CF_3CF_2CF_2$ | B24 |
| A79 | $CF_3$ | H | H | $CF_3CF_2CF_2$ | B24 |

TABLE 9-continued

Compounds of formula If:

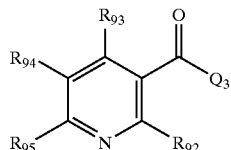

(If)

| Compd. no. | $R_{92}$ | $R_{93}$ | $R_{94}$ | $R_{95}$ | $Q_3$ |
|---|---|---|---|---|---|
| A80 | $F_2CH$ | H | H | $CF_3CF_2CF_2$ | B24 |
| A81 | HCC | H | H | $CF_3CF_2CF_2$ | B24 |
| A82 | $CH_3CC$ | H | H | $CF_3CF_2CF_2$ | B24 |
| A83 | $CH_2=CH$ | H | H | $CF_3CF_2CF_2$ | B24 |
| A84 | $CH_2=CHCH_2$ | H | H | $CF_3CF_2CF_2$ | B24 |
| A85 | $CH_3SO_2N(CH_3)$ | H | H | $CF_3CF_2CF_2$ | B24 |
| A86 | $(CH_3)_2N$ | H | H | $CF_3CF_2CF_2$ | B24 |
| A87 | $(CH_3)_2NSO_2$ | H | H | $CF_3CF_2CF_2$ | B24 |
| A88 | $ClCH_2$ | H | H | $CF_3CF_2CF_2$ | B24 |
| A89 | $CH_3SCH_2$ | H | H | $CF_3CF_2CF_2$ | B24 |
| A90 | $CH_3SOCH_2$ | H | H | $CF_3CF_2CF_2$ | B24 |
| A91 | $CH_3SO_2CH_2$ | H | H | $CF_3CF_2CF_2$ | B24 |
| A92 | [1,2,4]-triazol-1-yl-methyl | H | H | $CF_3CF_2CF_2$ | B24 |
| A93 | H | H | H | $CF_2Cl$ | B24 |
| A94 | $CH_3$ | H | H | $CF_2Cl$ | B24 |
| A95 | $CH_3CH_2$ | H | H | $CF_2Cl$ | B24 |
| A96 | cyclopropyl | H | H | $CF_2Cl$ | B24 |
| A97 | $(CH_3)_3C$ | H | H | $CF_2Cl$ | B24 |
| A98 | $(CH_3)_2CH$ | H | H | $CF_2Cl$ | B24 |
| A99 | $CH_3(CH_2)_2$ | H | H | $CF_2Cl$ | B24 |
| A100 | $CH_3OCH_2$ | H | H | $CF_2Cl$ | B24 |
| A101 | $CH_3O(CH_2)_2$ | H | H | $CF_2Cl$ | B24 |
| A102 | Ph | H | H | $CF_2Cl$ | B24 |
| A103 | PhO | H | H | $CF_2Cl$ | B24 |
| A104 | PhS | H | H | $CF_2Cl$ | B24 |
| A105 | PhSO | H | H | $CF_2Cl$ | B24 |
| A106 | $PhSO_2$ | H | H | $CF_2Cl$ | B24 |
| A107 | $CH_3S$ | H | H | $CF_2Cl$ | B24 |
| A108 | $CH_3SO$ | H | H | $CF_2Cl$ | B24 |
| A109 | $CF_3$ | H | H | $CF_2Cl$ | B24 |
| A110 | $F_2CH$ | H | H | $CF_2Cl$ | B24 |
| A111 | HCC | H | H | $CF_2Cl$ | B24 |
| A112 | $CH_3CC$ | H | H | $CF_2Cl$ | B24 |
| A113 | $CH_2=CH$ | H | H | $CF_2Cl$ | B24 |
| A114 | $CH_2=CHCH_2$ | H | H | $CF_2Cl$ | B24 |
| A115 | $CH_3SO_2N(CH_3)$ | H | H | $CF_2Cl$ | B24 |
| A116 | $(CH_3)_2N$ | H | H | $CF_2Cl$ | B24 |
| A117 | $(CH_3)_2NSO_2$ | H | H | $CF_2Cl$ | B24 |
| A118 | $ClCH_2$ | H | H | $CF_2Cl$ | B24 |
| A119 | $CH_3SCH_2$ | H | H | $CF_2Cl$ | B24 |
| A120 | $CH_3SOCH_2$ | H | H | $CF_2Cl$ | B24 |
| A121 | $CH_3SO_2CH_2$ | H | H | $CF_2Cl$ | B24 |
| A122 | [1,2,4]-triazol-1-yl-methyl | H | H | $CF_2Cl$ | B24 |
| A123 | H | H | H | $CHF_2$ | B24 |
| A124 | $CH_3$ | H | H | $CHF_2$ | B24 |
| A125 | $CH_3CH_2$ | H | H | $CHF_2$ | B24 |
| A126 | cyclopropyl | H | H | $CHF_2$ | B24 |
| A127 | $(CH_3)_3C$ | H | H | $CHF_2$ | B24 |
| A128 | $(CH_3)_2CH$ | H | H | $CHF_2$ | B24 |
| A129 | $CH_3(CH_2)_2$ | H | H | $CHF_2$ | B24 |
| A130 | $CH_3OCH_2$ | H | H | $CHF_2$ | B24 |
| A131 | $CH_3O(CH_2)_2$ | H | H | $CHF_2$ | B24 |
| A132 | Ph | H | H | $CHF_2$ | B24 |
| A133 | PhO | H | H | $CHF_2$ | B24 |
| A134 | PhS | H | H | $CHF_2$ | B24 |
| A135 | PhSO | H | H | $CHF_2$ | B24 |
| A136 | $PhSO_2$ | H | H | $CHF_2$ | B24 |
| A137 | $CH_3S$ | H | H | $CHF_2$ | B24 |
| A138 | $CH_3SO$ | H | H | $CHF_2$ | B24 |
| A139 | $CF_3$ | H | H | $CHF_2$ | B24 |
| A140 | $F_2CH$ | H | H | $CHF_2$ | B24 |
| A141 | HCC | H | H | $CHF_2$ | B24 |
| A142 | $CH_3CC$ | H | H | $CHF_2$ | B24 |
| A143 | $CH_2=CH$ | H | H | $CHF_2$ | B24 |

TABLE 9-continued

Compounds of formula If:

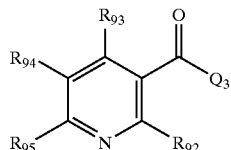

(If)

| Compd. no. | $R_{92}$ | $R_{93}$ | $R_{94}$ | $R_{95}$ | $Q_3$ |
|---|---|---|---|---|---|
| A144 | $CH_2$=$CHCH_2$ | H | H | $CHF_2$ | B24 |
| A145 | $CH_3SO_2N(CH_3)$ | H | H | $CHF_2$ | B24 |
| A146 | $(CH_3)_2N$ | H | H | $CHF_2$ | B24 |
| A147 | $(CH_3)_2NSO_2$ | H | H | $CHF_2$ | B24 |
| A148 | $ClCH_2$ | H | H | $CHF_2$ | B24 |
| A149 | $CH_3SCH_2$ | H | H | $CHF_2$ | B24 |
| A150 | $CH_3SOCH_2$ | H | H | $CHF_2$ | B24 |
| A151 | $CH_3SO_2CH_2$ | H | H | $CHF_2$ | B24 |
| A152 | [1,2,4]-triazol-1-yl-methyl | H | H | $CHF_2$ | B24 |
| A153 | H | H | H | $CCl_3$ | B24 |
| A154 | $CH_3$ | H | H | $CCl_3$ | B24 |
| A155 | $CH_3CH_2$ | H | H | $CCl_3$ | B24 |
| A156 | cyclopropyl | H | H | $CCl_3$ | B24 |
| A157 | $(CH_3)_3C$ | H | H | $CCl_3$ | B24 |
| A158 | $(CH_3)_2CH$ | H | H | $CCl_3$ | B24 |
| A159 | $CH_3(CH_2)_2$ | H | H | $CCl_3$ | B24 |
| A160 | $CH_3OCH_2$ | H | H | $CCl_3$ | B24 |
| A161 | $CH_3O(CH_2)_2$ | H | H | $CCl_3$ | B24 |
| A162 | Ph | H | H | $CCl_3$ | B24 |
| A163 | PhO | H | H | $CCl_3$ | B24 |
| A164 | PhS | H | H | $CCl_3$ | B24 |
| A165 | PhSO | H | H | $CCl_3$ | B24 |
| A166 | $PhSO_2$ | H | H | $CCl_3$ | B24 |
| A167 | $CH_3S$ | H | H | $CCl_3$ | B24 |
| A168 | $CH_3SO$ | H | H | $CCl_3$ | B24 |
| A169 | $CF_3$ | H | H | $CCl_3$ | B24 |
| A170 | $F_2CH$ | H | H | $CCl_3$ | B24 |
| A171 | HCC | H | H | $CCl_3$ | B24 |
| A172 | $CH_3CC$ | H | H | $CCl_3$ | B24 |
| A173 | $CH_2$=CH | H | H | $CCl_3$ | B24 |
| A174 | $CH_2$=$CHCH_2$ | H | H | $CCl_3$ | B24 |
| A175 | $CH_3SO_2N(CH_3)$ | H | H | $CCl_3$ | B24 |
| A176 | $(CH_3)_2N$ | H | H | $CCl_3$ | B24 |
| A177 | $(CH_3)_2NSO_2$ | H | H | $CCl_3$ | B24 |
| A178 | $ClCH_2$ | H | H | $CCl_3$ | B24 |
| A179 | $CH_3SCH_2$ | H | H | $CCl_3$ | B24 |
| A180 | $CH_3SOCH_2$ | H | H | $CCl_3$ | B24 |
| A181 | $CH_3SO_2CH_2$ | H | H | $CCl_3$ | B24 |
| A182 | [1,2,4]-triazol-1-yl-methyl | H | H | $CCl_3$ | B24 |
| A183 | H | H | $CH_3$ | $CF_3$ | B24 |
| A184 | $CH_3$ | H | $CH_3$ | $CF_3$ | B24 |
| A185 | $CH_3CH_2$ | H | $CH_3$ | $CF_3$ | B24 |
| A186 | cyclopropyl | H | $CH_3$ | $CF_3$ | B24 |
| A187 | $(CH_3)_3C$ | H | $CH_3$ | $CF_3$ | B24 |
| A188 | $(CH_3)_2CH$ | H | $CH_3$ | $CF_3$ | B24 |
| A189 | $CH_3(CH_2)_2$ | H | $CH_3$ | $CF_3$ | B24 |
| A190 | $CH_3OCH_2$ | H | $CH_3$ | $CF_3$ | B24 |
| A191 | $CH_3O(CH_2)_2$ | H | $CH_3$ | $CF_3$ | B24 |
| A192 | Ph | H | $CH_3$ | $CF_3$ | B24 |
| A193 | PhO | H | $CH_3$ | $CF_3$ | B24 |
| A194 | PhS | H | $CH_3$ | $CF_3$ | B24 |
| A195 | PhSO | H | $CH_3$ | $CF_3$ | B24 |
| A196 | $PhSO_2$ | H | $CH_3$ | $CF_3$ | B24 |
| A197 | $CH_3S$ | H | $CH_3$ | $CF_3$ | B24 |
| A198 | $CH_3SO$ | H | $CH_3$ | $CF_3$ | B24 |
| A199 | $CF_3$ | H | $CH_3$ | $CF_3$ | B24 |
| A200 | $F_2CH$ | H | $CH_3$ | $CF_3$ | B24 |
| A201 | HCC | H | $CH_3$ | $CF_3$ | B24 |
| A202 | $CH_3CC$ | H | $CH_3$ | $CF_3$ | B24 |
| A203 | $CH_2$=CH | H | $CH_3$ | $CF_3$ | B24 |
| A204 | $CH_2$=$CHCH_2$ | H | $CH_3$ | $CF_3$ | B24 |
| A205 | $CH_3SO_2N(CH_3)$ | H | $CH_3$ | $CF_3$ | B24 |
| A206 | $(CH_3)_2N$ | H | $CH_3$ | $CF_3$ | B24 |
| A207 | $(CH_3)_2NSO_2$ | H | $CH_3$ | $CF_3$ | B24 |

TABLE 9-continued

Compounds of formula If:

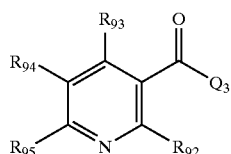

(If)

| Compd. no. | $R_{92}$ | $R_{93}$ | $R_{94}$ | $R_{95}$ | $Q_3$ |
|---|---|---|---|---|---|
| A208 | $ClCH_2$ | H | $CH_3$ | $CF_3$ | B24 |
| A209 | $CH_3SCH_2$ | H | $CH_3$ | $CF_3$ | B24 |
| A210 | $CH_3SOCH_2$ | H | $CH_3$ | $CF_3$ | B24 |
| A211 | $CH_3SO_2CH_2$ | H | $CH_3$ | $CF_3$ | B24 |
| A212 | H | H | $CH_3$ | $CF_3CF_2$ | B24 |
| A213 | $CH_3$ | H | $CH_3$ | $CF_3CF_2$ | B24 |
| A214 | $CH_3CH_2$ | H | $CH_3$ | $CF_3CF_2$ | B24 |
| A215 | cyclopropyl | H | $CH_3$ | $CF_3CF_2$ | B24 |
| A216 | $(CH_3)_3C$ | H | $CH_3$ | $CF_3CF_2$ | B24 |
| A217 | $(CH_3)_2CH$ | H | $CH_3$ | $CF_3CF_2$ | B24 |
| A218 | $CH_3(CH_2)_2$ | H | $CH_3$ | $CF_3CF_2$ | B24 |
| A219 | $CH_3OCH_2$ | H | $CH_3$ | $CF_3CF_2$ | B24 |
| A220 | $CH_3O(CH_2)_2$ | H | $CH_3$ | $CF_3CF_2$ | B24 |
| A221 | Ph | H | $CH_3$ | $CF_3CF_2$ | B24 |
| A222 | PhO | H | $CH_3$ | $CF_3CF_2$ | B24 |
| A223 | PhS | H | $CH_3$ | $CF_3CF_2$ | B24 |
| A224 | PhSO | H | $CH_3$ | $CF_3CF_2$ | B24 |
| A225 | $PhSO_2$ | H | $CH_3$ | $CF_3CF_2$ | B24 |
| A226 | $CH_3S$ | H | $CH_3$ | $CF_3CF_2$ | B24 |
| A227 | $CH_3SO$ | H | $CH_3$ | $CF_3CF_2$ | B24 |
| A228 | $CF_3$ | H | $CH_3$ | $CF_3CF_2$ | B24 |
| A229 | $F_2CH$ | H | $CH_3$ | $CF_3CF_2$ | B24 |
| A230 | HCC | H | $CH_3$ | $CF_3CF_2$ | B24 |
| A231 | $CH_3CC$ | H | $CH_3$ | $CF_3CF_2$ | B24 |
| A232 | $CH_2=CH$ | H | $CH_3$ | $CF_3CF_2$ | B24 |
| A233 | $CH_2=CHCH_2$ | H | $CH_3$ | $CF_3CF_2$ | B24 |
| A234 | $CH_3SO_2N(CH_3)$ | H | $CH_3$ | $CF_3CF_2$ | B24 |
| A235 | $(CH_3)_2N$ | H | $CH_3$ | $CF_3CF_2$ | B24 |
| A236 | $(CH_3)_2NSO_2$ | H | $CH_3$ | $CF_3CF_2$ | B24 |
| A237 | $ClCH_2$ | H | $CH_3$ | $CF_3CF_2$ | B24 |
| A238 | $CH_3SCH_2$ | H | $CH_3$ | $CF_3CF_2$ | B24 |
| A239 | $CH_3SOCH_2$ | H | $CH_3$ | $CF_3CF_2$ | B24 |
| A240 | $CH_3SO_2CH_2$ | H | $CH_3$ | $CF_3CF_2$ | B24 |
| A241 | H | H | $CH_3$ | $CF_3CF_2CF_2$ | B24 |
| A242 | $CH_3$ | H | $CH_3$ | $CF_3CF_2CF_2$ | B24 |
| A243 | $CH_3CH_2$ | H | $CH_3$ | $CF_3CF_2CF_2$ | B24 |
| A244 | cyclopropyl | H | $CH_3$ | $CF_3CF_2CF_2$ | B24 |
| A245 | $(CH_3)_3C$ | H | $CH_3$ | $CF_3CF_2CF_2$ | B24 |
| A246 | $(CH_3)_2CH$ | H | $CH_3$ | $CF_3CF_2CF_2$ | B24 |
| A247 | $CH_3(CH_2)_2$ | H | $CH_3$ | $CF_3CF_2CF_2$ | B24 |
| A248 | $CH_3OCH_2$ | H | $CH_3$ | $CF_3CF_2CF_2$ | B24 |
| A249 | $CH_3O(CH_2)_2$ | H | $CH_3$ | $CF_3CF_2CF_2$ | B24 |
| A250 | Ph | H | $CH_3$ | $CF_3CF_2CF_2$ | B24 |
| A251 | PhO | H | $CH_3$ | $CF_3CF_2CF_2$ | B24 |
| A252 | PhS | H | $CH_3$ | $CF_3CF_2CF_2$ | B24 |
| A253 | PhSO | H | $CH_3$ | $CF_3CF_2CF_2$ | B24 |
| A254 | $PhSO_2$ | H | $CH_3$ | $CF_3CF_2CF_2$ | B24 |
| A255 | $CH_3S$ | H | $CH_3$ | $CF_3CF_2CF_2$ | B24 |
| A256 | $CH_3SO$ | H | $CH_3$ | $CF_3CF_2CF_2$ | B24 |
| A257 | $CF_3$ | H | $CH_3$ | $CF_3CF_2CF_2$ | B24 |
| A258 | $F_2CH$ | H | $CH_3$ | $CF_3CF_2CF_2$ | B24 |
| A259 | HCC | H | $CH_3$ | $CF_3CF_2CF_2$ | B24 |
| A260 | $CH_3CC$ | H | $CH_3$ | $CF_3CF_2CF_2$ | B24 |
| A261 | $CH_2=CH$ | H | $CH_3$ | $CF_3CF_2CF_2$ | B24 |
| A262 | $CH_2=CHCH_2$ | H | $CH_3$ | $CF_3CF_2CF_2$ | B24 |
| A263 | $CH_3SO_2N(CH_3)$ | H | $CH_3$ | $CF_3CF_2CF_2$ | B24 |
| A264 | $(CH_3)_2N$ | H | $CH_3$ | $CF_3CF_2CF_2$ | B24 |
| A265 | $(CH_3)_2NSO_2$ | H | $CH_3$ | $CF_3CF_2CF_2$ | B24 |
| A266 | $ClCH_2$ | H | $CH_3$ | $CF_3CF_2CF_2$ | B24 |
| A267 | $CH_3SCH_2$ | H | $CH_3$ | $CF_3CF_2CF_2$ | B24 |
| A268 | $CH_3SOCH_2$ | H | $CH_3$ | $CF_3CF_2CF_2$ | B24 |
| A269 | $CH_3SO_2CH_2$ | H | $CH_3$ | $CF_3CF_2CF_2$ | B24 |
| A270 | H | H | $CH_3$ | $CF_2Cl$ | B24 |
| A271 | $CH_3$ | H | $CH_3$ | $CF_2Cl$ | B24 |

TABLE 9-continued

Compounds of formula If:

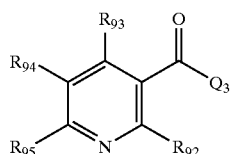

(If)

| Compd. no. | $R_{92}$ | $R_{93}$ | $R_{94}$ | $R_{95}$ | $Q_3$ |
|---|---|---|---|---|---|
| A272 | $CH_3CH_2$ | H | $CH_3$ | $CF_2Cl$ | B24 |
| A273 | cyclopropyl | H | $CH_3$ | $CF_2Cl$ | B24 |
| A274 | $(CH_3)_3C$ | H | $CH_3$ | $CF_2Cl$ | B24 |
| A275 | $(CH_3)_2CH$ | H | $CH_3$ | $CF_2Cl$ | B24 |
| A276 | $CH_3(CH_2)_2$ | H | $CH_3$ | $CF_2Cl$ | B24 |
| A277 | $CH_3OCH_2$ | H | $CH_3$ | $CF_2Cl$ | B24 |
| A278 | $CH_3O(CH_2)_2$ | H | $CH_3$ | $CF_2Cl$ | B24 |
| A279 | Ph | H | $CH_3$ | $CF_2Cl$ | B24 |
| A280 | PhO | H | $CH_3$ | $CF_2Cl$ | B24 |
| A281 | PhS | H | $CH_3$ | $CF_2Cl$ | B24 |
| A282 | PhSO | H | $CH_3$ | $CF_2Cl$ | B24 |
| A283 | $PhSO_2$ | H | $CH_3$ | $CF_2Cl$ | B24 |
| A284 | $CH_3S$ | H | $CH_3$ | $CF_2Cl$ | B24 |
| A285 | $CH_3SO$ | H | $CH_3$ | $CF_2Cl$ | B24 |
| A286 | $CF_3$ | H | $CH_3$ | $CF_2Cl$ | B24 |
| A287 | $F_2CH$ | H | $CH_3$ | $CF_2Cl$ | B24 |
| A288 | HCC | H | $CH_3$ | $CF_2Cl$ | B24 |
| A289 | $CH_3CC$ | H | $CH_3$ | $CF_2Cl$ | B24 |
| A290 | $CH_2=CH$ | H | $CH_3$ | $CF_2Cl$ | B24 |
| A291 | $CH_2=CHCH_2$ | H | $CH_3$ | $CF_2Cl$ | B24 |
| A292 | $CH_3SO_2N(CH_3)$ | H | $CH_3$ | $CF_2Cl$ | B24 |
| A293 | $(CH_3)_2N$ | H | $CH_3$ | $CF_2Cl$ | B24 |
| A294 | $(CH_3)_2NSO_2$ | H | $CH_3$ | $CF_2Cl$ | B24 |
| A295 | $ClCH_2$ | H | $CH_3$ | $CF_2Cl$ | B24 |
| A296 | $CH_3SCH_2$ | H | $CH_3$ | $CF_2Cl$ | B24 |
| A297 | $CH_3SOCH_2$ | H | $CH_3$ | $CF_2Cl$ | B24 |
| A298 | $CH_3SO_2CH_2$ | H | $CH_3$ | $CF_2Cl$ | B24 |
| A299 | H | H | $CH_3$ | $CHF_2$ | B24 |
| A300 | $CH_3$ | H | $CH_3$ | $CHF_2$ | B24 |
| A301 | $CH_3CH_2$ | H | $CH_3$ | $CHF_2$ | B24 |
| A302 | cyclopropyl | H | $CH_3$ | $CHF_2$ | B24 |
| A303 | $(CH_3)_3C$ | H | $CH_3$ | $CHF_2$ | B24 |
| A304 | $(CH_3)_2CH$ | H | $CH_3$ | $CHF_2$ | B24 |
| A305 | $CH_3(CH_2)_2$ | H | $CH_3$ | $CHF_2$ | B24 |
| A306 | $CH_3OCH_2$ | H | $CH_3$ | $CHF_2$ | B24 |
| A307 | $CH_3O(CH_2)_2$ | H | $CH_3$ | $CHF_2$ | B24 |
| A308 | Ph | H | $CH_3$ | $CHF_2$ | B24 |
| A309 | PhO | H | $CH_3$ | $CHF_2$ | B24 |
| A310 | PhS | H | $CH_3$ | $CHF_2$ | B24 |
| A311 | PhSO | H | $CH_3$ | $CHF_2$ | B24 |
| A312 | $PhSO_2$ | H | $CH_3$ | $CHF_2$ | B24 |
| A313 | $CH_3S$ | H | $CH_3$ | $CHF_2$ | B24 |
| A314 | $CH_3SO$ | H | $CH_3$ | $CHF_2$ | B24 |
| A315 | $CF_3$ | H | $CH_3$ | $CHF_2$ | B24 |
| A316 | $F_2CH$ | H | $CH_3$ | $CHF_2$ | B24 |
| A317 | HCC | H | $CH_3$ | $CHF_2$ | B24 |
| A318 | $CH_3CC$ | H | $CH_3$ | $CHF_2$ | B24 |
| A319 | $CH_2=CH$ | H | $CH_3$ | $CHF_2$ | B24 |
| A320 | $CH_2=CHCH_2$ | H | $CH_3$ | $CHF_2$ | B24 |
| A321 | $CH_3SO_2N(CH_3)$ | H | $CH_3$ | $CHF_2$ | B24 |
| A322 | $(CH_3)_2N$ | H | $CH_3$ | $CHF_2$ | B24 |
| A323 | $(CH_3)_2NSO_2$ | H | $CH_3$ | $CHF_2$ | B24 |
| A324 | $ClCH_2$ | H | $CH_3$ | $CHF_2$ | B24 |
| A325 | $CH_3SCH_2$ | H | $CH_3$ | $CHF_2$ | B24 |
| A326 | $CH_3SOCH_2$ | H | $CH_3$ | $CHF_2$ | B24 |
| A327 | $CH_3SO_2CH_2$ | H | $CH_3$ | $CHF_2$ | B24 |
| A328 | H | H | $CH_3$ | $CCl_3$ | B24 |
| A329 | $CH_3$ | H | $CH_3$ | $CCl_3$ | B24 |
| A330 | $CH_3CH_2$ | H | $CH_3$ | $CCl_3$ | B24 |
| A331 | $(CH_3)_3C$ | H | $CH_3$ | $CCl_3$ | B24 |
| A332 | $(CH_3)_2CH$ | H | $CH_3$ | $CCl_3$ | B24 |
| A333 | cyclopropyl | H | $CH_3$ | $CCl_3$ | B24 |
| A334 | $CH_3(CH_2)_2$ | H | $CH_3$ | $CCl_3$ | B24 |
| A335 | $CH_3OCH_2$ | H | $CH_3$ | $CCl_3$ | B24 |

TABLE 9-continued

Compounds of formula If:

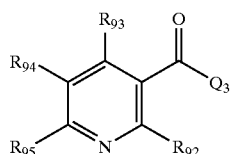

(If)

| Compd. no. | $R_{92}$ | $R_{93}$ | $R_{94}$ | $R_{95}$ | $Q_3$ |
|---|---|---|---|---|---|
| A336 | $CH_3O(CH_2)_2$ | H | $CH_3$ | $CCl_3$ | B24 |
| A337 | Ph | H | $CH_3$ | $CCl_3$ | B24 |
| A338 | PhO | H | $CH_3$ | $CCl_3$ | B24 |
| A339 | PhS | H | $CH_3$ | $CCl_3$ | B24 |
| A340 | PhSO | H | $CH_3$ | $CCl_3$ | B24 |
| A341 | $PhSO_2$ | H | $CH_3$ | $CCl_3$ | B24 |
| A342 | $CH_3S$ | H | $CH_3$ | $CCl_3$ | B24 |
| A343 | $CH_3SO$ | H | $CH_3$ | $CCl_3$ | B24 |
| A344 | $CF_3$ | H | $CH_3$ | $CCl_3$ | B24 |
| A345 | $F_2CH$ | H | $CH_3$ | $CCl_3$ | B24 |
| A346 | HCC | H | $CH_3$ | $CCl_3$ | B24 |
| A347 | $CH_3CC$ | H | $CH_3$ | $CCl_3$ | B24 |
| A348 | $CH_2=CH$ | H | $CH_3$ | $CCl_3$ | B24 |
| A349 | $CH_2=CHCH_2$ | H | $CH_3$ | $CCl_3$ | B24 |
| A350 | $CH_3SO_2N(CH_3)$ | H | $CH_3$ | $CCl_3$ | B24 |
| A351 | $(CH_3)_2N$ | H | $CH_3$ | $CCl_3$ | B24 |
| A352 | $(CH_3)_2NSO_2$ | H | $CH_3$ | $CCl_3$ | B24 |
| A353 | $ClCH_2$ | H | $CH_3$ | $CCl_3$ | B24 |
| A354 | $CH_3SCH_2$ | H | $CH_3$ | $CCl_3$ | B24 |
| A355 | $CH_3SOCH_2$ | H | $CH_3$ | $CCl_3$ | B24 |
| A356 | $CH_3SO_2CH_2$ | H | $CH_3$ | $CCl_3$ | B24 |
| A357 | H | H | Ph | $CF_3$ | B24 |
| A358 | $CH_3$ | H | Ph | $CF_3$ | B24 |
| A359 | $CH_3CH_2$ | H | Ph | $CF_3$ | B24 |
| A360 | cyclopropyl | H | Ph | $CF_3$ | B24 |
| A361 | $(CH_3)_3C$ | H | Ph | $CF_3$ | B24 |
| A362 | $(CH_3)_2CH$ | H | Ph | $CF_3$ | B24 |
| A363 | $CH_3(CH_2)_2$ | H | Ph | $CF_3$ | B24 |
| A364 | $CH_3OCH_2$ | H | Ph | $CF_3$ | B24 |
| A365 | $CH_3O(CH_2)_2$ | H | Ph | $CF_3$ | B24 |
| A366 | Ph | H | Ph | $CF_3$ | B24 |
| A367 | PhO | H | Ph | $CF_3$ | B24 |
| A368 | PhS | H | Ph | $CF_3$ | B24 |
| A369 | PhSO | H | Ph | $CF_3$ | B24 |
| A370 | $PhSO_2$ | H | Ph | $CF_3$ | B24 |
| A371 | $CH_3S$ | H | Ph | $CF_3$ | B24 |
| A372 | $CH_3SO$ | H | Ph | $CF_3$ | B24 |
| A373 | $CF_3$ | H | Ph | $CF_3$ | B24 |
| A374 | $F_2CH$ | H | Ph | $CF_3$ | B24 |
| A375 | HCC | H | Ph | $CF_3$ | B24 |
| A376 | $CH_3CC$ | H | Ph | $CF_3$ | B24 |
| A377 | $CH_2=CH$ | H | Ph | $CF_3$ | B24 |
| A378 | $CH_2=CHCH_2$ | H | Ph | $CF_3$ | B24 |
| A379 | $CH_3SO_2N(CH_3)$ | H | Ph | $CF_3$ | B24 |
| A380 | $(CH_3)_2N$ | H | Ph | $CF_3$ | B24 |
| A381 | $(CH_3)_2NSO_2$ | H | Ph | $CF_3$ | B24 |
| A382 | $ClCH_2$ | H | Ph | $CF_3$ | B24 |
| A383 | $CH_3SCH_2$ | H | Ph | $CF_3$ | B24 |
| A384 | $CH_3SOCH_2$ | H | Ph | $CF_3$ | B24 |
| A385 | $CH_3SO_2CH_2$ | H | Ph | $CF_3$ | B24 |
| A386 | H | H | Ph | $CF_3CF_2$ | B24 |
| A387 | $CH_3$ | H | Ph | $CF_3CF_2$ | B24 |
| A388 | $CH_3CH_2$ | H | Ph | $CF_3CF_2$ | B24 |
| A389 | cyclopropyl | H | Ph | $CF_3CF_2$ | B24 |
| A390 | $(CH_3)_3C$ | H | Ph | $CF_3CF_2$ | B24 |
| A391 | $(CH_3)_2CH$ | H | Ph | $CF_3CF_2$ | B24 |
| A392 | $CH_3(CH_2)_2$ | H | Ph | $CF_3CF_2$ | B24 |
| A393 | $CH_3OCH_2$ | H | Ph | $CF_3CF_2$ | B24 |
| A394 | $CH_3O(CH_2)_2$ | H | Ph | $CF_3CF_2$ | B24 |
| A395 | Ph | H | Ph | $CF_3CF_2$ | B24 |
| A396 | PhO | H | Ph | $CF_3CF_2$ | B24 |
| A397 | PhS | H | Ph | $CF_3CF_2$ | B24 |
| A398 | PhSO | H | Ph | $CF_3CF_2$ | B24 |
| A399 | $PhSO_2$ | H | Ph | $CF_3CF_2$ | B24 |

TABLE 9-continued

Compounds of formula If:

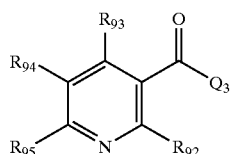

(If)

| Compd. no. | $R_{92}$ | $R_{93}$ | $R_{94}$ | $R_{95}$ | $Q_3$ |
|---|---|---|---|---|---|
| A400 | $CH_3S$ | H | Ph | $CF_3CF_2$ | B24 |
| A401 | $CH_3SO$ | H | Ph | $CF_3CF_2$ | B24 |
| A402 | $CF_3$ | H | Ph | $CF_3CF_2$ | B24 |
| A403 | $F_2CH$ | H | Ph | $CF_3CF_2$ | B24 |
| A404 | HCC | H | Ph | $CF_3CF_2$ | B24 |
| A405 | $CH_3CC$ | H | Ph | $CF_3CF_2$ | B24 |
| A406 | $CH_2=CH$ | H | Ph | $CF_3CF_2$ | B24 |
| A407 | $CH_2=CHCH_2$ | H | Ph | $CF_3CF_2$ | B24 |
| A408 | $CH_3SO_2N(CH_3)$ | H | Ph | $CF_3CF_2$ | B24 |
| A409 | $(CH_3)_2N$ | H | Ph | $CF_3CF_2$ | B24 |
| A410 | $(CH_3)_2NSO_2$ | H | Ph | $CF_3CF_2$ | B24 |
| A411 | $ClCH_2$ | H | Ph | $CF_3CF_2$ | B24 |
| A412 | $CH_3SCH_2$ | H | Ph | $CF_3CF_2$ | B24 |
| A413 | $CH_3SOCH_2$ | H | Ph | $CF_3CF_2$ | B24 |
| A414 | $CH_3SO_2CH_2$ | H | Ph | $CF_3CF_2$ | B24 |
| A415 | H | H | Ph | $CF_3CF_2CF_2$ | B24 |
| A416 | $CH_3$ | H | Ph | $CF_3CF_2CF_2$ | B24 |
| A417 | $CH_3CH_2$ | H | Ph | $CF_3CF_2CF_2$ | B24 |
| A418 | cyclopropyl | H | Ph | $CF_3CF_2CF_2$ | B24 |
| A419 | $(CH_3)_3C$ | H | Ph | $CF_3CF_2CF_2$ | B24 |
| A420 | $(CH_3)_2CH$ | H | Ph | $CF_3CF_2CF_2$ | B24 |
| A421 | $CH_3(CH_2)_2$ | H | Ph | $CF_3CF_2CF_2$ | B24 |
| A422 | $CH_3OCH_2$ | H | Ph | $CF_3CF_2CF_2$ | B24 |
| A423 | $CH_3O(CH_2)_2$ | H | Ph | $CF_3CF_2CF_2$ | B24 |
| A424 | Ph | H | Ph | $CF_3CF_2CF_2$ | B24 |
| A425 | PhO | H | Ph | $CF_3CF_2CF_2$ | B24 |
| A426 | PhS | H | Ph | $CF_3CF_2CF_2$ | B24 |
| A427 | PhSO | H | Ph | $CF_3CF_2CF_2$ | B24 |
| A428 | $PhSO_2$ | H | Ph | $CF_3CF_2CF_2$ | B24 |
| A429 | $CH_3S$ | H | Ph | $CF_3CF_2CF_2$ | B24 |
| A430 | $CH_3SO$ | H | Ph | $CF_3CF_2CF_2$ | B24 |
| A431 | $CF_3$ | H | Ph | $CF_3CF_2CF_2$ | B24 |
| A432 | $F_2CH$ | H | Ph | $CF_3CF_2CF_2$ | B24 |
| A433 | HCC | H | Ph | $CF_3CF_2CF_2$ | B24 |
| A434 | $CH_3CC$ | H | Ph | $CF_3CF_2CF_2$ | B24 |
| A435 | $CH_2=CH$ | H | Ph | $CF_3CF_2CF_2$ | B24 |
| A436 | $CH_2=CHCH_2$ | H | Ph | $CF_3CF_2CF_2$ | B24 |
| A437 | $CH_3SO_2N(CH_3)$ | H | Ph | $CF_3CF_2CF_2$ | B24 |
| A438 | $(CH_3)_2N$ | H | Ph | $CF_3CF_2CF_2$ | B24 |
| A439 | $(CH_3)_2NSO_2$ | H | Ph | $CF_3CF_2CF_2$ | B24 |
| A440 | $ClCH_2$ | H | Ph | $CF_3CF_2CF_2$ | B24 |
| A441 | $CH_3SCH_2$ | H | Ph | $CF_3CF_2CF_2$ | B24 |
| A442 | $CH_3SOCH_2$ | H | Ph | $CF_3CF_2CF_2$ | B24 |
| A443 | $CH_3SO_2CH_2$ | H | Ph | $CF_3CF_2CF_2$ | B24 |
| A444 | H | H | Ph | $CF_2Cl$ | B24 |
| A445 | $CH_3$ | H | Ph | $CF_2Cl$ | B24 |
| A446 | $CH_3CH_2$ | H | Ph | $CF_2Cl$ | B24 |
| A447 | cyclopropyl | H | Ph | $CF_2Cl$ | B24 |
| A448 | $(CH_3)_3C$ | H | Ph | $CF_2Cl$ | B24 |
| A449 | $(CH_3)_2CH$ | H | Ph | $CF_2Cl$ | B24 |
| A450 | $CH_3(CH_2)_2$ | H | Ph | $CF_2Cl$ | B24 |
| A451 | $CH_3OCH_2$ | H | Ph | $CF_2Cl$ | B24 |
| A452 | $CH_3O(CH_2)_2$ | H | Ph | $CF_2Cl$ | B24 |
| A453 | Ph | H | Ph | $CF_2Cl$ | B24 |
| A454 | PhO | H | Ph | $CF_2Cl$ | B24 |
| A455 | PhS | H | Ph | $CF_2Cl$ | B24 |
| A456 | PhSO | H | Ph | $CF_2Cl$ | B24 |
| A457 | $PhSO_2$ | H | Ph | $CF_2Cl$ | B24 |
| A458 | $CH_3S$ | H | Ph | $CF_2Cl$ | B24 |
| A459 | $CH_3SO$ | H | Ph | $CF_2Cl$ | B24 |
| A460 | $CF_3$ | H | Ph | $CF_2Cl$ | B24 |
| A461 | $F_2CH$ | H | Ph | $CF_2Cl$ | B24 |
| A462 | HCC | H | Ph | $CF_2Cl$ | B24 |
| A463 | $CH_3CC$ | H | Ph | $CF_2Cl$ | B24 |

TABLE 9-continued

Compounds of formula If:

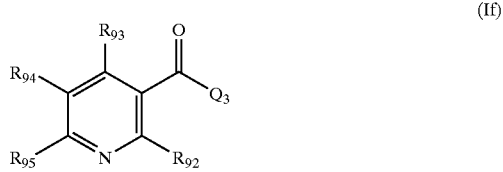

(If)

| Compd. no. | $R_{92}$ | $R_{93}$ | $R_{94}$ | $R_{95}$ | $Q_3$ |
|---|---|---|---|---|---|
| A464 | $CH_2=CH$ | H | Ph | $CF_2Cl$ | B24 |
| A465 | $CH_2=CHCH_2$ | H | Ph | $CF_2Cl$ | B24 |
| A466 | $CH_3SO_2N(CH_3)$ | H | Ph | $CF_2Cl$ | B24 |
| A467 | $(CH_3)_2N$ | H | Ph | $CF_2Cl$ | B24 |
| A468 | $(CH_3)_2NSO_2$ | H | Ph | $CF_2Cl$ | B24 |
| A469 | $ClCH_2$ | H | Ph | $CF_2Cl$ | B24 |
| A470 | $CH_3SCH_2$ | H | Ph | $CF_2Cl$ | B24 |
| A471 | $CH_3SOCH_2$ | H | Ph | $CF_2Cl$ | B24 |
| A472 | $CH_3SO_2CH_2$ | H | Ph | $CF_2Cl$ | B24 |
| A473 | H | H | Ph | $CHF_2$ | B24 |
| A474 | $CH_3$ | H | Ph | $CHF_2$ | B24 |
| A475 | $CH_3CH_2$ | H | Ph | $CHF_2$ | B24 |
| A476 | cyclopropyl | H | Ph | $CHF_2$ | B24 |
| A477 | $(CH_3)_3C$ | H | Ph | $CHF_2$ | B24 |
| A478 | $(CH_3)_2CH$ | H | Ph | $CHF_2$ | B24 |
| A479 | $CH_3(CH_2)_2$ | H | Ph | $CHF_2$ | B24 |
| A480 | $CH_3OCH_2$ | H | Ph | $CHF_2$ | B24 |
| A481 | $CH_3O(CH_2)_2$ | H | Ph | $CHF_2$ | B24 |
| A482 | Ph | H | Ph | $CHF_2$ | B24 |
| A483 | PhO | H | Ph | $CHF_2$ | B24 |
| A484 | PhS | H | Ph | $CHF_2$ | B24 |
| A485 | PhSO | H | Ph | $CHF_2$ | B24 |
| A486 | $PhSO_2$ | H | Ph | $CHF_2$ | B24 |
| A487 | $CH_3S$ | H | Ph | $CHF_2$ | B24 |
| A488 | $CH_3SO$ | H | Ph | $CHF_2$ | B24 |
| A489 | $CF_3$ | H | Ph | $CHF_2$ | B24 |
| A490 | $F_2CH$ | H | Ph | $CHF_2$ | B24 |
| A491 | HCC | H | Ph | $CHF_2$ | B24 |
| A492 | $CH_3CC$ | H | Ph | $CHF_2$ | B24 |
| A493 | $CH_2=CH$ | H | Ph | $CHF_2$ | B24 |
| A494 | $CH_2=CHCH_2$ | H | Ph | $CHF_2$ | B24 |
| A495 | $CH_3SO_2N(CH_3)$ | H | Ph | $CHF_2$ | B24 |
| A496 | $(CH_3)_2N$ | H | Ph | $CHF_2$ | B24 |
| A497 | $(CH_3)_2NSO_2$ | H | Ph | $CHF_2$ | B24 |
| A498 | $ClCH_2$ | H | Ph | $CHF_2$ | B24 |
| A499 | $CH_3SCH_2$ | H | Ph | $CHF_2$ | B24 |
| A500 | $CH_3SOCH_2$ | H | Ph | $CHF_2$ | B24 |
| A501 | $CH_3SO_2CH_2$ | H | Ph | $CHF_2$ | B24 |
| A502 | H | H | Ph | $CCl_3$ | B24 |
| A503 | $CH_3$ | H | Ph | $CCl_3$ | B24 |
| A504 | $CH_3CH_2$ | H | Ph | $CCl_3$ | B24 |
| A505 | cyclopropyl | H | Ph | $CCl_3$ | B24 |
| A506 | $(CH_3)_3C$ | H | Ph | $CCl_3$ | B24 |
| A507 | $(CH_3)_2CH$ | H | Ph | $CCl_3$ | B24 |
| A508 | $CH_3(CH_2)_2$ | H | Ph | $CCl_3$ | B24 |
| A509 | $CH_3OCH_2$ | H | Ph | $CCl_3$ | B24 |
| A510 | $CH_3O(CH_2)_2$ | H | Ph | $CCl_3$ | B24 |
| A511 | Ph | H | Ph | $CCl_3$ | B24 |
| A512 | PhO | H | Ph | $CCl_3$ | B24 |
| A513 | PhS | H | Ph | $CCl_3$ | B24 |
| A514 | PhSO | H | Ph | $CCl_3$ | B24 |
| A515 | $PhSO_2$ | H | Ph | $CCl_3$ | B24 |
| A516 | $CH_3S$ | H | Ph | $CCl_3$ | B24 |
| A517 | $CH_3SO$ | H | Ph | $CCl_3$ | B24 |
| A518 | $CF_3$ | H | Ph | $CCl_3$ | B24 |
| A519 | $F_2CH$ | H | Ph | $CCl_3$ | B24 |
| A520 | HCC | H | Ph | $CCl_3$ | B24 |
| A521 | $CH_3CC$ | H | Ph | $CCl_3$ | B24 |
| A522 | $CH_2=CH$ | H | Ph | $CCl_3$ | B24 |
| A523 | $CH_2=CHCH_2$ | H | Ph | $CCl_3$ | B24 |
| A524 | $CH_3SO_2N(CH_3)$ | H | Ph | $CCl_3$ | B24 |
| A525 | $(CH_3)_2N$ | H | Ph | $CCl_3$ | B24 |
| A526 | $(CH_3)_2NSO_2$ | H | Ph | $CCl_3$ | B24 |
| A527 | $ClCH_2$ | H | Ph | $CCl_3$ | B24 |

TABLE 9-continued

Compounds of formula If:

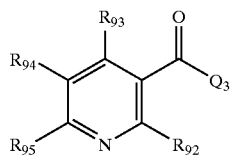

(If)

| Compd. no. | $R_{92}$ | $R_{93}$ | $R_{94}$ | $R_{95}$ | $Q_3$ |
|---|---|---|---|---|---|
| A528 | $CH_3SCH_2$ | H | Ph | $CCl_3$ | B24 |
| A529 | $CH_3SOCH_2$ | H | Ph | $CCl_3$ | B24 |
| A530 | $CH_3SO_2CH_2$ | H | Ph | $CCl_3$ | B24 |
| A531 | H | $CH_3$ | H | $CF_3$ | B24 |
| A532 | H | $CH_3CH_2$ | H | $CF_3$ | B24 |
| A533 | H | cyclopropyl | H | $CF_3$ | B24 |
| A534 | H | $(CH_3)_3CH$ | H | $CF_3$ | B24 |
| A535 | H | $(CH_3)_2CH$ | H | $CF_3$ | B24 |
| A536 | H | $CH_3(CH_2)_2$ | H | $CF_3$ | B24 |
| A537 | H | $CH_3OCH_2$ | H | $CF_3$ | B24 |
| A538 | H | $CH_3O(CH_2)_2$ | H | $CF_3$ | B24 |
| A539 | H | Ph | H | $CF_3$ | B24 |
| A540 | H | PhO | H | $CF_3$ | B24 |
| A541 | H | PhS | H | $CF_3$ | B24 |
| A542 | H | PhSO | H | $CF_3$ | B24 |
| A543 | H | $PhSO_2$ | H | $CF_3$ | B24 |
| A544 | H | $CH_3S$ | H | $CF_3$ | B24 |
| A545 | H | $CH_3SO$ | H | $CF_3$ | B24 |
| A546 | H | $CF_3$ | H | $CF_3$ | B24 |
| A547 | H | $F_2CH$ | H | $CF_3$ | B24 |
| A548 | H | HCC | H | $CF_3$ | B24 |
| A549 | H | $CH_3CC$ | H | $CF_3$ | B24 |
| A550 | H | $CH_2=CH$ | H | $CF_3$ | B24 |
| A551 | H | $CH_2=CHCH_2$ | H | $CF_3$ | B24 |
| A552 | H | $CH_3SO_2N(CH_3)$ | H | $CF_3$ | B24 |
| A553 | H | $(CH_3)_2N$ | H | $CF_3$ | B24 |
| A554 | H | $(CH_3)_2NSO_2$ | H | $CF_3$ | B24 |
| A555 | H | $CH_3SCH_2$ | H | $CF_3$ | B24 |
| A556 | H | $CH_3SOCH_2$ | H | $CF_3$ | B24 |
| A557 | H | $CH_3SO_2CH_2$ | H | $CF_3$ | B24 |
| A558 | H | $CH_3$ | H | $CF_3CF_2$ | B24 |
| A559 | H | $CH_3CH_2$ | H | $CF_3CF_2$ | B24 |
| A560 | H | cyclopropyl | H | $CF_3CF_2$ | B24 |
| A561 | H | $(CH_3)_3C$ | H | $CF_3CF_2$ | B24 |
| A562 | H | $(CH_3)_2CH$ | H | $CF_3CF_2$ | B24 |
| A563 | H | $CH_3(CH_2)_2$ | H | $CF_3CF_2$ | B24 |
| A564 | H | $CH_3OCH_2$ | H | $CF_3CF_2$ | B24 |
| A565 | H | $CH_3O(CH_2)_2$ | H | $CF_3CF_2$ | B24 |
| A566 | H | Ph | H | $CF_3CF_2$ | B24 |
| A567 | H | PhO | H | $CF_3CF_2$ | B24 |
| A568 | H | PhS | H | $CF_3CF_2$ | B24 |
| A569 | H | PhSO | H | $CF_3CF_2$ | B24 |
| A570 | H | $PhSO_2$ | H | $CF_3CF_2$ | B24 |
| A571 | H | $CH_3S$ | H | $CF_3CF_2$ | B24 |
| A572 | H | $CH_3SO$ | H | $CF_3CF_2$ | B24 |
| A573 | H | $CF_3$ | H | $CF_3CF_2$ | B24 |
| A574 | H | $F_2CH$ | H | $CF_3CF_2$ | B24 |
| A575 | H | HCC | H | $CF_3CF_2$ | B24 |
| A576 | H | $CH_3CC$ | H | $CF_3CF_2$ | B24 |
| A577 | H | $CH_2=CH$ | H | $CF_3CF_2$ | B24 |
| A578 | H | $CH_2=CHCH_2$ | H | $CF_3CF_2$ | B24 |
| A579 | H | $CH_3SO_2N(CH_3)$ | H | $CF_3CF_2$ | B24 |
| A580 | H | $(CH_3)_2N$ | H | $CF_3CF_2$ | B24 |
| A581 | H | $(CH_3)_2NSO_2$ | H | $CF_3CF_2$ | B24 |
| A582 | H | $CH_3SCH_2$ | H | $CF_3CF_2$ | B24 |
| A583 | H | $CH_3SOCH_2$ | H | $CF_3CF_2$ | B24 |
| A584 | H | $CH_3SO_2CH_2$ | H | $CF_3CF_2$ | B24 |
| A585 | H | $CH_3$ | H | $CF_3CF_2CF_2$ | B24 |
| A586 | H | $CH_3CH_2$ | H | $CF_3CF_2CF_2$ | B24 |
| A587 | H | cyclopropyl | H | $CF_3CF_2CF_2$ | B24 |
| A588 | H | $(CH_3)_3C$ | H | $CF_3CF_2CF_2$ | B24 |
| A589 | H | $(CH_3)_2CH$ | H | $CF_3CF_2CF_2$ | B24 |
| A590 | H | $CH_3(CH_2)_2$ | H | $CF_3CF_2CF_2$ | B24 |
| A591 | H | $CH_3OCH_2$ | H | $CF_3CF_2CF_2$ | B24 |

TABLE 9-continued

Compounds of formula If:

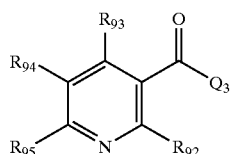

(If)

| Compd. no. | $R_{92}$ | $R_{93}$ | $R_{94}$ | $R_{95}$ | $Q_3$ |
|---|---|---|---|---|---|
| A592 | H | $CH_3O(CH_2)_2$ | H | $CF_3CF_2CF_2$ | B24 |
| A593 | H | Ph | H | $CF_3CF_2CF_2$ | B24 |
| A594 | H | PhO | H | $CF_3CF_2CF_2$ | B24 |
| A595 | H | PhS | H | $CF_3CF_2CF_2$ | B24 |
| A596 | H | PhSO | H | $CF_3CF_2CF_2$ | B24 |
| A597 | H | $PhSO_2$ | H | $CF_3CF_2CF_2$ | B24 |
| A598 | H | $CH_3S$ | H | $CF_3CF_2CF_2$ | B24 |
| A599 | H | $CH_3SO$ | H | $CF_3CF_2CF_2$ | B24 |
| A600 | H | $CF_3$ | H | $CF_3CF_2CF_2$ | B24 |
| A601 | H | $F_2CH$ | H | $CF_3CF_2CF_2$ | B24 |
| A602 | H | HCC | H | $CF_3CF_2CF_2$ | B24 |
| A603 | H | $CH_3CC$ | H | $CF_3CF_2CF_2$ | B24 |
| A604 | H | $CH_2=CH$ | H | $CF_3CF_2CF_2$ | B24 |
| A605 | H | $CH_2=CHCH_2$ | H | $CF_3CF_2CF_2$ | B24 |
| A606 | H | $CH_3SO_2N(CH_3)$ | H | $CF_3CF_2CF_2$ | B24 |
| A607 | H | $(CH_3)_2N$ | H | $CF_3CF_2CF_2$ | B24 |
| A608 | H | $(CH_3)_2NSO_2$ | H | $CF_3CF_2CF_2$ | B24 |
| A609 | H | $CH_3SCH_2$ | H | $CF_3CF_2CF_2$ | B24 |
| A610 | H | $CH_3SOCH_2$ | H | $CF_3CF_2CF_2$ | B24 |
| A611 | H | $CH_3SO_2CH_2$ | H | $CF_3CF_2CF_2$ | B24 |
| A612 | H | $CH_3$ | H | $CF_2Cl$ | B24 |
| A613 | H | $CH_3CH_2$ | H | $CF_2Cl$ | B24 |
| A614 | H | cyclopropyl | H | $CF_2Cl$ | B24 |
| A615 | H | $(CH_3)_3C$ | H | $CF_2Cl$ | B24 |
| A616 | H | $(CH_3)_2CH$ | H | $CF_2Cl$ | B24 |
| A617 | H | $CH_3(CH_2)_2$ | H | $CF_2Cl$ | B24 |
| A618 | H | $CH_3OCH_2$ | H | $CF_2Cl$ | B24 |
| A619 | H | $CH_3O(CH_2)_2$ | H | $CF_2Cl$ | B24 |
| A620 | H | Ph | H | $CF_2Cl$ | B24 |
| A621 | H | PhO | H | $CF_2Cl$ | B24 |
| A622 | H | PhS | H | $CF_2Cl$ | B24 |
| A623 | H | PhSO | H | $CF_2Cl$ | B24 |
| A624 | H | $PhSO_2$ | H | $CF_2Cl$ | B24 |
| A625 | H | $CH_3S$ | H | $CF_2Cl$ | B24 |
| A626 | H | $CH_3SO$ | H | $CF_2Cl$ | B24 |
| A627 | H | $CF_3$ | H | $CF_2Cl$ | B24 |
| A628 | H | $F_2CH$ | H | $CF_2Cl$ | B24 |
| A629 | H | HCC | H | $CF_2Cl$ | B24 |
| A630 | H | $CH_3CC$ | H | $CF_2Cl$ | B24 |
| A631 | H | $CH_2=CH$ | H | $CF_2Cl$ | B24 |
| A632 | H | $CH_2=CHCH_2$ | H | $CF_2Cl$ | B24 |
| A633 | H | $CH_3SO_2N(CH_3)$ | H | $CF_2Cl$ | B24 |
| A634 | H | $(CH_3)_2N$ | H | $CF_2Cl$ | B24 |
| A635 | H | $(CH_3)_2NSO_2$ | H | $CF_2Cl$ | B24 |
| A636 | H | $CH_3SCH_2$ | H | $CF_2Cl$ | B24 |
| A637 | H | $CH_3SOCH_2$ | H | $CF_2Cl$ | B24 |
| A638 | H | $CH_3SO_2CH_2$ | H | $CF_2Cl$ | B24 |
| A639 | H | $CH_3$ | H | $CHF_2$ | B24 |
| A640 | H | $CH_3CH_2$ | H | $CHF_2$ | B24 |
| A641 | H | cyclopropyl | H | $CHF_2$ | B24 |
| A642 | H | $(CH_3)_3C$ | H | $CHF_2$ | B24 |
| A643 | H | $(CH_3)_2CH$ | H | $CHF_2$ | B24 |
| A644 | H | $CH_3(CH_2)_2$ | H | $CHF_2$ | B24 |
| A645 | H | $CH_3OCH_2$ | H | $CHF_2$ | B24 |
| A646 | H | $CH_3O(CH_2)_2$ | H | $CHF_2$ | B24 |
| A647 | H | Ph | H | $CHF_2$ | B24 |
| A648 | H | PhO | H | $CHF_2$ | B24 |
| A649 | H | PhS | H | $CHF_2$ | B24 |
| A650 | H | PhSO | H | $CHF_2$ | B24 |
| A651 | H | $PhSO_2$ | H | $CHF_2$ | B24 |
| A652 | H | $CH_3S$ | H | $CHF_2$ | B24 |
| A653 | H | $CH_3SO$ | H | $CHF_2$ | B24 |
| A654 | H | $CF_3$ | H | $CHF_2$ | B24 |
| A655 | H | $F_2CH$ | H | $CHF_2$ | B24 |

TABLE 9-continued

Compounds of formula If:

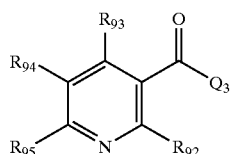

(If)

| Compd. no. | $R_{92}$ | $R_{93}$ | $R_{94}$ | $R_{95}$ | $Q_3$ |
|---|---|---|---|---|---|
| A656 | H | HCC | H | $CHF_2$ | B24 |
| A657 | H | $CH_3CC$ | H | $CHF_2$ | B24 |
| A658 | H | $CH_2$=CH | H | $CHF_2$ | B24 |
| A659 | H | $CH_2$=$CHCH_2$ | H | $CHF_2$ | B24 |
| A660 | H | $CH_3SO_2N(CH_3)$ | H | $CHF_2$ | B24 |
| A661 | H | $(CH_3)_2N$ | H | $CHF_2$ | B24 |
| A662 | H | $(CH_3)_2NSO_2$ | H | $CHF_2$ | B24 |
| A663 | H | $CH_3SCH_2$ | H | $CHF_2$ | B24 |
| A664 | H | $CH_3SOCH_2$ | H | $CHF_2$ | B24 |
| A665 | H | $CH_3SO_2CH_2$ | H | $CHF_2$ | B24 |
| A666 | H | $CH_3$ | H | $CCl_3$ | B24 |
| A667 | H | $CH_3CH_2$ | H | $CCl_3$ | B24 |
| A668 | H | cyclopropyl | H | $CCl_3$ | B24 |
| A669 | H | $(CH_3)_3C$ | H | $CCl_3$ | B24 |
| A670 | H | $(CH_3)_2CH$ | H | $CCl_3$ | B24 |
| A671 | H | $CH_3(CH_2)_2$ | H | $CCl_3$ | B24 |
| A672 | H | $CH_3OCH_2$ | H | $CCl_3$ | B24 |
| A673 | H | $CH_3O(CH_2)_2$ | H | $CCl_3$ | B24 |
| A674 | H | Ph | H | $CCl_3$ | B24 |
| A675 | H | PhO | H | $CCl_3$ | B24 |
| A676 | H | PhS | H | $CCl_3$ | B24 |
| A677 | H | PhSO | H | $CCl_3$ | B24 |
| A678 | H | $PhSO_2$ | H | $CCl_3$ | B24 |
| A679 | H | $CH_3S$ | H | $CCl_3$ | B24 |
| A680 | H | $CH_3SO$ | H | $CCl_3$ | B24 |
| A681 | H | $CF_3$ | H | $CCl_3$ | B24 |
| A682 | H | $F_2CH$ | H | $CCl_3$ | B24 |
| A683 | H | HCC | H | $CCl_3$ | B24 |
| A684 | H | $CH_3CC$ | H | $CCl_3$ | B24 |
| A685 | H | $CH_2$=CH | H | $CCl_3$ | B24 |
| A686 | H | $CH_2$=$CHCH_2$ | H | $CCl_3$ | B24 |
| A687 | H | $CH_3SO_2N(CH_3)$ | H | $CCl_3$ | B24 |
| A688 | H | $(CH_3)_2N$ | H | $CCl_3$ | B24 |
| A689 | H | $(CH_3)_2NSO_2$ | H | $CCl_3$ | B24 |
| A690 | H | $CH_3SCH_2$ | H | $CCl_3$ | B24 |
| A691 | H | $CH_3SOCH_2$ | H | $CCl_3$ | B24 |
| A692 | H | $CH_3SO_2CH_2$ | H | $CCl_3$ | B24 |
| A693 | H | $CH_3$ | $CH_3$ | $CF_3$ | B24 |
| A694 | H | $CH_3CH_2$ | $CH_3$ | $CF_3$ | B24 |
| A695 | H | cyclopropyl | $CH_3$ | $CF_3$ | B24 |
| A696 | H | $(CH_3)_3C$ | $CH_3$ | $CF_3$ | B24 |
| A697 | H | $(CH_3)_2CH$ | $CH_3$ | $CF_3$ | B24 |
| A698 | H | $CH_3(CH_2)_2$ | $CH_3$ | $CF_3$ | B24 |
| A699 | H | $CH_3OCH_2$ | $CH_3$ | $CF_3$ | B24 |
| A700 | H | $CH_3O(CH_2)_2$ | $CH_3$ | $CF_3$ | B24 |
| A701 | H | Ph | $CH_3$ | $CF_3$ | B24 |
| A702 | H | PhO | $CH_3$ | $CF_3$ | B24 |
| A703 | H | PhS | $CH_3$ | $CF_3$ | B24 |
| A704 | H | PhSO | $CH_3$ | $CF_3$ | B24 |
| A705 | H | $PhSO_2$ | $CH_3$ | $CF_3$ | B24 |
| A706 | H | $CH_3S$ | $CH_3$ | $CF_3$ | B24 |
| A707 | H | $CH_3SO$ | $CH_3$ | $CF_3$ | B24 |
| A708 | H | $CF_3$ | $CH_3$ | $CF_3$ | B24 |
| A709 | H | $F_2CH$ | $CH_3$ | $CF_3$ | B24 |
| A710 | H | HCC | $CH_3$ | $CF_3$ | B24 |
| A711 | H | $CH_3CC$ | $CH_3$ | $CF_3$ | B24 |
| A712 | H | $CH_2$=CH | $CH_3$ | $CF_3$ | B24 |
| A713 | H | $CH_2$=$CHCH_2$ | $CH_3$ | $CF_3$ | B24 |
| A714 | H | $CH_3SO_2N(CH_3)$ | $CH_3$ | $CF_3$ | B24 |
| A715 | H | $(CH_3)_2N$ | $CH_3$ | $CF_3$ | B24 |
| A716 | H | $(CH_3)_2NSO_2$ | $CH_3$ | $CF_3$ | B24 |
| A717 | H | $CH_3SCH_2$ | $CH_3$ | $CF_3$ | B24 |
| A718 | H | $CH_3SOCH_2$ | $CH_3$ | $CF_3$ | B24 |
| A719 | H | $CH_3SO_2CH_2$ | $CH_3$ | $CF_3$ | B24 |

TABLE 9-continued

Compounds of formula If:

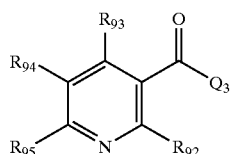

(If)

| Compd. no. | $R_{92}$ | $R_{93}$ | $R_{94}$ | $R_{95}$ | $Q_3$ |
|---|---|---|---|---|---|
| A720 | H | $CH_3$ | $CH_3$ | $CF_3CF_2$ | B24 |
| A721 | H | $CH_3CH_2$ | $CH_3$ | $CF_3CF_2$ | B24 |
| A722 | H | cyclopropyl | $CH_3$ | $CF_3CF_2$ | B24 |
| A723 | H | $(CH_3)_3C$ | $CH_3$ | $CF_3CF_2$ | B24 |
| A724 | H | $(CH_3)_2CH$ | $CH_3$ | $CF_3CF_2$ | B24 |
| A725 | H | $CH_3(CH_2)_2$ | $CH_3$ | $CF_3CF_2$ | B24 |
| A726 | H | $CH_3OCH_2$ | $CH_3$ | $CF_3CF_2$ | B24 |
| A727 | H | $CH_3O(CH_2)_2$ | $CH_3$ | $CF_3CF_2$ | B24 |
| A728 | H | Ph | $CH_3$ | $CF_3CF_2$ | B24 |
| A729 | H | PhO | $CH_3$ | $CF_3CF_2$ | B24 |
| A730 | H | PhS | $CH_3$ | $CF_3CF_2$ | B24 |
| A731 | H | PhSO | $CH_3$ | $CF_3CF_2$ | B24 |
| A732 | H | $PhSO_2$ | $CH_3$ | $CF_3CF_2$ | B24 |
| A733 | H | $CH_3S$ | $CH_3$ | $CF_3CF_2$ | B24 |
| A734 | H | $CH_3SO$ | $CH_3$ | $CF_3CF_2$ | B24 |
| A735 | H | $CF_3$ | $CH_3$ | $CF_3CF_2$ | B24 |
| A736 | H | $F_2CH$ | $CH_3$ | $CF_3CF_2$ | B24 |
| A737 | H | HCC | $CH_3$ | $CF_3CF_2$ | B24 |
| A738 | H | $CH_3CC$ | $CH_3$ | $CF_3CF_2$ | B24 |
| A739 | H | $CH_2=CH$ | $CH_3$ | $CF_3CF_2$ | B24 |
| A740 | H | $CH_2=CHCH_2$ | $CH_3$ | $CF_3CF_2$ | B24 |
| A741 | H | $CH_3SO_2N(CH_3)$ | $CH_3$ | $CF_3CF_2$ | B24 |
| A742 | H | $(CH_3)_2N$ | $CH_3$ | $CF_3CF_2$ | B24 |
| A743 | H | $(CH_3)_2NSO_2$ | $CH_3$ | $CF_3CF_2$ | B24 |
| A744 | H | $CH_3SCH_2$ | $CH_3$ | $CF_3CF_2$ | B24 |
| A745 | H | $CH_3SOCH_2$ | $CH_3$ | $CF_3CF_2$ | B24 |
| A746 | H | $CH_3SO_2CH_2$ | $CH_3$ | $CF_3CF_2$ | B24 |
| A747 | H | $CH_3$ | $CH_3$ | $CF_3CF_2CF_2$ | B24 |
| A748 | H | $CH_3CH_2$ | $CH_3$ | $CF_3CF_2CF_2$ | B24 |
| A749 | H | cyclopropyl | $CH_3$ | $CF_3CF_2CF_2$ | B24 |
| A750 | H | $(CH_3)_3C$ | $CH_3$ | $CF_3CF_2CF_2$ | B24 |
| A751 | H | $(CH_3)_2CH$ | $CH_3$ | $CF_3CF_2CF_2$ | B24 |
| A752 | H | $CH_3(CH_2)_2$ | $CH_3$ | $CF_3CF_2CF_2$ | B24 |
| A753 | H | $CH_3OCH_2$ | $CH_3$ | $CF_3CF_2CF_2$ | B24 |
| A754 | H | $CH_3O(CH_2)_2$ | $CH_3$ | $CF_3CF_2CF_2$ | B24 |
| A755 | H | Ph | $CH_3$ | $CF_3CF_2CF_2$ | B24 |
| A756 | H | PhO | $CH_3$ | $CF_3CF_2CF_2$ | B24 |
| A757 | H | PhS | $CH_3$ | $CF_3CF_2CF_2$ | B24 |
| A758 | H | PhSO | $CH_3$ | $CF_3CF_2CF_2$ | B24 |
| A759 | H | $PhSO_2$ | $CH_3$ | $CF_3CF_2CF_2$ | B24 |
| A760 | H | $CH_3S$ | $CH_3$ | $CF_3CF_2CF_2$ | B24 |
| A761 | H | $CH_3SO$ | $CH_3$ | $CF_3CF_2CF_2$ | B24 |
| A762 | H | $CF_3$ | $CH_3$ | $CF_3CF_2CF_2$ | B24 |
| A763 | H | $F_2CH$ | $CH_3$ | $CF_3CF_2CF_2$ | B24 |
| A764 | H | HCC | $CH_3$ | $CF_3CF_2CF_2$ | B24 |
| A765 | H | $CH_3CC$ | $CH_3$ | $CF_3CF_2CF_2$ | B24 |
| A766 | H | $CH_2=CH$ | $CH_3$ | $CF_3CF_2CF_2$ | B24 |
| A767 | H | $CH_2=CHCH_2$ | $CH_3$ | $CF_3CF_2CF_2$ | B24 |
| A768 | H | $CH_3SO_2N(CH_3)$ | $CH_3$ | $CF_3CF_2CF_2$ | B24 |
| A769 | H | $(CH_3)_2N$ | $CH_3$ | $CF_3CF_2CF_2$ | B24 |
| A770 | H | $(CH_3)_2NSO_2$ | $CH_3$ | $CF_3CF_2CF_2$ | B24 |
| A771 | H | $CH_3SCH_2$ | $CH_3$ | $CF_3CF_2CF_2$ | B24 |
| A772 | H | $CH_3SOCH_2$ | $CH_3$ | $CF_3CF_2CF_2$ | B24 |
| A773 | H | $CH_3SO_2CH_2$ | $CH_3$ | $CF_3CF_2CF_2$ | B24 |
| A774 | H | $CH_3$ | $CH_3$ | $CF_2Cl$ | B24 |
| A775 | H | $CH_3CH_2$ | $CH_3$ | $CF_2Cl$ | B24 |
| A776 | H | cyclopropyl | $CH_3$ | $CF_2Cl$ | B24 |
| A777 | H | $(CH_3)_3C$ | $CH_3$ | $CF_2Cl$ | B24 |
| A778 | H | $(CH_3)_2CH$ | $CH_3$ | $CF_2Cl$ | B24 |
| A779 | H | $CH_3(CH_2)_2$ | $CH_3$ | $CF_2Cl$ | B24 |
| A780 | H | $CH_3OCH_2$ | $CH_3$ | $CF_2Cl$ | B24 |
| A781 | H | $CH_3O(CH_2)_2$ | $CH_3$ | $CF_2Cl$ | B24 |
| A782 | H | Ph | $CH_3$ | $CF_2Cl$ | B24 |
| A783 | H | PhO | $CH_3$ | $CF_2Cl$ | B24 |

TABLE 9-continued

Compounds of formula If:

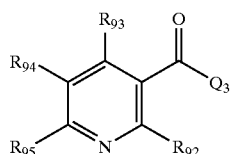

(If)

| Compd. no. | $R_{92}$ | $R_{93}$ | $R_{94}$ | $R_{95}$ | $Q_3$ |
|---|---|---|---|---|---|
| A784 | H | PhS | $CH_3$ | $CF_2Cl$ | B24 |
| A785 | H | PhSO | $CH_3$ | $CF_2Cl$ | B24 |
| A786 | H | $PhSO_2$ | $CH_3$ | $CF_2Cl$ | B24 |
| A787 | H | $CH_3S$ | $CH_3$ | $CF_2Cl$ | B24 |
| A788 | H | $CH_3SO$ | $CH_3$ | $CF_2Cl$ | B24 |
| A789 | H | $CF_3$ | $CH_3$ | $CF_2Cl$ | B24 |
| A790 | H | $F_2CH$ | $CH_3$ | $CF_2Cl$ | B24 |
| A791 | H | HCC | $CH_3$ | $CF_2Cl$ | B24 |
| A792 | H | $CH_3CC$ | $CH_3$ | $CF_2Cl$ | B24 |
| A793 | H | $CH_2=CH$ | $CH_3$ | $CF_2Cl$ | B24 |
| A794 | H | $CH_2=CHCH_2$ | $CH_3$ | $CF_2Cl$ | B24 |
| A795 | H | $CH_3SO_2N(CH_3)$ | $CH_3$ | $CF_2Cl$ | B24 |
| A796 | H | $(CH_3)_2N$ | $CH_3$ | $CF_2Cl$ | B24 |
| A797 | H | $(CH_3)_2NSO_2$ | $CH_3$ | $CF_2Cl$ | B24 |
| A798 | H | $CH_3SCH_2$ | $CH_3$ | $CF_2Cl$ | B24 |
| A799 | H | $CH_3SOCH_2$ | $CH_3$ | $CF_2Cl$ | B24 |
| A800 | H | $CH_3SO_2CH_2$ | $CH_3$ | $CF_2Cl$ | B24 |
| A801 | H | $CH_3$ | $CH_3$ | $CHF_2$ | B24 |
| A802 | H | $CH_3CH_2$ | $CH_3$ | $CHF_2$ | B24 |
| A803 | H | cyclopropyl | $CH_3$ | $CHF_2$ | B24 |
| A804 | H | $(CH_3)_3C$ | $CH_3$ | $CHF_2$ | B24 |
| A805 | H | $(CH_3)_2CH$ | $CH_3$ | $CHF_2$ | B24 |
| A806 | H | $CH_3(CH_2)_2$ | $CH_3$ | $CHF_2$ | B24 |
| A807 | H | $CH_3OCH_2$ | $CH_3$ | $CHF_2$ | B24 |
| A808 | H | $CH_3O(CH_2)_2$ | $CH_3$ | $CHF_2$ | B24 |
| A809 | H | Ph | $CH_3$ | $CHF_2$ | B24 |
| A810 | H | PhO | $CH_3$ | $CHF_2$ | B24 |
| A811 | H | PhS | $CH_3$ | $CHF_2$ | B24 |
| A812 | H | PhSO | $CH_3$ | $CHF_2$ | B24 |
| A813 | H | $PhSO_2$ | $CH_3$ | $CHF_2$ | B24 |
| A814 | H | $CH_3S$ | $CH_3$ | $CHF_2$ | B24 |
| A815 | H | $CH_3SO$ | $CH_3$ | $CHF_2$ | B24 |
| A816 | H | $CF_3$ | $CH_3$ | $CHF_2$ | B24 |
| A817 | H | $F_2CH$ | $CH_3$ | $CHF_2$ | B24 |
| A818 | H | HCC | $CH_3$ | $CHF_2$ | B24 |
| A819 | H | $CH_3CC$ | $CH_3$ | $CHF_2$ | B24 |
| A820 | H | $CH_2=CH$ | $CH_3$ | $CHF_2$ | B24 |
| A821 | H | $CH_2=CHCH_2$ | $CH_3$ | $CHF_2$ | B24 |
| A822 | H | $CH_3SO_2N(CH_3)$ | $CH_3$ | $CHF_2$ | B24 |
| A823 | H | $(CH_3)_2N$ | $CH_3$ | $CHF_2$ | B24 |
| A824 | H | $(CH_3)_2NSO_2$ | $CH_3$ | $CHF_2$ | B24 |
| A825 | H | $CH_3SCH_2$ | $CH_3$ | $CHF_2$ | B24 |
| A826 | H | $CH_3SOCH_2$ | $CH_3$ | $CHF_2$ | B24 |
| A827 | H | $CH_3SO_2CH_2$ | $CH_3$ | $CHF_2$ | B24 |
| A828 | H | $CH_3$ | $CH_3$ | $CCl_3$ | B24 |
| A829 | H | $CH_3CH_2$ | $CH_3$ | $CCl_3$ | B24 |
| A830 | H | cyclopropyl | $CH_3$ | $CCl_3$ | B24 |
| A831 | H | $(CH_3)_3C$ | $CH_3$ | $CCl_3$ | B24 |
| A832 | H | $(CH_3)_2CH$ | $CH_3$ | $CCl_3$ | B24 |
| A833 | H | $CH_3(CH_2)_2$ | $CH_3$ | $CCl_3$ | B24 |
| A834 | H | $CH_3OCH_2$ | $CH_3$ | $CCl_3$ | B24 |
| A835 | H | $CH_3O(CH_2)_2$ | $CH_3$ | $CCl_3$ | B24 |
| A836 | H | Ph | $CH_3$ | $CCl_3$ | B24 |
| A837 | H | PhO | $CH_3$ | $CCl_3$ | B24 |
| A838 | H | PhS | $CH_3$ | $CCl_3$ | B24 |
| A839 | H | PhSO | $CH_3$ | $CCl_3$ | B24 |
| A840 | H | $PhSO_2$ | $CH_3$ | $CCl_3$ | B24 |
| A841 | H | $CH_3S$ | $CH_3$ | $CCl_3$ | B24 |
| A842 | H | $CH_3SO$ | $CH_3$ | $CCl_3$ | B24 |
| A843 | H | $CF_3$ | $CH_3$ | $CCl_3$ | B24 |
| A844 | H | $F_2CH$ | $CH_3$ | $CCl_3$ | B24 |
| A845 | H | HCC | $CH_3$ | $CCl_3$ | B24 |
| A846 | H | $CH_3CC$ | $CH_3$ | $CCl_3$ | B24 |
| A847 | H | $CH_2=CH$ | $CH_3$ | $CCl_3$ | B24 |

TABLE 9-continued

Compounds of formula If:

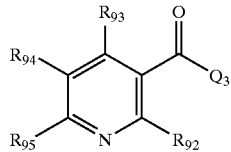

(If)

| Compd. no. | $R_{92}$ | $R_{93}$ | $R_{94}$ | $R_{95}$ | $Q_3$ |
|---|---|---|---|---|---|
| A848 | H | $CH_2=CHCH_2$ | $CH_3$ | $CCl_3$ | B24 |
| A849 | H | $CH_3SO_2N(CH_3)$ | $CH_3$ | $CCl_3$ | B24 |
| A850 | H | $(CH_3)_2N$ | $CH_3$ | $CCl_3$ | B24 |
| A851 | H | $(CH_3)_2NSO_2$ | $CH_3$ | $CCl_3$ | B24 |
| A852 | H | $CH_3SCH_2$ | $CH_3$ | $CCl_3$ | B24 |
| A853 | H | $CH_3SOCH_2$ | $CH_3$ | $CCl_3$ | B24 |
| A854 | H | $CH_3SO_2CH_2$ | $CH_3$ | $CCl_3$ | B24 |
| A855 | H | $CH_3$ | Ph | $CF_3$ | B24 |
| A856 | H | $CH_3CH_2$ | Ph | $CF_3$ | B24 |
| A857 | H | $(CH_3)_2CH$ | Ph | $CF_3$ | B24 |
| A858 | H | $(CH_3)_2CH$ | Ph | $CF_3$ | B24 |
| A859 | H | cyclopropyl | Ph | $CF_3$ | B24 |
| A860 | H | $CH_3(CH_2)_2$ | Ph | $CF_3$ | B24 |
| A861 | H | $CH_3OCH_2$ | Ph | $CF_3$ | B24 |
| A862 | H | $CH_3O(CH_2)_2$ | Ph | $CF_3$ | B24 |
| A863 | H | Ph | Ph | $CF_3$ | B24 |
| A864 | H | PhO | Ph | $CF_3$ | B24 |
| A865 | H | PhS | Ph | $CF_3$ | B24 |
| A866 | H | PhSO | Ph | $CF_3$ | B24 |
| A867 | H | $PhSO_2$ | Ph | $CF_3$ | B24 |
| A868 | H | $CH_3S$ | Ph | $CF_3$ | B24 |
| A869 | H | $CH_3SO$ | Ph | $CF_3$ | B24 |
| A870 | H | $CF_3$ | Ph | $CF_3$ | B24 |
| A871 | H | $F_2CH$ | Ph | $CF_3$ | B24 |
| A872 | H | HCC | Ph | $CF_3$ | B24 |
| A873 | H | $CH_3CC$ | Ph | $CF_3$ | B24 |
| A874 | H | $CH_2=CH$ | Ph | $CF_3$ | B24 |
| A875 | H | $CH_2=CHCH_2$ | Ph | $CF_3$ | B24 |
| A876 | H | $CH_3SO_2N(CH_3)$ | Ph | $CF_3$ | B24 |
| A877 | H | $(CH_3)_2N$ | Ph | $CF_3$ | B24 |
| A878 | H | $(CH_3)_2NSO_2$ | Ph | $CF_3$ | B24 |
| A879 | H | $CH_3SCH_2$ | Ph | $CF_3$ | B24 |
| A880 | H | $CH_3SOCH_2$ | Ph | $CF_3$ | B24 |
| A881 | H | $CH_3SO_2CH_2$ | Ph | $CF_3$ | B24 |
| A882 | H | $CH_3$ | Ph | $CF_3CF_2$ | B24 |
| A883 | H | $CH_3CH_2$ | Ph | $CF_3CF_2$ | B24 |
| A884 | H | cyclopropyl | Ph | $CF_3CF_2$ | B24 |
| A885 | H | $(CH_3)_3C$ | Ph | $CF_3CF_2$ | B24 |
| A886 | H | $(CH_3)_2CH$ | Ph | $CF_3CF_2$ | B24 |
| A887 | H | $CH_3(CH_2)_2$ | Ph | $CF_3CF_2$ | B24 |
| A888 | H | $CH_3OCH_2$ | Ph | $CF_3CF_2$ | B24 |
| A889 | H | $CH_3O(CH_2)_2$ | Ph | $CF_3CF_2$ | B24 |
| A890 | H | Ph | Ph | $CF_3CF_2$ | B24 |
| A891 | H | PhO | Ph | $CF_3CF_2$ | B24 |
| A892 | H | PhS | Ph | $CF_3CF_2$ | B24 |
| A893 | H | PhSO | Ph | $CF_3CF_2$ | B24 |
| A894 | H | $PhSO_2$ | Ph | $CF_3CF_2$ | B24 |
| A895 | H | $CH_3S$ | Ph | $CF_3CF_2$ | B24 |
| A896 | H | $CH_3SO$ | Ph | $CF_3CF_2$ | B24 |
| A897 | H | $CF_3$ | Ph | $CF_3CF_2$ | B24 |
| A898 | H | $F_2CH$ | Ph | $CF_3CF_2$ | B24 |
| A899 | H | HCC | Ph | $CF_3CF_2$ | B24 |
| A900 | H | $CH_3CC$ | Ph | $CF_3CF_2$ | B24 |
| A901 | H | $CH_2=CH$ | Ph | $CF_3CF_2$ | B24 |
| A902 | H | $CH_2=CHCH_2$ | Ph | $CF_3CF_2$ | B24 |
| A903 | H | $CH_3SO_2N(CH_3)$ | Ph | $CF_3CF_2$ | B24 |
| A904 | H | $(CH_3)_2N$ | Ph | $CF_3CF_2$ | B24 |
| A905 | H | $(CH_3)_2NSO_2$ | Ph | $CF_3CF_2$ | B24 |
| A906 | H | $CH_3SCH_2$ | Ph | $CF_3CF_2$ | B24 |
| A907 | H | $CH_3SOCH_2$ | Ph | $CF_3CF_2$ | B24 |
| A908 | H | $CH_3SO_2CH_2$ | Ph | $CF_3CF_2$ | B24 |
| A909 | H | $CH_3$ | Ph | $CF_3CF_2CF_2$ | B24 |
| A910 | H | $CH_3CH_2$ | Ph | $CF_3CF_2CF_2$ | B24 |
| A911 | H | cyclopropyl | Ph | $CF_3CF_2CF_2$ | B24 |

TABLE 9-continued

Compounds of formula If:

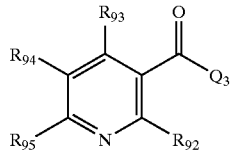

(If)

| Compd. no. | $R_{92}$ | $R_{93}$ | $R_{94}$ | $R_{95}$ | $Q_3$ |
|---|---|---|---|---|---|
| A912 | H | $(CH_3)_3C$ | Ph | $CF_3CF_2CF_2$ | B24 |
| A913 | H | $(CH_3)_2CH$ | Ph | $CF_3CF_2CF_2$ | B24 |
| A914 | H | $CH_3(CH_2)_2$ | Ph | $CF_3CF_2CF_2$ | B24 |
| A915 | H | $CH_3OCH_2$ | Ph | $CF_3CF_2CF_2$ | B24 |
| A916 | H | $CH_3O(CH_2)_2$ | Ph | $CF_3CF_2CF_2$ | B24 |
| A917 | H | Ph | Ph | $CF_3CF_2CF_2$ | B24 |
| A918 | H | PhO | Ph | $CF_3CF_2CF_2$ | B24 |
| A919 | H | PhS | Ph | $CF_3CF_2CF_2$ | B24 |
| A920 | H | PhSO | Ph | $CF_3CF_2CF_2$ | B24 |
| A921 | H | $PhSO_2$ | Ph | $CF_3CF_2CF_2$ | B24 |
| A922 | H | $CH_3S$ | Ph | $CF_3CF_2CF_2$ | B24 |
| A923 | H | $CH_3SO$ | Ph | $CF_3CF_2CF_2$ | B24 |
| A924 | H | $CF_3$ | Ph | $CF_3CF_2CF_2$ | B24 |
| A925 | H | $F_2CH$ | Ph | $CF_3CF_2CF_2$ | B24 |
| A926 | H | HCC | Ph | $CF_3CF_2CF_2$ | B24 |
| A927 | H | $CH_3CC$ | Ph | $CF_3CF_2CF_2$ | B24 |
| A928 | H | $CH_2=CH$ | Ph | $CF_3CF_2CF_2$ | B24 |
| A929 | H | $CH_2=CHCH_2$ | Ph | $CF_3CF_2CF_2$ | B24 |
| A930 | H | $CH_3SO_2N(CH_3)$ | Ph | $CF_3CF_2CF_2$ | B24 |
| A931 | H | $(CH_3)_2N$ | Ph | $CF_3CF_2CF_2$ | B24 |
| A932 | H | $(CH_3)_2NSO_2$ | Ph | $CF_3CF_2CF_2$ | B24 |
| A933 | H | $CH_3SCH_2$ | Ph | $CF_3CF_2CF_2$ | B24 |
| A934 | H | $CH_3SOCH_2$ | Ph | $CF_3CF_2CF_2$ | B24 |
| A935 | H | $CH_3SO_2CH_2$ | Ph | $CF_3CF_2CF_2$ | B24 |
| A936 | H | $CH_3$ | Ph | $CF_2Cl$ | B24 |
| A937 | H | $CH_3CH_2$ | Ph | $CF_2Cl$ | B24 |
| A938 | H | cyclopropyl | Ph | $CF_2Cl$ | B24 |
| A939 | H | $(CH_3)_3C$ | Ph | $CF_2Cl$ | B24 |
| A940 | H | $(CH_3)_2CH$ | Ph | $CF_2Cl$ | B24 |
| A941 | H | $CH_3(CH_2)_2$ | Ph | $CF_2Cl$ | B24 |
| A942 | H | $CH_3OCH_2$ | Ph | $CF_2Cl$ | B24 |
| A943 | H | $CH_3O(CH_2)_2$ | Ph | $CF_2Cl$ | B24 |
| A944 | H | Ph | Ph | $CF_2Cl$ | B24 |
| A945 | H | PhO | Ph | $CF_2Cl$ | B24 |
| A946 | H | PhS | Ph | $CF_2Cl$ | B24 |
| A947 | H | PhSO | Ph | $CF_2Cl$ | B24 |
| A948 | H | $PhSO_2$ | Ph | $CF_2Cl$ | B24 |
| A949 | H | $CH_3S$ | Ph | $CF_2Cl$ | B24 |
| A950 | H | $CH_3SO$ | Ph | $CF_2Cl$ | B24 |
| A951 | H | $CF_3$ | Ph | $CF_2Cl$ | B24 |
| A952 | H | $F_2CH$ | Ph | $CF_2Cl$ | B24 |
| A953 | H | HCC | Ph | $CF_2Cl$ | B24 |
| A954 | H | $CH_3CC$ | Ph | $CF_2Cl$ | B24 |
| A955 | H | $CH_2=CH$ | Ph | $CF_2Cl$ | B24 |
| A956 | H | $CH_2=CHCH_2$ | Ph | $CF_2Cl$ | B24 |
| A957 | H | $CH_3SO_2N(CH_3)$ | Ph | $CF_2Cl$ | B24 |
| A958 | H | $(CH_3)_2N$ | Ph | $CF_2Cl$ | B24 |
| A959 | H | $(CH_3)_2NSO_2$ | Ph | $CF_2Cl$ | B24 |
| A960 | H | $CH_3SCH_2$ | Ph | $CF_2Cl$ | B24 |
| A961 | H | $CH_3SOCH_2$ | Ph | $CF_2Cl$ | B24 |
| A962 | H | $CH_3SO_2CH_2$ | Ph | $CF_2Cl$ | B24 |
| A963 | H | $CH_3$ | Ph | $CHF_2$ | B24 |
| A964 | H | $CH_3CH_2$ | Ph | $CHF_2$ | B24 |
| A965 | H | $(CH_3)_3C$ | Ph | $CHF_2$ | B24 |
| A966 | H | $(CH_3)_2CH$ | Ph | $CHF_2$ | B24 |
| A967 | H | cyclopropyl | Ph | $CHF_2$ | B24 |
| A968 | H | $CH_3(CH_2)_2$ | Ph | $CHF_2$ | B24 |
| A969 | H | $CH_3OCH_2$ | Ph | $CHF_2$ | B24 |
| A970 | H | $CH_3O(CH_2)_2$ | Ph | $CHF_2$ | B24 |
| A971 | H | Ph | Ph | $CHF_2$ | B24 |
| A972 | H | PhO | Ph | $CHF_2$ | B24 |
| A973 | H | PhS | Ph | $CHF_2$ | B24 |
| A974 | H | PhSO | Ph | $CHF_2$ | B24 |
| A975 | H | $PhSO_2$ | Ph | $CHF_2$ | B24 |

TABLE 9-continued

Compounds of formula If:

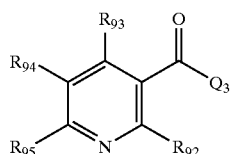

(If)

| Compd. no. | $R_{92}$ | $R_{93}$ | $R_{94}$ | $R_{95}$ | $Q_3$ |
|---|---|---|---|---|---|
| A976 | H | $CH_3S$ | Ph | $CHF_2$ | B24 |
| A977 | H | $CH_3SO$ | Ph | $CHF_2$ | B24 |
| A978 | H | $CF_3$ | Ph | $CHF_2$ | B24 |
| A979 | H | $F_2CH$ | Ph | $CHF_2$ | B24 |
| A980 | H | HCC | Ph | $CHF_2$ | B24 |
| A981 | H | $CH_3CC$ | Ph | $CHF_2$ | B24 |
| A982 | H | $CH_2=CH$ | Ph | $CHF_2$ | B24 |
| A983 | H | $CH_2=CHCH_2$ | Ph | $CHF_2$ | B24 |
| A984 | H | $CH_3SO_2N(CH_3)$ | Ph | $CHF_2$ | B24 |
| A985 | H | $(CH_3)_2N$ | Ph | $CHF_2$ | B24 |
| A986 | H | $(CH_3)_2NSO_2$ | Ph | $CHF_2$ | B24 |
| A987 | H | $CH_3SCH_2$ | Ph | $CHF_2$ | B24 |
| A988 | H | $CH_3SOCH_2$ | Ph | $CHF_2$ | B24 |
| A989 | H | $CH_3SO_2CH_2$ | Ph | $CHF_2$ | B24 |
| A990 | H | $CH_3$ | Ph | $CCl_3$ | B24 |
| A991 | H | $CH_3CH_2$ | Ph | $CCl_3$ | B24 |
| A992 | H | $(CH_3)_3C$ | Ph | $CCl_3$ | B24 |
| A993 | H | $(CH_3)_2CH$ | Ph | $CCl_3$ | B24 |
| A994 | H | cyclopropyl | Ph | $CCl_3$ | B24 |
| A995 | H | $CH_3(CH_2)_2$ | Ph | $CCl_3$ | B24 |
| A996 | H | $CH_3OCH_2$ | Ph | $CCl_3$ | B24 |
| A997 | H | $CH_3O(CH_2)_2$ | Ph | $CCl_3$ | B24 |
| A998 | H | Ph | Ph | $CCl_3$ | B24 |
| A999 | H | PhO | Ph | $CCl_3$ | B24 |
| A1000 | H | PhS | Ph | $CCl_3$ | B24 |
| A1001 | H | PhSO | Ph | $CCl_3$ | B24 |
| A1002 | H | $PhSO_2$ | Ph | $CCl_3$ | B24 |
| A1003 | H | $CH_3S$ | Ph | $CCl_3$ | B24 |
| A1004 | H | $CH_3SO$ | Ph | $CCl_3$ | B24 |
| A1005 | H | $CF_3$ | Ph | $CCl_3$ | B24 |
| A1006 | H | $F_2CH$ | Ph | $CCl_3$ | B24 |
| A1007 | H | HCC | Ph | $CCl_3$ | B24 |
| A1008 | H | $CH_3CC$ | Ph | $CCl_3$ | B24 |
| A1009 | H | $CH_2=CH$ | Ph | $CCl_3$ | B24 |
| A1010 | H | $CH_2=CHCH_2$ | Ph | $CCl_3$ | B24 |
| A1011 | H | $CH_3SO_2N(CH_3)$ | Ph | $CCl_3$ | B24 |
| A1012 | H | $(CH_3)_2N$ | Ph | $CCl_3$ | B24 |
| A1013 | H | $(CH_3)_2NSO_2$ | Ph | $CCl_3$ | B24 |
| A1014 | H | $CH_3SCH_2$ | Ph | $CCl_3$ | B24 |
| A1015 | H | $CH_3SOCH_2$ | Ph | $CCl_3$ | B24 |
| A1016 | H | $CH_3SO_2CH_2$ | Ph | $CCl_3$ | B24 |
| A1017 | F | H | H | $CF_3$ | B24 |
| A1018 | Cl | H | H | $CF_3$ | B24 |
| A1019 | Br | H | H | $CF_3$ | B24 |
| A1020 | CN | H | H | $CF_3$ | B24 |
| A1021 | $CH_3SO_2O$ | H | H | $CF_3$ | B24 |
| A1022 | $CH_3O$ | H | H | $CF_3$ | B24 |
| A1023 | $CH_2CH_3O$ | H | H | $CF_3$ | B24 |
| A1024 | $CH_2CH=CH_2O$ | H | H | $CF_3$ | B24 |
| A1025 | $HCCCH_2O$ | H | H | $CF_3$ | B24 |
| A1026 | S-benzyl | H | H | $CF_3$ | B24 |
| A1027 | $SO_2$-benzyl | H | H | $CF_3$ | B24 |
| A1028 | $ClCH_2$ | H | H | $CF_3$ | B24 |
| A1029 | $BrCH_2$ | H | H | $CF_3$ | B24 |
| A1030 | $FCH_2$ | H | H | $CF_3$ | B24 |
| A1031 | $CHF_2CH_2$ | H | H | $CF_3$ | B24 |
| A1032 | $CF_3CH_2$ | H | H | $CF_3$ | B24 |
| A1033 | triazolylmethyl | H | H | $CF_3$ | B24 |
| A1034 | $CHCl_2CH_2$ | H | H | $CF_3$ | B24 |
| A1035 | $ClCH=CH$ | H | H | $CF_3$ | B24 |
| A1036 | $Cl_2C=CH$ | H | H | $CF_3$ | B24 |
| A1037 | $CF_3CH=CH$ | H | H | $CF_3$ | B24 |
| A1038 | ClCC | H | H | $CF_3$ | B24 |
| A1039 | Ph | H | H | $CF_3$ | B24 |

TABLE 9-continued

Compounds of formula If:

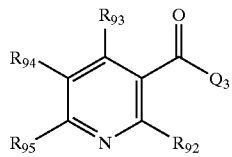

(If)

| Compd. no. | $R_{92}$ | $R_{93}$ | $R_{94}$ | $R_{95}$ | $Q_3$ |
|---|---|---|---|---|---|
| A1040 | $CH_3$ | $CH_3$ | H | $CF_3$ | B24 |
| A1041 | $CH_3$ | OH | H | $CF_3$ | B24 |
| A1042 | $CH_3$ | F | H | $CF_3$ | B24 |
| A1043 | $CH_3$ | Cl | H | $CF_3$ | B24 |
| A1044 | F | $CH_3$ | H | $CF_3$ | B24 |
| A1045 | Cl | $CH_3$ | H | $CF_3$ | B24 |
| A1046 | H | F | H | $CF_3$ | B24 |
| A1047 | H | Cl | H | $CF_3$ | B24 |
| A1048 | H | Br | H | $CF_3$ | B24 |
| A1049 | H | OH | H | $CF_3$ | B24 |
| A1050 | H | $OCH_3$ | H | $CF_3$ | B24 |
| A1051 | H | $OCHF_2$ | H | $CF_3$ | B24 |
| A1052 | H | $OSO_2CH_3$ | H | $CF_3$ | B24 |
| A1053 | H | $OSO_2CF_3$ | H | $CF_3$ | B24 |
| A1054 | H | $ClCH_2$ | H | $CF_3$ | B24 |
| A1055 | H | $BrCH_2$ | H | $CF_3$ | B24 |
| A1056 | H | $FCH_2$ | H | $CF_3$ | B24 |
| A1057 | H | $CHF_2CH_2$ | H | $CF_3$ | B24 |
| A1058 | H | $CF_3CH_2$ | H | $CF_3$ | B24 |
| A1059 | H | triazolylmethyl | H | $CF_3$ | B24 |
| A1060 | H | $CHCl_2CH_2$ | H | $CF_3$ | B24 |
| A1061 | H | ClCH=CH | H | $CF_3$ | B24 |
| A1062 | H | $Cl_2$C=CH | H | $CF_3$ | B24 |
| A1063 | H | $CF_3$CH=CH | H | $CF_3$ | B24 |
| A1064 | H | ClCC | H | $CF_3$ | B24 |
| A1065 | H | $CH_3$C(O) | H | $CF_3$ | B24 |
| A1066 | H | phenyl | H | $CF_3$ | B24 |
| A1067 | H | $SO_2CH_3$ | H | $CF_3$ | B24 |
| A1068 | H | $SO_2CF_3$ | H | $CF_3$ | B24 |
| A1069 | H | CN | H | $CF_3$ | B24 |
| A1070 | H | $NO_2$ | H | $CF_3$ | B24 |
| A1071 | $CH_3$ | H | F | $CF_3$ | B24 |
| A1072 | $CH_3$ | H | Cl | $CF_3$ | B24 |
| A1073 | $CH_3$ | H | Br | $CF_3$ | B24 |
| A1074 | $CH_3$ | H | CN | $CF_3$ | B24 |
| A1075 | $CH_3$ | H | $CH_3O$ | $CF_3$ | B24 |
| A1076 | $CH_3$ | H | $CH_3S$ | $CF_3$ | B24 |
| A1077 | $CH_3$ | H | $CH_3SO$ | $CF_3$ | B24 |
| A1078 | $CH_3$ | H | $CH_3SO_2$ | $CF_3$ | B24 |

TABLE 9a

Compounds of formula Ig:

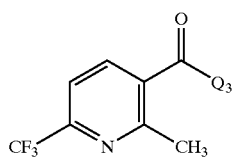

(Ig)

| $Q_3$ | $Q_3$ | $Q_3$ | $Q_3$ | $Q_3$ | $Q_3$ | $Q_3$ | $Q_3$ | $Q_3$ | $Q_3$ | $Q_3$ | $Q_3$ |
|---|---|---|---|---|---|---|---|---|---|---|---|
| B1 | B2 | B3 | B4 | B5 | B6 | B7 | B8 | B9 | B10 | B11 | B12 |
| B13 | B14 | B15 | B16 | B17 | B18 | B19 | B20 | B21 | B22 | B23 | B24 |
| B25 | B26 | B27 | B28 | B29 | B30 | B31 | B32 | B33 | B34 | B35 | B36 |
| B37 | B38 | B39 | B40 | B41 | B42 | B43 | B44 | B45 | B46 | B47 | B48 |
| B49 | B50 | B51 | B52 | B53 | B54 | B55 | B56 | B57 | B58 | B59 | B60 |
| B61 | B62 | B63 | B64 | B65 | B66 | B67 | B68 | B69 | B70 | B71 | B72 |
| B73 | B74 | B75 | B76 | B77 | B78 | B79 | B80 | B81 | B82 | B83 | B84 |
| B85 | B86 | B87 | B88 | B89 | B90 | B91 | B92 | B93 | B94 | B95 | B96 |

TABLE 9a-continued

Compounds of formula Ig:

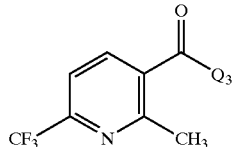

(Ig)

| $Q_3$ | $Q_3$ | $Q_3$ | $Q_3$ | $Q_3$ | $Q_3$ | $Q_3$ | $Q_3$ | $Q_3$ | $Q_3$ | $Q_3$ | $Q_3$ |
|---|---|---|---|---|---|---|---|---|---|---|---|
| B97 | B98 | B99 | B100 | B101 | B102 | B103 | B104 | B105 | B106 | B107 | B108 |
| B109 | B110 | B111 | B112 | B113 | B114 | B115 | B116 | B117 | B118 | B119 | B120 |
| B121 | B122 | B123 | B124 | B125 | B126 | B127 | B128 | B129 | B130 | B131 | B132 |
| B133 | B134 | B135 | B136 | B137 | B138 | B139 | B140 | B141 | B142 | B143 | B144 |
| B145 | B146 | B147 | B148 | B149 | B150 | B151 | B152 | B153 | B154 | B155 | B156 |
| B157 | B158 | B159 | B160 | B161 | B162 | B163 | B164 | B165 | B166 | B167 | B168 |
| B169 | B170 | B171 | B172 | B173 | B174 | B175 | B176 | B177 | B178 | B179 | B180 |
| B181 | B182 | B183 | B184 | B185 | B186 | B187 | B188 | B189 | B190 | B191 | B192 |
| B193 | B194 | B195 | B196 | B197 | B198 | B199 | B200 | B201 | B202 | B203 | B204 |
| B205 | B206 | B207 | B208 | B209 | B210 | B211 | B212 | B213 | B214 | B215 | B216 |
| B217 | B218 | B219 | B220 | B221 | B222 | B223 | B224 | B225 | B226 | B227 | B228 |
| B229 | B230 | B231 | B232 | B233 | B234 | B235 | B236 | B237 | B238 | B239 | B240 |
| B241 | B242 | B243 | B244 | B245 | B246 | B247 | B248 | B249 | B250 | B251 | B252 |
| B253 | B254 | B255 | B256 | B257 | B258 | B259 | B260 | B261 | B262 | B263 | B264 |
| B265 | B266 | B267 | B268 | B269 | B270 | B271 | B272 | B273 | B274 | B275 | B276 |
| B277 | B278 | B279 | B280 | B281 | B282 | B283 | B284 | B285 | B286 | B287 | B288 |
| B289 | B290 | B291 | B292 | B293 | B294 | B295 | B296 | B297 | B298 | B299 | B300 |
| B301 | B302 | B303 | B304 | B305 | B306 | B307 | B308 | B309 | B310 | B311 | B312 |
| B313 | B314 | B315 | B316 | B317 | B318 | B319 | B320 | B321 | B322 | B323 | B324 |
| B325 | B326 | B327 | B328 | B329 | B330 | B331 | B332 | B333 | B334 | B335 | B336 |
| B337 | B338 | B339 | B340 | B341 | B342 | B343 | B344 | B345 | B346 | B347 | B348 |
| B349 | B350 | B351 | B352 | B353 | B354 | B355 | B356 | B357 | B358 | B359 | B360 |
| B361 | B362 | B363 | B364 | B365 | B366 | B367 | B368 | B369 | B370 | B371 | B372 |
| B373 | B374 | B375 | B376 | B377 | B378 | B379 | B380 | B381 | B382 | B383 | B384 |
| B385 | B386 | B387 | B388 | B389 | B390 | B391 | B392 | B393 | B394 | B395 | B396 |
| B397 | B398 | B399 | B400 | B401 | B402 | B403 | B404 | B405 | B406 | B407 | B408 |
| B409 | B410 | B411 | B412 | B413 | B414 | B415 | B416 | B417 | B418 | B419 | B420 |
| B421 | B422 | B423 | B424 | B425 | B426 | B427 | B428 | B429 | B430 | B431 | B432 |
| B433 | B434 | B435 | B436 | B437 | B438 | B439 | B440 | B441 | B442 | B443 | B444 |
| B445 | B446 | B447 | B448 | B449 | B450 | B451 | B452 | B453 | B454 | B455 | B456 |
| B457 | B458 | B459 | B460 | B461 | B462 | B463 | B464 | B465 | B466 | B467 | B468 |
| B469 | B470 | B471 | B472 | B473 | B474 | B475 | B476 | B477 | B478 | B479 | B480 |
| B481 | B482 | B483 | B484 | B485 | B486 | B487 | B488 | B489 | B490 | B491 | B492 |
| B493 | B494 | B495 | B496 | B497 | B498 | B499 | B500 | B501 | B502 | B503 | B504 |
| B505 | B506 | B507 | B508 | B509 | B510 | B511 | B512 | B513 | B514 | B515 | B516 |
| B517 | B518 | B519 | B520 | B521 | B522 | B523 | B524 | B525 | B526 | B527 | B528 |
| B529 | B530 | B531 | B532 | B533 | B534 | B535 | B536 | B537 | B538 | B539 | B540 |
| B541 | B542 | B543 | B544 | B545 | B546 | B547 | B548 | B549 | B550 | B551 | B552 |
| B553 | B554 | B555 | B556 | B557 | B558 | B559 | B560 | B561 | B562 | B563 | B564 |
| B565 | B566 | B567 | B568 | B569 | B570 | B571 | B572 | B573 | B574 | B575 | B576 |
| B577 | B578 | B579 | B580 | B581 | B582 | B583 | B584 | B585 | B586 | B587 | B588 |
| B589 | B590 | B591 | B592 | B593 | B594 | B595 | B596 | B597 | B598 | B599 | B600 |
| B601 | B602 | B603 | B604 | B605 | B606 | B607 | B608 | B609 | B610 | B611 | B612 |
| B613 | B614 | B615 | B616 | B617 | B618 | B619 | B620 | B621 | B622 | B623 | B624 |
| B625 | B626 | B627 | B628 | B629 | B630 | B631 | B632 | B633 | B634 | B635 | B636 |
| B637 | B638 | B639 | B640 | B641 | B642 | B643 | B644 | B645 | B646 | B647 | B648 |
| B649 | B650 | B651 | B652 | B653 | B654 | B655 | B656 | B657 | B658 | B659 | B660 |
| B661 | B662 | B663 | B664 | B665 | B666 | B667 | B668 | B669 | B670 | B671 | B672 |
| B773 | B774 | B775 | B776 | B777 | B778 | B779 | B780 | B781 | B782 | B783 | B784 |
| B785 | B786 | B787 | B788 | B789 | B790 | B791 | B792 | B793 | B794 | B795 | B796 |
| B797 | B798 | B799 | B800 | B801 | B802 | B803 | B804 | B805 | B806 | B807 | B808 |
| B809 | B810 | B811 | B812 | B813 | B814 | B815 | B816 | B817 | B818 | B819 | B820 |
| B821 | B822 | B823 | B824 | B825 | B826 | B827 | B828 | B829 | B830 | B831 | B832 |
| B833 | B834 | B835 | B836 | B837 | B838 | B839 | B840 | B841 | B842 | B843 | B844 |
| B845 | B846 | B847 | B848 | B849 | B850 | B851 | B852 | B853 | B854 | B855 | B856 |
| B857 | B858 | B859 | B860 | B861 | B862 | B863 | B864 | B865 | B866 | B867 | B868 |
| B869 | B870 | B871 | B872 | B873 | B874 | B875 | B876 | B877 | B878 | B879 | B880 |
| B881 | B882 | B883 | B884 | B885 | B886 | B887 | B888 | B889 | B890 | B891 | B892 |
| B893 | B894 | B895 | B896 | B897 | B898 | B899 | B900 | B901 | B902 | B903 | B904 |
| B905 | B906 | B907 | B908 | B909 | B910 | B911 | B912 | B913 | B914 | B915 | B916 |
| B917 | B918 | B919 | B920 | B921 | B922 | B923 | B924 | B925 | B926 | B927 | B928 |
| B929 | B930 | B931 | B932 | B933 | B934 | B935 | B936 | B937 | B938 | B939 | B940 |
| B941 | B942 | B943 | B944 | B945 | B946 | B947 | B948 | B949 | B950 | B951 | B952 |
| B953 | B954 | B955 | B956 | B957 | B958 | B959 | B960 | B961 | B962 | B963 | B964 |
| B965 | B966 | B967 | B968 | B969 | B970 | B971 | B972 | B973 | B974 | B975 | B976 |

TABLE 9a-continued

Compounds of formula Ig:

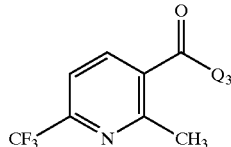

(Ig)

| $Q_3$ | $Q_3$ | $Q_3$ | $Q_3$ | $Q_3$ | $Q_3$ | $Q_3$ | $Q_3$ | $Q_3$ | $Q_3$ | $Q_3$ | $Q_3$ |
|---|---|---|---|---|---|---|---|---|---|---|---|
| B977 | B978 | B979 | B980 | B981 | B982 | B983 | B984 | B985 | B986 | B987 | B988 |
| B989 | B990 | B991 | B992 | B993 | B994 | B995 | B996 | B997 | B998 | B999 | B1000 |
| B1001 | B1002 | B1003 | B1004 | B1005 | B1006 | B1007 | B1008 | B1009 | B1010 | B1011 | B1012 |
| B1013 | B1014 | B1015 | B1016 | B1017 | B1018 | B1019 | B1020 | B1021 | B1022 | B1023 | B1024 |
| B1025 | B1026 | B1027 | B1028 | B1029 | B1030 | B1031 | B1032 | B1033 | B1034 | B1035 | B1036 |
| B1037 | B1038 | B1039 | B1040 | B1041 | B1042 | B1043 | B1044 | B1045 | B1046 | B1047 | B1048 |
| B1049 | B1050 | B1051 | B1052 | B1053 | B1054 | B1055 | B1056 | B1057 | B1058 | B1059 | B1060 |
| B1061 | B1062 | B1063 | B1064 | B1065 | B1066 | B1067 | B1068 | B1069 | B1070 | B1071 | B1072 |
| B1073 | B1074 | B1075 | B1076 | B1077 | B1078 | B1079 | B1080 | B1081 | B1082 | B1083 | |

TABLE 10

Compounds of formula Ih:

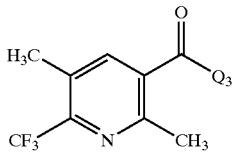

(Ih)

| $Q_3$ | $Q_3$ | $Q_3$ | $Q_3$ | $Q_3$ | $Q_3$ | $Q_3$ | $Q_3$ | $Q_3$ | $Q_3$ | $Q_3$ | $Q_3$ |
|---|---|---|---|---|---|---|---|---|---|---|---|
| B1 | B2 | B3 | B4 | B5 | B6 | B7 | B8 | B9 | B10 | B11 | B12 |
| B13 | B14 | B15 | B16 | B17 | B18 | B19 | B20 | B21 | B22 | B23 | B24 |
| B25 | B26 | B27 | B28 | B29 | B30 | B31 | B32 | B33 | B34 | B35 | B36 |
| B37 | B38 | B39 | B40 | B41 | B42 | B43 | B44 | B45 | B46 | B47 | B48 |
| B49 | B50 | B51 | B52 | B53 | B54 | B55 | B56 | B57 | B58 | B59 | B60 |
| B61 | B62 | B63 | B64 | B65 | B66 | B67 | B68 | B69 | B70 | B71 | B72 |
| B73 | B74 | B75 | B76 | B77 | B78 | B79 | B80 | B81 | B82 | B83 | B84 |
| B85 | B86 | B87 | B88 | B89 | B90 | B91 | B92 | B93 | B94 | B95 | B96 |
| B97 | B98 | B99 | B100 | B101 | B102 | B103 | B104 | B105 | B106 | B107 | B108 |
| B109 | B110 | B111 | B112 | B113 | B114 | B115 | B116 | B117 | B118 | B119 | B120 |
| B121 | B122 | B123 | B124 | B125 | B126 | B127 | B128 | B129 | B130 | B131 | B132 |
| B133 | B134 | B135 | B136 | B137 | B138 | B139 | B140 | B141 | B142 | B143 | B144 |
| B145 | B146 | B147 | B148 | B149 | B150 | B151 | B152 | B153 | B154 | B155 | B156 |
| B157 | B158 | B159 | B160 | B161 | B162 | B163 | B164 | B165 | B166 | B167 | B168 |
| B169 | B170 | B171 | B172 | B173 | B174 | B175 | B176 | B177 | B178 | B179 | B180 |
| B181 | B182 | B183 | B184 | B185 | B186 | B187 | B188 | B189 | B190 | B191 | B192 |
| B193 | B194 | B195 | B196 | B197 | B198 | B199 | B200 | B201 | B202 | B203 | B204 |
| B205 | B206 | B207 | B208 | B209 | B210 | B211 | B212 | B213 | B214 | B215 | B216 |
| B217 | B218 | B219 | B220 | B221 | B222 | B223 | B224 | B225 | B226 | B227 | B228 |
| B229 | B230 | B231 | B232 | B233 | B234 | B235 | B236 | B237 | B238 | B239 | B240 |
| B241 | B242 | B243 | B244 | B245 | B246 | B247 | B248 | B249 | B250 | B251 | B252 |
| B253 | B254 | B255 | B256 | B257 | B258 | B259 | B260 | B261 | B262 | B263 | B264 |
| B265 | B266 | B267 | B268 | B269 | B270 | B271 | B272 | B273 | B274 | B275 | B276 |
| B277 | B278 | B279 | B280 | B281 | B282 | B283 | B284 | B285 | B286 | B287 | B288 |
| B289 | B290 | B291 | B292 | B293 | B294 | B295 | B296 | B297 | B298 | B299 | B300 |
| B301 | B302 | B303 | B304 | B305 | B306 | B307 | B308 | B309 | B310 | B311 | B312 |
| B313 | B314 | B315 | B316 | B317 | B318 | B319 | B320 | B321 | B322 | B323 | B324 |
| B325 | B326 | B327 | B328 | B329 | B330 | B331 | B332 | B333 | B334 | B335 | B336 |
| B337 | B338 | B339 | B340 | B341 | B342 | B343 | B344 | B345 | B346 | B347 | B348 |
| B349 | B350 | B351 | B352 | B353 | B354 | B355 | B356 | B357 | B358 | B359 | B360 |
| B361 | B362 | B363 | B364 | B365 | B366 | B367 | B368 | B369 | B370 | B371 | B372 |
| B373 | B374 | B375 | B376 | B377 | B378 | B379 | B380 | B381 | B382 | B383 | B384 |
| B385 | B386 | B387 | B388 | B389 | B390 | B391 | B392 | B393 | B394 | B395 | B396 |
| B397 | B398 | B399 | B400 | B401 | B402 | B403 | B404 | B405 | B406 | B407 | B408 |
| B409 | B410 | B411 | B412 | B413 | B414 | B415 | B416 | B417 | B418 | B419 | B420 |
| B421 | B422 | B423 | B424 | B425 | B426 | B427 | B428 | B429 | B430 | B431 | B432 |
| B433 | B434 | B435 | B436 | B437 | B438 | B439 | B440 | B441 | B442 | B443 | B444 |
| B445 | B446 | B447 | B448 | B449 | B450 | B451 | B452 | B453 | B454 | B455 | B456 |

TABLE 10-continued

Compounds of formula Ih:

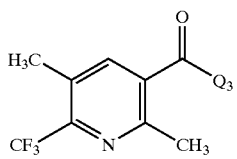

(Ih)

| Q₃ | Q₃ | Q₃ | Q₃ | Q₃ | Q₃ | Q₃ | Q₃ | Q₃ | Q₃ | Q₃ | Q₃ |
|---|---|---|---|---|---|---|---|---|---|---|---|
| B457 | B458 | B459 | B460 | B461 | B462 | B463 | B464 | B465 | B466 | B467 | B468 |
| B469 | B470 | B471 | B472 | B473 | B474 | B475 | B476 | B477 | B478 | B479 | B480 |
| B481 | B482 | B483 | B484 | B485 | B486 | B487 | B488 | B489 | B490 | B491 | B492 |
| B493 | B494 | B495 | B496 | B497 | B498 | B499 | B500 | B501 | B502 | B503 | B504 |
| B505 | B506 | B507 | B508 | B509 | B510 | B511 | B512 | B513 | B514 | B515 | B516 |
| B517 | B518 | B519 | B520 | B521 | B522 | B523 | B524 | B525 | B526 | B527 | B528 |
| B529 | B530 | B531 | B532 | B533 | B534 | B535 | B536 | B537 | B538 | B539 | B540 |
| B541 | B542 | B543 | B544 | B545 | B546 | B547 | B548 | B549 | B550 | B551 | B552 |
| B553 | B554 | B555 | B556 | B557 | B558 | B559 | B560 | B561 | B562 | B563 | B564 |
| B565 | B566 | B567 | B568 | B569 | B570 | B571 | B572 | B573 | B574 | B575 | B576 |
| B577 | B578 | B579 | B580 | B581 | B582 | B583 | B584 | B585 | B586 | B587 | B588 |
| B589 | B590 | B591 | B592 | B593 | B594 | B595 | B596 | B597 | B598 | B599 | B600 |
| B601 | B602 | B603 | B604 | B605 | B606 | B607 | B608 | B609 | B610 | B611 | B612 |
| B613 | B614 | B615 | B616 | B617 | B618 | B619 | B620 | B621 | B622 | B623 | B624 |
| B625 | B626 | B627 | B628 | B629 | B630 | B631 | B632 | B633 | B634 | B635 | B636 |
| B637 | B638 | B639 | B640 | B641 | B642 | B643 | B644 | B645 | B646 | B647 | B648 |
| B649 | B650 | B651 | B652 | B653 | B654 | B655 | B656 | B657 | B658 | B659 | B660 |
| B661 | B662 | B663 | B664 | B665 | B666 | B667 | B668 | B669 | B670 | B671 | B672 |
| B773 | B774 | B775 | B776 | B777 | B778 | B779 | B780 | B781 | B782 | B783 | B784 |
| B785 | B786 | B787 | B788 | B789 | B790 | B791 | B792 | B793 | B794 | B795 | B796 |
| B797 | B798 | B799 | B800 | B801 | B802 | B803 | B804 | B805 | B806 | B807 | B808 |
| B809 | B810 | B811 | B812 | B813 | B814 | B815 | B816 | B817 | B818 | B819 | B820 |
| B821 | B822 | B823 | B824 | B825 | B826 | B827 | B828 | B829 | B830 | B831 | B832 |
| B833 | B834 | B835 | B836 | B837 | B838 | B839 | B840 | B841 | B842 | B843 | B844 |
| B845 | B846 | B847 | B848 | B849 | B850 | B851 | B852 | B853 | B854 | B855 | B856 |
| B857 | B858 | B859 | B860 | B861 | B862 | B863 | B864 | B865 | B866 | B867 | B868 |
| B869 | B870 | B871 | B872 | B873 | B874 | B875 | B876 | B877 | B878 | B879 | B880 |
| B881 | B882 | B883 | B884 | B885 | B886 | B887 | B888 | B889 | B890 | B891 | B892 |
| B893 | B894 | B895 | B896 | B897 | B898 | B899 | B900 | B901 | B902 | B903 | B904 |
| B905 | B906 | B907 | B908 | B909 | B910 | B911 | B912 | B913 | B914 | B915 | B916 |
| B917 | B918 | B919 | B920 | B921 | B922 | B923 | B924 | B925 | B926 | B927 | B928 |
| B929 | B930 | B931 | B932 | B933 | B934 | B935 | B936 | B937 | B938 | B939 | B940 |
| B941 | B942 | B943 | B944 | B945 | B946 | B947 | B948 | B949 | B950 | B951 | B952 |
| B953 | B954 | B955 | B956 | B957 | B958 | B959 | B960 | B961 | B962 | B963 | B964 |
| B965 | B966 | B967 | B968 | B969 | B970 | B971 | B972 | B973 | B974 | B975 | B976 |
| B977 | B978 | B979 | B980 | B981 | B982 | B983 | B984 | B985 | B986 | B987 | B988 |
| B989 | B990 | B991 | B992 | B993 | B994 | B995 | B996 | B997 | B998 | B999 | B1000 |
| B1001 | B1002 | B1003 | B1004 | B1005 | B1006 | B1007 | B1008 | B1009 | B1010 | B1011 | B1012 |
| B1013 | B1014 | B1015 | B1016 | B1017 | B1018 | B1019 | B1020 | B1021 | B1022 | B1023 | B1024 |
| B1025 | B1026 | B1027 | B1028 | B1029 | B1030 | B1031 | B1032 | B1033 | B1034 | B1035 | B1036 |
| B1037 | B1038 | B1039 | B1040 | B1041 | B1042 | B1043 | B1044 | B1045 | B1046 | B1047 | B1048 |
| B1049 | B1050 | B1051 | B1052 | B1053 | B1054 | B1055 | B1056 | B1057 | B1058 | B1059 | B1060 |
| B1061 | B1062 | B1063 | B1064 | B1065 | B1066 | B1067 | B1068 | B1069 | B1070 | B1071 | B1072 |
| B1073 | B1074 | B1075 | B1076 | B1077 | B1078 | B1079 | B1080 | B1081 | B1082 | B1083 | |

TABLE 11

Compounds of formula Ik:

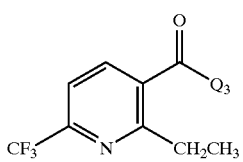

(Ik)

| Q₃ | Q₃ | Q₃ | Q₃ | Q₃ | Q₃ | Q₃ | Q₃ | Q₃ | Q₃ | Q₃ | Q₃ |
|---|---|---|---|---|---|---|---|---|---|---|---|
| B1 | B2 | B3 | B4 | B5 | B6 | B7 | B8 | B9 | B10 | B11 | B12 |
| B13 | B14 | B15 | B16 | B17 | B18 | B19 | B20 | B21 | B22 | B23 | B24 |
| B25 | B26 | B27 | B28 | B29 | B30 | B31 | B32 | B33 | B34 | B35 | B36 |

TABLE 11-continued

Compounds of formula Ik:

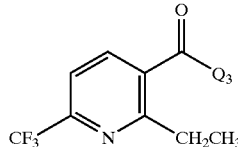

(Ik)

| Q3 | Q3 | Q3 | Q3 | Q3 | Q3 | Q3 | Q3 | Q3 | Q3 | Q3 | Q3 |
|---|---|---|---|---|---|---|---|---|---|---|---|
| B37 | B38 | B39 | B40 | B41 | B42 | B43 | B44 | B45 | B46 | B47 | B48 |
| B49 | B50 | B51 | B52 | B53 | B54 | B55 | B56 | B57 | B58 | B59 | B60 |
| B61 | B62 | B63 | B64 | B65 | B66 | B67 | B68 | B69 | B70 | B71 | B72 |
| B73 | B74 | B75 | B76 | B77 | B78 | B79 | B80 | B81 | B82 | B83 | B84 |
| B85 | B86 | B87 | B88 | B89 | B90 | B91 | B92 | B93 | B94 | B95 | B96 |
| B97 | B98 | B99 | B100 | B101 | B102 | B103 | B104 | B105 | B106 | B107 | B108 |
| B109 | B110 | B111 | B112 | B113 | B114 | B115 | B116 | B117 | B118 | B119 | B120 |
| B121 | B122 | B123 | B124 | B125 | B126 | B127 | B128 | B129 | B130 | B131 | B132 |
| B133 | B134 | B135 | B136 | B137 | B138 | B139 | B140 | B141 | B142 | B143 | B144 |
| B145 | B146 | B147 | B148 | B149 | B150 | B151 | B152 | B153 | B154 | B155 | B156 |
| B157 | B158 | B159 | B160 | B161 | B162 | B163 | B164 | B165 | B166 | B167 | B168 |
| B169 | B170 | B171 | B172 | B173 | B174 | B175 | B176 | B177 | B178 | B179 | B180 |
| B181 | B182 | B183 | B184 | B185 | B186 | B187 | B188 | B189 | B190 | B191 | B192 |
| B193 | B194 | B195 | B196 | B197 | B198 | B199 | B200 | B201 | B202 | B203 | B204 |
| B205 | B206 | B207 | B208 | B209 | B210 | B211 | B212 | B213 | B214 | B215 | B216 |
| B217 | B218 | B219 | B220 | B221 | B222 | B223 | B224 | B225 | B226 | B227 | B228 |
| B229 | B230 | B231 | B232 | B233 | B234 | B235 | B236 | B237 | B238 | B239 | B240 |
| B241 | B242 | B243 | B244 | B245 | B246 | B247 | B248 | B249 | B250 | B251 | B252 |
| B253 | B254 | B255 | B256 | B257 | B258 | B259 | B260 | B261 | B262 | B263 | B264 |
| B265 | B266 | B267 | B268 | B269 | B270 | B271 | B272 | B273 | B274 | B275 | B276 |
| B277 | B278 | B279 | B280 | B281 | B282 | B283 | B284 | B285 | B286 | B287 | B288 |
| B289 | B290 | B291 | B292 | B293 | B294 | B295 | B296 | B297 | B298 | B299 | B300 |
| B301 | B302 | B303 | B304 | B305 | B306 | B307 | B308 | B309 | B310 | B311 | B312 |
| B313 | B314 | B315 | B316 | B317 | B318 | B319 | B320 | B321 | B322 | B323 | B324 |
| B325 | B326 | B327 | B328 | B329 | B330 | B331 | B332 | B333 | B334 | B335 | B336 |
| B337 | B338 | B339 | B340 | B341 | B342 | B343 | B344 | B345 | B346 | B347 | B348 |
| B349 | B350 | B351 | B352 | B353 | B354 | B355 | B356 | B357 | B358 | B359 | B360 |
| B361 | B362 | B363 | B364 | B365 | B366 | B367 | B368 | B369 | B370 | B371 | B372 |
| B373 | B374 | B375 | B376 | B377 | B378 | B379 | B380 | B381 | B382 | B383 | B384 |
| B385 | B386 | B387 | B388 | B389 | B390 | B391 | B392 | B393 | B394 | B395 | B396 |
| B397 | B398 | B399 | B400 | B401 | B402 | B403 | B404 | B405 | B406 | B407 | B408 |
| B409 | B410 | B411 | B412 | B413 | B414 | B415 | B416 | B417 | B418 | B419 | B420 |
| B421 | B422 | B423 | B424 | B425 | B426 | B427 | B428 | B429 | B430 | B431 | B432 |
| B433 | B434 | B435 | B436 | B437 | B438 | B439 | B440 | B441 | B442 | B443 | B444 |
| B445 | B446 | B447 | B448 | B449 | B450 | B451 | B452 | B453 | B454 | B455 | B456 |
| B457 | B458 | B459 | B460 | B461 | B462 | B463 | B464 | B465 | B466 | B467 | B468 |
| B469 | B470 | B471 | B472 | B473 | B474 | B475 | B476 | B477 | B478 | B479 | B480 |
| B481 | B482 | B483 | B484 | B485 | B486 | B487 | B488 | B489 | B490 | B491 | B492 |
| B493 | B494 | B495 | B496 | B497 | B498 | B499 | B500 | B501 | B502 | B503 | B504 |
| B505 | B506 | B507 | B508 | B509 | B510 | B511 | B512 | B513 | B514 | B515 | B516 |
| B517 | B518 | B519 | B520 | B521 | B522 | B523 | B524 | B525 | B526 | B527 | B528 |
| B529 | B530 | B531 | B532 | B533 | B534 | B535 | B536 | B537 | B538 | B539 | B540 |
| B541 | B542 | B543 | B544 | B545 | B546 | B547 | B548 | B549 | B550 | B551 | B552 |
| B553 | B554 | B555 | B556 | B557 | B558 | B559 | B560 | B561 | B562 | B563 | B564 |
| B565 | B566 | B567 | B568 | B569 | B570 | B571 | B572 | B573 | B574 | B575 | B576 |
| B577 | B578 | B579 | B580 | B581 | B582 | B583 | B584 | B585 | B586 | B587 | B588 |
| B589 | B590 | B591 | B592 | B593 | B594 | B595 | B596 | B597 | B598 | B599 | B600 |
| B601 | B602 | B603 | B604 | B605 | B606 | B607 | B608 | B609 | B610 | B611 | B612 |
| B613 | B614 | B615 | B616 | B617 | B618 | B619 | B620 | B621 | B622 | B623 | B624 |
| B625 | B626 | B627 | B628 | B629 | B630 | B631 | B632 | B633 | B634 | B635 | B636 |
| B637 | B638 | B639 | B640 | B641 | B642 | B643 | B644 | B645 | B646 | B647 | B648 |
| B649 | B650 | B651 | B652 | B653 | B654 | B655 | B656 | B657 | B658 | B659 | B660 |
| B661 | B662 | B663 | B664 | B665 | B666 | B667 | B668 | B669 | B670 | B671 | B672 |
| B773 | B774 | B775 | B776 | B777 | B778 | B779 | B780 | B781 | B782 | B783 | B784 |
| B785 | B786 | B787 | B788 | B789 | B790 | B791 | B792 | B793 | B794 | B795 | B796 |
| B797 | B798 | B799 | B800 | B801 | B802 | B803 | B804 | B805 | B806 | B807 | B808 |
| B809 | B810 | B811 | B812 | B813 | B814 | B815 | B816 | B817 | B818 | B819 | B820 |
| B821 | B822 | B823 | B824 | B825 | B826 | B827 | B828 | B829 | B830 | B831 | B832 |
| B833 | B834 | B835 | B836 | B837 | B838 | B839 | B840 | B841 | B842 | B843 | B844 |
| B845 | B846 | B847 | B848 | B849 | B850 | B851 | B852 | B853 | B854 | B855 | B856 |
| B857 | B858 | B859 | B860 | B861 | B862 | B863 | B864 | B865 | B866 | B867 | B868 |
| B869 | B870 | B871 | B872 | B873 | B874 | B875 | B876 | B877 | B878 | B879 | B880 |
| B881 | B882 | B883 | B884 | B885 | B886 | B887 | B888 | B889 | B890 | B891 | B892 |
| B893 | B894 | B895 | B896 | B897 | B898 | B899 | B900 | B901 | B902 | B903 | B904 |
| B905 | B906 | B907 | B908 | B909 | B910 | B911 | B912 | B913 | B914 | B915 | B916 |

TABLE 11-continued

Compounds of formula Ik:

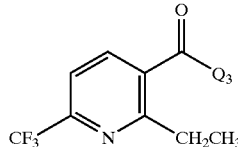

(Ik)

| Q₃ | Q₃ | Q₃ | Q₃ | Q₃ | Q₃ | Q₃ | Q₃ | Q₃ | Q₃ | Q₃ | Q₃ |
|---|---|---|---|---|---|---|---|---|---|---|---|
| B917 | B918 | B919 | B920 | B921 | B922 | B923 | B924 | B925 | B926 | B927 | B928 |
| B929 | B930 | B931 | B932 | B933 | B934 | B935 | B936 | B937 | B938 | B939 | B940 |
| B941 | B942 | B943 | B944 | B945 | B946 | B947 | B948 | B949 | B950 | B951 | B952 |
| B953 | B954 | B955 | B956 | B957 | B958 | B959 | B960 | B961 | B962 | B963 | B964 |
| B965 | B966 | B967 | B968 | B969 | B970 | B971 | B972 | B973 | B974 | B975 | B976 |
| B977 | B978 | B979 | B980 | B981 | B982 | B983 | B984 | B985 | B986 | B987 | B988 |
| B989 | B990 | B991 | B992 | B993 | B994 | B995 | B996 | B997 | B998 | B999 | B1000 |
| B1001 | B1002 | B1003 | B1004 | B1005 | B1006 | B1007 | B1008 | B1009 | B1010 | B1011 | B1012 |
| B1013 | B1014 | B1015 | B1016 | B1017 | B1018 | B1019 | B1020 | B1021 | B1022 | B1023 | B1024 |
| B1025 | B1026 | B1027 | B1028 | B1029 | B1030 | B1031 | B1032 | B1033 | B1034 | B1035 | B1036 |
| B1037 | B1038 | B1039 | B1040 | B1041 | B1042 | B1043 | B1044 | B1045 | B1046 | B1047 | B1048 |
| B1049 | B1050 | B1051 | B1052 | B1053 | B1054 | B1055 | B1056 | B1057 | B1058 | B1059 | B1060 |
| B1061 | B1062 | B1063 | B1064 | B1065 | B1066 | B1067 | B1068 | B1069 | B1070 | B1071 | B1072 |
| B1073 | B1074 | B1075 | B1076 | B1077 | B1078 | B1079 | B1080 | B1081 | B1082 | B1083 | |

TABLE 12

Compounds of formula Im:

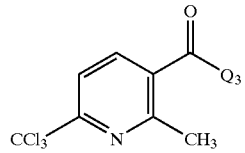

(Im)

| Q₃ | Q₃ | Q₃ | Q₃ | Q₃ | Q₃ | Q₃ | Q₃ | Q₃ | Q₃ | Q₃ | Q₃ |
|---|---|---|---|---|---|---|---|---|---|---|---|
| B1 | B2 | B3 | B4 | B5 | B6 | B7 | B8 | B9 | B10 | B11 | B12 |
| B13 | B14 | B15 | B16 | B17 | B18 | B19 | B20 | B21 | B22 | B23 | B24 |
| B25 | B26 | B27 | B28 | B29 | B30 | B31 | B32 | B33 | B34 | B35 | B36 |
| B37 | B38 | B39 | B40 | B41 | B42 | B43 | B44 | B45 | B46 | B47 | B48 |
| B49 | B50 | B51 | B52 | B53 | B54 | B55 | B56 | B57 | B58 | B59 | B60 |
| B61 | B62 | B63 | B64 | B65 | B66 | B67 | B68 | B69 | B70 | B71 | B72 |
| B73 | B74 | B75 | B76 | B77 | B78 | B79 | B80 | B81 | B82 | B83 | B84 |
| B85 | B86 | B87 | B88 | B89 | B90 | B91 | B92 | B93 | B94 | B95 | B96 |
| B97 | B98 | B99 | B100 | B101 | B102 | B103 | B104 | B105 | B106 | B107 | B108 |
| B109 | B110 | B111 | B112 | B113 | B114 | B115 | B116 | B117 | B118 | B119 | B120 |
| B121 | B122 | B123 | B124 | B125 | B126 | B127 | B128 | B129 | B130 | B131 | B132 |
| B133 | B134 | B135 | B136 | B137 | B138 | B139 | B140 | B141 | B142 | B143 | B144 |
| B145 | B146 | B147 | B148 | B149 | B150 | B151 | B152 | B153 | B154 | B155 | B156 |
| B157 | B158 | B159 | B160 | B161 | B162 | B163 | B164 | B165 | B166 | B167 | B168 |
| B169 | B170 | B171 | B172 | B173 | B174 | B175 | B176 | B177 | B178 | B179 | B180 |
| B181 | B182 | B183 | B184 | B185 | B186 | B187 | B188 | B189 | B190 | B191 | B192 |
| B193 | B194 | B195 | B196 | B197 | B198 | B199 | B200 | B201 | B202 | B203 | B204 |
| B205 | B206 | B207 | B208 | B209 | B210 | B211 | B212 | B213 | B214 | B215 | B216 |
| B217 | B218 | B219 | B220 | B221 | B222 | B223 | B224 | B225 | B226 | B227 | B228 |
| B229 | B230 | B231 | B232 | B233 | B234 | B235 | B236 | B237 | B238 | B239 | B240 |
| B241 | B242 | B243 | B244 | B245 | B246 | B247 | B248 | B249 | B250 | B251 | B252 |
| B253 | B254 | B255 | B256 | B257 | B258 | B259 | B260 | B261 | B262 | B263 | B264 |
| B265 | B266 | B267 | B268 | B269 | B270 | B271 | B272 | B273 | B274 | B275 | B276 |
| B277 | B278 | B279 | B280 | B281 | B282 | B283 | B284 | B285 | B286 | B287 | B288 |
| B289 | B290 | B291 | B292 | B293 | B294 | B295 | B296 | B297 | B298 | B299 | B300 |
| B301 | B302 | B303 | B304 | B305 | B306 | B307 | B308 | B309 | B310 | B311 | B312 |
| B313 | B314 | B315 | B316 | B317 | B318 | B319 | B320 | B321 | B322 | B323 | B324 |
| B325 | B326 | B327 | B328 | B329 | B330 | B331 | B332 | B333 | B334 | B335 | B336 |
| B337 | B338 | B339 | B340 | B341 | B342 | B343 | B344 | B345 | B346 | B347 | B348 |
| B349 | B350 | B351 | B352 | B353 | B354 | B355 | B356 | B357 | B358 | B359 | B360 |
| B361 | B362 | B363 | B364 | B365 | B366 | B367 | B368 | B369 | B370 | B371 | B372 |
| B373 | B374 | B375 | B376 | B377 | B378 | B379 | B380 | B381 | B382 | B383 | B384 |
| B385 | B386 | B387 | B388 | B389 | B390 | B391 | B392 | B393 | B394 | B395 | B396 |

TABLE 12-continued

Compounds of formula Im:

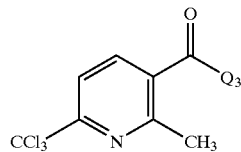

(Im)

| $Q_3$ | $Q_3$ | $Q_3$ | $Q_3$ | $Q_3$ | $Q_3$ | $Q_3$ | $Q_3$ | $Q_3$ | $Q_3$ | $Q_3$ | $Q_3$ |
|---|---|---|---|---|---|---|---|---|---|---|---|
| B397 | B398 | B399 | B400 | B401 | B402 | B403 | B404 | B405 | B406 | B407 | B408 |
| B409 | B410 | B411 | B412 | B413 | B414 | B415 | B416 | B417 | B418 | B419 | B420 |
| B421 | B422 | B423 | B424 | B425 | B426 | B427 | B428 | B429 | B430 | B431 | B432 |
| B433 | B434 | B435 | B436 | B437 | B438 | B439 | B440 | B441 | B442 | B443 | B444 |
| B445 | B446 | B447 | B448 | B449 | B450 | B451 | B452 | B453 | B454 | B455 | B456 |
| B457 | B458 | B459 | B460 | B461 | B462 | B463 | B464 | B465 | B466 | B467 | B468 |
| B469 | B470 | B471 | B472 | B473 | B474 | B475 | B476 | B477 | B478 | B479 | B480 |
| B481 | B482 | B483 | B484 | B485 | B486 | B487 | B488 | B489 | B490 | B491 | B492 |
| B493 | B494 | B495 | B496 | B497 | B498 | B499 | B500 | B501 | B502 | B503 | B504 |
| B505 | B506 | B507 | B508 | B509 | B510 | B511 | B512 | B513 | B514 | B515 | B516 |
| B517 | B518 | B519 | B520 | B521 | B522 | B523 | B524 | B525 | B526 | B527 | B528 |
| B529 | B530 | B531 | B532 | B533 | B534 | B535 | B536 | B537 | B538 | B539 | B540 |
| B541 | B542 | B543 | B544 | B545 | B546 | B547 | B548 | B549 | B550 | B551 | B552 |
| B553 | B554 | B555 | B556 | B557 | B558 | B559 | B560 | B561 | B562 | B563 | B564 |
| B565 | B566 | B567 | B568 | B569 | B570 | B571 | B572 | B573 | B574 | B575 | B576 |
| B577 | B578 | B579 | B580 | B581 | B582 | B583 | B584 | B585 | B586 | B587 | B588 |
| B589 | B590 | B591 | B592 | B593 | B594 | B595 | B596 | B597 | B598 | B599 | B600 |
| B601 | B602 | B603 | B604 | B605 | B606 | B607 | B608 | B609 | B610 | B611 | B612 |
| B613 | B614 | B615 | B616 | B617 | B618 | B619 | B620 | B621 | B622 | B623 | B624 |
| B625 | B626 | B627 | B628 | B629 | B630 | B631 | B632 | B633 | B634 | B635 | B636 |
| B637 | B638 | B639 | B640 | B641 | B642 | B643 | B644 | B645 | B646 | B647 | B648 |
| B649 | B650 | B651 | B652 | B653 | B654 | B655 | B656 | B657 | B658 | B659 | B660 |
| B661 | B662 | B663 | B664 | B665 | B666 | B667 | B668 | B669 | B670 | B671 | B672 |
| B773 | B774 | B775 | B776 | B777 | B778 | B779 | B780 | B781 | B782 | B783 | B784 |
| B785 | B786 | B787 | B788 | B789 | B790 | B791 | B792 | B793 | B794 | B795 | B796 |
| B797 | B798 | B799 | B800 | B801 | B802 | B803 | B804 | B805 | B806 | B807 | B808 |
| B809 | B810 | B811 | B812 | B813 | B814 | B815 | B816 | B817 | B818 | B819 | B820 |
| B821 | B822 | B823 | B824 | B825 | B826 | B827 | B828 | B829 | B830 | B831 | B832 |
| B833 | B834 | B835 | B836 | B837 | B838 | B839 | B840 | B841 | B842 | B843 | B844 |
| B845 | B846 | B847 | B848 | B849 | B850 | B851 | B852 | B853 | B854 | B855 | B856 |
| B857 | B858 | B859 | B860 | B861 | B862 | B863 | B864 | B865 | B866 | B867 | B868 |
| B869 | B870 | B871 | B872 | B873 | B874 | B875 | B876 | B877 | B878 | B879 | B880 |
| B881 | B882 | B883 | B884 | B885 | B886 | B887 | B888 | B889 | B890 | B891 | B892 |
| B893 | B894 | B895 | B896 | B897 | B898 | B899 | B900 | B901 | B902 | B903 | B904 |
| B905 | B906 | B907 | B908 | B909 | B910 | B911 | B912 | B913 | B914 | B915 | B916 |
| B917 | B918 | B919 | B920 | B921 | B922 | B923 | B924 | B925 | B926 | B927 | B928 |
| B929 | B930 | B931 | B932 | B933 | B934 | B935 | B936 | B937 | B938 | B939 | B940 |
| B941 | B942 | B943 | B944 | B945 | B946 | B947 | B948 | B949 | B950 | B951 | B952 |
| B953 | B954 | B955 | B956 | B957 | B958 | B959 | B960 | B961 | B962 | B963 | B964 |
| B965 | B966 | B967 | B968 | B969 | B970 | B971 | B972 | B973 | B974 | B975 | B976 |
| B977 | B978 | B979 | B980 | B981 | B982 | B983 | B984 | B985 | B986 | B987 | B988 |
| B989 | B990 | B991 | B992 | B993 | B994 | B995 | B996 | B997 | B998 | B999 | B1000 |
| B1001 | B1002 | B1003 | B1004 | B1005 | B1006 | B1007 | B1008 | B1009 | B1010 | B1011 | B1012 |
| B1013 | B1014 | B1015 | B1016 | B1017 | B1018 | B1019 | B1020 | B1021 | B1022 | B1023 | B1024 |
| B1025 | B1026 | B1027 | B1028 | B1029 | B1030 | B1031 | B1032 | B1033 | B1034 | B1035 | B1036 |
| B1037 | B1038 | B1039 | B1040 | B1041 | B1042 | B1043 | B1044 | B1045 | B1046 | B1047 | B1048 |
| B1049 | B1050 | B1051 | B1052 | B1053 | B1054 | B1055 | B1056 | B1057 | B1058 | B1059 | B1060 |
| B1061 | B1062 | B1063 | B1064 | B1065 | B1066 | B1067 | B1068 | B1069 | B1070 | B1071 | B1072 |
| B1073 | B1074 | B1075 | B1076 | B1077 | B1078 | B1079 | B1080 | B1081 | B1082 | B1083 | |

TABLE 13

Compounds of formula In:

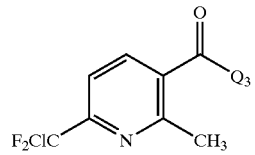

(In)

| $Q_3$ | $Q_3$ | $Q_3$ | $Q_3$ | $Q_3$ | $Q_3$ | $Q_3$ | $Q_3$ | $Q_3$ | $Q_3$ | $Q_3$ | $Q_3$ |
|---|---|---|---|---|---|---|---|---|---|---|---|
| B1 | B2 | B3 | B4 | B5 | B6 | B7 | B8 | B9 | B10 | B11 | B12 |
| B13 | B14 | B15 | B16 | B17 | B18 | B19 | B20 | B21 | B22 | B23 | B24 |
| B25 | B26 | B27 | B28 | B29 | B30 | B31 | B32 | B33 | B34 | B35 | B36 |
| B37 | B38 | B39 | B40 | B41 | B42 | B43 | B44 | B45 | B46 | B47 | B48 |
| B49 | B50 | B51 | B52 | B53 | B54 | B55 | B56 | B57 | B58 | B59 | B60 |
| B61 | B62 | B63 | B64 | B65 | B66 | B67 | B68 | B69 | B70 | B71 | B72 |
| B73 | B74 | B75 | B76 | B77 | B78 | B79 | B80 | B81 | B82 | B83 | B84 |
| B85 | B86 | B87 | B88 | B89 | B90 | B91 | B92 | B93 | B94 | B95 | B96 |
| B97 | B98 | B99 | B100 | B101 | B102 | B103 | B104 | B105 | B106 | B107 | B108 |
| B109 | B110 | B111 | B112 | B113 | B114 | B115 | B116 | B117 | B118 | B119 | B120 |
| B121 | B122 | B123 | B124 | B125 | B126 | B127 | B128 | B129 | B130 | B131 | B132 |
| B133 | B134 | B135 | B136 | B137 | B138 | B139 | B140 | B141 | B142 | B143 | B144 |
| B145 | B146 | B147 | B148 | B149 | B150 | B151 | B152 | B153 | B154 | B155 | B156 |
| B157 | B158 | B159 | B160 | B161 | B162 | B163 | B164 | B165 | B166 | B167 | B168 |
| B169 | B170 | B171 | B172 | B173 | B174 | B175 | B176 | B177 | B178 | B179 | B180 |
| B181 | B182 | B183 | B184 | B185 | B186 | B187 | B188 | B189 | B190 | B191 | B192 |
| B193 | B194 | B195 | B196 | B197 | B198 | B199 | B200 | B201 | B202 | B203 | B204 |
| B205 | B206 | B207 | B208 | B209 | B210 | B211 | B212 | B213 | B214 | B215 | B216 |
| B217 | B218 | B219 | B220 | B221 | B222 | B223 | B224 | B225 | B226 | B227 | B228 |
| B229 | B230 | B231 | B232 | B233 | B234 | B235 | B236 | B237 | B238 | B239 | B240 |
| B241 | B242 | B243 | B244 | B245 | B246 | B247 | B248 | B249 | B250 | B251 | B252 |
| B253 | B254 | B255 | B256 | B257 | B258 | B259 | B260 | B261 | B262 | B263 | B264 |
| B265 | B266 | B267 | B268 | B269 | B270 | B271 | B272 | B273 | B274 | B275 | B276 |
| B277 | B278 | B279 | B280 | B281 | B282 | B283 | B284 | B285 | B286 | B287 | B288 |
| B289 | B290 | B291 | B292 | B293 | B294 | B295 | B296 | B297 | B298 | B299 | B300 |
| B301 | B302 | B303 | B304 | B305 | B306 | B307 | B308 | B309 | B310 | B311 | B312 |
| B313 | B314 | B315 | B316 | B317 | B318 | B319 | B320 | B321 | B322 | B323 | B324 |
| B325 | B326 | B327 | B328 | B329 | B330 | B331 | B332 | B333 | B334 | B335 | B336 |
| B337 | B338 | B339 | B340 | B341 | B342 | B343 | B344 | B345 | B346 | B347 | B348 |
| B349 | B350 | B351 | B352 | B353 | B354 | B355 | B356 | B357 | B358 | B359 | B360 |
| B361 | B362 | B363 | B364 | B365 | B366 | B367 | B368 | B369 | B370 | B371 | B372 |
| B373 | B374 | B375 | B376 | B377 | B378 | B379 | B380 | B381 | B382 | B383 | B384 |
| B385 | B386 | B387 | B388 | B389 | B390 | B391 | B392 | B393 | B394 | B395 | B396 |
| B397 | B398 | B399 | B400 | B401 | B402 | B403 | B404 | B405 | B406 | B407 | B408 |
| B409 | B410 | B411 | B412 | B413 | B414 | B415 | B416 | B417 | B418 | B419 | B420 |
| B421 | B422 | B423 | B424 | B425 | B426 | B427 | B428 | B429 | B430 | B431 | B432 |
| B433 | B434 | B435 | B436 | B437 | B438 | B439 | B440 | B441 | B442 | B443 | B444 |
| B445 | B446 | B447 | B448 | B449 | B450 | B451 | B452 | B453 | B454 | B455 | B456 |
| B457 | B458 | B459 | B460 | B461 | B462 | B463 | B464 | B465 | B466 | B467 | B468 |
| B469 | B470 | B471 | B472 | B473 | B474 | B475 | B476 | B477 | B478 | B479 | B480 |
| B481 | B482 | B483 | B484 | B485 | B486 | B487 | B488 | B489 | B490 | B491 | B492 |
| B493 | B494 | B495 | B496 | B497 | B498 | B499 | B500 | B501 | B502 | B503 | B504 |
| B505 | B506 | B507 | B508 | B509 | B510 | B511 | B512 | B513 | B514 | B515 | B516 |
| B517 | B518 | B519 | B520 | B521 | B522 | B523 | B524 | B525 | B526 | B527 | B528 |
| B529 | B530 | B531 | B532 | B533 | B534 | B535 | B536 | B537 | B538 | B539 | B540 |
| B541 | B542 | B543 | B544 | B545 | B546 | B547 | B548 | B549 | B550 | B551 | B552 |
| B553 | B554 | B555 | B556 | B557 | B558 | B559 | B560 | B561 | B562 | B563 | B564 |
| B565 | B566 | B567 | B568 | B569 | B570 | B571 | B572 | B573 | B574 | B575 | B576 |
| B577 | B578 | B579 | B580 | B581 | B582 | B583 | B584 | B585 | B586 | B587 | B588 |
| B589 | B590 | B591 | B592 | B593 | B594 | B595 | B596 | B597 | B598 | B599 | B600 |
| B601 | B602 | B603 | B604 | B605 | B606 | B607 | B608 | B609 | B610 | B611 | B612 |
| B613 | B614 | B615 | B616 | B617 | B618 | B619 | B620 | B621 | B622 | B623 | B624 |
| B625 | B626 | B627 | B628 | B629 | B630 | B631 | B632 | B633 | B634 | B635 | B636 |
| B637 | B638 | B639 | B640 | B641 | B642 | B643 | B644 | B645 | B646 | B647 | B648 |
| B649 | B650 | B651 | B652 | B653 | B654 | B655 | B656 | B657 | B658 | B659 | B660 |
| B661 | B662 | B663 | B664 | B665 | B666 | B667 | B668 | B669 | B670 | B671 | B672 |
| B773 | B774 | B775 | B776 | B777 | B778 | B779 | B780 | B781 | B782 | B783 | B784 |
| B785 | B786 | B787 | B788 | B789 | B790 | B791 | B792 | B793 | B794 | B795 | B796 |
| B797 | B798 | B799 | B800 | B801 | B802 | B803 | B804 | B805 | B806 | B807 | B808 |
| B809 | B810 | B811 | B812 | B813 | B814 | B815 | B816 | B817 | B818 | B819 | B820 |
| B821 | B822 | B823 | B824 | B825 | B826 | B827 | B828 | B829 | B830 | B831 | B832 |
| B833 | B834 | B835 | B836 | B837 | B838 | B839 | B840 | B841 | B842 | B843 | B844 |
| B845 | B846 | B847 | B848 | B849 | B850 | B851 | B852 | B853 | B854 | B855 | B856 |
| B857 | B858 | B859 | B860 | B861 | B862 | B863 | B864 | B865 | B866 | B867 | B868 |
| B869 | B870 | B871 | B872 | B873 | B874 | B875 | B876 | B877 | B878 | B879 | B880 |

TABLE 13-continued

Compounds of formula In:

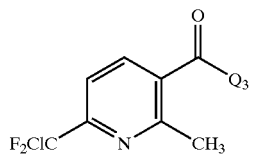

(In)

| Q₃ | Q₃ | Q₃ | Q₃ | Q₃ | Q₃ | Q₃ | Q₃ | Q₃ | Q₃ | Q₃ | Q₃ |
|---|---|---|---|---|---|---|---|---|---|---|---|
| B881 | B882 | B883 | B884 | B885 | B886 | B887 | B888 | B889 | B890 | B891 | B892 |
| B893 | B894 | B895 | B896 | B897 | B898 | B899 | B900 | B901 | B902 | B903 | B904 |
| B905 | B906 | B907 | B908 | B909 | B910 | B911 | B912 | B913 | B914 | B915 | B916 |
| B917 | B918 | B919 | B920 | B921 | B922 | B923 | B924 | B925 | B926 | B927 | B928 |
| B929 | B930 | B931 | B932 | B933 | B934 | B935 | B936 | B937 | B938 | B939 | B940 |
| B941 | B942 | B943 | B944 | B945 | B946 | B947 | B948 | B949 | B950 | B951 | B952 |
| B953 | B954 | B955 | B956 | B957 | B958 | B959 | B960 | B961 | B962 | B963 | B964 |
| B965 | B966 | B967 | B968 | B969 | B970 | B971 | B972 | B973 | B974 | B975 | B976 |
| B977 | B978 | B979 | B980 | B981 | B982 | B983 | B984 | B985 | B986 | B987 | B988 |
| B989 | B990 | B991 | B992 | B993 | B994 | B995 | B996 | B997 | B998 | B999 | B1000 |
| B1001 | B1002 | B1003 | B1004 | B1005 | B1006 | B1007 | B1008 | B1009 | B1010 | B1011 | B1012 |
| B1013 | B1014 | B1015 | B1016 | B1017 | B1018 | B1019 | B1020 | B1021 | B1022 | B1023 | B1024 |
| B1025 | B1026 | B1027 | B1028 | B1029 | B1030 | B1031 | B1032 | B1033 | B1034 | B1035 | B1036 |
| B1037 | B1038 | B1039 | B1040 | B1041 | B1042 | B1043 | B1044 | B1045 | B1046 | B1047 | B1048 |
| B1049 | B1050 | B1051 | B1052 | B1053 | B1054 | B1055 | B1056 | B1057 | B1058 | B1059 | B1060 |
| B1061 | B1062 | B1063 | B1064 | B1065 | B1066 | B1067 | B1068 | B1069 | B1070 | B1071 | B1072 |
| B1073 | B1074 | B1075 | B1076 | B1077 | B1078 | B1079 | B1080 | B1081 | B1082 | B1083 | |

TABLE 14

Compounds of formula Io:

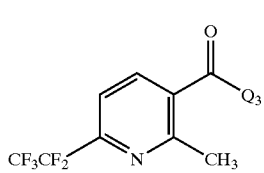

(Io)

| Q₃ | Q₃ | Q₃ | Q₃ | Q₃ | Q₃ | Q₃ | Q₃ | Q₃ | Q₃ | Q₃ | Q₃ |
|---|---|---|---|---|---|---|---|---|---|---|---|
| B1 | B2 | B3 | B4 | B5 | B6 | B7 | B8 | B9 | B10 | B11 | B12 |
| B13 | B14 | B15 | B16 | B17 | B18 | B19 | B20 | B21 | B22 | B23 | B24 |
| B25 | B26 | B27 | B28 | B29 | B30 | B31 | B32 | B33 | B34 | B35 | B36 |
| B37 | B38 | B39 | B40 | B41 | B42 | B43 | B44 | B45 | B46 | B47 | B48 |
| B49 | B50 | B51 | B52 | B53 | B54 | B55 | B56 | B57 | B58 | B59 | B60 |
| B61 | B62 | B63 | B64 | B65 | B66 | B67 | B68 | B69 | B70 | B71 | B72 |
| B73 | B74 | B75 | B76 | B77 | B78 | B79 | B80 | B81 | B82 | B83 | B84 |
| B85 | B86 | B87 | B88 | B89 | B90 | B91 | B92 | B93 | B94 | B95 | B96 |
| B97 | B98 | B99 | B100 | B101 | B102 | B103 | B104 | B105 | B106 | B107 | B108 |
| B109 | B110 | B111 | B112 | B113 | B114 | B115 | B116 | B117 | B118 | B119 | B120 |
| B121 | B122 | B123 | B124 | B125 | B126 | B127 | B128 | B129 | B130 | B131 | B132 |
| B133 | B134 | B135 | B136 | B137 | B138 | B139 | B140 | B141 | B142 | B143 | B144 |
| B145 | B146 | B147 | B148 | B149 | B150 | B151 | B152 | B153 | B154 | B155 | B156 |
| B157 | B158 | B159 | B160 | B161 | B162 | B163 | B164 | B165 | B166 | B167 | B168 |
| B169 | B170 | B171 | B172 | B173 | B174 | B175 | B176 | B177 | B178 | B179 | B180 |
| B181 | B182 | B183 | B184 | B185 | B186 | B187 | B188 | B189 | B190 | B191 | B192 |
| B193 | B194 | B195 | B196 | B197 | B198 | B199 | B200 | B201 | B202 | B203 | B204 |
| B205 | B206 | B207 | B208 | B209 | B210 | B211 | B212 | B213 | B214 | B215 | B216 |
| B217 | B218 | B219 | B220 | B221 | B222 | B223 | B224 | B225 | B226 | B227 | B228 |
| B229 | B230 | B231 | B232 | B233 | B234 | B235 | B236 | B237 | B238 | B239 | B240 |
| B241 | B242 | B243 | B244 | B245 | B246 | B247 | B248 | B249 | B250 | B251 | B252 |
| B253 | B254 | B255 | B256 | B257 | B258 | B259 | B260 | B261 | B262 | B263 | B264 |
| B265 | B266 | B267 | B268 | B269 | B270 | B271 | B272 | B273 | B274 | B275 | B276 |
| B277 | B278 | B279 | B280 | B281 | B282 | B283 | B284 | B285 | B286 | B287 | B288 |
| B289 | B290 | B291 | B292 | B293 | B294 | B295 | B296 | B297 | B298 | B299 | B300 |
| B301 | B302 | B303 | B304 | B305 | B306 | B307 | B308 | B309 | B310 | B311 | B312 |
| B313 | B314 | B315 | B316 | B317 | B318 | B319 | B320 | B321 | B322 | B323 | B324 |
| B325 | B326 | B327 | B328 | B329 | B330 | B331 | B332 | B333 | B334 | B335 | B336 |
| B337 | B338 | B339 | B340 | B341 | B342 | B343 | B344 | B345 | B346 | B347 | B348 |
| B349 | B350 | B351 | B352 | B353 | B354 | B355 | B356 | B357 | B358 | B359 | B360 |

TABLE 14-continued

Compounds of formula Io:

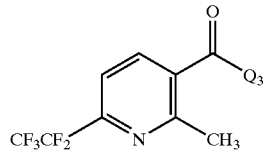

(Io)

| $Q_3$ | $Q_3$ | $Q_3$ | $Q_3$ | $Q_3$ | $Q_3$ | $Q_3$ | $Q_3$ | $Q_3$ | $Q_3$ | $Q_3$ | $Q_3$ |
|---|---|---|---|---|---|---|---|---|---|---|---|
| B361 | B362 | B363 | B364 | B365 | B366 | B367 | B368 | B369 | B370 | B371 | B372 |
| B373 | B374 | B375 | B376 | B377 | B378 | B379 | B380 | B381 | B382 | B383 | B384 |
| B385 | B386 | B387 | B388 | B389 | B390 | B391 | B392 | B393 | B394 | B395 | B396 |
| B397 | B398 | B399 | B400 | B401 | B402 | B403 | B404 | B405 | B406 | B407 | B408 |
| B409 | B410 | B411 | B412 | B413 | B414 | B415 | B416 | B417 | B418 | B419 | B420 |
| B421 | B422 | B423 | B424 | B425 | B426 | B427 | B428 | B429 | B430 | B431 | B432 |
| B433 | B434 | B435 | B436 | B437 | B438 | B439 | B440 | B441 | B442 | B443 | B444 |
| B445 | B446 | B447 | B448 | B449 | B450 | B451 | B452 | B453 | B454 | B455 | B456 |
| B457 | B458 | B459 | B460 | B461 | B462 | B463 | B464 | B465 | B466 | B467 | B468 |
| B469 | B470 | B471 | B472 | B473 | B474 | B475 | B476 | B477 | B478 | B479 | B480 |
| B481 | B482 | B483 | B484 | B485 | B486 | B487 | B488 | B489 | B490 | B491 | B492 |
| B493 | B494 | B495 | B496 | B497 | B498 | B499 | B500 | B501 | B502 | B503 | B504 |
| B505 | B506 | B507 | B508 | B509 | B510 | B511 | B512 | B513 | B514 | B515 | B516 |
| B517 | B518 | B519 | B520 | B521 | B522 | B523 | B524 | B525 | B526 | B527 | B528 |
| B529 | B530 | B531 | B532 | B533 | B534 | B535 | B536 | B537 | B538 | B539 | B540 |
| B541 | B542 | B543 | B544 | B545 | B546 | B547 | B548 | B549 | B550 | B551 | B552 |
| B553 | B554 | B555 | B556 | B557 | B558 | B559 | B560 | B561 | B562 | B563 | B564 |
| B565 | B566 | B567 | B568 | B569 | B570 | B571 | B572 | B573 | B574 | B575 | B576 |
| B577 | B578 | B579 | B580 | B581 | B582 | B583 | B584 | B585 | B586 | B587 | B588 |
| B589 | B590 | B591 | B592 | B593 | B594 | B595 | B596 | B597 | B598 | B599 | B600 |
| B601 | B602 | B603 | B604 | B605 | B606 | B607 | B608 | B609 | B610 | B611 | B612 |
| B613 | B614 | B615 | B616 | B617 | B618 | B619 | B620 | B621 | B622 | B623 | B624 |
| B625 | B626 | B627 | B628 | B629 | B630 | B631 | B632 | B633 | B634 | B635 | B636 |
| B637 | B638 | B639 | B640 | B641 | B642 | B643 | B644 | B645 | B646 | B647 | B648 |
| B649 | B650 | B651 | B652 | B653 | B654 | B655 | B656 | B657 | B658 | B659 | B660 |
| B661 | B662 | B663 | B664 | B665 | B666 | B667 | B668 | B669 | B670 | B671 | B672 |
| B773 | B774 | B775 | B776 | B777 | B778 | B779 | B780 | B781 | B782 | B783 | B784 |
| B785 | B786 | B787 | B788 | B789 | B790 | B791 | B792 | B793 | B794 | B795 | B796 |
| B797 | B798 | B799 | B800 | B801 | B802 | B803 | B804 | B805 | B806 | B807 | B808 |
| B809 | B810 | B811 | B812 | B813 | B814 | B815 | B816 | B817 | B818 | B819 | B820 |
| B821 | B822 | B823 | B824 | B825 | B826 | B827 | B828 | B829 | B830 | B831 | B832 |
| B833 | B834 | B835 | B836 | B837 | B838 | B839 | B840 | B841 | B842 | B843 | B844 |
| B845 | B846 | B847 | B848 | B849 | B850 | B851 | B852 | B853 | B854 | B855 | B856 |
| B857 | B858 | B859 | B860 | B861 | B862 | B863 | B864 | B865 | B866 | B867 | B868 |
| B869 | B870 | B871 | B872 | B873 | B874 | B875 | B876 | B877 | B878 | B879 | B880 |
| B881 | B882 | B883 | B884 | B885 | B886 | B887 | B888 | B889 | B890 | B891 | B892 |
| B893 | B894 | B895 | B896 | B897 | B898 | B899 | B900 | B901 | B902 | B903 | B904 |
| B905 | B906 | B907 | B908 | B909 | B910 | B911 | B912 | B913 | B914 | B915 | B916 |
| B917 | B918 | B919 | B920 | B921 | B922 | B923 | B924 | B925 | B926 | B927 | B928 |
| B929 | B930 | B931 | B932 | B933 | B934 | B935 | B936 | B937 | B938 | B939 | B940 |
| B941 | B942 | B943 | B944 | B945 | B946 | B947 | B948 | B949 | B950 | B951 | B952 |
| B953 | B954 | B955 | B956 | B957 | B958 | B959 | B960 | B961 | B962 | B963 | B964 |
| B965 | B966 | B967 | B968 | B969 | B970 | B971 | B972 | B973 | B974 | B975 | B976 |
| B977 | B978 | B979 | B980 | B981 | B982 | B983 | B984 | B985 | B986 | B987 | B988 |
| B989 | B990 | B991 | B992 | B993 | B994 | B995 | B996 | B997 | B998 | B999 | B1000 |
| B1001 | B1002 | B1003 | B1004 | B1005 | B1006 | B1007 | B1008 | B1009 | B1010 | B1011 | B1012 |
| B1013 | B1014 | B1015 | B1016 | B1017 | B1018 | B1019 | B1020 | B1021 | B1022 | B1023 | B1024 |
| B1025 | B1026 | B1027 | B1028 | B1029 | B1030 | B1031 | B1032 | B1033 | B1034 | B1035 | B1036 |
| B1037 | B1038 | B1039 | B1040 | B1041 | B1042 | B1043 | B1044 | B1045 | B1046 | B1047 | B1048 |
| B1049 | B1050 | B1051 | B1052 | B1053 | B1054 | B1055 | B1056 | B1057 | B1058 | B1059 | B1060 |
| B1061 | B1062 | B1063 | B1064 | B1065 | B1066 | B1067 | B1068 | B1069 | B1070 | B1071 | B1072 |
| B1073 | B1074 | B1075 | B1076 | B1077 | B1078 | B1079 | B1080 | B1081 | B1082 | B1083 | |

TABLE 15

Compounds of formula Ip:

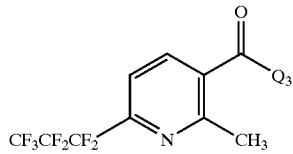

(Ip)

| $Q_3$ | $Q_3$ | $Q_3$ | $Q_3$ | $Q_3$ | $Q_3$ | $Q_3$ | $Q_3$ | $Q_3$ | $Q_3$ | $Q_3$ | $Q_3$ |
|---|---|---|---|---|---|---|---|---|---|---|---|
| B1 | B2 | B3 | B4 | B5 | B6 | B7 | B8 | B9 | B10 | B11 | B12 |
| B13 | B14 | B15 | B16 | B17 | B18 | B19 | B20 | B21 | B22 | B23 | B24 |
| B25 | B26 | B27 | B28 | B29 | B30 | B31 | B32 | B33 | B34 | B35 | B36 |
| B37 | B38 | B39 | B40 | B41 | B42 | B43 | B44 | B45 | B46 | B47 | B48 |
| B49 | B50 | B51 | B52 | B53 | B54 | B55 | B56 | B57 | B58 | B59 | B60 |
| B61 | B62 | B63 | B64 | B65 | B66 | B67 | B68 | B69 | B70 | B71 | B72 |
| B73 | B74 | B75 | B76 | B77 | B78 | B79 | B80 | B81 | B82 | B83 | B84 |
| B85 | B86 | B87 | B88 | B89 | B90 | B91 | B92 | B93 | B94 | B95 | B96 |
| B97 | B98 | B99 | B100 | B101 | B102 | B103 | B104 | B105 | B106 | B107 | B108 |
| B109 | B110 | B111 | B112 | B113 | B114 | B115 | B116 | B117 | B118 | B119 | B120 |
| B121 | B122 | B123 | B124 | B125 | B126 | B127 | B128 | B129 | B130 | B131 | B132 |
| B133 | B134 | B135 | B136 | B137 | B138 | B139 | B140 | B141 | B142 | B143 | B144 |
| B145 | B146 | B147 | B148 | B149 | B150 | B151 | B152 | B153 | B154 | B155 | B156 |
| B157 | B158 | B159 | B160 | B161 | B162 | B163 | B164 | B165 | B166 | B167 | B168 |
| B169 | B170 | B171 | B172 | B173 | B174 | B175 | B176 | B177 | B178 | B179 | B180 |
| B181 | B182 | B183 | B184 | B185 | B186 | B187 | B188 | B189 | B190 | B191 | B192 |
| B193 | B194 | B195 | B196 | B197 | B198 | B199 | B200 | B201 | B202 | B203 | B204 |
| B205 | B206 | B207 | B208 | B209 | B210 | B211 | B212 | B213 | B214 | B215 | B216 |
| B217 | B218 | B219 | B220 | B221 | B222 | B223 | B224 | B225 | B226 | B227 | B228 |
| B229 | B230 | B231 | B232 | B233 | B234 | B235 | B236 | B237 | B238 | B239 | B240 |
| B241 | B242 | B243 | B244 | B245 | B246 | B247 | B248 | B249 | B250 | B251 | B252 |
| B253 | B254 | B255 | B256 | B257 | B258 | B259 | B260 | B261 | B262 | B263 | B264 |
| B265 | B266 | B267 | B268 | B269 | B270 | B271 | B272 | B273 | B274 | B275 | B276 |
| B277 | B278 | B279 | B280 | B281 | B282 | B283 | B284 | B285 | B286 | B287 | B288 |
| B289 | B290 | B291 | B292 | B293 | B294 | B295 | B296 | B297 | B298 | B299 | B300 |
| B301 | B302 | B303 | B304 | B305 | B306 | B307 | B308 | B309 | B310 | B311 | B312 |
| B313 | B314 | B315 | B316 | B317 | B318 | B319 | B320 | B321 | B322 | B323 | B324 |
| B325 | B326 | B327 | B328 | B329 | B330 | B331 | B332 | B333 | B334 | B335 | B336 |
| B337 | B338 | B339 | B340 | B341 | B342 | B343 | B344 | B345 | B346 | B347 | B348 |
| B349 | B350 | B351 | B352 | B353 | B354 | B355 | B356 | B357 | B358 | B359 | B360 |
| B361 | B362 | B363 | B364 | B365 | B366 | B367 | B368 | B369 | B370 | B371 | B372 |
| B373 | B374 | B375 | B376 | B377 | B378 | B379 | B380 | B381 | B382 | B383 | B384 |
| B385 | B386 | B387 | B388 | B389 | B390 | B391 | B392 | B393 | B394 | B395 | B396 |
| B397 | B398 | B399 | B400 | B401 | B402 | B403 | B404 | B405 | B406 | B407 | B408 |
| B409 | B410 | B411 | B412 | B413 | B414 | B415 | B416 | B417 | B418 | B419 | B420 |
| B421 | B422 | B423 | B424 | B425 | B426 | B427 | B428 | B429 | B430 | B431 | B432 |
| B433 | B434 | B435 | B436 | B437 | B438 | B439 | B440 | B441 | B442 | B443 | B444 |
| B445 | B446 | B447 | B448 | B449 | B450 | B451 | B452 | B453 | B454 | B455 | B456 |
| B457 | B458 | B459 | B460 | B461 | B462 | B463 | B464 | B465 | B466 | B467 | B468 |
| B469 | B470 | B471 | B472 | B473 | B474 | B475 | B476 | B477 | B478 | B479 | B480 |
| B481 | B482 | B483 | B484 | B485 | B486 | B487 | B488 | B489 | B490 | B491 | B492 |
| B493 | B494 | B495 | B496 | B497 | B498 | B499 | B500 | B501 | B502 | B503 | B504 |
| B505 | B506 | B507 | B508 | B509 | B510 | B511 | B512 | B513 | B514 | B515 | B516 |
| B517 | B518 | B519 | B520 | B521 | B522 | B523 | B524 | B525 | B526 | B527 | B528 |
| B529 | B530 | B531 | B532 | B533 | B534 | B535 | B536 | B537 | B538 | B539 | B540 |
| B541 | B542 | B543 | B544 | B545 | B546 | B547 | B548 | B549 | B550 | B551 | B552 |
| B553 | B554 | B555 | B556 | B557 | B558 | B559 | B560 | B561 | B562 | B563 | B564 |
| B565 | B566 | B567 | B568 | B569 | B570 | B571 | B572 | B573 | B574 | B575 | B576 |
| B577 | B578 | B579 | B580 | B581 | B582 | B583 | B584 | B585 | B586 | B587 | B588 |
| B589 | B590 | B591 | B592 | B593 | B594 | B595 | B596 | B597 | B598 | B599 | B600 |
| B601 | B602 | B603 | B604 | B605 | B606 | B607 | B608 | B609 | B610 | B611 | B612 |
| B613 | B614 | B615 | B616 | B617 | B618 | B619 | B620 | B621 | B622 | B623 | B624 |
| B625 | B626 | B627 | B628 | B629 | B630 | B631 | B632 | B633 | B634 | B635 | B636 |
| B637 | B638 | B639 | B640 | B641 | B642 | B643 | B644 | B645 | B646 | B647 | B648 |
| B649 | B650 | B651 | B652 | B653 | B654 | B655 | B656 | B657 | B658 | B659 | B660 |
| B661 | B662 | B663 | B664 | B665 | B666 | B667 | B668 | B669 | B670 | B671 | B672 |
| B773 | B774 | B775 | B776 | B777 | B778 | B779 | B780 | B781 | B782 | B783 | B784 |
| B785 | B786 | B787 | B788 | B789 | B790 | B791 | B792 | B793 | B794 | B795 | B796 |
| B797 | B798 | B799 | B800 | B801 | B802 | B803 | B804 | B805 | B806 | B807 | B808 |
| B809 | B810 | B811 | B812 | B813 | B814 | B815 | B816 | B817 | B818 | B819 | B820 |
| B821 | B822 | B823 | B824 | B825 | B826 | B827 | B828 | B829 | B830 | B831 | B832 |
| B833 | B834 | B835 | B836 | B837 | B838 | B839 | B840 | B841 | B842 | B843 | B844 |
| B845 | B846 | B847 | B848 | B849 | B850 | B851 | B852 | B853 | B854 | B855 | B856 |
| B857 | B858 | B859 | B860 | B861 | B862 | B863 | B864 | B865 | B866 | B867 | B868 |
| B869 | B870 | B871 | B872 | B873 | B874 | B875 | B876 | B877 | B878 | B879 | B880 |

TABLE 15-continued

Compounds of formula Ip:

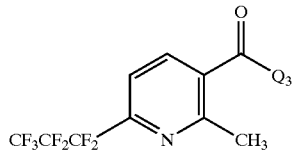
(Ip)

| $Q_3$ | $Q_3$ | $Q_3$ | $Q_3$ | $Q_3$ | $Q_3$ | $Q_3$ | $Q_3$ | $Q_3$ | $Q_3$ | $Q_3$ | $Q_3$ |
|---|---|---|---|---|---|---|---|---|---|---|---|
| B881 | B882 | B883 | B884 | B885 | B886 | B887 | B888 | B889 | B890 | B891 | B892 |
| B893 | B894 | B895 | B896 | B897 | B898 | B899 | B900 | B901 | B902 | B903 | B904 |
| B905 | B906 | B907 | B908 | B909 | B910 | B911 | B912 | B913 | B914 | B915 | B916 |
| B917 | B918 | B919 | B920 | B921 | B922 | B923 | B924 | B925 | B926 | B927 | B928 |
| B929 | B930 | B931 | B932 | B933 | B934 | B935 | B936 | B937 | B938 | B939 | B940 |
| B941 | B942 | B943 | B944 | B945 | B946 | B947 | B948 | B949 | B950 | B951 | B952 |
| B953 | B954 | B955 | B956 | B957 | B958 | B959 | B960 | B961 | B962 | B963 | B964 |
| B965 | B966 | B967 | B968 | B969 | B970 | B971 | B972 | B973 | B974 | B975 | B976 |
| B977 | B978 | B979 | B980 | B981 | B982 | B983 | B984 | B985 | B986 | B987 | B988 |
| B989 | B990 | B991 | B992 | B993 | B994 | B995 | B996 | B997 | B998 | B999 | B1000 |
| B1001 | B1002 | B1003 | B1004 | B1005 | B1006 | B1007 | B1008 | B1009 | B1010 | B1011 | B1012 |
| B1013 | B1014 | B1015 | B1016 | B1017 | B1018 | B1019 | B1020 | B1021 | B1022 | B1023 | B1024 |
| B1025 | B1026 | B1027 | B1028 | B1029 | B1030 | B1031 | B1032 | B1033 | B1034 | B1035 | B1036 |
| B1037 | B1038 | B1039 | B1040 | B1041 | B1042 | B1043 | B1044 | B1045 | B1046 | B1047 | B1048 |
| B1049 | B1050 | B1051 | B1052 | B1053 | B1054 | B1055 | B1056 | B1057 | B1058 | B1059 | B1060 |
| B1061 | B1062 | B1063 | B1064 | B1065 | B1066 | B1067 | B1068 | B1069 | B1070 | B1071 | B1072 |
| B1073 | B1074 | B1075 | B1076 | B1077 | B1078 | B1079 | B1080 | B1081 | B1082 | B1083 | |

TABLE 16

Compounds of formula Iq:

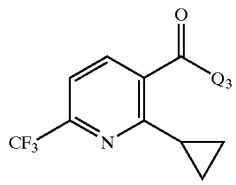
(Iq)

| $Q_3$ | $Q_3$ | $Q_3$ | $Q_3$ | $Q_3$ | $Q_3$ | $Q_3$ | $Q_3$ | $Q_3$ | $Q_3$ | $Q_3$ | $Q_3$ |
|---|---|---|---|---|---|---|---|---|---|---|---|
| B1 | B2 | B3 | B4 | B5 | B6 | B7 | B8 | B9 | B10 | B11 | B12 |
| B13 | B14 | B15 | B16 | B17 | B18 | B19 | B20 | B21 | B22 | B23 | B24 |
| B25 | B26 | B27 | B28 | B29 | B30 | B31 | B32 | B33 | B34 | B35 | B36 |
| B37 | B38 | B39 | B40 | B41 | B42 | B43 | B44 | B45 | B46 | B47 | B48 |
| B49 | B50 | B51 | B52 | B53 | B54 | B55 | B56 | B57 | B58 | B59 | B60 |
| B61 | B62 | B63 | B64 | B65 | B66 | B67 | B68 | B69 | B70 | B71 | B72 |
| B73 | B74 | B75 | B76 | B77 | B78 | B79 | B80 | B81 | B82 | B83 | B84 |
| B85 | B86 | B87 | B88 | B89 | B90 | B91 | B92 | B93 | B94 | B95 | B96 |
| B97 | B98 | B99 | B100 | B101 | B102 | B103 | B104 | B105 | B106 | B107 | B108 |
| B109 | B110 | B111 | B112 | B113 | B114 | B115 | B116 | B117 | B118 | B119 | B120 |
| B121 | B122 | B123 | B124 | B125 | B126 | B127 | B128 | B129 | B130 | B131 | B132 |
| B133 | B134 | B135 | B136 | B137 | B138 | B139 | B140 | B141 | B142 | B143 | B144 |
| B145 | B146 | B147 | B148 | B149 | B150 | B151 | B152 | B153 | B154 | B155 | B156 |
| B157 | B158 | B159 | B160 | B161 | B162 | B163 | B164 | B165 | B166 | B167 | B168 |
| B169 | B170 | B171 | B172 | B173 | B174 | B175 | B176 | B177 | B178 | B179 | B180 |
| B181 | B182 | B183 | B184 | B185 | B186 | B187 | B188 | B189 | B190 | B191 | B192 |
| B193 | B194 | B195 | B196 | B197 | B198 | B199 | B200 | B201 | B202 | B203 | B204 |
| B205 | B206 | B207 | B208 | B209 | B210 | B211 | B212 | B213 | B214 | B215 | B216 |
| B217 | B218 | B219 | B220 | B221 | B222 | B223 | B224 | B225 | B226 | B227 | B228 |
| B229 | B230 | B231 | B232 | B233 | B234 | B235 | B236 | B237 | B238 | B239 | B240 |
| B241 | B242 | B243 | B244 | B245 | B246 | B247 | B248 | B249 | B250 | B251 | B252 |
| B253 | B254 | B255 | B256 | B257 | B258 | B259 | B260 | B261 | B262 | B263 | B264 |
| B265 | B266 | B267 | B268 | B269 | B270 | B271 | B272 | B273 | B274 | B275 | B276 |
| B277 | B278 | B279 | B280 | B281 | B282 | B283 | B284 | B285 | B286 | B287 | B288 |
| B289 | B290 | B291 | B292 | B293 | B294 | B295 | B296 | B297 | B298 | B299 | B300 |
| B301 | B302 | B303 | B304 | B305 | B306 | B307 | B308 | B309 | B310 | B311 | B312 |
| B313 | B314 | B315 | B316 | B317 | B318 | B319 | B320 | B321 | B322 | B323 | B324 |
| B325 | B326 | B327 | B328 | B329 | B330 | B331 | B332 | B333 | B334 | B335 | B336 |

TABLE 16-continued

Compounds of formula Iq:

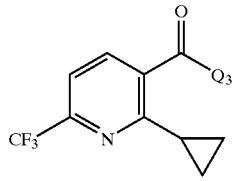

(Iq)

| Q₃ | Q₃ | Q₃ | Q₃ | Q₃ | Q₃ | Q₃ | Q₃ | Q₃ | Q₃ | Q₃ | Q₃ |
|---|---|---|---|---|---|---|---|---|---|---|---|
| B337 | B338 | B339 | B340 | B341 | B342 | B343 | B344 | B345 | B346 | B347 | B348 |
| B349 | B350 | B351 | B352 | B353 | B354 | B355 | B356 | B357 | B358 | B359 | B360 |
| B361 | B362 | B363 | B364 | B365 | B366 | B367 | B368 | B369 | B370 | B371 | B372 |
| B373 | B374 | B375 | B376 | B377 | B378 | B379 | B380 | B381 | B382 | B383 | B384 |
| B385 | B386 | B387 | B388 | B389 | B390 | B391 | B392 | B393 | B394 | B395 | B396 |
| B397 | B398 | B399 | B400 | B401 | B402 | B403 | B404 | B405 | B406 | B407 | B408 |
| B409 | B410 | B411 | B412 | B413 | B414 | B415 | B416 | B417 | B418 | B419 | B420 |
| B421 | B422 | B423 | B424 | B425 | B426 | B427 | B428 | B429 | B430 | B431 | B432 |
| B433 | B434 | B435 | B436 | B437 | B438 | B439 | B440 | B441 | B442 | B443 | B444 |
| B445 | B446 | B447 | B448 | B449 | B450 | B451 | B452 | B453 | B454 | B455 | B456 |
| B457 | B458 | B459 | B460 | B461 | B462 | B463 | B464 | B465 | B466 | B467 | B468 |
| B469 | B470 | B471 | B472 | B473 | B474 | B475 | B476 | B477 | B478 | B479 | B480 |
| B481 | B482 | B483 | B484 | B485 | B486 | B487 | B488 | B489 | B490 | B491 | B492 |
| B493 | B494 | B495 | B496 | B497 | B498 | B499 | B500 | B501 | B502 | B503 | B504 |
| B505 | B506 | B507 | B508 | B509 | B510 | B511 | B512 | B513 | B514 | B515 | B516 |
| B517 | B518 | B519 | B520 | B521 | B522 | B523 | B524 | B525 | B526 | B527 | B528 |
| B529 | B530 | B531 | B532 | B533 | B534 | B535 | B536 | B537 | B538 | B539 | B540 |
| B541 | B542 | B543 | B544 | B545 | B546 | B547 | B548 | B549 | B550 | B551 | B552 |
| B553 | B554 | B555 | B556 | B557 | B558 | B559 | B560 | B561 | B562 | B563 | B564 |
| B565 | B566 | B567 | B568 | B569 | B570 | B571 | B572 | B573 | B574 | B575 | B576 |
| B577 | B578 | B579 | B580 | B581 | B582 | B583 | B584 | B585 | B586 | B587 | B588 |
| B589 | B590 | B591 | B592 | B593 | B594 | B595 | B596 | B597 | B598 | B599 | B600 |
| B601 | B602 | B603 | B604 | B605 | B606 | B607 | B608 | B609 | B610 | B611 | B612 |
| B613 | B614 | B615 | B616 | B617 | B618 | B619 | B620 | B621 | B622 | B623 | B624 |
| B625 | B626 | B627 | B628 | B629 | B630 | B631 | B632 | B633 | B634 | B635 | B636 |
| B637 | B638 | B639 | B640 | B641 | B642 | B643 | B644 | B645 | B646 | B647 | B648 |
| B649 | B650 | B651 | B652 | B653 | B654 | B655 | B656 | B657 | B658 | B659 | B660 |
| B661 | B662 | B663 | B664 | B665 | B666 | B667 | B668 | B669 | B670 | B671 | B672 |
| B773 | B774 | B775 | B776 | B777 | B778 | B779 | B780 | B781 | B782 | B783 | B784 |
| B785 | B786 | B787 | B788 | B789 | B790 | B791 | B792 | B793 | B794 | B795 | B796 |
| B797 | B798 | B799 | B800 | B801 | B802 | B803 | B804 | B805 | B806 | B807 | B808 |
| B809 | B810 | B811 | B812 | B813 | B814 | B815 | B816 | B817 | B818 | B819 | B820 |
| B821 | B822 | B823 | B824 | B825 | B826 | B827 | B828 | B829 | B830 | B831 | B832 |
| B833 | B834 | B835 | B836 | B837 | B838 | B839 | B840 | B841 | B842 | B843 | B844 |
| B845 | B846 | B847 | B848 | B849 | B850 | B851 | B852 | B853 | B854 | B855 | B856 |
| B857 | B858 | B859 | B860 | B861 | B862 | B863 | B864 | B865 | B866 | B867 | B868 |
| B869 | B870 | B871 | B872 | B873 | B874 | B875 | B876 | B877 | B878 | B879 | B880 |
| B881 | B882 | B883 | B884 | B885 | B886 | B887 | B888 | B889 | B890 | B891 | B892 |
| B893 | B894 | B895 | B896 | B897 | B898 | B899 | B900 | B901 | B902 | B903 | B904 |
| B905 | B906 | B907 | B908 | B909 | B910 | B911 | B912 | B913 | B914 | B915 | B916 |
| B917 | B918 | B919 | B920 | B921 | B922 | B923 | B924 | B925 | B926 | B927 | B928 |
| B929 | B930 | B931 | B932 | B933 | B934 | B935 | B936 | B937 | B938 | B939 | B940 |
| B941 | B942 | B943 | B944 | B945 | B946 | B947 | B948 | B949 | B950 | B951 | B952 |
| B953 | B954 | B955 | B956 | B957 | B958 | B959 | B960 | B961 | B962 | B963 | B964 |
| B965 | B966 | B967 | B968 | B969 | B970 | B971 | B972 | B973 | B974 | B975 | B976 |
| B977 | B978 | B979 | B980 | B981 | B982 | B983 | B984 | B985 | B986 | B987 | B988 |
| B989 | B990 | B991 | B992 | B993 | B994 | B995 | B996 | B997 | B998 | B999 | B1000 |
| B1001 | B1002 | B1003 | B1004 | B1005 | B1006 | B1007 | B1008 | B1009 | B1010 | B1011 | B1012 |
| B1013 | B1014 | B1015 | B1016 | B1017 | B1018 | B1019 | B1020 | B1021 | B1022 | B1023 | B1024 |
| B1025 | B1026 | B1027 | B1028 | B1029 | B1030 | B1031 | B1032 | B1033 | B1034 | B1035 | B1036 |
| B1037 | B1038 | B1039 | B1040 | B1041 | B1042 | B1043 | B1044 | B1045 | B1046 | B1047 | B1048 |
| B1049 | B1050 | B1051 | B1052 | B1053 | B1054 | B1055 | B1056 | B1057 | B1058 | B1059 | B1060 |
| B1061 | B1062 | B1063 | B1064 | B1065 | B1066 | B1067 | B1068 | B1069 | B1070 | B1071 | B1072 |
| B1073 | B1074 | B1075 | B1076 | B1077 | B1078 | B1079 | B1080 | B1081 | B1082 | B1083 | |

TABLE 17

Compounds of formula Ir:

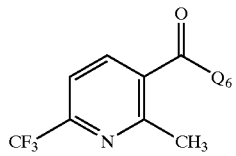

(Ir)

| $Q_6$ | $Q_6$ | $Q_6$ | $Q_6$ | $Q_6$ | $Q_6$ | $Q_6$ | $Q_6$ | $Q_6$ | $Q_6$ | $Q_6$ | $Q_6$ |
|---|---|---|---|---|---|---|---|---|---|---|---|
| C1 | C2 | C3 | C4 | C5 | C6 | C7 | C8 | C9 | C10 | C11 | C12 |
| C13 | C14 | C15 | C16 | C17 | C18 | C19 | C20 | C21 | C22 | C23 | C24 |
| C25 | C26 | C27 | C28 | C29 | C30 | C31 | C32 | C33 | C34 | C35 | C36 |
| C37 | C38 | C39 | C40 | C41 | C42 | C43 | C44 | C45 | C46 | C47 | C48 |
| C49 | C50 | C51 | C52 | C53 | C54 | C55 | C56 | C57 | C58 | C59 | C60 |
| C61 | C62 | C63 | C64 | C65 | C66 | C67 | C68 | C69 | C70 | C71 | C72 |
| C73 | C74 | C75 | C76 | C77 | C78 | C79 | C80 | C81 | C82 | C83 | C84 |
| C85 | C86 | C87 | C88 | C89 | C90 | C91 | C92 | C93 | C94 | C95 | C96 |
| C97 | C98 | C99 | C100 | C101 | C102 | C103 | C104 | C105 | C106 | C107 | C108 |
| C109 | C110 | C111 | C112 | C113 | C114 | C115 | C116 | C117 | C118 | C119 | C120 |
| C121 | C122 | C123 | C124 | C125 | C126 | C127 | C128 | C129 | C130 | C131 | C132 |
| C133 | C134 | C135 | C136 | C137 | C138 | C139 | C140 | C141 | C142 | C143 | C144 |
| C145 | C146 | C147 | C148 | C149 | C150 | C151 | | | | | |

TABLE 18

Compounds of formula Is:

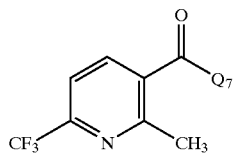

(Is)

| $Q_7$ | $Q_7$ | $Q_7$ | $Q_7$ | $Q_7$ | $Q_7$ | $Q_7$ | $Q_7$ | $Q_7$ | $Q_7$ | $Q_7$ | $Q_7$ |
|---|---|---|---|---|---|---|---|---|---|---|---|
| D1 | D2 | D3 | D4 | D5 | D6 | D7 | D8 | D9 | D10 | D11 | D12 |
| D13 | D14 | D15 | D16 | D17 | D18 | D19 | D20 | D21 | D22 | D23 | D24 |
| D25 | D26 | D27 | D28 | D29 | D30 | D31 | D32 | D33 | D34 | D35 | D36 |
| D37 | D38 | D39 | D40 | D41 | D42 | D43 | D44 | D45 | D46 | D47 | D48 |
| D49 | D50 | D51 | D52 | D53 | D54 | D55 | D56 | D57 | D58 | D59 | D60 |
| D61 | D62 | D63 | D64 | D65 | D66 | D67 | D68 | D69 | D70 | D71 | D72 |
| D73 | D74 | D75 | D76 | D77 | D78 | D79 | D80 | D81 | D82 | D83 | D84 |
| D85 | D86 | D87 | D88 | D89 | D90 | D91 | D92 | D93 | D94 | D95 | D96 |
| D97 | D98 | D99 | D100 | D101 | D102 | D103 | D104 | D105 | D106 | D107 | D108 |
| D109 | D110 | D111 | D112 | D113 | D114 | D115 | D116 | D117 | D118 | D119 | D120 |
| D121 | D122 | D123 | D124 | D125 | D126 | D127 | D128 | D129 | D130 | D131 | D132 |
| D133 | D134 | D135 | D136 | D137 | D138 | D139 | D140 | | | | |

TABLE 19

Compounds of formula Iv:

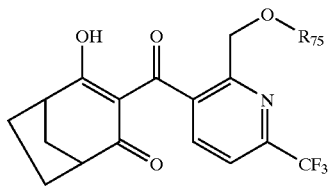

(Iv)

| Compd. no. | $R_{75}$ |
|---|---|
| E1 | $CH_2OCH_3$ |
| E2 | $CH_2OC_2H_5$ |

TABLE 19-continued

Compounds of formula Iv:

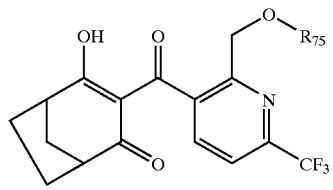

(Iv)

| Compd. no. | $R_{75}$ |
|---|---|
| E3 | $CH_2O$-n-propyl |
| E4 | $CH_2O$-isopropyl |

TABLE 19-continued

Compounds of formula Iv:

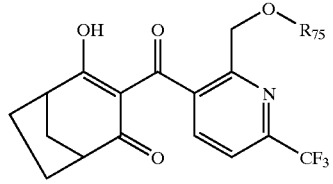

(Iv)

| Compd. no. | $R_{75}$ |
|---|---|
| E5 | $CH_2$O-n-butyl |
| E6 | $CH_2$O-isobutyl |
| E7 | $CH_2$O-tert-butyl |
| E8 | $(CH_2)_2OCH_3$ |
| E9 | $(CH_2)_2$O-ethyl |
| E10 | $(CH_2)_2$O-n-propyl |
| E11 | $(CH_2)_2$O-isopropyl |

TABLE 19-continued

Compounds of formula Iv:

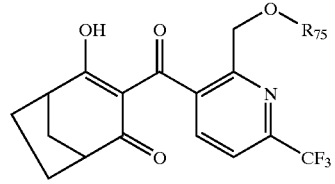

(Iv)

| Compd. no. | $R_{75}$ |
|---|---|
| E12 | $(CH_2)_2$O-n-butyl |
| E13 | $(CH_2)_2$O-isobutyl |
| E14 | $(CH_2)_2$O-tert-butyl |
| E15 | $(CH_2)_2O(CH_2)_2OCH_3$ |
| E16 | $(CH_2)_2O(CH_2)_2OCH_3$ |
| E17 | $C_2H_5$ |

TABLE 20

Physical data for Tables 5 to 19 (figures = m.p. in ° C.):

| Compound | Phys. data | Compound | Phys. data | Compound | Phys. data |
|---|---|---|---|---|---|
| A2 | 150–151 | C46 | 159–161 | A2-B1058 | 88–89 |
| A3 | 148–149 | C91 | 141–143 | A2-B1066 | viscous |
| A4 | 143–144 | C146 | 99–101 | A2-B1067 | resinous oil |
| A5 | 81–82 | C149 | 148–150 | A2-B1069 | oil |
| A6 | 148–150 | A2-B1 | 90–92 | A2-B1069 | viscous oil |
| A7 | 105–106 | A2-B68 | 120–121 | A8-B1 | 97–98 |
| A8 | 123–124 | A2-B2 | resin | A7-B1 | oil |
| A9 | 73–74 | A2-B90 | resin | A3-B1 | 42–44 |
| A10 | 165–167 | A2-B93 | 95–96 | A94-B1 | 57–58 |
| A15 | 164–166 | A2-B46 | 61–62 cis-rac | A66-B24 | 80–82 |
| A17 | 99–100 | A2-B46 | 83–84 trans-rac | A64-B1 | 49–51 |
| A26 | 143–144 | A2-B91 | resin | A154-B1 | 94–95 |
| A27 | 107–108 | A2-B1081 | oil | A6-B1 | 123–124 |
| A29 | 173–174 | A2-B1082 | resin | A6-B24 | oil |
| A30 | 178–181 | A2-B1083 | resin | A34-B1 | 53–54 |
| A31 | 209–210 | A2-B29 | 87–88 | A2-B25 | oil |
| A32 | 145–146 | A2-B73 | resin | A2-B925 | oil |
| A34 | 170–171 | A2-B95 | 106–107 | E8 | 55–56 |
| A64 | 134–135 | A2-B31 | 151–153 | E17 | 99–101 |
| A94 | 134–135 | A2-B75 | amorphous | | |
| A154 | 108–110 | A2-B24 | oil | | |
| B1057 | 166–167 | A2-B5 | resin | | |
| B1058 | crystalline | A2-C91 | resin | | |
| B1061 | crystalline | A2-C146 | oil | | |
| B1063 | crystalline | A2-B112 | resin | | |
| B1065 | oil | A2-D140 | oil | | |
| B1066 | 150–152 | A2-B1057 | amorphous | | |
| B1067 | 122–123 | A2-B1063 | oil | | |
| B1069 | 117–118 | A2-B1061 | oil | | |
| B1070 | crystalline | A2-B133 | oil | | |

Compounds of formulae 2.1 and 2.3 to 2.13.c are known by the names imazamox, imazethapyr, imazaquin, imazapyr, dimethenamid, atrazine, terbuthylazine, simazine, terbutyrn, cyanazine, ametryn, terbumeton, prohexadione calcium, sethoxydim, clethodim, tepraloxydim, flumetsulam, metosulam, pyridate, bromoxynil, ioxynil, sulcotrione, carfentrazone, sulfentrazone, isoxaflutole, glufosinate, primisulfuron, prosulfuron, rimsulfuron, halosulfuron, nicosulfuron, ethoxysulfuron, flazasulfuron and thifensulfuron and are described in the Pesticide Manual, eleventh ed., British Crop Protection Council, 1997 under the entry numbers 412, 415, 414, 413, 240, 34, 692, 651, 693, 168, 20, 691, 595, 648, 146, 49, 339, 495, 626, 88, 425, 664, 112, 665, 436, 382, 589, 613, 644, 389, 519, 287, 325 and 704. The compound of formula 2.13 wherein $Y_1$, $Y_3$ and $Y_4$ are methine, $Y_2$ is C—I, $R_{74}$ is COOMe, $Y_5$ is nitrogen, $Y_6$ is methyl and $Y_7$ is methoxy is known by the name iodosulfuron (especially the sodium salt) from AGROW No. 296, Jan. 16, 1998, page 22. The compound of formula 2.13 wherein $Y_1$, $Y_2$, $Y_3$ and $Y_4$ are methine, $R_{74}$ is trifluoromethyl, $Y_5$ is nitrogen, $Y_6$ is trifluoromethyl and $Y_7$ is methoxy is known by the name tritosulfuron and described in DE-A-40 38 430. The compound of formula 2.13 wherein $Y_1$ is NH—CHO, $Y_2$, $Y_3$ and $Y_4$ are methine, $R_{74}$ is CONMe$_2$, $Y_5$ is methine and $Y_6$ and $Y_7$ are methoxy is described, for example, in WO 95/29899.

The S enantiomer of the compound of formula 2.12 is registered under the CAS-Reg. No. [35597-44-5]. The compound of the general formula 2.2, aRS,1'S(–)N-(1'-methyl-2'-methoxy-ethyl)-N-chloroacetyl-2-ethyl-6-methylaniline, and a compound of the general formula 2.3, (1S,aRS)-2-chloro-N-(2,4-dimethyl-3-thienyl)-N-(2-methoxy-1-methylethyl)-acetamide, are described, for example, in WO 97/34485. The compound of formula 2.9 wherein $R_{69}$ is NO$_2$ is known by the name mesotrione and is described, for example, in U.S. Pat. No. 5,006,158. The compound of formula 2.6 wherein $R_{62}$ is ethoxy, $R_{63}$ is fluorine, Y is methine, $R_{64}$ is methoxycarbonyl, $R_{65}$ is hydrogen and $R_{66}$ is chlorine is known by the name cloransulam, for example from AGROW No. 261, Aug. 2, 1996, page 21. The compound of formula 2.6 wherein $R_{62}$ is methoxy, $R_{63}$ is hydrogen, Y is C—F, $R_{64}$ is fluorine, $R_{65}$ is hydrogen and $R_{66}$ is fluorine, is known by the name florasulam and described in U.S. Pat. No. 5,163,995.

Furthermore, the following compounds of the composition according to the invention are described in the Pesticide Manual, eleventh ed., British Crop Protection Council, 1997:

| Compound of formula (name) | Pesticide Manual eleventh ed., Entry No.: |
|---|---|
| 2.14 (metribuzin) | 497 |
| 2.15 (aclonifen) | 8 |
| 2.16 (glyphosate) | 383 |
| 2.17 (bentazone) | 65 |
| 2.18 (pendimethalin) | 557 |
| 2.19 (dicamba) | 210 |
| 2.20 (butylate) | 100 |
| 2.22 (clomazone) | 150 |
| 2.23 (2,4-D) | 192 |
| 2.24 (flumiclorac) | 340 |
| 2.25 (fluthiacet-methyl) | 359 |
| 2.26 (flurtamone) | 356 |
| 2.27 (flumioxazin) | 341 |
| 2.28 (paraquat) | 550 |
| 2.29 (azafenidin) | 37 |
| 2.30 (fluthiamid) | 51 |
| 2.33 (sulfosate) | 383 |
| 2.34 (asulam) | 33 |
| 2.35 (norflurazon) | 526 |
| 2.36 (terbacil) | 689 |
| 2.37 (thiazopyr) | 702 |
| 2.38 (dithiopyr) | 259 |
| 2.39 (hexazinone) | 400 |
| 2.40 (diuron) | 260 |
| 2.41 (MCPA) | 455 |
| 2.42 (mecoprop) | 459 |
| 2.43 (tebuthiuron) | 683 |

The compound of formula 2.7 wherein $R_{67}$ is hydrogen and its preparation are described in U.S. Pat. No. 3,790,571; the compound of formula 2.6 wherein $R_{62}$ is ethoxy, Z is nitrogen, $R_{63}$ is fluorine, $R_{64}$ is chlorine, $R_{65}$ is hydrogen and $R_{66}$ is chlorine is described in U.S. Pat. No. 5,498,773. The compound of formula 2.21 and its preparation are described in U.S. Pat. No. 5,183,492; the compound of formula 2.22 is described by the name isoxachlortole in AGROW No. 296 Jan. 16, 1998, page 22. The compound of formula 2.31 is described under the name fentrazamide in The 1997 British Crop Protection Conference—Weeds, Conference Proceedings Vol.1,2–8, pages 67 to 72; the compound of formula 2.32 is described under the name JV 485 (isoxapropazol) in The 1997 British Crop Protection Conference—Weeds, Conference Proceedings Vol.1, 3A-2, pages 93 to 98. The compound of formula 2.44 is known by the name pethoxamid and is described, for example in EP-A-0 206 251. The compound of formula 2.45 is known by the name procarbazone and is described, for example, in EP-A-0 507 171; the compound of formula 2.46 is known by the name fluazolate and is described, for example, in U.S. Pat. No. 5,530,126. The compound of formula 2.47 is known by the name cinidon-ethyl and is described, for example, in DE-A-4 037 840. The compound of formula 2.48 is known by the name benzfendizone and is described, for example, in WO 97/08953. The compound of formula 2.49 is known as diflufenzopyr and is described, for example, in EP-A-0 646 315. The compound of formula 2.50 (amicarbazone) and its preparation are disclosed in DD 298 393 and in U.S. Pat. No. 5,194,085. The compound of formula 2.51 (flufenpyr-ethyl) is described in Abstracts of Papers American Chemical Society, (2000) Vol.220, No. Part 1, pp. AGRO 174.

It is extremely surprising that the combination of the active ingredient of formula I with one or more active ingredients selected from formulae 2.1 to 2.51 exceeds the additive effect on the weeds to be controlled that is to be expected in principle, and thus broadens the range of action of the individual active ingredients especially in two respects: Firstly, the rates of application of the individual compounds of formulae 1 and 2.1 to 2.51 are reduced while a good level of action is maintained and, secondly, the composition according to the invention achieves a high level of weed control also in those cases where the individual substances, in the range of low rates of application, have become unusable from the agronomic standpoint. The result is a considerable broadening of the spectrum of weeds and an additional increase in selectivity in respect of the crops of useful plants, as is necessary and desirable in the event of an unintentional overdose of active ingredient. The composition according to the invention, while retaining excellent control of weeds in crops of useful plants, also enables greater flexibility in succeeding crops.

The composition according to the invention can be used against a large number of agronomically important weeds, such as Stellaria, Nasturtium, Agrostis, Digitaria, Avena, Setaria, Sinapis, Lolium, Solanum, Phaseolus, Echinochloa, Scirpus, Monochoria, Sagittaria, Bromus, Alopecurus, Sorghum halepense, Rottboellia, Cyperus, Abutilon, Sida, Xanthium, Amaranthus, Chenopodium, Ipomoea, Chrysanthemum, Galium, Viola and Veronica. The composition according to the invention is suitable for all methods of application conventionally used in agriculture, e.g. pre-emergence application, post-emergence application and seed dressing. The composition according to the invention is suitable especially for controlling weeds in crops of useful plants, such as cereals, rape, sugar beet, sugar cane, plantation crops, rice, maize and soybeans, and also for non-selective weed control. "Crops" are to be understood to mean also those crops which have been made tolerant to herbicides or classes of herbicides as a result of conventional methods of breeding or genetic engineering. The invention relates also to a method of controlling undesired plant growth in crops of useful plants, which comprises allowing a herbicidally effective amount of a composition according to the invention to act on the crop plant or the locus thereof.

The composition according to the invention comprises the active ingredient of formula I and the active ingredients of formulae 2.1 to 2.51 in any mixing ratio, but usually has an excess of one component over the others. Generally, the mixing ratios (ratios by weight) of the active ingredient of formula I and the mixing partners of formulae 2.1 to 2.51 are from 1:2000 to 2000:1, especially from 200:1 to 1:200. The rate of application may vary within wide limits and depends on the nature of the soil, the method of application (pre- or post-emergence; seed dressing; application to the seed furrow; no tillage application etc.), the crop plant, the weed to be controlled, the prevailing climatic conditions, and other factors governed by the method of application, the time of application and the target crop. The active ingredient mixture according to the invention can generally be applied at a rate of from 1 to 5000 g of active ingredient mixture/ha. The mixtures of the compound of formula I with the compounds of formulae 2.1 to 2.51 may be used in unmodified form, that is to say as obtained in the synthesis. ,Preferably, however, they are formulated in customary manner, together with the adjuvants conventionally used in formulation technology, such as solvents, solid carriers or surfactants, for example into emulsifiable concentrates, a combination of a suspension and an emulsion (suspoemulsion), directly sprayable or dilutable solutions, dilute emulsions, wettable powders, soluble powders, dusts, granules or microcapsules. As with the nature of the compositions, the methods of application, such as spraying, atomising, dusting, wetting, scattering or pouring, are chosen in accordance with the intended objectives and the prevailing circumstances.

The formulations, i.e. the compositions, preparations or mixtures comprising the compounds (active ingredients) of formulae 1 and 2.1 to 2.51 and, where appropriate, one or more solid or liquid formulation adjuvants, are prepared in a manner known per se, e.g. by intimately mixing and/or grinding the active ingredients with the formulation adjuvants, e.g. solvents or solid carriers. In addition, surface-active compounds (surfactants) may also be used in the preparation of the formulations.

Examples of solvents and solid carriers are given, for example, in WO 97/34485, page 6.

Depending on the nature of the compound of formula I to be formulated, suitable surface-active compounds are non-ionic, cationic and/or anionic surfactants and surfactant mixtures having good emulsifying, dispersing and wetting properties.

Examples of suitable anionic, non-ionic and cationic surfactants are listed, for example, in WO 97/34485, pages 7 and 8.

Also suitable in the preparation of the herbicidal compositions according to the invention are the surfactants conventionally used in formulation technology, which are described, inter alia, in "McCutcheon's Detergents and Emulsifiers Annual" MC Publishing Corp., Ridgewood N.J., 1981, Stache, H., "Tensid-Taschenbuch", Carl Hanser Verlag, Munich/Vienna, 1981 and M. and J. Ash, "Encyclopedia of Surfactants", Vol I–III, Chemical Publishing Co., New York, 1980–81.

The herbicidal formulations usually contain from 0.1 to 99% by weight, especially from 0.1 to 95% by weight, of active ingredient mixture comprising a compound of formula I and the compounds of formulae 2.1 to 2.51, from 1 to 99.9% by weight of a solid or liquid formulation adjuvant, and from 0 to 25% by weight, especially from 0.1 to 25% by weight, of a surfactant.

Whereas commercial products are usually formulated as concentrates, the end user will normally employ dilute formulations. The compositions may also comprise further ingredients, such as stabilisers, e.g. vegetable oils or epoxidised vegetable oils (epoxidised coconut oil, rapeseed oil or soybean oil), antifoams, e.g. silicone oil, preservatives, viscosity regulators, binders, tackifiers, and also fertilisers or other active ingredients. Preferred formulations have especially the following compositions: (%=percent by weight)

| Emulsifiable concentrates: | |
|---|---|
| active ingredient mixture: | 1 to 90%, preferably 5 to 20% |
| surfactant: | 1 to 30%, preferably 10 to 20% |
| liquid carrier: | 5 to 94%, preferably 70 to 85% |
| Dusts: | |
| active ingredient mixture: | 0.1 to 10%, preferably 0.1 to 5% |
| solid carrier: | 99.9 to 90%, preferably 99.9 to 99% |
| Suspension concentrates: | |
| active ingredient mixture: | 5 to 75%, preferably 10 to 50% |
| water: | 94 to 24%, preferably 88 to 30% |
| surfactant: | 1 to 40%, preferably 2 to 30% |
| Wettable powders: | |
| active ingredient mixture: | 0.5 to 90%, preferably 1 to 80% |
| surfactant: | 0.5 to 20%, preferably 1 to 15% |
| solid carrier: | 5 to 95%, preferably 15 to 90% |
| Granules: | |
| active ingredient mixture: | 0.1 to 30%, preferably 0.1 to 15% |
| solid carrier: | 99.5 to 70%, preferably 97 to 85% |

(% = percent by weight)

The following Examples illustrate the invention further, but do not limit the invention.

| F1. Emulsifiable concentrates | a) | b) | c) | d) |
|---|---|---|---|---|
| active ingredient mixture | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7–8 mol of ethylene oxide) | — | 4% | — | 2% |

-continued

| F1. Emulsifiable concentrates | a) | b) | c) | d) |
|---|---|---|---|---|
| cyclohexanone | — | — | 10% | 20% |
| arom. hydrocarbon mixture $C_9$–$C_{12}$ | 85% | 78% | 55% | 16% |

Emulsions of any desired concentration can be obtained from such concentrates by dilution with water.

| F2. Solutions | a) | b) | c) | d) |
|---|---|---|---|---|
| active ingredient mixture | 5% | 10% | 50% | 90% |
| 1-methoxy-3-(3-methoxy-propoxy)-propane | — | 20% | 20% | — |
| polyethylene glycol MW 400 | 20% | 10% | — | — |
| N-methyl-2-pyrrolidone | — | — | 30% | 10% |
| arom. hydrocarbon mixture $C_9$–$C_{12}$ | 75% | 60% | — | — |

The solutions are suitable for use in the form of microdrops.

| F3. Wettable powders | a) | b) | c) | d) |
|---|---|---|---|---|
| active ingredient mixture | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7–8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

| F4. Coated granules | a) | b) | c) |
|---|---|---|---|
| active ingredient mixture | 0.1% | 5% | 15% |
| highly dispersed silicic acid | 0.9% | 2% | 2% |
| inorganic carrier (Æ0.1–1 mm) e.g. $CaCO_3$ or $SiO_2$ | 99.0% | 93% | 83% |

The active ingredient is dissolved in methylene chloride and applied to the carrier by spraying, and the solvent is then evaporated off in vacuo.

| F5. Coated granules | a) | b) | c) |
|---|---|---|---|
| active ingredient mixture | 0.1% | 5% | 15% |
| polyethylene glycol MW 200 | 1.0% | 2% | 3% |
| highly dispersed silicic acid | 0.9% | 1% | 2% |
| inorganic carrier (Æ0.1–1 mm) e.g. $CaCO_3$ or $SiO_2$ | 98.0% | 92% | 80% |

The finely ground active ingredient is uniformly applied, in a mixer, to the carrier moistened with polyethylene glycol. Non-dusty coated granules are obtained in this manner.

| F6. Extruder granules | a) | b) | c) | d) |
|---|---|---|---|---|
| active ingredient mixture | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

| F7. Dusts | a) | b) | c) |
|---|---|---|---|
| active ingredient mixture | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient mixture | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

It is often more practical for the compound of formula I and the mixing partner or partners of formulae 2.1 to 2.51 to be formulated separately and to be brought together in the desired mixing ratio in the applicator in the form of a "tank mixture" in water shortly before application.

BIOLOGICAL EXAMPLES

A synergistic effect exists whenever the action of the active ingredient combination of compounds of formula 1 and 2.1 to 2.51 is greater than the sum of the actions of the active ingredients applied separately.

The herbicidal action to be expected We for a given combination of two herbicides can be calculated as follows (see COLBY, S. R., "Calculating synergistic and antagonistic response of herbicide combinations", Weeds 15, pages 20–22, 1967):

$$We = X + [Y \cdot (100-X)/100]$$

wherein:
X=percentage herbicidal action on treatment with the compound of formula I at a rate of application of p kg per hectare, compared with the untreated control (=0%).
Y=percentage herbicidal action on treatment with a compound of formula 2.1 to 2.51 at a rate of application of q kg per hectare, compared with the untreated control.

We=expected herbicidal action (percentage herbicidal action compared with the untreated control) following treatment with the compounds of formulae 1 and 2.1 to 2.51 at a rate of application of p+q kg of active ingredient per hectare.

When the action actually observed is greater than the value to be expected We, there is a synergistic effect.

The synergistic effect of the combinations of a compound of formula I with the compounds of formulae 2.1 to 2.51 is demonstrated in the following Examples.

Experiment Description—Pre-emergence Test

Monocotyledonous and dicotyledonous test plants are sown in standard soil in plastics pots. Directly after sowing, the test substances are applied in aqueous suspension by spraying (500 liters of water/ha). The rates of application depend on the optimum doses ascertained under field conditions and greenhouse conditions. The test plants are then grown on in the greenhouse under optimum conditions. The tests are evaluated after 36 days (% action, 100%=plant has died, 0%=no phytotoxic action). Examples of the synergistic action of the compositions according to the invention are given in the following Tables B1 to B6:

Mixture A contains as active ingredients 915 g/liter of the compound of formula 2.2a and 45 g/liter of the compound of formula 3.1.

TABLE B1

| Test plant: | Compd. 1.001 [25 g/ha] | Mixture A [900 g/ha] | Compd. 1.001 [25 g/ha] + mixture A [900 g/ha] | We according to Colby |
|---|---|---|---|---|
| Sorghum | 30 | 20 | 90 | 44 |
| Chenopodium | 0 | 0 | 100 | 0 |
| Sida | 0 | 70 | 100 | 70 |

TABLE B2

| Test plant: | Compd. 1.001 [12.5 g/ha] | Mixture A [900 g/ha] | Compd. 1.001 [12.5 g/ha] + mixture A [900 g/ha] | We according to Colby |
|---|---|---|---|---|
| Sorghum | 0 | 20 | 80 | 20 |
| Chenopodium | 0 | 0 | 95 | 0 |
| Sida | 0 | 70 | 95 | 70 |

TABLE B3

| Test plant: | Compd. 1.001 [6.25 g/ha] | Mixture A [900 g/ha] | Compd. 1.001 [6.25 g/ha] + mixture A [900 g/ha] | We according to Colby |
|---|---|---|---|---|
| Sorghum | 0 | 20 | 70 | 20 |
| Chenopodium | 0 | 0 | 95 | 0 |
| Sida | 0 | 70 | 95 | 70 |

TABLE B4

| Test plant: | Compd. 1.001 [25 g/ha] | Mixture A [300 g/ha] | Compd. 1.001 [25 g/ha] + mixture A [300 g/ha] | We according to Colby |
|---|---|---|---|---|
| Chenopodium | 0 | 0 | 90 | 0 |
| Ipomoea | 30 | 0 | 100 | 30 |
| Sida | 0 | 0 | 40 | 0 |

TABLE B5

| Test plant: | Compd. 1.001 [12.5 g/ha] | Mixture A [300 g/ha] | Compd. 1.001 [12.5 g/ha] + mixture A [300 g/ha] | We according to Colby |
|---|---|---|---|---|
| Chenopodium | 0 | 0 | 80 | 0 |
| Ipomoea | 0 | 0 | 60 | 0 |
| Sida | 0 | 0 | 40 | 0 |

TABLE B6

| Test plant: | Compd. 1.001 [6.25 g/ha] | Mixture A [300 g/ha] | Compd. 1.001 [6.25 g/ha] + mixture A [300 g/ha] | We according to Colby |
|---|---|---|---|---|
| Chenopodium | 0 | 0 | 80 | 0 |
| Ipomoea | 0 | 0 | 60 | 0 |
| Sida | 0 | 0 | 40 | 0 |

Experiment Description—Post-emergence Test

The test plants are grown to the 2- to 3-leaf stage in plastics pots under greenhouse conditions. A standard soil is used as cultivation substrate. At the 2- to 3-leaf stage, the herbicide is applied to the test plants on its own and as a mixture. The application is carried out using an aqueous suspension of the test substances in 500 liters of water/ha. The rates of application depend on the optimum doses ascertained under field conditions and greenhouse conditions. The tests are evaluated after 33 days (% action, 100%=plant has died, 0%=no phytotoxic action). Examples of the synergistic action of the compositions according to the invention are given in the following Tables B7 to B10:

Mixture A contains as active ingredients 915 g/liter of the compound of formula 2.2a and 45 g/liter of the compound of formula 3.1.

TABLE B7

Post-emergence test:

| Test plant: | Compd. 1.001 [12.5 g/ha] | Mixture A [900 g/ha] | Compd. 1.001 [12.5 g/ha] + mixture A [900 g/ha] | We according to Colby |
|---|---|---|---|---|
| Ipomoea | 0 | 0 | 80 | 0 |
| Polygonum | 0 | 20 | 100 | 20 |
| Xanthium | 80 | 0 | 100 | 80 |

TABLE B8

Post-emergence test:

| Test plant: | Compd. 1.001 [12.5 g/ha] | Mixture A [300 g/ha] | Compd. 1.001 [12.5 g/ha] + mixture A [300 g/ha] | We according to Colby |
|---|---|---|---|---|
| Ipomoea | 0 | 0 | 80 | 0 |
| Polygonum | 0 | 0 | 70 | 0 |
| Xanthium | 80 | 0 | 98 | 80 |

TABLE B9

Post-emergence test:

| Test plant: | Compd. 1.001 [6.25 g/ha] | Mixture A [900 g/ha] | Compd. 1.001 [6.25 g/ha] + mixture A [900 g/ha] | We according to Colby |
|---|---|---|---|---|
| Ipomoea | 0 | 0 | 70 | 0 |
| Polygonum | 0 | 20 | 70 | 20 |
| Xanthium | 70 | 0 | 80 | 70 |

TABLE B10

Post-emergence test:

| Test plant: | Compd. 1.001 [6.25 g/ha] | Mixture A [300 g/ha] | Compd. 1.001 [6.25 g/ha] + mixture A [300 g/ha] | We according to Colby |
|---|---|---|---|---|
| Ipomoea | 0 | 0 | 80 | 0 |
| Polygonum | 0 | 0 | 70 | 0 |
| Xanthium | 70 | 0 | 70 | 70 |

In the following Tables, evaluation is carried out after 14 days:

TABLE B11

Pre-emergence action:

| Test plant: | Compd. E8 [50 g/ha] | Compd. 2.18 [500 g/ha] | Compd. E8 [50 g/ha] + compd. 2.18 [500 g/ha] | We according to Colby |
|---|---|---|---|---|
| Polygonum | 50 | 80 | 95 | 90 |

TABLE B12

Pre-emergence action:

| Test plant: | Compd. E8 [100 g/ha] | Compd. 2.14 [250 g/ha] | Compd. E8 [100 g/ha] + compd. 2.14 [250 g/ha] | We according to Colby |
|---|---|---|---|---|
| Polygonum | 50 | 50 | 90 | 75 |

TABLE B13

Pre-emergence action:

| Test plant: | Compd. E8 [100 g/ha] | Compd. 2.14 [125 g/ha] | Compd. E8 [100 g/ha] + compd. 2.14 [125 g/ha] | We according to Colby |
|---|---|---|---|---|
| Polygonum | 50 | 30 | 90 | 65 |

TABLE B14

Pre-emergence action: Compound no. 2.13a corresponds to formula 2.13 wherein $R_{74}$ is —$CH_2CH_2CF_3$, $Y_1$, $Y_2$, $Y_3$ and $Y_4$ are each methine, $Y_5$ is nitrogen and $Y_6$ is methyl.

| Test plant: | Compd. E8 [100 g/ha] | Compd. 2.13a [60 g/ha] | Compd. E8 [100 g/ha] + compd. 2.13a [60 g/ha] | We according to Colby |
|---|---|---|---|---|
| Polygonum | 50 | 80 | 95 | 90 |

TABLE B15

Pre-emergence action:

| Test plant: | Compd. E8 [50 g/ha] | Compd. 2.30 [60 g/ha] | Compd. E8 [50 g/ha] + compd. 2.30 [60 g/ha] | We according to Colby |
|---|---|---|---|---|
| Polygonum | 50 | 30 | 90 | 65 |

TABLE B16

Pre-emergence action:

| Test plant: | Compd. E8 [50 g/ha] | Compd. 2.21 [30 g/ha] | Compd. E8 [50 g/ha] + compd. 2.21 [30 g/ha] | We according to Colby |
|---|---|---|---|---|
| Polygonum | 50 | 50 | 100 | 75 |

TABLE B17

Pre-emergence action: Compound no. 2.4.a corresponds to formula 2.4 wherein $R_{57}$ is chlorine, $R_{58}$ is ethyl and $R_{59}$ is tert-butyl.

| Test plant: | Compd. E8 [50 g/ha] | Compd. 2.4.a [125 g/ha] | Compd. E8 [50 g/ha] + compd. 2.4.a [125 g/ha] | We according to Colby |
|---|---|---|---|---|
| Polygonum | 50 | 30 | 85 | 65 |

TABLE B18

Pre-emergence action:

| Test plant: | Compd. 1.001 [25 g/ha] | Compd. 2.2.b [300 g/ha] | Compd. 1.001 [25 g/ha] + compd. 2.2.b [300 g/ha] | We according to Colby |
|---|---|---|---|---|
| Chenopodium | 80 | 0 | 95 | 80 |
| Solanum | 80 | 40 | 98 | 88 |
| Cyperus | 0 | 0 | 50 | 0 |

TABLE B19

Pre-emergence action: Compound no. 2.3.a corresponds to formula 2.3 wherein $R_{56}$ is CH(Me)—$CH_2$OMe.

| Test plant: | Compd. 1.001 [12.5 g/ha] | Compd. 2.3.a [100 g/ha] | Compd. 1.001 [12.5 g/ha] + compd. 2.3.a [100 g/ha] | We according to Colby |
|---|---|---|---|---|
| Chenopodium | 80 | 20 | 90 | 84 |
| Solanum | 75 | 60 | 90 | 90 |
| Cyperus | 0 | 20 | 60 | 20 |

TABLE B20

Pre-emergence action: Compound no. 2.2.c corresponds to formula 2.2 wherein $R_{53}$ and $R_{54}$ are ethyl and $R_{55}$ is $CH_2$OMe.

| Test plant: | Compd. 1.001 [12.5 g/ha] | Compd. 2.2.c [100 g/ha] | Compd. 1.001 [12.5 g/ha] + compd. 2.2.c [100 g/ha] | We according to Colby |
|---|---|---|---|---|
| Chenopodium | 80 | 20 | 90 | 84 |
| Solanum | 75 | 50 | 95 | 88 |
| Cyperus | 0 | 0 | 30 | 0 |

TABLE B21

Pre-emergence action: Compound no. 2.2.d corresponds to formula 2.2 wherein $R_{53}$ is ethyl, $R_{54}$ is methyl and $R_{55}$ is $CH_2$—$CH_2CH_3$.

| Test plant: | Compd. 1.001 [12.5 g/ha] | Compd. 2.2.d [100 g/ha] | Compd. 1.001 [12.5 g/ha] + compd. 2.2.d [100 g/ha] | We according to Colby |
|---|---|---|---|---|
| Solanum | 75 | 60 | 95 | 90 |

TABLE B22

Pre-emergence action:

| Test plant: | Compd. 1.001 [25 g/ha] | Compd. 2.30 [100 g/ha] | Compd. 1.001 [25 g/ha] + compd. 2.30 [100 g/ha] | We according to Colby |
|---|---|---|---|---|
| Cyperus | 10 | 0 | 60 | 10 |

In the following Tables, evaluation is carried out after 31 days:

TABLE B23

Pre-emergence action: Compound no. 2.4.a corresponds to the compound of formula 2.4 wherein $R_{57}$ is chlorine, $R_{58}$ is ethyl and $R_{59}$ is isopropyl.

| Test plant: | Compd. 1.001 [25 g/ha] | Compd. 2.4.a [250 g/ha] | Compd. 1.001 [25 g/ha] + compd. 2.4.a [250 g/ha] | We according to Colby |
|---|---|---|---|---|
| Polygonum | 0 | 20 | 80 | 20 |

TABLE B24

Pre-emergence action: Compound no. 2.4.b corresponds to the compound of formula 2.4 wherein $R_{57}$ is chlorine, $R_{58}$ is ethyl and $R_{59}$ is ethyl.

| Test plant: | Compd. 1.001 [25 g/ha] | Compd. 2.4.b [125 g/ha] | Compd. 1.001 [25 g/ha] + compd. 2.4.b [125 g/ha] | We according to Colby |
|---|---|---|---|---|
| Polygonum | 0 | 0 | 40 | 0 |

TABLE B25

Pre-emergence action: Compound no. 2.4.c corresponds to the compound of formula 2.4 wherein $R_{57}$ is chlorine, $R_{58}$ is ethyl and $R_{59}$ is tert-butyl.

| Test plant: | Compd. 1.001 [25 g/ha] | Compd. 2.4.c [250 g/ha] | Compd. 1.001 [25 g/ha] + compd. 2.4.c [250 g/ha] | We according to Colby |
|---|---|---|---|---|
| Ipomoea | 70 | 0 | 90 | 70 |
| Xanthium | 80 | 0 | 100 | 80 |

TABLE B26

Pre-emergence action: Compound no. 2.4.d corresponds to the compound of formula 2.4 wherein $R_{57}$ is methylthio, $R_{58}$ is ethyl and $R_{59}$ is tert-butyl.

| Test plant: | Compd. 1.001 [25 g/ha] | Compd. 2.4.d [250 g/ha] | Compd. 1.001 [25 g/ha] + compd. 2.4.d [250 g/ha] | We according to Colby |
|---|---|---|---|---|
| Ipomoea | 70 | 0 | 80 | 70 |
| Xanthium | 80 | 10 | 95 | 82 |

TABLE B27

Pre-emergence action:

| Test plant: | Compd. 1.001 [25 g/ha] | Compd. 2.14 [125 g/ha] | Compd. 1.001 [25 g/ha] + compd. 2.14 [125 g/ha] | We according to Colby |
|---|---|---|---|---|
| Ipomoea | 70 | 0 | 85 | 70 |
| Xanthium | 80 | 20 | 100 | 84 |

TABLE B28

Pre-emergence action: Compound no. 2.6.a corresponds to the compound of formula 2.6 wherein $R_{62}$ is hydrogen, $R_{63}$ is methyl, $R_{64}$ is fluorine, $R_{65}$ is hydrogen, Y is nitrogen, Z is methine and $R_{66}$ is fluorine.

| Test plant: | Compd. 1.001 [50 g/ha] | Compd. 2.6.a [30 g/ha] | Compd. 1.001 [50 g/ha] + compd. 2.6.a [30 g/ha] | We according to Colby |
|---|---|---|---|---|
| Polygonum | 0 | 30 | 90 | 30 |

In the following Tables, evaluation is carried out after 21 days:

TABLE B29

Post-emergence action: Compound no. 2.7.a corresponds to the compound of formula 2.7 wherein $R_{67}$ is —C(O)—S-n-octyl.

| Test plant: | Compd. 1.001 [25 g/ha] | Compd. 2.7.a [250 g/ha] | Compd. 1.001 [25 g/ha] + compd. 2.7.a [250 g/ha] | We according to Colby |
|---|---|---|---|---|
| Ipomoea | 30 | 10 | 80 | 30 |
| Polygonum | 75 | 0 | 95 | 75 |
| Xanthium | 90 | 10 | 100 | 91 |

TABLE B30

Post-emergence action:

| Test plant: | Compd. 1.001 [25 g/ha] | Compd. 2.19 [250 g/ha] | Compd. 1.001 [25 g/ha] + compd. 2.19 [250 g/ha] | We according to Colby |
|---|---|---|---|---|
| Ipomoea | 30 | 60 | 95 | 72 |

TABLE B31

Post-emergence action:

| Test plant: | Compd. 1.001 [25 g/ha] | Compd. 2.16 [360 g/ha] | Compd. 1.001 [25 g/ha] + compd. 2.16 [360 g/ha] | We according to Colby |
|---|---|---|---|---|
| Ipomoea | 30 | 20 | 70 | 46 |
| Polygonum | 75 | 10 | 90 | 84 |

TABLE B32

Post-emergence action:

| Test plant: | Compd. 1.001 [12.5 g/ha] | Compd. 2.33 [360 g/ha] | Compd. 1.001 [12.5 g/ha] + compd. 2.33 [360 g/ha] | We according to Colby |
|---|---|---|---|---|
| Polygonum | 30 | 0 | 90 | 30 |

TABLE B33

Post-emergence action: Compound no. 2.12.a corresponds to the compound of formula 2.12 wherein $R_{73}$ is $NH_2$.

| Test plant: | Compd. 1.001 [25 g/ha] | Compd. 2.12.a [400 g/ha] | Compd. 1.001 [25 g/ha] + compd. 2.33 [400 g/ha] | We according to Colby |
|---|---|---|---|---|
| Ipomoea | 30 | 20 | 90 | 44 |

TABLE B34

Post-emergence action:

| Test plant: | Compd. 1.001 [12.5 g/ha] | Compd. 2.25 [2 g/ha] | Compd. 1.001 [12.5 g/ha] + compd. 2.25 [2 g/ha] | We according to Colby |
|---|---|---|---|---|
| Ipomoea | 30 | 0 | 50 | 30 |
| Polygonum | 30 | 0 | 40 | 30 |

TABLE B35

Post-emergence action: Compound no. 2.1.a corresponds to the compound of formula 2.1 wherein $R_{52}$ is hydrogen and $R_{51}$ is ethyl.

| Test plant: | Compd. 1.001 [12.5 g/ha] | Compd. 2.1.a [30 g/ha] | Compd. 1.001 [12.5 g/ha] + compd. 2.1.a [30 g/ha] | We according to Colby |
|---|---|---|---|---|
| Polygonum | 30 | 30 | 70 | 51 |

TABLE B36

Post-emergence action: Compound no. 2.1.b corresponds to the compound of formula 2.1 wherein $R_{51}$ is $CH_2OMe$ and $R_{52}$ is hydrogen.

| Test plant: | Compd. 1.001 [25 g/ha] | Compd. 2.1.b [30 g/ha] | Compd. 1.001 [25 g/ha] + compd. 2.1.b [30 g/ha] | We according to Colby |
|---|---|---|---|---|
| Polygonum | 75 | 30 | 90 | 83 |

In the following Tables, evaluation is carried out after 23 days:

TABLE B37

Pre-emergence action: Compound no. 2.13.b corresponds to formula 2.13 wherein $R_{74}$ is —COOMe, $Y_1$, $Y_2$, $Y_3$ and $Y_4$ are each methine, $Y_5$ is methine and $Y_6$ and $Y_7$ are difluoromethoxy.

| Test plant: | Compd. 1.001 [6 g/ha] | Compd. 2.13.b [15 g/ha] | Compd. 1.001 [6 g/ha] + compd. 2.13.b [15 g/ha] | We according to Colby |
|---|---|---|---|---|
| Chenopodium | 50 | 70 | 95 | 85 |

TABLE B38

Pre-emergence action:

| Test plant: | Compd. 1.001 [6 g/ha] | Compd. 2.13.c [60 g/ha] | Compd. 1.001 [6 g/ha] + compd. 2.13.c [60 g/ha] | We according to Colby |
|---|---|---|---|---|
| Chenopodium | 50 | 10 | 85 | 55 |

TABLE B39

Pre-emergence action: Compound no. 2.13.d corresponds to the compound of formula 2.13 wherein $Y_1$, $Y_2$, $Y_3$ and $Y_4$ are methine, $R_{74}$ is trifluoromethyl, $Y_5$ is nitrogen, $Y_6$ is trifluoromethyl and $Y_7$ is methoxy.

| Test plant: | Compd. 1.001 [6 g/ha] | Compd. 2.13d [7.5 g/ha] | Compd. 1.001 [6 g/ha] + compd. 2.13.d [7.5 g/ha] | We according to Colby |
|---|---|---|---|---|
| Amaranthus | 10 | 80 | 95 | 82 |

It has surprisingly been shown that special safeners are suitable for mixing with the synergistic composition according to the invention. The present invention accordingly relates also to a herbicidally selective composition for controlling grasses and weeds in crops of useful plants, especially in maize crops, that comprises a compound of formula I, one or more compounds selected from the compounds of formulae 2.1 to 2.51, and a safener (counter agent, antidote), and that protects the useful plants, but not the weeds, against the phytotoxic action of the herbicide, as well as to the use of such a composition in the control of weeds in crops of useful plants.

There is also proposed in accordance with the invention a herbicidally selective composition that, in addition to comprising customary inert formulation adjuvants, such as carriers, solvents and wetting agents, comprises as active ingredient a mixture of
a) a herbicidally-synergistically effective amount of a compound of formula I and one or more compounds selected from the compounds of formulae 2.1 to 2.51 and
b) a herbicidally-antagonistically effective amount of a compound selected from the compound of formula 3.1

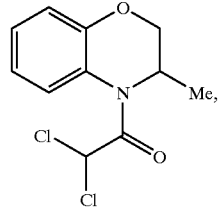

(3.1)

and the compound of formula 3.2

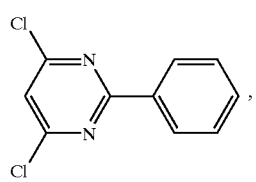

(3.2)

and the compound of formula 3.3

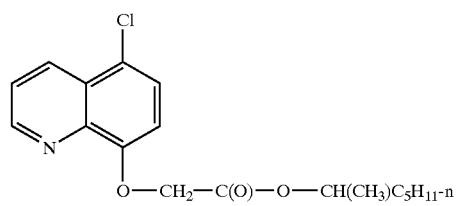

(3.3)

and the compound of formula 3.4

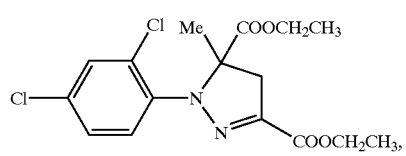

(3.4)

and the compound of formula 3.5

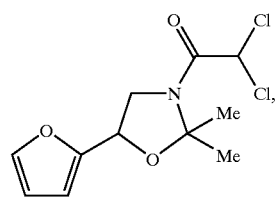

(3.5)

and the compound of formula 3.6

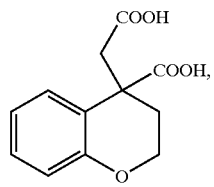

(3.6)

and the compound of formula 3.7

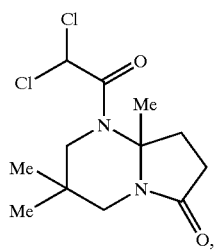

(3.7)

and the compound of formula 3.8

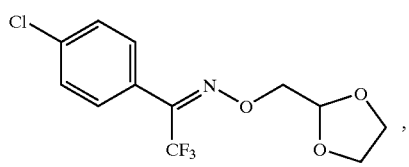

(3.8)

and of formula 3.9

$Cl_2CHCON(CH_2CH=CH_2)_2$       (3.9), and of formula 3.10

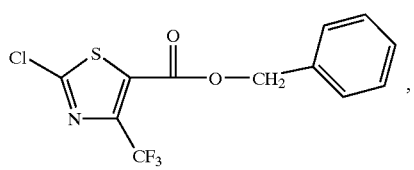

(3.10)

and of formula 3.11

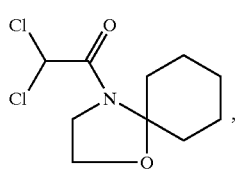

(3.11)

and of formula 3.12

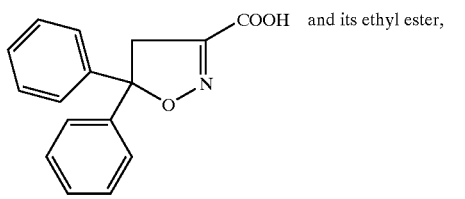

(3.12)

and of formula 3.13

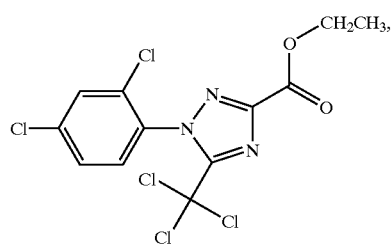

(3.13)

and of formula 3.14

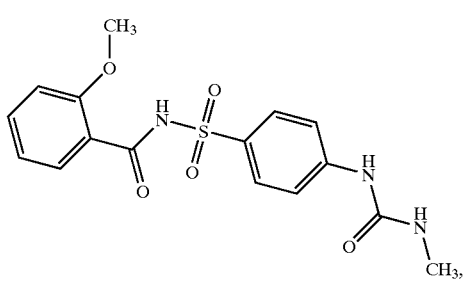

(3.14)

and of formula 3.15

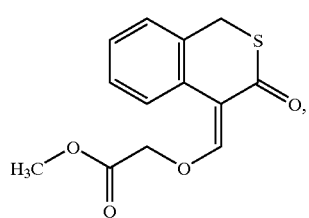

(3.15)

and of formula 3.16

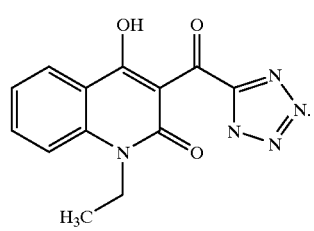

(3.16)

The invention relates also to a herbicidally selective herbicidal composition that, in addition to comprising customary inert formulation adjuvants, such as carriers, solvents and wetting agents, comprises as active ingredient a mixture of a) a herbicidally effective amount of a compound of formula I and
b) a herbicidally-antagonistically effective amount of a compound selected from the compounds of formulae 3.1, 3.2, 3.3, 3.4, 3.5, 3.6, 3.7, 3.8, 3.9, 3.10, 3.11, 3.12, 3.13, 3.14, 3.15 and 3.16.

Preferred compositions according to the invention comprise as safener a compound selected from the compounds of formulae 3.1, 3.3 and 3.8. Those safeners are especially suitable for compositions according to the invention that comprise the above-mentioned preferred compounds of formula I and optionally of formulae 2.1 to 2.51.

Combinations of compounds of formula I with the compound of formula 3.1 have been shown to be especially effective compositions, with special preference being given to compound no. 1.001 as the compound of formula I. That composition is preferably used together with the compound of formula 2.2a

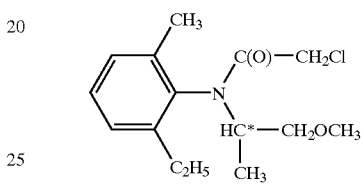

(2.2a, aRS, 1'S(−)N-(1'-Methyl-2'-methoxyethyl-N-chloroacetyl-2-ethyl-6-methylaniline).

The invention relates also to a method for the selective control of weeds in crops of useful plants, which comprises treating the useful plants, seeds or cuttings thereof, or the area of cultivation thereof, with a herbicidally effective amount of the herbicide of formula I, as appropriate one or more herbicides selected from the compounds of formulae 2.1 to 2.51, and a herbicidally-antagonistically effective amount of a safener of formulae 3.1 to 3.16.

The compounds of formulae 3.1 to 3.16 are known and are described, for example, in the Pesticide Manual, eleventh ed., British Crop Protection Council, 1997 under the entry numbers 61 (formula 3.1, benoxacor), 304 (formula 3.2, fenclorim), 154 (formula 3.3, cloquintocet), 462 (formula 3.4, mefenpyr-diethyl), 377 (formula 3.5, furilazol), 363 (formula 3.8, fluxofenim), 213 (formula 3.9, dichlormid) and 350 (formula 3.10, flurazole). The compound of formula 3.11 is known by the name MON 4660 (Monsanto) and is described, for example, in EP-A-0 436 483.

The compound of formula 3.6 (AC 304 415) is described, for example, in EP-A-0 613 618, and the compound of formula 3.7 in DE-A-2 948 535. The compounds of formula 3.12 are described in DE-A-4 331 448, and the compound of formula 3.13 in DE-A-3 525 205. The compound of formula 3.14 is known, for example, from U.S. Pat. No. 5,215,570 and the compound of formula 3.15 from EP-A-0 929 543. The compound of formula 3.16 is described in WO 99/00020. In addition to the compound of formula 3.16, the other 3-(5-tetrazolylcarbonyl)-2-quinolones described in WO 99/00020, especially the compounds specifically disclosed in Tables 1 and 2 on pages 21 to 29, are suitable for protecting the crop plants against the phytotoxic action of the compounds of formula I.

As crop plants that can be protected by the safeners of formulae 3.1 to 3.16 against the damaging effect of the above-mentioned herbicides there come into consideration especially cereals, cotton, soybeans, sugar beet, sugar cane, plantation crops, rape, maize and rice, more especially maize. "Crops" are to be understood to mean also those crops which have been made tolerant to herbicides or classes of herbicides as a result of conventional methods of breeding or genetic engineering.

The weeds to be controlled may be both monocotyledonous and dicotyledonous weeds, e.g. Stellaria, Agrostis, Digitaria, Avena, Apera, Brachiaria, Phalaris, Setaria, Sinapis, Lolium, Solanum, Echinochloa, Scirpus, Monochoria, Sagittaria, Panicum, Bromus, Alopecurus, *Sorghum halepense, Sorghum bicolor*, Rottboellia, Cyperus, Abutilon, Sida, Xanthium, Amaranthus, Chenopodium, Ipomoea, Chrysanthemum, Galium, Viola and Veronica.

Areas of cultivation include the areas of ground on which the crop plants are already growing or which have already been sown with the seeds of those crop plants, as well as ground intended for cultivation with such crop plants.

Depending on the intended use, a safener of formula 3.1 to 3.16 can be used in the pretreatment of the seed of the crop plant (dressing of the seeds or cuttings) or can be introduced into the soil before or after sowing. It can, however, also be applied, either alone or together with the herbicide, after emergence of the plants. The treatment of the plants or seeds with the safener can therefore in principle be carried out independently of the time at which the herbicide is applied. The plants can, however, also be treated by simultaneous application of herbicide and safener (e.g. in the form of a tank mixture). The ratio of the rate of application of safener to the rate of application of herbicide depends largely on the method of application. In the case of field treatment, which is carried out either using a tank mixture comprising a combination of safener and herbicide or by separate application of safener and herbicide, the ratio of herbicides to safener is generally from 100:1 to 1:10, preferably from 20:1 to 1:1. In the case of field treatment it is usual to apply from 0.001 to 0.5 kg of safener/ha, preferably from 0.001 to 0.25 kg of safener/ha.

The rate of application of herbicides is generally from 0.001 to 5 kg/ha, but preferably from 0.005 to 0.5 kg/ha. The compositions according to the invention are suitable for all methods of application conventionally used in agriculture, e.g. pre-emergence application, post-emergence application and seed dressing. In the case of seed dressing, generally from 0.001 to 10 g of safener/kg of seed, preferably from 0.05 to 2 g of safener/kg of seed, are applied. When the safener is applied in liquid form shortly before sowing, with soaking of the seeds, then advantageously the safener solutions used contain the active ingredient in a concentration of from 1 to 10,000 ppm, preferably from 100 to 1000 ppm.

For the purpose of application, the safeners of formulae 3.1 to 3.16 or combinations of those safeners with the herbicide of formula I and, as appropriate, one or more herbicides selected from formulae 2.1 to 2.51 are advantageously formulated together with adjuvants customary in formulation technology, e.g. into emulsifiable concentrates, coatable pastes, directly sprayable or dilutable solutions, dilute emulsions, wettable powders, soluble powders, dusts, granules or microcapsules.

Such formulations are described, for example, in WO 97/34485, pages 9 to 13. The formulations are prepared in known manner, e.g. by intimately mixing and/or grinding the active ingredients with liquid or solid formulation adjuvants, e.g. solvents or solid carriers. In addition, surface-active compounds (surfactants) can also be used in the preparation of the formulations. Solvents and solid carriers suitable for that purpose are mentioned, e.g., in WO 97/34485, page 6.

Depending on the nature of the compounds of formulae I, 2.1 to 2.51 and 3.1 to,3.16 to be formulated, there come into consideration as surface-active compounds non-ionic, cationic and/or anionic surfactants and surfactant mixtures having good emulsifying, dispersing and wetting properties. Examples of suitable anionic, non-ionic and cationic surfactants are listed, for example, on pages 7 and 8 of WO 97/34485. Also suitable for the preparation of the herbicidal compositions according to the invention are the surfactants conventionally employed in formulation technology, which are described, inter alia, in "McCutcheon's Detergents and Emulsifiers Annual" MC Publishing Corp., Ridgewood N.J., 1981, Stache, H., "Tensid-Taschenbuch", Carl Hanser Verlag, Munich/Vienna, 1981 and M. and J. Ash, "Encyclopedia of Surfactants", Vol. I–III, Chemical Publishing Co., New York, 1980–81.

The herbicidal formulations usually contain from 0.1 to 99% by weight, especially from 0.1 to 95% by weight, of active ingredient mixture comprising a compound of formula I, a compound selected from the compounds of formulae 2.1 to 2.51 and the compounds of formulae 3.1 to 3.16, from 1 to 99.9% by weight of a solid or liquid formulation adjuvant and from 0 to 25% by weight, especially from 0.1 to 25% by weight, of a surfactant. Whereas commercial products are usually formulated as concentrates, the end user will normally employ dilute formulations.

The compositions may also comprise further ingredients, such as stabilisers, e.g. vegetable oils or epoxidised vegetable oils (epoxidised coconut oil, rapeseed oil or soybean oil), anti-foams, e.g. silicone oil, preservatives, viscosity regulators, binders, tackifiers, and also fertilisers or other active ingredients. For the use of safeners of formulae 3.1 to 3.16, or of compositions comprising them, in the protection of crop plants against the damaging effects of herbicides of formulae I and 2.1 to 2.51, various methods and techniques come into consideration, such as, for example, the following:

i) Seed Dressing a) Dressing of the seeds with a wettable powder formulation of a compound of formulae 3.1 to 3.16 by shaking in a vessel until uniformly distributed over the seed surface (dry dressing). In that procedure approximately from 1 to 500 g of compound of formulae 3.1 to 3.16 (4 g to 2 kg of wettable powder) are used per 100 kg of seed.

b) Dressing of the seeds with an emulsifiable concentrate of a compound of formulae 3.1 to 3.16 according to method a) (wet dressing).

c) Dressing by immersing the seeds for from 1 to 72 hours in a liquor comprising from 100 to 1000 ppm of a compound of formulae 3.1 to 3.16 and optionally subsequently drying the seeds (immersion dressing).

Dressing the seed or treating the germinated seedling are naturally the preferred methods of application, because treatment with the active ingredients is directed entirely at the target crop. Generally from 1 to 1000 g of antidote, preferably from 5 to 250 g of antidote, are used per 100 kg of seed, but depending on the methodology, which also enables the addition of other active ingredients or micronutrients, the concentration limits indicated can be varied up or down (repeat dressing).

ii) Application as a Tank Mixture

A liquid formulation of a mixture of antidote and herbicide is used (ratio by weight of the one to the other from 10:1 to 1:100), the rate of application of herbicide being from 0.005 to 5.0 kg per hectare. Such tank mixtures are applied before or after sowing.

iii) Application to the Seed Furrow

The compounds of formulae 3.1 to 3.16 are introduced into the open, sown seed furrow in the form of an emulsifiable concentrate, wettable powder or granules. Once the seed furrow has been covered over, the herbicide is applied in the usual manner in the pre-emergence process.

iv) Controlled Release of Active Ingredient

The compounds of formulae 3.1 to 3.16 are applied in solution to mineral granule carriers or polymerised granules (urea/formaldehyde) and dried. If desired, it is also possible to apply a coating that allows the active ingredient to be released in metered amounts over a specific period of time (coated granules).

Preferred formulations have especially the following compositions: (%=percent by weight)

Emulsifiable concentrates:

| | |
|---|---|
| active ingredient mixture: | 1 to 90%, preferably 5 to 20% |
| surfactant: | 1 to 30%, preferably 10 to 20% |
| liquid carrier: | 5 to 94%, preferably 70 to 85% |

Dusts:

| | |
|---|---|
| active ingredient mixture: | 0.1 to 10%, preferably 0.1 to 5% |
| solid carrier: | 99.9 to 90%, preferably 99.9 to 99% |

Suspension concentrates:

| | |
|---|---|
| active ingredient mixture: | 5 to 75%, preferably 10 to 50% |
| water: | 94 to 24%, preferably 88 to 30% |
| surfactant: | 1 to 40%, preferably 2 to 30% |

Wettable powders:

| | |
|---|---|
| active ingredient mixture: | 0.5 to 90%, preferably 1 to 80% |
| surfactant: | 0.5 to 20%, preferably 1 to 15% |
| solid carrier: | 5 to 95%, preferably 15 to 90% |

Granules:

| | |
|---|---|
| active ingredient mixture: | 0.1 to 30%, preferably 0.1 to 15% |
| solid carrier: | 99.5 to 70%, preferably 97 to 85% |

The following Examples illustrate the invention further, but do not limit the invention.

Formulation Examples for Mixtures of Herbicides of Formula I, Optionally Herbicides of Formulae 2.1 to 2.51, and Safeners of Formulae 3.1 to 3.16 (%=Percent by Weight)

F1. Emulsifiable concentrates

| | a) | b) | c) | d) |
|---|---|---|---|---|
| active ingredient mixture | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7–8 mol of ethylene oxide) | — | 4% | — | 2% |
| cyclohexanone | — | — | 10% | 20% |
| aromatic hydrocarbon mixture $C_9$–$C_{12}$ | 85% | 78% | 55% | 16% |

Emulsions of any desired concentration can be obtained from such concentrates by dilution with water.

F2. Solutions

| | a) | b) | c) | d) |
|---|---|---|---|---|
| active ingredient mixture | 5% | 10% | 50% | 90% |
| 1-methoxy-3-(3-methoxy-propoxy)-propane | — | 20% | 20% | — |
| polyethylene glycol MW 400 | 20% | 10% | — | — |
| N-methyl-2-pyrrolidone | — | — | 30% | 10% |
| aromatic hydrocarbon mixture $C_9$–$C_{12}$ | 75% | 60% | — | — |

The solutions are suitable for use in the form of microdrops.

F3. Wettable powders

| | a) | b) | c) | d) |
|---|---|---|---|---|
| active ingredient mixture | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7–8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

F4. Coated granules

| | a) | b) | c) |
|---|---|---|---|
| active ingredient mixture | 0.1% | 5% | 15% |
| highly dispersed silicic acid | 0.9% | 2% | 2% |
| inorganic carrier (Æ0.1–1 mm) e.g. $CaCO_3$ or $SiO_2$ | 99.0% | 93% | 83% |

The active ingredient is dissolved in methylene chloride and applied to the carrier by spraying, and the solvent is then evaporated off in vacuo.

F5. Coated granules

| | a) | b) | c) |
|---|---|---|---|
| active ingredient mixture | 0.1% | 5% | 15% |
| polyethylene glycol MW 200 | 1.0% | 2% | 3% |
| highly dispersed silicic acid | 0.9% | 1% | 2% |
| inorganic carrier (Æ0.1–1 mm) e.g. $CaCO_3$ or $SiO_2$ | 98.0% | 92% | 80% |

The finely ground active ingredient is uniformly applied, in a mixer, to the carrier moistened with polyethylene glycol. Non-dusty coated granules are obtained in this manner.

F6. Extruder granules

|  | a) | b) | c) | d) |
|---|---|---|---|---|
| active ingredient mixture | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

F7. Dusts

|  | a) | b) | c) |
|---|---|---|---|
| active ingredient mixture | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

F8. Suspension concentrates

|  | a) | b) | c) | d) |
|---|---|---|---|---|
| active ingredient mixture | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

It is often more practical for the compounds of formulae I, 2.1 to 2.51 and 3.1 to 3.16 to be formulated separately and then to be brought together in the desired mixing ratio in the applicator in the form of a "tank mixture" in water shortly before application.

The ability of the safeners of formulae 3.1 to 3.16 to protect crop plants against the phytotoxic action of herbicides of formula I is illustrated in the following Examples.

Biological Example: Safening Action

The test plants are grown in plastics pots under greenhouse conditions to the 4-leaf stage. At that stage, the herbicides alone, and the mixtures of the herbicides with the test compounds that are to be tested as safeners, are applied to the test plants. The application is in the form of an aqueous suspension of the test compounds prepared from a 25% wettable powder (Example F3, b)) with 500 liters of water/ha. 4 weeks after application, the phytotoxic action of the herbicides on the crop plants, e.g. maize and cereals, is evaluated using a percentage scale. 100% denotes that the test plant has died, 0% denotes no phytotoxic action.

The results obtained in this test demonstrate that damage to the crop plant caused by the herbicide of formula I in combination with one or more herbicides selected from formulae 2.1 to 2.51 can be significantly reduced by the compounds of formulae 3.1 to 3.16. Examples of the safening action are given in the following Table B40:

TABLE B40

| Test plant | Compd. 1.001 [50 g/ha] | Compd. 1.001 [50 g/ha] + compd. 3.3 [50 g/ha] | Compd. 1.001 [50 g/ha] + compd. 3.1 [50 g/ha] | Compd. 1.001 [50 g/ha] + compd. 3.8 [50 g/ha] |
|---|---|---|---|---|
| Maize | 50 | 5 | 5 | 0 |
| Abutilon | 100 | 100 | 100 | 100 |
| Setaria | 100 | 100 | 100 | 100 |

The same results are obtained when the mixtures are formulated in accordance with Examples F1, F2 and F4 to F8.

What is claimed is:

1. A herbicidally selective composition that, in addition to comprising customary inert formulation adjuvants, comprises as active ingredient a mixture a) a herbicidally effective amount of a compound of formula Ia

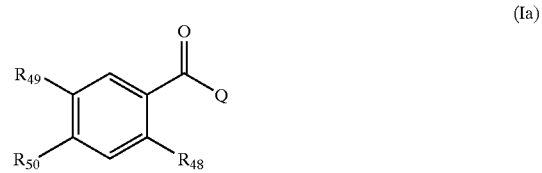

(Ia)

$R_{48}$ is $C_1$–$C_6$alkyl, $C_2$–$C_6$alkenyl, $C_2$–$C_6$haloalkenyl, $C_2$–$C_6$alkynyl, $C_2$–$C_6$alkynl, $C_3$–$C_6$cycloalkyl, $C_1$–$C_6$haloalkyl, $C_1$–$C_4$alkoxy-$C_1$–$C_4$alkyl or $C_1$–$C_4$alkoxy-$C_1$–$C_4$alkoxy-$C_1$–$C_4$;

$R_{49}$ is hydrogen;

$R_{50}$ $C_1$–$C_6$haloalkyl, $C_1$–$C_4$alkoxy-$C_1$–$C_4$alkyl or $C_1$–$C_4$alkoxy-$C_1$–$C_4$alkoxy-$C_1$–$C_4$; wherein one substituent selected from $R_{48}$ and $R_{50}$ can be $C_1$–$C_4$alkoxy-$C_1$–$C_4$alkyl or $C_1$–$C_4$alkoxy-$C_1$–$C_4$alkoxy-$C_1$–$C_4$alkyl and Q is the group $Q_2$

($Q_2$)

wherein $R_{23}$ is hydroxy and

Y is oxygen, sulfur, a chemical bond or a $C_1$–$C_4$alkylene bridge; or an agronomically acceptable salt of such a compound, and b) a synergistically effective amount of one or more compounds selected from a compound of formula 2.1

(2.1)

wherein $R_{51}$ is $CH_2$—OMe, ethyl or hydrogen;
$R_{52}$ is hydrogen or $R_{51}$ and $R_{52}$ together are the group —CH=CH—CH=CH—;
and a compound of formula 2.2

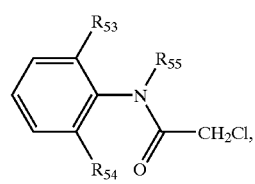
(2.2)

wherein $R_{53}$ is ethyl, $R_{54}$ is methyl or ethyl and $R_{55}$ is —CH(Me)-CH$_2$OMe, <S>—CH(Me)-CH$_2$OMe, CH$_2$OMe or CH$_2$O—CH$_2$CH$_3$;
and a compound of formula 2.3

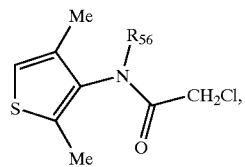
(2.3)

wherein $R_{56}$ is CH(Me)-CH$_2$OMe or <S>CH(Me)-CH$_2$OMe;
a compound of formula 2.4

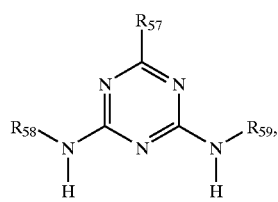
(2.4)

wherein $R_{57}$ is chlorine, methoxy or methylthio, $R_{58}$ is ethyl and $R_{59}$ is ethyl, isopropyl, —C(CN)(CH$_3$)—CH$_3$ or tert-butyl;

and a compound of formula 2.6

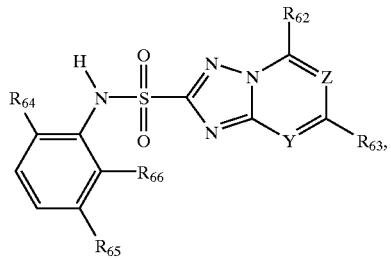
(2.6)

wherein $R_{62}$ is hydrogen, methoxy or ethoxy, $R_{63}$ is hydrogen, methyl, methoxy or fluorine, $R_{64}$ is COOMe, fluorine or chlorine, $R_{65}$ is hydrogen or methyl, Y is methine, C—F or nitrogen, Z is methine or nitrogen and $R_{66}$ is fluorine or chlorine;
and a compound of formula 2.7

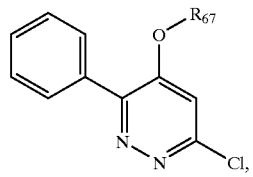
(2.7)

wherein $R_{67}$ is hydrogen or —C(O)—S-n-octyl;
and a compound of formula 2.12

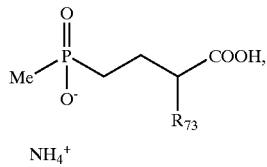
(2.12)

wherein $R_{73}$ is NH$_2$ or <S>NH$_2$;
a compound of formula 2.13

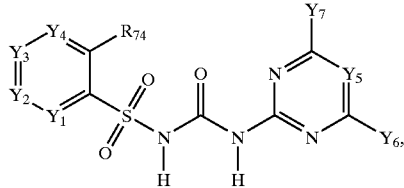
(2.13)

wherein $Y_1$ is nitrogen, methine, H—CHO or N-Me, $Y_2$ is nitrogen, methine or C—I, $Y_3$ is methine, $Y_4$ is methine or $Y_3$ and $Y_4$ together are sulfur or C—Cl, $Y_5$ is nitrogen or methine, $Y_6$ is methyl, difluoromethoxy, trifluoromethyl or methox , $Y_7$ is methoxy or difluoromethoxy and $R_{74}$ is CONMe$_2$, COOMe, COOC$_2$H$_5$, trifluoromethyl, CH$_2$—H$_2$CF$_3$ or SO$_2$CH$_2$CH$_3$, or a sodium salt thereof;

and the compound of formula 2.13.c

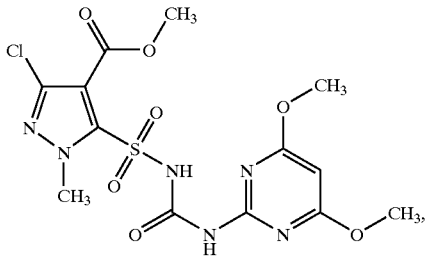
(2.13.c)

and the compound of formula 2.14

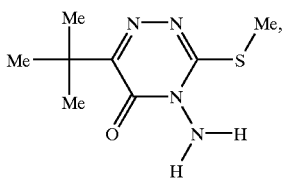
(2.14)

and the compound of formula 2.16

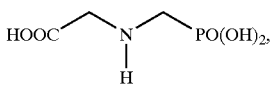
(2.16)

and the compound of formula 2.18

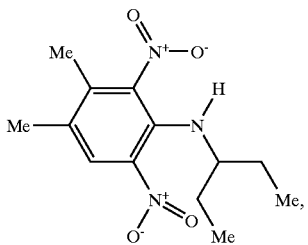
(2.18)

and the compound of formula 2.19

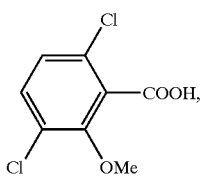
(2.19)

and the compound 2.21

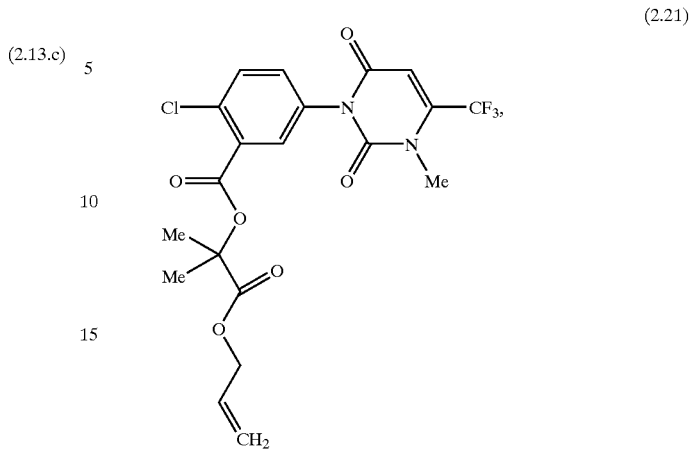
(2.21)

and the compound of formula 2.25

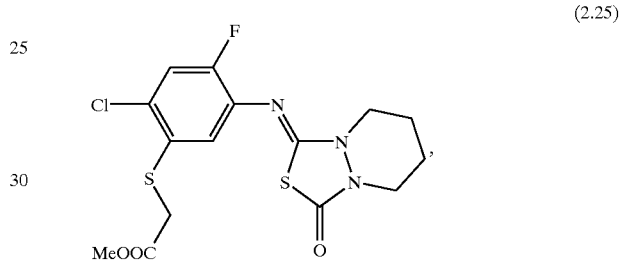
(2.25)

and the compound of formula 2.30

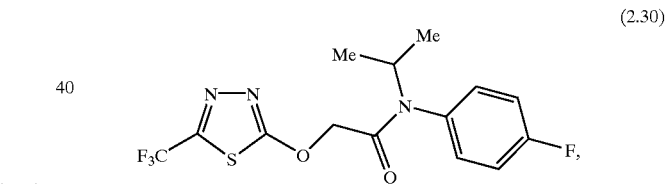
(2.30)

and the compound of formula 2.33

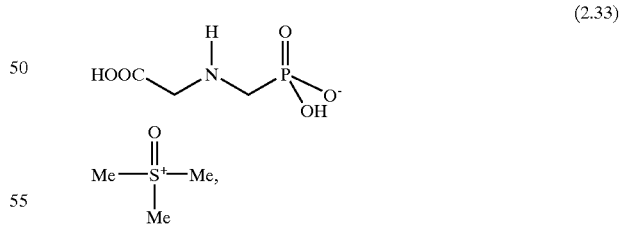
(2.33)

2. A method of controlling undesired plant growth crops of useful plants, which comprises allowing a herbicidally effective amount of a composition according to claim 1 to act on the crop plant or the locus thereof.

3. A method according to claim 2, wherein the crop plant is maize or sugar cane.

4. A method according to claim 2, wherein the crops of useful plants are treated with the mentioned composition at rates of application corresponding to a total amount of active ingredient of from 1 to 5000 g per hectare.

5. A herbicidally selective composition according to claim 1 that, in addition to comprising customary inert formulation adjuvants, such as carriers, solvents and wetting agents, comprises as active ingredient a mixture of
- a) a herbicidally-synergistically effective amount of a compound of formula (Ia) and one or more compounds selected from the compounds of formulae 2.1 to 2.51 and
- b) a herbicidally-antagonistically effective amount of a compound selected from the compound of formula 3.1

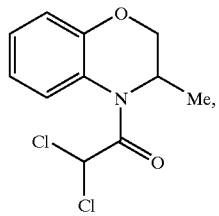

(3.1)

and the compound of formula 3.2

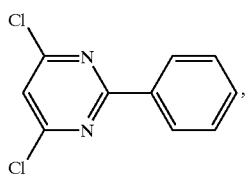

(3.2)

and the compound of formula 3.3

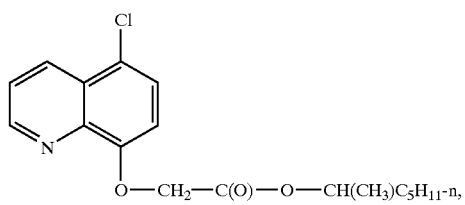

(3.3)

and the compound of formula 3.4

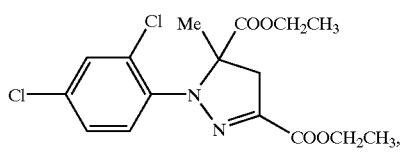

(3.4)

and the compound of formula 3.5

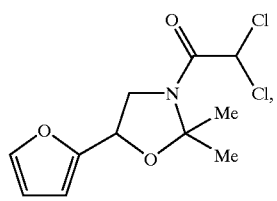

(3.5)

and the compound of formula 3.6

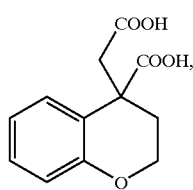

(3.6)

and the compound of formula 3.7

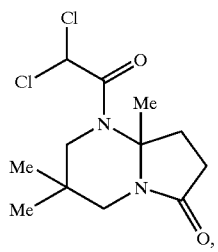

(3.7)

and the compound of formula 3.8

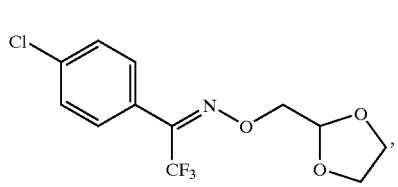

(3.8)

and of formula 3.9

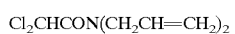

$Cl_2CHCON(CH_2CH=CH_2)_2$ (3.9), and of formula 3.10

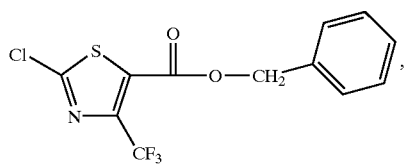

(3.10)

and of formula 3.11

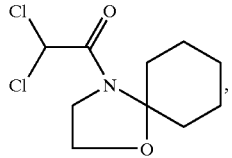

(3.11)

and of formula 3.12

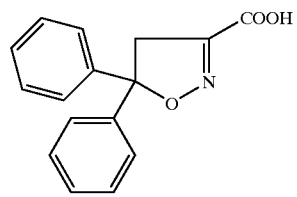

(3.12)

and its ethyl ester, and of formula 3.13

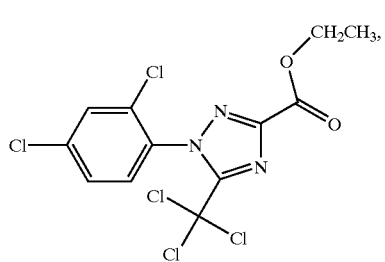

(3.13)

and of formula 3.14

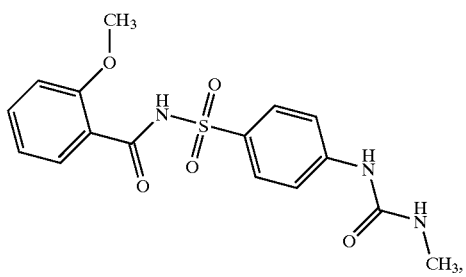

and of formula 3.15

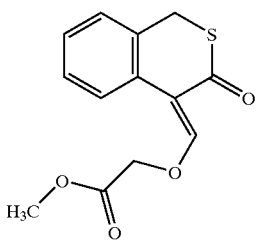

and of formula 3.16

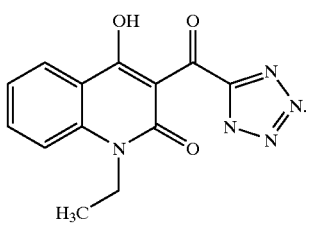

6. A method for the selective control of weeds and grasses in crops of useful plants, which comprises treating the useful plants, seeds or cuttings thereof, or the area of cultivation thereof, with a herbicidally-synergistically effective amount of a corn position according to claim 5.

7. A method according to claim 6, wherein the rate of application of herbicides is from 1 to 5000 g/ha and the rate of application of safener is from 0.001 to 0.5 kg/ha.

8. A method according to claim 6, wherein the crops of useful plants are maize or sugar cane.

9. A herbicidally selective composition that, in addition to comprising customary inert formulation adjuvants, such as carriers, solvents and wetting agents, comprise as active ingredient a mixture of
   a) a herbicidally effective amount of a compound of formula (Ia)

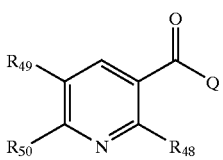

wherein $R_{48}$ is $C_1$–$C_6$alkyl, $C_2$–$C_6$alkenyl, $C_2$–$C_6$haloalkenyl, $C_2$–$C_6$-alkynyl, $C_2$–$C_6$haloalkynyl, $C_3$–$C_6$cycloalkyl, $C_1$–$C_6$haloalkyl, $C_1$–$C_4$alkoxy-$C_1$–$C_4$alkyl or $C_1$–$C_4$alkoxy-$C_1$–$C_4$alkyl;

$R_{49}$ is hydrogen;

$R_{50}$ is $C_1$–$C_6$haloalkyl, $C_1$–$C_4$alkoxy-$C_1$–$C_4$alkyl or $C_1$–$C_4$alkoxy-$C_1$–$C_4$alkoxy-$C_1$–$C_4$; wherein one substituent selected from $R_{48}$ and $R_{50}$ can be $C_1$–$C_4$alkoxy-$C_1$–$C_4$alkyl or $C_1$–$C_4$alkoxy-$C_1$–$C_4$alkoxy-$C_1$–$C_4$alkyl and Q is the group $Q_2$

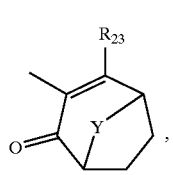

wherein $R_{23}$ is hydroxy and

Y is oxygen, sulfur, a chemical bond or a $C_1$–$C_4$alkylene bridge; or an agronomically acceptable salt of such a compound, and b) a herbicidally-antagonistically effective amount of a compound selected from the compound of formula 3.1

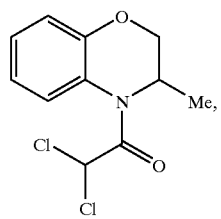

and the compound of formula 3.2

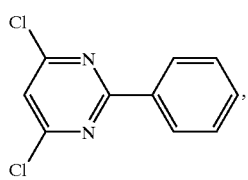

and the compound of formula 3.3

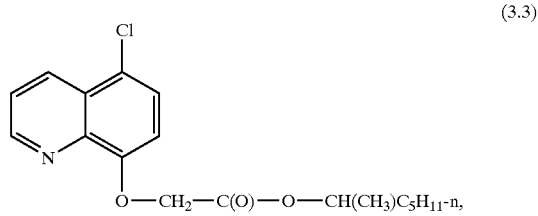

and the compound of formula 3.4

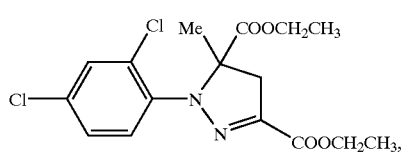

and the compound of formula 3.5

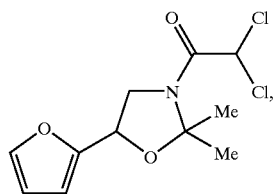
(3.5)

and the compound of formula 3.6

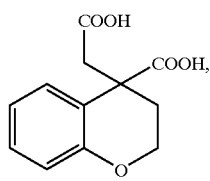
(3.6)

and the compound of formula 3.7

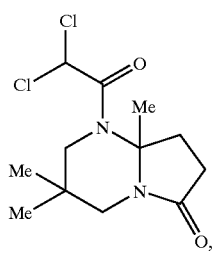
(3.7)

and the compound of formula 3.8

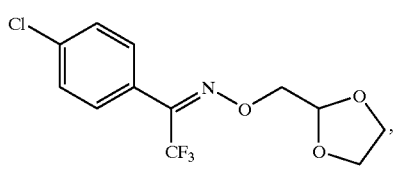
(3.8)

and of formula 3.9

$Cl_2CHCON(CH_2CH\!=\!CH_2)_2$
(3.9), and of formula 3.10

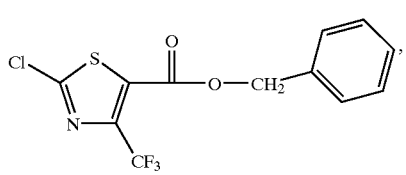
(3.10)

and of formula 3.11

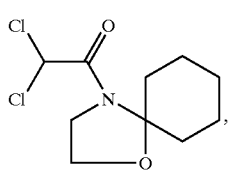
(3.11)

and of formula 3.12

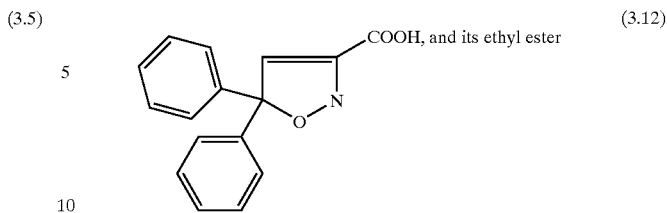
(3.12)

and of formula 3.13

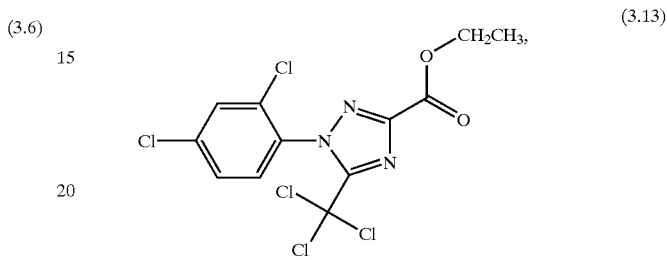
(3.13)

and of formula 3.14

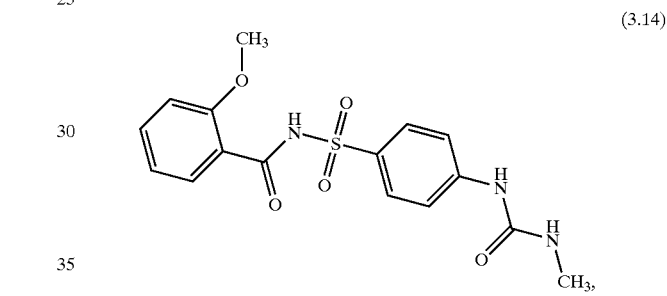
(3.14)

and of formula 3.15

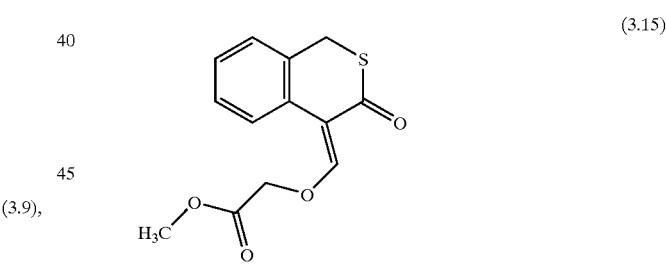
(3.15)

and of formula 3.16

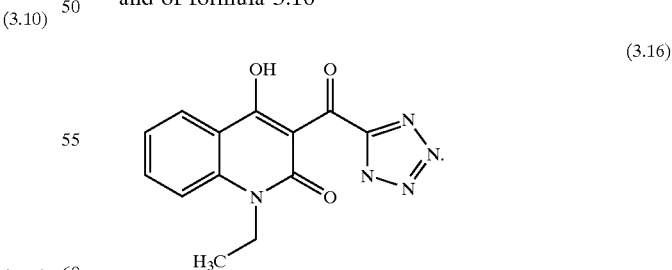
(3.16)

10. A method for the selective control of weeds and grasses in crops of useful plants, which comprises treating the useful plants, seeds or cuttings thereof, or the area of cultivation thereof, with a herbicidally-synergistically effective amount of a composition according to claim 9.

* * * * *

UNITED STATES PATENT AND TRADEMARK OFFICE
CERTIFICATE OF CORRECTION

PATENT NO. : 6,890,885 B2
DATED : May 10, 2005
INVENTOR(S) : Willy T. Rüegg

It is certified that error appears in the above-identified patent and that said Letters Patent is hereby corrected as shown below:

<u>Title page,</u>
Item [73], Assignee, should read -- Syngenta Crop Protection, Inc., --.

Signed and Sealed this

Twenty-eighth Day of March, 2006

JON W. DUDAS
*Director of the United States Patent and Trademark Office*

UNITED STATES PATENT AND TRADEMARK OFFICE
CERTIFICATE OF CORRECTION

PATENT NO. : 6,890,885 B2  Page 1 of 2
APPLICATION NO. : 10/201405
DATED : May 10, 2005
INVENTOR(S) : Willy T. Rüegg It is certified that error appears in the above-identified patent and that said Letters Patent is hereby corrected as shown below:

Column 206, lines 35-40, formula Ia should appear as follows:

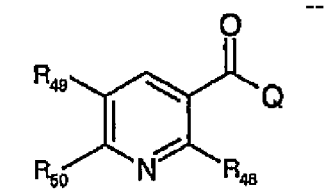

Column 206, lines 43, claim 1 "$C_2$–$C_6$alkynl" should read --$C_2$–$C_6$haloalkynyl--.

Column 206, line 45, claim 1 "$C_1$–$C_4$alkoxy-$C_1$–$C_4$alkoxy-$C_1$–$C_4$" should read --$C_1$–$C_4$alkoxy-$C_1$–$C_4$alkoxy-$C_1$–$C_4$alkyl--.

Column 206, line 49, claim 1 "$C_1$–$C_4$alkoxy-$C_1$–$C_4$alkoxy-$C_1$–$C_4$" should read --$C_1$–$C_4$alkoxy-$C_1$–$C_4$alkoxy–$C_1$–$C_4$alkyl--.

Column 208, line 60, claim 1 "H–CHO" should read --NH–CHO--.

Column 208, line 64, claim 1 "methox" should read --methoxy--.

Column 208, line 66, claim 1 "$CH_2$–$H_2CF_3$" should read --$CH_2$–$CH_2CF_3$--.

Column 213, line 43, claim 6, "corn position" should read --composition--.

Column 213, line 67, claim 9, "$C_1$–$C_4$alkoxy-$C_1$–$C_4$alkyl" should read --$C_1$–$C_4$alkoxy-$C_1$–$C_4$alkoxy-$C_1$–$C_4$alkyl--.

UNITED STATES PATENT AND TRADEMARK OFFICE
CERTIFICATE OF CORRECTION

| | |
|---|---|
| PATENT NO. | : 6,890,885 B2 |
| APPLICATION NO. | : 10/201405 |
| DATED | : May 10, 2005 |
| INVENTOR(S) | : Willy T. Rüegg |

It is certified that error appears in the above-identified patent and that said Letters Patent is hereby corrected as shown below:

Column 214, line 4, claim 9 "$C_1$–$C_4$alkoxy-$C_1$–$C_4$alkoxy-$C_1$–$C_4$" should read --$C_1$–$C_4$alkoxy-$C_1$–$C_4$alkoxy-$C_1$–$C_4$alkyl--.

Signed and Sealed this

Sixth Day of November, 2007

JON W. DUDAS
*Director of the United States Patent and Trademark Office*